(12) United States Patent
Buechter et al.

(10) Patent No.: US 7,101,676 B2
(45) Date of Patent: Sep. 5, 2006

(54) METHODS FOR IDENTIFYING COMPOUNDS WHICH INHIBIT BINDING OF NUCLEOCAPSID 7 PROTEIN TO HIV-1 RNA

(76) Inventors: Douglas Buechter, 9 Wellsweep La., Killingworth, CT (US) 06419; Xiaohong Hou, 2261 Longhill Rd., Guilford, CT (US) 06437; William G. Rice, 87 Mill Rd., Madison, CT (US) 06443; Christopher W. Marlor, 11 Robertson Dr., Bethany, CT (US) 06524; Wengang Yang, 55A Branford La., Branford, CT (US) 06511

( * ) Notice: Subject to any disclaimer, the term of this patent is extended or adjusted under 35 U.S.C. 154(b) by 0 days.

(21) Appl. No.: 10/339,217

(22) Filed: Jan. 9, 2003

(65) Prior Publication Data

US 2003/0198648 A1 Oct. 23, 2003

Related U.S. Application Data

(60) Provisional application No. 60/347,369, filed on Jan. 11, 2002.

(51) Int. Cl.
*G01N 33/53* (2006.01)

(52) U.S. Cl. .................. 435/7.1; 435/5; 435/6; 435/91.2; 435/456; 435/235.1; 435/69.1; 424/184.1; 424/207.1; 424/208.1; 530/300; 530/350

(58) Field of Classification Search ............ 435/5, 435/6, 7.1, 91.2, 456, 235.1, 69.1; 424/207.1, 424/208.1, 184.1, 93.2, 188.1, 204.1; 530/300, 530/350
See application file for complete search history.

(56) References Cited

U.S. PATENT DOCUMENTS

| | | | |
|---|---|---|---|
| 5,652,260 A | 7/1997 | Kun et al. | 514/457 |
| 5,652,367 A | 7/1997 | Kun et al. | 546/141 |
| 5,668,291 A | 9/1997 | Domagala et al. | 546/316 |
| 5,670,518 A | 9/1997 | Kun et al. | 514/309 |
| 5,733,921 A | 3/1998 | Bolton et al. | 514/373 |
| 5,734,081 A | 3/1998 | Domagala et al. | 564/82 |
| 5,753,674 A | 5/1998 | Kun et al. | 514/309 |
| 5,783,384 A | 7/1998 | Verdine | 435/6 |
| 5,877,185 A | 3/1999 | Kun et al. | 514/309 |
| 5,889,034 A | 3/1999 | Bolton et al. | 514/373 |
| 5,929,114 A | 7/1999 | Domagala et al. | 514/562 |
| 6,001,863 A | 12/1999 | Bolton et al. | 514/373 |
| 6,004,978 A | 12/1999 | Kun et al. | 514/309 |
| 6,008,190 A | 12/1999 | Meade et al. | 514/6 |
| 6,046,228 A | 4/2000 | Rice et al. | 514/441 |
| 6,133,270 A | 10/2000 | Bolton et al. | 514/258 |
| 6,225,323 B1 | 5/2001 | Yatscoff et al. | 514/292 |
| 6,242,478 B1 | 6/2001 | Welker et al. | 514/439 |

FOREIGN PATENT DOCUMENTS

WO    WO 9609406    *  3/1996

OTHER PUBLICATIONS

Tummino et al. The in vitro ejection of zinc from human immunodeficiency virus (HIV) type 1 nucleocapsid protein by disulfide benzamides with cellular anti–HIV activity. Proc. Natl. Acad. Sci. Feb. 1996, vol. 93, pp. 969–973.*

Domagala et al. A new class of anti–HIV agents targeted toward the nucleocapsid NCp7: the 2,2'–dithiobisbenzamides. Bioorg. Med. Chem. 1997, vol. 5(3) 569–579.*

Domagala et al. 2,2'–dithiobisbenzamides and 2–benzisothiazolones: two new classes of antiretroviral agents: SAR and mechanistic consideration. Drug Design Discovery, 1997, vol. 15(1), 49–61.*

Rice et al. Inhibition of HIV–1 infectivity by zinc–ejecting aromatic C–nitroso compounds. Nature, vol. 361, 1993, pp. 473–475.*

Rice et al. The site of antiviral action of 3–nitrosobenzamide on the infectivity process of human immunodeficiency virus in human lymphocytes. Proc. Natl. Acad. Sci. vol. 90, 1993, pp. 9721–9724.*

Rice et al. Inhibitors of HIV nucleocapsid protein zinc fingers as candidates for the treatment of AIDS. Science. vol. 270, 1995, 1194–1197.*

Tummino et al. The human immunodeficiency virus type 1 (HIV–1) nucleocapsid protein zinc ejection activity of disulfide benzamides and benzisothiazolones: correlation with anti–HIV and virucidal activities. Antimicrobial Agents and Chemotherapy. vol. 41 (2), 1997, pp. 394–400.*

Aldovini A, and Young RA, Mutations of RNA and Protein Sequences Involved in Human Immunodeficiency Virus Type 1 Packaging Result in Production of Noninfectious Virus, J Virol May 1990, 64(5):1920–1926.

Altschul, et al., Basic Local Alignment Search Tool, (1990) J. Mol. Biol. 215:403–410.

Amara et al., Control of a Mucosal Challenge and Prevention of AIDS by a Multiprotein DNA/MVA Vaccine, Science Apr. 6, 2001;292(5514): 69–74.

(Continued)

*Primary Examiner*—James Housel
*Assistant Examiner*—Emily M. Le
(74) *Attorney, Agent, or Firm*—Wilmer Cutler Pickering Hale & Dorr LLP

(57) ABSTRACT

The present invention relates to methods of identifying a molecule from a library of molecules that inhibits binding of human immunodeficiency virus nucleocapsid 7 polypeptide (NCp7) to an oligonucleotide which comprises admixing an NCp7 polypeptide with at one labeled HIV-1 psi-site oligonucleotide and an amount of the molecule to be tested under binding conditions; and determining the amount of oligonucleotide bound to the NCp7 polypeptide, wherein a decrease in the amount of oligonucleotide bound in the presence of the molecule compared with the amount of oligonucleotide bound in the absence of the molecule indicates that the molecule inhibits binding of NCp7 polypeptide to the oligonucleotide.

9 Claims, 7 Drawing Sheets

OTHER PUBLICATIONS

Amarasinghe et al., NMR Structure of the HIV–1 Nucleocapsid Protein Bound to Stem–Loop SL2 of the Ψ–RNA Packaging Signal. Implications for Genome Recognition, J Mol Biol Aug. 11, 2000;301(2):491–511.

Basrur et al., Inactivation of HIV–1 Nucleocapsid Protein P7 by Pyridinioalkanoyl Thioesters, J Biol Chem May 19, 2000;275(20):14890–14897.

Berg, Potential Metal–Binding Domains in Nucleic Acid Binding Proteins, Science Apr. 25, 1986; 232(4749):485–487.

Darlix, et al., First Glimpses at Structure–function Relationships of the Nucleocapsid Protein of Retroviruses, J Mol Biol Dec. 8, 1995; 254(4):523–537.

De Guzman et al., Structure of the HIV–1 Nucleocapsid Protein Bound to the SL3 Ψ–RNA Recognition Element, Science Jan. 16, 1998; 279(5349):384–388.

de Rocquigny H. et al., First Large Scale Chemical Synthesis of the 72 Amino Acid HIV–1 Nucleocapsid Protein NCp7 in an Active Form, Biochem Biophys Res Commun Oct. 31, 1991;180(2):1010–8.

Dorfman et al., Mapping of Functionally Important Residues of a Cysteine–Histidine Box in the Human Immunodeficiency Virus Type 1 Nucleocapsid Protein, J Virol Oct. 1993;67(10):6159–69.

Gorelick, et al., Strict Conservation of the Retroviral Nucleocapsid Protein Zinc Finger is Strongly Influenced by its Roles in Viral Processes: Characterization of HIV–1, Particles Containing Mutant Nucleocapsid Zinc–Coordinating Sequences, Virology Mar. 30, 1999;256(1):92–104.

Guo, J, et al., Zinc Finger Structures in the Human Immunodeficiency Virus Type 1 Nucleocapsid Protein Facilitate Efficient Minus– and Plus–Strand Transfer, J Virol Oct. 2000;74(19):8980–8.

Huang M, et al., Anti–HIV Agents That Selectively Target Retroviral Nucleocapsid Protein Zinc Fingers without Affecting Cellular Zinc Finger Proteins, J Med Chem Apr. 23, 1998;41(9):1371–81.

Maynard AT, et al., Reactivity of the HIV–1 nucleocapsid protein p7 zinc finger domains from the perspective of density–functional theory, Proc Natl Acad Sci USA Sep. 29, 1998;95(20);11578–83.

Maynard AT and Covell DG, Reactivity of Zinc Finger Cores; Analysis of Protein Packing and Electrostatic Screening, J Am Chem Soc Feb. 14, 2001;123(6):1047–58.

McDonnell NB, et al., Zinc Ejection as a New Rationale for the Use of Cystamine and Related Disulfide–Containing Antiviral Agents in the Treatment of AIDS, J Med Chem Jun. 20, 1997;40(13):1969–76.

Ramboarina S. et al., Structural Investigation on the Requirement of CCHH Zinc Finger Type in Nucleocapsid Protein of Human Immunodeficiency Virus 1, Biochemistry Jul. 27, 1999;38(30):9600–7.

Rice WG, et al., Inhibition of Multiple Phases of Human Immunodeficiency Virus Type 1.

South TL, et al., The Nucleocapsid Protein Isolated from HIV–1 Particles Binds Zinc and Forms Retroviral–Type Zinc Fingers, Biochemistry Aug. 28, 1990;29(34):7786–9.

South TL and Summers MF, Zinc Fingers, Adv Inorg Biochem 1990;8:199–248.

Takahashi K, et al., Two Basic Regions of NCp7 Are Sufficient for Conformational Conversion of HIV–1 Dimerization Initiation Site from Kissing–loop Dimer to Extended–duplex Dimer, Biol Chem Aug. 17, 2001;276(33):31274–8.

Turpin JA, et al., Synthesis and Biological Properties of Novel Pyridinioalkanoyl Thioesters (PATE) as Anti–HIV–1 Agents That Target the Viral Nucleocapsid Protein Zinc Fingers, J Med Chem Jan.14, 1999;42(1):67–86.

Vuilleumier C, et al., Nucleic Acid Sequence Discrimination by the HIV–1 Nucleocapsid Protein NCp7: A Fluorescence Study, Biochemistry Dec. 21, 1999;38(51);16816–25.

Williams MC, et al., Mechanism for nucleic acid chaperone activity of HIV–1 nucleocapsid protein revealed by single molecule stretching, Proc Natl Acad Sci USA May 22, 2001;98(11):6121–6.

Rice, et al., Inhibitors of HIV Nucleocapsid Protein Zinc Fingers as Candidates for the Treatment of AIDS, Science Nov. 17, 1995;270(5239): 1194–97.

Rice, et al. The Site of Antiviral Action of 3–nitrosobenzamide on the Infectivity Process of Human Immunodeficiency Virus in Human Lymphocytes, Proc. Natl. Acad. Sci. USA Oct. 15, 1993; 90(20): 9721–24.

Tummino, et al. The vitro Ejection of Zinc From Human Immunodeficiency Virus (HIV) typ 1 Nucleocapsid Protein by Disulfide Benzamides with Cellular Anti–HIV Activity, Proc. Natl. Acad. Sci. USA Feb. 6, 1996;93(3): 969–73.

Liitsola, K. et al., "Genetic Characterization of HIV–1 Strains in the Baltic Countries and Russia," *Scand J. Infect. Dis. 1996*; 28: 537–541.

International Search Report for Application No. PCT/US03/00801. Mailing Date Jun. 22, 2005; Total 6 pages.

* cited by examiner

SEQUENCE LISTING

<160> NUMBER OF SEQ ID NOS: 144

<210> SEQ ID NO 1
<211> LENGTH: 50
<212> TYPE: PRT
<213> ORGANISM: Artificial Sequence
<220> FEATURE:
<223> OTHER INFORMATION: NCp7 protein

<400> SEQUENCE: 1

Met Gln Arg Gly Asn Phe Arg Asn Gln Arg Lys Ile Lys Cys Phe Asn
1               5                   10                  15

Cys Gly Lys Glu Gly His Ile Ala Asn Cys Arg Ala Pro Arg Lys Arg
            20                  25                  30

Gly Cys Trp Lys Gly Lys Glu Gly His Gln Met Lys Asp Cys Thr Glu
        35                  40                  45

Gln Ala
    50

<210> SEQ ID NO 2
<211> LENGTH: 18
<212> TYPE: PRT
<213> ORGANISM: Artificial Sequence
<220> FEATURE:
<223> OTHER INFORMATION: first zinc finger of NCp7 protein

<400> SEQUENCE: 2

Val Lys Cys Phe Asn Cys Gly Lys Glu Gly His Thr Ala Arg Asn Cys
1               5                   10                  15

Arg Ala

-continued

```
<210> SEQ ID NO 3
<211> LENGTH: 18
<212> TYPE: PRT
<213> ORGANISM: Artificial Sequence
<220> FEATURE:
<223> OTHER INFORMATION: second zinc finger of NCp7 protein

<400> SEQUENCE: 3

Lys Gly Cys Trp Lys Cys Gly Lys Glu Gly His Gln Met Lys Asp Cys
 1               5                  10                  15

Thr Glu

<210> SEQ ID NO 4
<211> LENGTH: 36
<212> TYPE: PRT
<213> ORGANISM: Artificial Sequence
<220> FEATURE:
<223> OTHER INFORMATION: first and second zinc fingers of NCp7 protein

<400> SEQUENCE: 4

Val Lys Cys Phe Asn Cys Gly Lys Glu Gly His Thr Ala Arg Asn Cys
 1               5                  10                  15

Arg Ala Lys Gly Cys Trp Lys Cys Gly Lys Glu Gly His Gln Met Lys
                20                  25                  30

Asp Cys Thr Glu
            35

<210> SEQ ID NO 5
<211> LENGTH: 117
<212> TYPE: DNA
<213> ORGANISM: HIV-1

<400> SEQUENCE: 5
aggacucggc uugcugaagc gcgcacggca agaggcgagg ggcggcgacu ggugaguacg        60
ccaaaaauuu ugacuagcgg aggcuagaag gagagagaug ggugcgagag cgucggu         117

<210> SEQ ID NO 6
<211> LENGTH: 117
<212> TYPE: DNA
<213> ORGANISM: HIV-1

<400> SEQUENCE: 6
aggactcggc ttgctgaagc gcgcacggca agaggcgagg ggcggcgact ggtgagtacg        60
ccaaaaattt tgactagcgg aggctagaag gagagagatg ggtgcgagag cgtcggt         117

<210> SEQ ID NO 7
<211> LENGTH: 20
<212> TYPE: DNA
<213> ORGANISM: Artificial Sequence
<220> FEATURE:
<223> OTHER INFORMATION: SL3 RNA sequence

<400> SEQUENCE: 7
ggacuagcgg aggcuagucc                                                    20

<210> SEQ ID NO 8
<211> LENGTH: 20
<212> TYPE: DNA
<213> ORGANISM: Artificial Sequence
<220> FEATURE:
<223> OTHER INFORMATION: SL3 DNA sequence
```

-continued

```
<400> SEQUENCE: 8
ggactagcgg aggctagtcc                                              20

<210> SEQ ID NO 9
<211> LENGTH: 20
<212> TYPE: DNA
<213> ORGANISM: Artificial Sequence
<220> FEATURE:
<223> OTHER INFORMATION: SL3 A4 DNA sequence

<400> SEQUENCE: 9
ggactagcaa aagctagtcc                                              20

<210> SEQ ID NO 10
<211> LENGTH: 57
<212> TYPE: PRT
<213> ORGANISM: Artificial Sequence
<220> FEATURE:
<223> OTHER INFORMATION: NCp7 protein

<400> SEQUENCE: 10

Ala Arg Ile Leu Ala Glu Ala Met Ser Gln Val Thr Asn Thr Ala Val
 1               5                  10                  15

Met Met Gln Arg Asn Asn Phe Lys Gly Gln Arg Lys Ile Ile Lys Cys
            20                  25                  30

Phe Asn Cys Gly Lys Glu Gly His Leu Ala Lys Asn Cys Arg Ala Pro
        35                  40                  45

Arg Lys Lys Gly Cys Trp Lys Cys Gly
    50                  55

<210> SEQ ID NO 11
<211> LENGTH: 59
<212> TYPE: PRT
<213> ORGANISM: Artificial Sequence
<220> FEATURE:
<223> OTHER INFORMATION: NCp7 protein

<400> SEQUENCE: 11

Ala Arg Val Leu Ala Glu Ala Met Ser Gln Val Ser Gly Val Gly Ala
 1               5                  10                  15

Ala Ile Met Met Gln Lys Ser Asn Phe Lys Gly Pro Lys Arg Met Ile
            20                  25                  30

Lys Cys Phe Asn Cys Gly Lys Glu Gly His Leu Ala Arg Asn Cys Arg
        35                  40                  45

Ala Pro Arg Lys Arg Gly Cys Trp Lys Cys Gly
    50                  55

<210> SEQ ID NO 12
<211> LENGTH: 59
<212> TYPE: PRT
<213> ORGANISM: Artificial Sequence
<220> FEATURE:
<223> OTHER INFORMATION: NCp7 protein

<400> SEQUENCE: 12

Ala Arg Val Leu Ala Glu Ala Met Ser Gln Val Thr Gln Pro Ala Thr
 1               5                  10                  15

Ile Met Met Gln Lys Gly Asn Phe Arg Asn Gln Arg Lys Thr Val Lys
            20                  25                  30
```

```
Cys Phe Asn Cys Gly Lys Glu Gly His Ile Ala Lys Asn Cys Arg Ala
        35                  40                  45

Pro Arg Lys Lys Gly Cys Trp Lys Cys Gly Arg
 50                  55

<210> SEQ ID NO 13
<211> LENGTH: 60
<212> TYPE: PRT
<213> ORGANISM: Artificial Sequence
<220> FEATURE:
<223> OTHER INFORMATION: NCp7 protein

<400> SEQUENCE: 13

Ala Arg Val Leu Ala Glu Ala Met Ser Gln Val Thr Gly Ser Ala Ala
 1               5                  10                  15

Thr Ile Met Met Gln Arg Gly Asn Ile Arg Asn Gln Arg Lys Thr Val
                20                  25                  30

Lys Cys Phe Asn Cys Gly Lys Glu Gly His Ile Ala Arg Asn Cys Arg
            35                  40                  45

Ala Pro Arg Lys Lys Gly Cys Trp Lys Cys Gly Lys
 50                  55                  60

<210> SEQ ID NO 14
<211> LENGTH: 59
<212> TYPE: PRT
<213> ORGANISM: Artificial Sequence
<220> FEATURE:
<223> OTHER INFORMATION: NCp7 protein

<400> SEQUENCE: 14

Ala Arg Val Leu Ala Glu Ala Met Ser Gln Val Thr Gln Ser Ala Thr
 1               5                  10                  15

Met Met Met Gln Arg Gly Asn Phe Arg Asn Gln Lys Lys Thr Val Lys
                20                  25                  30

Cys Phe Asn Cys Gly Lys Glu Gly His Ile Ala Lys Asn Cys Arg Ala
        35                  40                  45

Pro Arg Lys Lys Gly Cys Trp Lys Cys Gly Arg
 50                  55

<210> SEQ ID NO 15
<211> LENGTH: 59
<212> TYPE: PRT
<213> ORGANISM: Artificial Sequence
<220> FEATURE:
<223> OTHER INFORMATION: NCp7 protein

<400> SEQUENCE: 15

Ala Arg Val Leu Ala Glu Ala Met Ser Gln Val Thr Asn Ser Pro Ala
 1               5                  10                  15

Ile Met Met Gln Arg Gly Asn Phe Arg Asn Gln Arg Lys Ile Val Lys
                20                  25                  30

Cys Phe Asn Cys Gly Lys Glu Gly His Ile Ala Lys Asn Cys Arg Ala
        35                  40                  45

Pro Arg Lys Arg Gly Cys Trp Lys Cys Gly Lys
 50                  55

<210> SEQ ID NO 16
<211> LENGTH: 59
<212> TYPE: PRT
<213> ORGANISM: Artificial Sequence
<220> FEATURE:
<223> OTHER INFORMATION: NCp7 protein
```

-continued

<400> SEQUENCE: 16

Ala Arg Val Leu Ala Glu Ala Met Ser Gln Val Thr Gln Pro Ala Thr
1               5                   10                  15

Ile Met Met Gln Arg Gly Asn Phe Arg Asn Gln Arg Lys Thr Val Lys
            20                  25                  30

Cys Phe Asn Cys Gly Lys Glu Gly His Ile Ala Lys Asn Cys Arg Ala
        35                  40                  45

Pro Arg Lys Lys Gly Cys Trp Lys Cys Gly Arg
    50                  55

<210> SEQ ID NO 17
<211> LENGTH: 58
<212> TYPE: PRT
<213> ORGANISM: Artificial Sequence
<220> FEATURE:
<223> OTHER INFORMATION: NCp7 protein

<400> SEQUENCE: 17

Ala Arg Val Leu Ala Glu Ala Met Ser Gln Val Thr Ala Ser Ala Thr
1               5                   10                  15

Ile Met Met Gln Arg Gly Asn Phe Lys Asn Gln Arg Lys Thr Val Lys
            20                  25                  30

Cys Phe Asn Cys Gly Lys Glu Gly His Ile Ala Lys Asn Cys Arg Ala
        35                  40                  45

Pro Arg Lys Lys Gly Cys Trp Lys Cys Gly
    50                  55

<210> SEQ ID NO 18
<211> LENGTH: 500
<212> TYPE: PRT
<213> ORGANISM: HIV-1

<400> SEQUENCE: 18

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Lys Tyr Arg Leu Lys
            20                  25                  30

His Ile Val Trp Ala Ser Arg Glu Leu Glu Arg Phe Ala Leu Asn Pro
        35                  40                  45

Gly Leu Leu Glu Thr Ser Glu Gly Cys Lys Gln Ile Ile Gly Gln Leu
    50                  55                  60

Gln Pro Ala Val Gln Thr Gly Ser Glu Glu Leu Lys Ser Leu Phe Asn
65                  70                  75                  80

Thr Val Ala Thr Leu Tyr Cys Val His Glu Arg Ile Glu Val Lys Asp
                85                  90                  95

Thr Lys Glu Ala Leu Glu Lys Ile Glu Glu Gln Ala Lys Ser Lys
            100                 105                 110

Lys Lys Ala Gln Gln Ala Thr Ala Asp Thr Arg Asn Ser Ser Gln Val
        115                 120                 125

Ser Gln Asn Tyr Pro Ile Val Gln Asn Leu Gln Gly Gln Met Ile His
    130                 135                 140

Gln Ala Ile Ser Pro Arg Thr Leu Asn Ala Trp Val Lys Val Ile Glu
145                 150                 155                 160

Glu Lys Ala Phe Ser Pro Glu Val Ile Pro Met Phe Thr Ala Leu Ser
                165                 170                 175

Glu Gly Ala Thr Pro Gln Asp Leu Asn Thr Met Leu Asn Thr Val Gly
            180                 185                 190

```
Gly His Gln Ala Ala Met Gln Met Leu Lys Glu Thr Ile Asn Glu Glu
        195                 200                 205

Ala Ala Glu Trp Asp Arg Leu His Pro Pro Gln Ala Gly Pro Val Ala
        210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Ser Asn Pro Pro Val
                245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Gly Ala Thr Leu Glu Glu Met Met Thr Ala Cys Gln Gly
            340                 345                 350

Val Gly Gly Pro Ser His Lys Ala Arg Val Leu Ala Glu Ala Met Ser
        355                 360                 365

Gln Ala Thr Asn Leu Asn Gly Ala Ala Met Met Gln Arg Ser Asn Phe
    370                 375                 380

Lys Gly Pro Arg Lys Ile Val Lys Cys Phe Asn Cys Gly Lys Glu Gly
385                 390                 395                 400

His Ile Ala Arg Asn Cys Lys Ala Pro Arg Lys Lys Gly Cys Trp Lys
                405                 410                 415

Cys Gly Ser Glu Gly His Gln Met Lys Asp Cys Thr Glu Arg Gln Ala
            420                 425                 430

Asn Phe Leu Gly Lys Ile Trp Pro Ser His Lys Gly Arg Pro Gly Asn
        435                 440                 445

Phe Leu Gln Asn Arg Pro Glu Pro Thr Ala Pro Ala Glu Ser Phe
    450                 455                 460

Gly Phe Gly Glu Glu Ile Thr Pro Ser Gln Lys Gln Glu Gln Lys Asn
465                 470                 475                 480

Gln Glu Pro Gln Pro Leu Thr Ser Leu Arg Ser Leu Phe Gly Asn Asp
                485                 490                 495

Pro Leu Leu Pro
        500

<210> SEQ ID NO 19
<211> LENGTH: 95
<212> TYPE: PRT
<213> ORGANISM: HIV-1

<400> SEQUENCE: 19

Leu Asn Lys Ile Val Arg Met Tyr Ser Pro Val Ser Ile Leu Asp Ile
1               5                   10                  15

Arg Gln Gly Pro Lys Glu Pro Phe Arg Asp Tyr Val Asp Arg Phe Phe
            20                  25                  30

Lys Thr Leu Arg Ala Glu Gln Ala Thr Gln Glu Val Lys Gly Trp Met
        35                  40                  45

Thr Asp Thr Leu Leu Val Gln Asn Ala Asn Pro Asp Cys Lys Thr Ile
    50                  55                  60
```

```
Leu Arg Ala Leu Gly Pro Gly Ala Thr Leu Glu Glu Met Met Thr Ala
 65                  70                  75                  80

Cys Gln Gly Val Gly Pro Ser Pro Lys Ala Arg Val Phe Ser
                 85                  90                  95

<210> SEQ ID NO 20
<211> LENGTH: 139
<212> TYPE: PRT
<213> ORGANISM: HIV-1

<400> SEQUENCE: 20

Leu Asn Lys Ile Val Arg Met Tyr Ser Pro Val Ser Ile Leu Asp Ile
  1               5                  10                  15

Arg Gln Gly Pro Lys Glu Pro Phe Arg Asp Tyr Val Asp Arg Phe Phe
                 20                  25                  30

Lys Thr Leu Arg Ala Glu Gln Ala Thr Gln Glu Val Lys Gly Trp Met
                 35                  40                  45

Thr Asp Thr Leu Leu Val Gln Asn Ala Asn Pro Asp Cys Lys Thr Ile
 50                  55                  60

Leu Arg Ala Leu Gly Pro Gly Ala Thr Leu Glu Glu Met Met Thr Ala
 65                  70                  75                  80

Cys Gln Gly Val Gly Gly Pro Ser His Lys Ala Arg Val Leu Ala Glu
                 85                  90                  95

Ala Met Ser Gln Ala Ser Gly Ala Thr Ile Met Met Gln Lys Ser Asn
                100                 105                 110

Phe Lys Gly Pro Arg Arg Met Ile Lys Cys Phe Asn Cys Gly Lys Glu
                115                 120                 125

Gly His Leu Ala Arg Asn Cys Arg Ala Pro Arg
                130                 135

<210> SEQ ID NO 21
<211> LENGTH: 95
<212> TYPE: PRT
<213> ORGANISM: HIV-1

<400> SEQUENCE: 21

Leu Asn Lys Ile Val Arg Met Tyr Ser Pro Val Ser Ile Leu Asp Ile
  1               5                  10                  15

Arg Gln Gly Pro Lys Glu Pro Phe Arg Asp Tyr Val Asp Arg Phe Phe
                 20                  25                  30

Lys Thr Leu Arg Ala Glu Gln Ala Thr Gln Glu Val Lys Gly Trp Met
                 35                  40                  45

Thr Asp Thr Leu Leu Val Gln Asn Ala Asn Pro Asp Cys Lys Thr Ile
 50                  55                  60

Leu Arg Ala Leu Gly Pro Gly Ala Thr Leu Glu Glu Met Met Thr Ala
 65                  70                  75                  80

Cys Gln Gly Val Gly Gly Pro Ser His Lys Ala Arg Val Phe Ser
                 85                  90                  95

<210> SEQ ID NO 22
<211> LENGTH: 139
<212> TYPE: PRT
<213> ORGANISM: HIV-1
```

<400> SEQUENCE: 22

```
Leu Asn Lys Ile Val Arg Met Tyr Ser Pro Val Ser Ile Leu Asp Ile
 1               5                  10                  15

Arg Gln Gly Pro Lys Glu Pro Phe Arg Asp Tyr Val Asp Arg Phe Phe
            20                  25                  30

Lys Thr Leu Arg Ala Gly Gln Ala Thr Gln Glu Val Lys Gly Trp Met
        35                  40                  45

Thr Asp Thr Leu Leu Val Gln Asn Ala Asn Pro Asp Cys Lys Thr Ile
 50                  55                  60

Leu Arg Ala Leu Gly Pro Gly Ala Thr Leu Glu Glu Met Met Thr Ala
 65                  70                  75                  80

Cys Gln Gly Val Gly Gly Pro Gly His Lys Ala Arg Val Leu Ala Glu
                85                  90                  95

Ala Met Ser Gln Ala Thr Gly Ala Ala Met Met Gln Lys Ser Asn
                100                 105                 110

Phe Lys Gly Pro Lys Arg Met Ile Lys Cys Phe Asn Cys Gly Lys Glu
            115                 120                 125

Gly His Leu Ala Arg Asn Cys Arg Ala Pro Arg
        130                 135
```

<210> SEQ ID NO 23
<211> LENGTH: 139
<212> TYPE: PRT
<213> ORGANISM: HIV-1

<400> SEQUENCE: 23

```
Leu Asn Lys Ile Val Arg Met Tyr Ser Pro Val Ser Ile Leu Asp Ile
 1               5                  10                  15

Arg Gln Gly Pro Lys Glu Pro Phe Arg Asp Tyr Val Asp Arg Phe Phe
            20                  25                  30

Lys Thr Leu Arg Ala Glu Gln Ala Thr Gln Glu Val Lys Gly Trp Met
        35                  40                  45

Thr Asp Thr Leu Leu Val Gln Asn Ala Asn Pro Asp Cys Lys Thr Ile
 50                  55                  60

Leu Lys Ala Leu Gly Ser Gly Ala Thr Leu Glu Glu Met Met Thr Ala
 65                  70                  75                  80

Cys Gln Gly Val Gly Gly Pro Gly His Lys Ala Arg Val Leu Ala Glu
                85                  90                  95

Ala Met Ser Gln Val Ser Gly Thr Thr Val Met Met Gln Lys Ser Asn
                100                 105                 110

Phe Lys Gly Pro Lys Arg Thr Val Lys Cys Phe Asn Cys Gly Lys Glu
            115                 120                 125

Gly His Leu Ala Arg Asn Cys Arg Ala Pro Arg
        130                 135
```

<210> SEQ ID NO 24
<211> LENGTH: 139
<212> TYPE: PRT
<213> ORGANISM: HIV-1

<400> SEQUENCE: 24

```
Leu Asn Lys Ile Val Arg Met Tyr Ser Pro Val Ser Ile Leu Asp Ile
 1               5                  10                  15

Arg Gln Gly Pro Lys Glu Pro Phe Arg Asp Tyr Val Asp Arg Phe Phe
            20                  25                  30
```

```
Lys Thr Leu Arg Ala Glu Gln Ala Thr Gln Glu Val Lys Gly Trp Met
        35                  40                  45

Thr Asp Thr Leu Leu Val Gln Asn Ala Asn Pro Asp Cys Lys Thr Ile
    50                  55                  60

Leu Lys Ala Leu Gly Pro Gly Ala Thr Leu Glu Glu Met Met Thr Ala
65                  70                  75                  80

Cys Gln Gly Val Gly Gly Pro Gly His Lys Ala Arg Val Leu Ala Glu
                85                  90                  95

Ala Met Ser Gln Val Ser Gly Thr Thr Val Met Met Gln Lys Ser Asn
            100                 105                 110

Phe Lys Gly Pro Lys Arg Thr Ile Lys Cys Phe Asn Cys Gly Lys Glu
        115                 120                 125

Gly His Leu Ala Arg Asn Cys Arg Ala Pro Arg
    130                 135
```

<210> SEQ ID NO 25
<211> LENGTH: 139
<212> TYPE: PRT
<213> ORGANISM: HIV-1

<400> SEQUENCE: 25

```
Leu Asn Lys Ile Val Arg Met Tyr Ser Pro Thr Ser Ile Leu Asp Ile
1               5                   10                  15

Lys Gln Gly Pro Lys Glu Ser Phe Arg Asp Tyr Val Asp Arg Phe Phe
            20                  25                  30

Lys Thr Leu Arg Ala Glu Gln Ala Thr Gln Glu Val Lys Asn Trp Met
        35                  40                  45

Thr Asp Thr Leu Leu Val Gln Asn Ala Asn Pro Asp Cys Lys Thr Ile
    50                  55                  60

Leu Arg Ala Leu Gly Pro Gly Ala Thr Leu Glu Glu Met Met Thr Ala
65                  70                  75                  80

Cys Gln Gly Val Gly Gly Pro Ser His Lys Ala Arg Val Leu Ala Glu
                85                  90                  95

Ala Met Ser Gln Ala Ser Gly Ala Thr Val Met Met Gln Lys Gly Asn
            100                 105                 110

Phe Lys Gly Pro Lys Arg Met Ile Lys Cys Phe Asn Cys Gly Lys Glu
        115                 120                 125

Gly His Leu Ala Arg Asn Cys Arg Ala Pro Arg
    130                 135
```

<210> SEQ ID NO 26
<211> LENGTH: 139
<212> TYPE: PRT
<213> ORGANISM: HIV-1

<400> SEQUENCE: 26

```
Leu Asn Lys Ile Val Arg Met Tyr Ser Pro Val Ser Ile Leu Asp Ile
1               5                   10                  15

Lys Gln Gly Pro Lys Glu Pro Phe Arg Asp Tyr Val Asp Arg Phe Phe
            20                  25                  30

Lys Thr Leu Arg Ala Glu Gln Cys Thr Gln Glu Val Lys Gly Trp Met
        35                  40                  45

Thr Asp Thr Leu Leu Val Gln Asn Ala Asn Pro Asp Cys Lys Thr Ile
    50                  55                  60

Leu Arg Ala Leu Gly Pro Gly Ala Thr Leu Glu Glu Met Met Thr Ala
65                  70                  75                  80
```

```
Cys Gln Gly Val Gly Gly Pro Ser His Lys Ala Arg Ile Leu Ala Glu
                85                  90                  95

Ala Met Ser Gln Val Ser Gly Ala Thr Ile Met Met Gln Lys Ser Asn
            100                 105                 110

Phe Lys Gly Pro Lys Arg Met Ile Lys Cys Phe Asn Cys Gly Lys Glu
        115                 120                 125

Gly His Leu Ala Arg Asn Cys Arg Ala Pro Arg
    130                 135
```

<210> SEQ ID NO 27
<211> LENGTH: 139
<212> TYPE: PRT
<213> ORGANISM: HIV-1

<400> SEQUENCE: 27

```
Leu Asn Lys Ile Val Arg Met Tyr Ser Pro Val Ser Ile Leu Asp Ile
  1               5                  10                  15

Arg Gln Gly Pro Lys Glu Pro Phe Arg Asp Tyr Val Asp Arg Phe Phe
             20                  25                  30

Lys Thr Leu Arg Ala Glu Gln Ala Thr Gln Glu Val Lys Asn Trp Met
         35                  40                  45

Thr Asp Thr Leu Leu Val Gln Asn Ala Asn Pro Asp Cys Lys Asn Ile
 50                  55                  60

Leu Arg Ala Leu Gly Pro Gly Ala Thr Leu Glu Glu Met Met Thr Ala
 65                  70                  75                  80

Cys Gln Gly Val Gly Gly Pro Gly His Lys Ala Arg Val Leu Ala Glu
                85                  90                  95

Ala Met Ser Gln Val Ser Gly Pro Thr Val Met Met Gln Lys Ser Asn
            100                 105                 110

Phe Lys Gly Pro Arg Lys Met Ile Lys Cys Phe Asn Cys Gly Lys Glu
        115                 120                 125

Gly His Leu Ala Arg Asn Cys Arg Ala Pro Arg
    130                 135
```

<210> SEQ ID NO 28
<211> LENGTH: 141
<212> TYPE: PRT
<213> ORGANISM: HIV-1

<400> SEQUENCE: 28

```
Leu Asn Lys Ile Val Arg Met Tyr Ser Pro Val Ser Ile Leu Asp Ile
  1               5                  10                  15

Arg Gln Gly Pro Lys Glu Pro Phe Arg Asp Tyr Val Asp Arg Phe Phe
             20                  25                  30

Lys Thr Leu Arg Ala Glu Gln Ala Thr Gln Glu Val Lys Gly Trp Met
         35                  40                  45

Thr Asp Thr Leu Leu Val Gln Asn Ala Asn Pro Asp Cys Lys Thr Ile
 50                  55                  60

Leu Arg Ala Leu Gly Pro Gly Ala Thr Leu Glu Glu Met Met Thr Ala
 65                  70                  75                  80

Cys Gln Gly Val Gly Gly Pro Gly His Lys Ala Arg Val Leu Ala Glu
                85                  90                  95

Ala Met Ser Gln Ala Ser Gly Ala Ala Ala Ile Met Met Gln Lys
            100                 105                 110
```

```
Ser Asn Phe Lys Gly Pro Arg Arg Met Ile Lys Cys Phe Asn Cys Gly
        115                 120                 125

Lys Glu Gly His Leu Ala Arg Asn Cys Arg Ala Pro Arg
    130                 135                 140

<210> SEQ ID NO 29
<211> LENGTH: 141
<212> TYPE: PRT
<213> ORGANISM: HIV-1

<400> SEQUENCE: 29

Leu Asn Lys Ile Val Arg Met Tyr Ser Pro Val Ser Ile Leu Asp Ile
  1               5                  10                  15

Arg Gln Gly Pro Lys Glu Pro Phe Arg Asp Tyr Val Asp Arg Phe Phe
             20                  25                  30

Lys Thr Leu Arg Ala Glu Gln Ala Thr Gln Glu Val Lys Gly Trp Met
         35                  40                  45

Thr Glu Thr Leu Leu Val Gln Asn Ala Asn Pro Asp Cys Lys Thr Ile
     50                  55                  60

Leu Arg Ala Leu Gly Ser Gly Ala Thr Leu Glu Glu Met Met Thr Ala
 65                  70                  75                  80

Cys Gln Gly Val Gly Gly Pro Ser His Lys Ala Arg Val Leu Ala Glu
                 85                  90                  95

Ala Met Ser Gln Ala Ser Gly Ala Ala Thr Ala Ile Met Met Gln Lys
            100                 105                 110

Ser Asn Phe Lys Gly Pro Arg Arg Met Ile Lys Cys Phe Asn Cys Gly
        115                 120                 125

Lys Glu Gly His Leu Ala Arg Asn Cys Arg Ala Pro Arg
    130                 135                 140

<210> SEQ ID NO 30
<211> LENGTH: 141
<212> TYPE: PRT
<213> ORGANISM: HIV-1

<400> SEQUENCE: 30

Leu Asn Lys Ile Val Arg Met Tyr Ser Pro Val Gly Ile Leu Asp Ile
  1               5                  10                  15

Lys Gln Gly Pro Lys Glu Pro Phe Arg Asp Tyr Val Asp Arg Phe Phe
             20                  25                  30

Lys Thr Leu Arg Ala Glu Gln Ala Thr Gln Glu Val Lys Gly Trp Met
         35                  40                  45

Thr Asp Thr Leu Leu Val Gln Asn Ala Asn Pro Asp Cys Lys Thr Ile
     50                  55                  60

Leu Arg Ala Leu Gly Pro Gly Ala Thr Leu Glu Glu Met Met Thr Ala
 65                  70                  75                  80

Cys Gln Gly Val Gly Gly Pro Ser His Lys Ala Lys Val Leu Ala Glu
                 85                  90                  95

Ala Met Ser Gln Ala Ser Gly Ala Ala Pro Ala Ile Met Met Gln Lys
            100                 105                 110

Ser Asn Phe Lys Gly Pro Arg Arg Met Ile Lys Cys Phe Asn Cys Gly
        115                 120                 125

Lys Glu Gly His Leu Ala Arg Asn Cys Arg Ala Pro Arg
    130                 135                 140
```

```
<210> SEQ ID NO 31
<211> LENGTH: 513
<212> TYPE: PRT
<213> ORGANISM: HIV-1

<400> SEQUENCE: 31
```

| | | | | | | | | | | | | | | | |
|---|---|---|---|---|---|---|---|---|---|---|---|---|---|---|---|
| Met | Gly | Ala | Arg | Ala | Ser | Val | Leu | Ser | Gly | Lys | Leu | Asp | Ala | Trp | |
| 1 | | | | 5 | | | | | 10 | | | | | 15 | |
| Glu | Lys | Ile | Arg | Leu | Arg | Pro | Gly | Gly | Lys | Lys | Lys | Tyr | Arg | Leu | Lys |
| | | | 20 | | | | | 25 | | | | | 30 | | |
| His | Leu | Val | Trp | Ala | Ser | Arg | Glu | Leu | Glu | Arg | Phe | Ala | Leu | Asn | Pro |
| | | | 35 | | | | 40 | | | | | 45 | | | |
| Ser | Leu | Leu | Glu | Thr | Gly | Glu | Gly | Cys | Gln | Gln | Ile | Met | Glu | Gln | Leu |
| | 50 | | | | | 55 | | | | | 60 | | | | |
| Gln | Ser | Ala | Leu | Arg | Thr | Gly | Thr | Glu | Glu | Leu | Arg | Ser | Leu | Tyr | Asn |
| 65 | | | | | 70 | | | | | 75 | | | | | 80 |
| Thr | Val | Val | Thr | Leu | Tyr | Cys | Val | His | Gln | Arg | Ile | Glu | Val | Lys | Asp |
| | | | | 85 | | | | | 90 | | | | | 95 | |
| Thr | Lys | Glu | Ala | Leu | Asp | Lys | Val | Glu | Glu | Ile | Lys | Asn | Lys | Ser | Lys |
| | | | 100 | | | | | 105 | | | | | 110 | | |
| Gln | Lys | Lys | Gln | Gln | Ala | Glu | Ala | Asp | Thr | Gly | Asn | Ser | Asn | Lys | Val |
| | | 115 | | | | | 120 | | | | | 125 | | | |
| Ser | Gln | Asn | Phe | Pro | Ile | Val | Gln | Asn | Ala | Gln | Gly | Gln | Met | Val | His |
| | 130 | | | | | 135 | | | | | 140 | | | | |
| Gln | Ala | Ile | Ser | Pro | Arg | Thr | Leu | Asn | Ala | Trp | Val | Lys | Val | Val | Glu |
| 145 | | | | | 150 | | | | | 155 | | | | | 160 |
| Glu | Lys | Ala | Phe | Ser | Pro | Glu | Val | Ile | Pro | Met | Phe | Ser | Ala | Leu | Ser |
| | | | | 165 | | | | | 170 | | | | | 175 | |
| Glu | Gly | Ala | Thr | Pro | Gln | Asp | Leu | Asn | Met | Met | Leu | Asn | Ile | Val | Gly |
| | | | 180 | | | | | 185 | | | | | 190 | | |
| Gly | His | Gln | Ala | Ala | Met | Gln | Met | Leu | Lys | Glu | Thr | Ile | Asn | Asp | Glu |
| | | 195 | | | | | 200 | | | | | 205 | | | |
| Ala | Ala | Glu | Trp | Asp | Arg | Val | His | Pro | Val | His | Ala | Gly | Pro | Ile | Pro |
| | 210 | | | | | 215 | | | | | 220 | | | | |
| Pro | Gly | Gln | Met | Arg | Glu | Pro | Arg | Gly | Ser | Asp | Ile | Ala | Gly | Thr | Thr |
| 225 | | | | | 230 | | | | | 235 | | | | | 240 |
| Ser | Thr | Leu | Gln | Glu | Gln | Val | Gly | Trp | Met | Thr | Ser | Asn | Pro | Pro | Val |
| | | | | 245 | | | | | 250 | | | | | 255 | |
| Pro | Val | Gly | Asp | Ile | Tyr | Arg | Arg | Trp | Ile | Ile | Leu | Gly | Leu | Asn | Lys |
| | | | 260 | | | | | 265 | | | | | 270 | | |
| Ile | Val | Arg | Met | Tyr | Ser | Pro | Val | Ser | Ile | Leu | Asp | Ile | Lys | Gln | Gly |
| | | 275 | | | | | 280 | | | | | 285 | | | |
| Pro | Lys | Glu | Pro | Phe | Arg | Asp | Tyr | Val | Asp | Arg | Phe | Phe | Lys | Ala | Leu |
| | 290 | | | | | 295 | | | | | 300 | | | | |
| Arg | Ala | Glu | Gln | Ala | Thr | Gln | Glu | Val | Lys | Gly | Trp | Met | Thr | Glu | Thr |
| 305 | | | | | 310 | | | | | 315 | | | | | 320 |
| Leu | Leu | Val | Gln | Asn | Ala | Asn | Pro | Asp | Cys | Lys | Thr | Ile | Leu | Arg | Gly |
| | | | | 325 | | | | | 330 | | | | | 335 | |
| Leu | Gly | Gln | Gly | Ala | Thr | Leu | Glu | Glu | Met | Met | Thr | Ala | Cys | Gln | Gly |
| | | | 340 | | | | | 345 | | | | | 350 | | |
| Val | Gly | Gly | Pro | Ser | His | Lys | Ala | Arg | Val | Leu | Ala | Glu | Ala | Met | Ser |
| | | 355 | | | | | 360 | | | | | 365 | | | |
| Gln | Ala | Gln | Gln | Thr | Asn | Ile | Met | Met | Gln | Arg | Ser | Asn | Phe | Lys | Gly |
| | 370 | | | | | 375 | | | | | 380 | | | | |

-continued

```
Gln Lys Lys Ile Lys Cys Phe Asn Cys Gly Arg Glu Gly His Leu Ala
385                 390                 395                 400

Arg Asn Cys Arg Ala Pro Arg Lys Lys Gly Cys Trp Lys Cys Gly Gln
                405                 410                 415

Glu Gly His Gln Met Lys Asp Cys Thr Glu Arg Gln Ala Asn Phe Leu
            420                 425                 430

Gly Lys Ile Trp Pro Ser His Lys Gly Arg Pro Gly Asn Phe Leu Gln
        435                 440                 445

Ser Arg Pro Glu Pro Thr Ala Pro Pro Ala Glu Ser Phe Gly Phe Gly
    450                 455                 460

Glu Asn Thr Gly Pro Ser Pro Lys Gln Glu Gln Ser Phe Gly Ile Gly
465                 470                 475                 480

Glu Asn Val Ala Pro Ser Pro Lys Gln Glu Pro Lys Lys Glu Glu Leu
                485                 490                 495

Tyr Pro Leu Thr Ser Leu Lys Ser Leu Phe Gly Asn Asp Pro Leu Leu
            500                 505                 510

Gln

<210> SEQ ID NO 32
<211> LENGTH: 496
<212> TYPE: PRT
<213> ORGANISM: HIV-1

<400> SEQUENCE: 32

Met Gly Ala Arg Ala Ser Val Leu Ser Gly Gly Lys Leu Asp Ser Trp
1               5                   10                  15

Glu Lys Ile Arg Leu Arg Pro Gly Gly Lys Lys Lys Tyr Arg Leu Lys
            20                  25                  30

His Leu Val Trp Ala Ser Arg Glu Leu Glu Arg Phe Ala Leu Asn Pro
        35                  40                  45

Ser Leu Leu Glu Thr Gly Glu Gly Cys Gln Gln Leu Met Gly Gln Leu
    50                  55                  60

Gln Pro Ala Leu Gly Thr Gly Thr Glu Glu Leu Arg Ser Leu Tyr Asn
65                  70                  75                  80

Thr Leu Ala Thr Leu Tyr Cys Val His His Arg Ile Glu Ile Lys Asp
                85                  90                  95

Thr Lys Glu Ala Leu Asp Lys Ile Glu Glu Ile Gln Asn Lys Ser Lys
            100                 105                 110

Gln Lys Lys Gln Gln Ala Ala Ala Asp Thr Gly Asn Ser Ser Asn Val
        115                 120                 125

Ser Gln Asn Tyr Pro Ile Val Gln Asn Ala Gln Gly Gln Met Val His
    130                 135                 140

Gln Pro Val Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Met Met Leu Asn Ile Val Gly
            180                 185                 190

Gly His Gln Ala Ala Met Gln Met Leu Lys Asp Thr Ile Asn Glu Glu
        195                 200                 205

Ala Ala Glu Trp Asp Arg Leu His Pro Val Gln Ala Gly Pro Ile Ala
    210                 215                 220

Pro Gly Gln Met Arg Asp Pro Arg Gly Ser Asp Ile Ala Gly Thr Thr
225                 230                 235                 240
```

```
Ser Thr Leu Gln Glu Gln Ile Gly Trp Met Thr Gly Asn Pro Pro Ile
            245                 250                 255

Pro Val Gly Asp Ile Tyr Arg Arg Trp Ile Ile Leu Gly Leu Asn Lys
            260                 265                 270

Ile Val Arg Met Tyr Ser Pro Val Ser Ile Leu Asp Ile Lys Gln Gly
            275                 280                 285

Pro Lys Glu Pro Phe Arg Asp Tyr Val Asp Arg Phe Phe Lys Ala Leu
            290                 295                 300

Arg Ala Glu Gln Ala Thr Gln Glu Val Lys Gly Trp Met Thr Asp Thr
305                 310                 315                 320

Leu Leu Ile Gln Asn Ala Asn Pro Asp Cys Lys Ser Ile Leu Arg Ala
            325                 330                 335

Leu Gly Thr Gly Ala Thr Leu Glu Glu Met Met Thr Ala Cys Gln Gly
            340                 345                 350

Val Gly Gly Pro Ser His Lys Ala Arg Val Leu Ala Glu Ala Met Ser
            355                 360                 365

Gln Val Gln Gln Thr Asn Val Met Met Gln Arg Ser Asn Phe Lys Gly
            370                 375                 380

Gln Lys Arg Ile Lys Cys Phe Asn Cys Gly Lys Glu Gly His Leu Ala
385                 390                 395                 400

Arg Asn Cys Arg Ala Pro Arg Lys Lys Gly Cys Trp Lys Cys Gly Arg
            405                 410                 415

Glu Gly His Gln Met Lys Asp Cys Thr Glu Arg Gln Ala Asn Phe Leu
            420                 425                 430

Gly Lys Ile Trp Pro Ser Ser Lys Gly Arg Pro Gly Asn Phe Leu Gln
            435                 440                 445

Ser Arg Pro Glu Pro Thr Ala Pro Pro Ala Glu Ser Phe Gly Phe Gly
            450                 455                 460

Glu Glu Ile Ala Pro Ser Pro Lys Gln Glu Pro Lys Glu Lys Glu Lys
465                 470                 475                 480

Glu Leu Tyr Pro Leu Thr Ser Leu Lys Ser Leu Phe Gly Ser Asp Pro
            485                 490                 495

<210> SEQ ID NO 33
<211> LENGTH: 152
<212> TYPE: PRT
<213> ORGANISM: HIV-1
<220> FEATURE:
<221> NAME/KEY: VARIANT
<222> LOCATION: 52
<223> OTHER INFORMATION: Xaa = Any Amino Acid

<400> SEQUENCE: 33

Asn Tyr Pro Ile Val Gln Asn Leu Gln Gly Gln Met Val His Gln Ala
1               5                  10                  15

Leu Ser Pro Arg Thr Leu Asn Ala Trp Val Lys Val Ile Glu Glu Lys
            20                  25                  30

Ala Phe Ser Pro Glu Val Ile Pro Met Phe Thr Ala Leu Ser Glu Gly
            35                  40                  45

Ala Thr Pro Xaa Asp Leu Asn Thr Met Leu Asn Thr Val Gly Gly His
            50                  55                  60

Gln Ala Ala Met Gln Met Leu Lys Asp Thr Ile Asn Glu Glu Ala Ala
65                  70                  75                  80

Glu Trp Asp Arg Leu His Pro Val His Ala Gly Pro Ile Ala Pro Gly
            85                  90                  95
```

```
Gln Met Arg Glu Pro Arg Gly Ser Asp Ile Ala Gly Thr Thr Ser Thr
            100                 105                 110

Leu Gln Glu Gln Ile Ala Trp Met Thr Ser Asn Pro Pro Ile Pro Val
        115                 120                 125

Gly Asp Ile Tyr Lys Arg Trp Ile Ile Leu Gly Leu Asn Lys Ile Val
    130                 135                 140

Arg Met Tyr Ser Pro Val Ser Ile
145                 150

<210> SEQ ID NO 34
<211> LENGTH: 94
<212> TYPE: PRT
<213> ORGANISM: HIV-1

<400> SEQUENCE: 34

Ser Gln Asn Tyr Pro Ile Val Gln Asn Leu Gln Gly Gln Met Val His
1               5                   10                  15

Gln Ala Ile Ser Pro Arg Thr Leu Asn Ala Trp Val Lys Val Ile Glu
            20                  25                  30

Glu Lys Ala Phe Ser Pro Glu Val Ile Pro Met Phe Ser Ala Leu Ser
        35                  40                  45

Glu Gly Ala Thr Pro Gln Asp Leu Asn Thr Met Leu Asn Thr Val Gly
    50                  55                  60

Gly His Gln Ala Ala Met Gln Met Leu Lys Asp Thr Ile Asn Glu Glu
65                  70                  75                  80

Ala Ala Glu Trp Asp Arg Thr His Pro Val His Ala Gly Pro
                85                  90

<210> SEQ ID NO 35
<211> LENGTH: 510
<212> TYPE: PRT
<213> ORGANISM: Simian-HIV

<400> SEQUENCE: 35

Met Gly Val Arg Asn Ser Val Leu Ser Gly Lys Lys Ala Asp Glu Leu
1               5                   10                  15

Glu Lys Ile Arg Leu Arg Pro Asn Gly Lys Lys Lys Tyr Met Leu Lys
            20                  25                  30

His Val Val Trp Ala Ala Asn Glu Leu Asp Arg Phe Gly Leu Ala Glu
        35                  40                  45

Ser Leu Leu Glu Asn Lys Glu Gly Cys Gln Lys Ile Leu Ser Val Leu
    50                  55                  60

Ala Pro Leu Val Pro Thr Gly Ser Glu Asn Leu Lys Ser Leu Tyr Asn
65                  70                  75                  80

Thr Val Cys Val Ile Trp Cys Ile His Ala Glu Lys Val Lys His
                85                  90                  95

Thr Glu Glu Ala Lys Gln Ile Val Gln Arg His Leu Val Val Glu Thr
            100                 105                 110

Gly Thr Thr Glu Thr Met Pro Lys Thr Ser Arg Pro Thr Ala Pro Ser
        115                 120                 125

Ser Gly Arg Gly Gly Asn Tyr Pro Val Gln Gln Ile Gly Gly Asn Tyr
    130                 135                 140

Val His Leu Pro Leu Ser Pro Arg Thr Leu Asn Ala Trp Val Lys Leu
145                 150                 155                 160

Ile Glu Glu Lys Lys Phe Gly Ala Glu Val Val Pro Gly Phe Gln Ala
                165                 170                 175
```

-continued

```
Leu Ser Glu Gly Cys Thr Pro Tyr Asp Ile Asn Gln Met Leu Asn Cys
            180                 185                 190
Val Gly Asp His Gln Ala Ala Met Gln Ile Ile Arg Asp Ile Ile Asn
        195                 200                 205
Glu Glu Ala Ala Asp Trp Asp Leu Gln His Pro Gln Pro Ala Pro Gln
    210                 215                 220
Gln Gly Gln Leu Arg Glu Pro Ser Gly Ser Asp Ile Ala Gly Thr Thr
225                 230                 235                 240
Ser Ser Val Asp Glu Gln Ile Gln Trp Met Tyr Arg Gln Gln Asn Pro
                245                 250                 255
Ile Pro Val Gly Asn Ile Tyr Arg Arg Trp Ile Gln Leu Gly Leu Gln
            260                 265                 270
Lys Cys Val Arg Met Tyr Asn Pro Thr Asn Ile Leu Asp Val Lys Gln
        275                 280                 285
Gly Pro Lys Glu Pro Phe Gln Ser Tyr Val Asp Arg Phe Tyr Lys Ser
    290                 295                 300
Leu Arg Ala Glu Gln Thr Asp Ala Ala Val Lys Asn Trp Met Thr Gln
305                 310                 315                 320
Thr Leu Leu Ile Gln Asn Ala Asn Pro Asp Cys Lys Leu Val Leu Lys
                325                 330                 335
Gly Leu Gly Val Asn Pro Thr Leu Glu Glu Met Leu Thr Ala Cys Gln
            340                 345                 350
Gly Val Gly Gly Pro Gly Gln Lys Ala Arg Leu Met Ala Glu Ala Leu
        355                 360                 365
Lys Glu Ala Leu Ala Pro Val Pro Ile Pro Phe Ala Ala Ala Gln Gln
    370                 375                 380
Arg Gly Pro Arg Lys Pro Ile Lys Cys Trp Asn Cys Gly Lys Glu Gly
385                 390                 395                 400
His Ser Ala Arg Gln Cys Arg Ala Pro Arg Arg Gln Gly Cys Trp Lys
                405                 410                 415
Cys Gly Lys Met Asp His Val Met Ala Lys Cys Pro Asp Arg Gln Ala
            420                 425                 430
Gly Phe Leu Gly Leu Gly Pro Trp Gly Lys Lys Pro Arg Asn Phe Pro
        435                 440                 445
Met Ala Gln Val His Gln Gly Leu Ile Pro Thr Ala Pro Pro Glu Asp
    450                 455                 460
Pro Ala Val Asp Leu Leu Lys Asn Tyr Met Gln Leu Gly Lys Gln Gln
465                 470                 475                 480
Arg Glu Lys Gln Arg Glu Ser Arg Glu Lys Pro Tyr Lys Glu Val Thr
                485                 490                 495
Glu Asp Leu Leu His Leu Asn Ser Leu Phe Gly Gly Asp Gln
            500                 505                 510

<210> SEQ ID NO 36
<211> LENGTH: 133
<212> TYPE: PRT
<213> ORGANISM: HIV-1

<400> SEQUENCE: 36

Met Gly Ala Arg Ala Ser Val Leu Ser Gly Gly Glu Leu Asp Lys Trp
 1               5                  10                  15
Glu Lys Ile Arg Leu Arg Pro Gly Arg Lys Lys Gln Tyr Lys Leu Lys
                20                  25                  30
His Ile Val Trp Ala Ser Arg Glu Leu Glu Arg Phe Ala Ile Asn Pro
            35                  40                  45
```

```
Ser Leu Leu Glu Thr Ser Glu Gly Cys Arg Gln Ile Leu Gly Gln Leu
    50                  55                  60

Gln Pro Ser Leu Gln Thr Gly Ser Glu Glu Leu Lys Ser Leu Tyr Asn
 65                  70                  75                  80

Thr Ile Ala Val Leu Tyr Cys Val His Gln Arg Ile Asn Val Lys Asp
                 85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
            115                 120                 125

Val Ser Gln Asn Tyr
    130
```

<210> SEQ ID NO 37
<211> LENGTH: 133
<212> TYPE: PRT
<213> ORGANISM: HIV-1

<400> SEQUENCE: 37

```
Met Gly Ala Arg Ala Ser Val Leu Ser Gly Gly Glu Leu Asp Lys Trp
  1               5                  10                  15

Glu Lys Ile Arg Leu Arg Pro Gly Arg Lys Lys Gln Tyr Lys Leu Lys
                 20                  25                  30

His Ile Val Trp Ala Ser Arg Glu Leu Glu Arg Phe Ala Ile Asn Pro
             35                  40                  45

Ser Leu Leu Glu Thr Ser Glu Gly Cys Arg Gln Ile Leu Gly Gln Leu
    50                  55                  60

Gln Pro Ser Leu Gln Thr Gly Ser Glu Glu Leu Lys Ser Leu Tyr Asn
 65                  70                  75                  80

Thr Ile Ala Val Leu Tyr Cys Val His Gln Arg Ile Asn Val Lys Asp
                 85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
            115                 120                 125

Val Ser Gln Asn Tyr
    130
```

<210> SEQ ID NO 38
<211> LENGTH: 133
<212> TYPE: PRT
<213> ORGANISM: HIV-1

<400> SEQUENCE: 38

```
Met Gly Ala Arg Ala Ser Val Leu Ser Gly Gly Glu Leu Asp Lys Trp
  1               5                  10                  15

Glu Lys Ile Arg Leu Arg Pro Gly Arg Lys Lys Gln Tyr Lys Leu Lys
                 20                  25                  30

His Ile Val Trp Ala Ser Arg Glu Leu Glu Arg Phe Ala Ile Asn Pro
             35                  40                  45

Ser Leu Leu Glu Thr Thr Glu Gly Cys Arg Gln Ile Leu Gly Gln Leu
    50                  55                  60

Gln Pro Ser Leu Gln Thr Gly Ser Glu Glu Leu Lys Ser Leu Tyr Asn
 65                  70                  75                  80

Thr Ile Ala Val Leu Tyr Cys Val His Gln Arg Ile Asn Val Lys Asp
                 85                  90                  95
```

```
Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
            115                 120                 125

Val Ser Gln Asn Tyr
    130

<210> SEQ ID NO 39
<211> LENGTH: 133
<212> TYPE: PRT
<213> ORGANISM: HIV-1

<400> SEQUENCE: 39

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
            20                  25                  30

His Ile Val Trp Ala Ser Arg Glu Leu Glu Arg Phe Ala Ile Asn Pro
            35                  40                  45

Ser Leu Leu Glu Thr Ser Glu Gly Cys Arg Gln Ile Leu Gly Gln Leu
    50                  55                  60

Gln Pro Ser Leu Gln Thr Gly Ser Glu Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
            115                 120                 125

Val Ser Gln Asn Tyr
    130

<210> SEQ ID NO 40
<211> LENGTH: 133
<212> TYPE: PRT
<213> ORGANISM: HIV-1

<400> SEQUENCE: 40

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
            20                  25                  30

His Ile Val Trp Ala Ser Arg Glu Leu Glu Arg Phe Ala Ile Asn Pro
            35                  40                  45

Ser Leu Leu Glu Thr Ser Glu Gly Cys Arg Gln Ile Leu Gly Gln Leu
    50                  55                  60

Gln Pro Ser Leu Gln Thr Gly Ser Glu Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
            115                 120                 125

Val Ser Gln Asn Tyr
    130
```

```
<210> SEQ ID NO 41
<211> LENGTH: 133
<212> TYPE: PRT
<213> ORGANISM: HIV-1

<400> SEQUENCE: 41
```

Met Gly Ala Arg Ala Ser Val Leu Ser Gly Gly Glu Leu Glu Lys Trp
1               5                   10                  15

Glu Lys Ile Arg Leu Arg Pro Gly Arg Lys Lys Gln Tyr Lys Leu Lys
            20                  25                  30

His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
    50                  55                  60

Gln Pro Ser Leu Gln Thr Gly Ser Glu Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
            115                 120                 125

Val Ser Gln Asn Tyr
        130

```
<210> SEQ ID NO 42
<211> LENGTH: 133
<212> TYPE: PRT
<213> ORGANISM: HIV-1

<400> SEQUENCE: 42
```

Met Gly Ala Arg Ala Ser Val Leu Ser Gly Gly Glu Leu Asp Lys Trp
1               5                   10                  15

Glu Lys Ile Arg Leu Arg Pro Gly Arg Lys Lys Gln Tyr Lys Leu Lys
            20                  25                  30

His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
    50                  55                  60

Gln Pro Ser Leu Gln Thr Gly Ser Glu Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
            115                 120                 125

Val Ser Gln Asn Tyr
        130

```
<210> SEQ ID NO 43
<211> LENGTH: 133
<212> TYPE: PRT
<213> ORGANISM: HIV-1
```

-continued

```
<400> SEQUENCE: 43

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
             20                  25                  30

His Ile Val Trp Ala Ser Arg Glu Leu Glu Arg Phe Ala Ile Asn Pro
         35                  40                  45

Ser Leu Leu Glu Thr Ser Glu Gly Cys Arg Gln Ile Leu Gly Gln Leu
     50                  55                  60

Gln Pro Ser Leu Gln Thr Gly Ser Glu Leu Lys Ser Leu Tyr Asn
 65                  70                  75                  80

Thr Ile Ala Val Leu Tyr Cys Val His Gln Arg Ile Asn Val Lys Asp
                 85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
            115                 120                 125

Val Ser Gln Asn Tyr
        130

<210> SEQ ID NO 44
<211> LENGTH: 133
<212> TYPE: PRT
<213> ORGANISM: HIV-1

<400> SEQUENCE: 44

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
             20                  25                  30

His Ile Val Trp Ala Ser Arg Glu Leu Glu Arg Phe Ala Ile Asn Pro
         35                  40                  45

Ser Leu Leu Glu Thr Ser Glu Gly Cys Arg Gln Ile Leu Gly Gln Leu
     50                  55                  60

Gln Pro Ser Leu Gln Thr Gly Ser Glu Leu Lys Ser Leu Tyr Asn
 65                  70                  75                  80

Thr Ile Ala Val Leu Tyr Cys Val His Gln Arg Ile Asn Val Lys Asp
                 85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
            115                 120                 125

Val Ser Gln Asn Tyr
        130

<210> SEQ ID NO 45
<211> LENGTH: 133
<212> TYPE: PRT
<213> ORGANISM: HIV-1

<400> SEQUENCE: 45

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
             20                  25                  30
```

-continued

His Ile Val Trp Ala Ser Arg Glu Leu Glu Arg Phe Ala Ile Asn Pro
            35                  40                  45

Ser Leu Leu Glu Thr Ser Glu Gly Cys Arg Gln Ile Leu Gly Gln Leu
 50                  55                  60

Gln Pro Ser Leu Gln Thr Gly Ser Glu Glu Leu Lys Ser Leu Tyr Asn
 65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Glu Gln Asn Lys Ser Lys
                100                 105                 110

Lys Lys Ala Gln Gln Ala Ala Ala Asp Thr Gly Asn Lys Ser Ser Gln
            115                 120                 125

Val Ser Gln Asn Tyr
        130

<210> SEQ ID NO 46
<211> LENGTH: 133
<212> TYPE: PRT
<213> ORGANISM: HIV-1

<400> SEQUENCE: 46

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
                20                  25                  30

His Ile Val Trp Ala Ser Arg Glu Leu Glu Arg Phe Ala Ile Asn Pro
            35                  40                  45

Ser Leu Leu Glu Thr Ser Glu Gly Cys Arg Gln Ile Leu Gly Gln Leu
 50                  55                  60

Gln Pro Ser Leu Gln Thr Gly Ser Glu Glu Leu Lys Ser Leu Tyr Asn
 65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Glu Gln Asn Lys Ser Lys
                100                 105                 110

Lys Lys Ala Gln Gln Ala Ala Ala Asp Thr Gly Asn Lys Ser Ser Gln
            115                 120                 125

Val Ser Gln Asn Tyr
        130

<210> SEQ ID NO 47
<211> LENGTH: 133
<212> TYPE: PRT
<213> ORGANISM: HIV-1

<400> SEQUENCE: 47

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
                20                  25                  30

His Ile Val Trp Ala Ser Arg Glu Leu Glu Arg Phe Ala Ile Asn Pro
            35                  40                  45

Ser Leu Leu Glu Thr Ser Glu Gly Cys Arg Gln Ile Leu Gly Gln Leu
 50                  55                  60

Gln Pro Ser Leu Gln Thr Gly Ser Glu Glu Leu Lys Ser Leu Tyr Asn
 65                  70                  75                  80

```
Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
            115                 120                 125

Val Ser Gln Asn Tyr
        130

<210> SEQ ID NO 48
<211> LENGTH: 133
<212> TYPE: PRT
<213> ORGANISM: HIV-1

<400> SEQUENCE: 48

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
            20                  25                  30

His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
    50                  55                  60

Gln Pro Ser Leu Gln Thr Gly Ser Glu Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
            115                 120                 125

Val Ser Gln Asn Tyr
        130

<210> SEQ ID NO 49
<211> LENGTH: 133
<212> TYPE: PRT
<213> ORGANISM: HIV-1

<400> SEQUENCE: 49

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
            20                  25                  30

His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
    50                  55                  60

Gln Pro Ser Leu Gln Thr Gly Ser Glu Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110
```

```
Lys Lys Ala Gln Gln Ala Ala Ala Asp Thr Gly Asn Lys Ser Ser Gln
        115                 120                 125

Val Ser Gln Asn Tyr
        130

<210> SEQ ID NO 50
<211> LENGTH: 133
<212> TYPE: PRT
<213> ORGANISM: HIV-1

<400> SEQUENCE: 50

Met Gly Ala Arg Ala Ser Val Leu Ser Gly Gly Glu Leu Asp Lys Trp
  1               5                  10                  15

Glu Lys Ile Arg Leu Arg Pro Gly Arg Lys Lys Gln Tyr Lys Leu Lys
             20                  25                  30

His Ile Val Trp Ala Ser Arg Glu Leu Glu Arg Phe Ala Ile Asn Pro
         35                  40                  45

Ser Leu Leu Glu Thr Ser Glu Gly Cys Arg Gln Ile Leu Gly Gln Leu
     50                  55                  60

Gln Pro Ser Leu Gln Thr Gly Ser Glu Glu Leu Lys Ser Leu Tyr Asn
 65                  70                  75                  80

Thr Ile Ala Val Leu Tyr Cys Val His Gln Arg Ile Asn Val Lys Asp
                 85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
        115                 120                 125

Val Ser Gln Asn Tyr
        130

<210> SEQ ID NO 51
<211> LENGTH: 133
<212> TYPE: PRT
<213> ORGANISM: HIV-1

<400> SEQUENCE: 51

Met Gly Ala Arg Ala Ser Val Leu Ser Gly Gly Glu Leu Asp Lys Trp
  1               5                  10                  15

Glu Lys Ile Arg Leu Arg Pro Gly Arg Lys Lys Gln Tyr Lys Leu Lys
             20                  25                  30

His Ile Val Trp Ala Ser Arg Glu Leu Glu Arg Phe Ala Ile Asn Pro
         35                  40                  45

Ser Leu Leu Glu Thr Ser Glu Gly Cys Arg Gln Ile Leu Gly Gln Leu
     50                  55                  60

Gln Pro Ser Leu Gln Thr Gly Ser Glu Glu Leu Lys Ser Leu Tyr Asn
 65                  70                  75                  80

Thr Ile Ala Val Leu Tyr Cys Val His Gln Arg Ile Asn Val Lys Asp
                 85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
        115                 120                 125

Val Ser Gln Asn Tyr
        130
```

```
<210> SEQ ID NO 52
<211> LENGTH: 133
<212> TYPE: PRT
<213> ORGANISM: HIV-1

<400> SEQUENCE: 52
```

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
             20                  25                  30

His Ile Val Trp Ala Ser Arg Glu Leu Glu Arg Phe Ala Ile Asn Pro
         35                  40                  45

Ser Leu Leu Glu Thr Ser Glu Gly Cys Arg Gln Ile Leu Gly Gln Leu
     50                  55                  60

Gln Pro Ser Leu Gln Thr Gly Ser Glu Glu Leu Lys Ser Leu Tyr Asn
 65                  70                  75                  80

Thr Ile Ala Val Leu Tyr Cys Val His Gln Arg Ile Asn Val Lys Asp
                 85                  90                  95

Thr Lys Glu Ala Leu Asp Lys Val Glu Glu Glu Gln Asn Lys Ser Lys
            100                 105                 110

Lys Lys Ala Gln Gln Ala Ala Ala Asp Thr Gly Asn Lys Ser Ser Gln
        115                 120                 125

Val Ser Gln Asn Tyr
        130

```
<210> SEQ ID NO 53
<211> LENGTH: 133
<212> TYPE: PRT
<213> ORGANISM: HIV-1

<400> SEQUENCE: 53
```

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
             20                  25                  30

His Ile Val Trp Ala Ser Arg Glu Leu Glu Arg Phe Ala Ile Asn Pro
         35                  40                  45

Ser Leu Leu Glu Thr Ser Glu Gly Cys Arg Gln Ile Leu Gly Gln Leu
     50                  55                  60

Gln Pro Ser Leu Gln Thr Gly Ser Glu Glu Leu Lys Ser Leu Tyr Asn
 65                  70                  75                  80

Thr Ile Ala Val Leu Tyr Cys Val His Gln Arg Ile Asn Val Lys Asp
                 85                  90                  95

Thr Lys Glu Ala Leu Asp Lys Val Glu Glu Glu Gln Asn Lys Ser Lys
            100                 105                 110

Lys Lys Ala Gln Gln Ala Ala Ala Asp Thr Gly Asn Lys Ser Ser Gln
        115                 120                 125

Val Ser Gln Asn Tyr
        130

```
<210> SEQ ID NO 54
<211> LENGTH: 133
<212> TYPE: PRT
<213> ORGANISM: HIV-1
```

```
<400> SEQUENCE: 54

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
            20                  25                  30

His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
 50                  55                  60

Gln Pro Ser Leu Gln Thr Gly Ser Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110

Lys Lys Ala Gln Gln Ala Ala Asp Thr Gly Asn Lys Ser Ser Gln
            115                 120                 125

Val Ser Gln Asn Tyr
            130

<210> SEQ ID NO 55
<211> LENGTH: 133
<212> TYPE: PRT
<213> ORGANISM: HIV-1

<400> SEQUENCE: 55

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
            20                  25                  30

His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
 50                  55                  60

Gln Pro Ser Leu Gln Thr Gly Ser Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110

Lys Lys Ala Gln Gln Ala Ala Asp Thr Gly Asn Lys Ser Ser Gln
            115                 120                 125

Val Ser Gln Asn Tyr
            130

<210> SEQ ID NO 56
<211> LENGTH: 133
<212> TYPE: PRT
<213> ORGANISM: HIV-1

<400> SEQUENCE: 56

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
            20                  25                  30
```

His Ile Val Trp Ala Ser Arg Glu Leu Glu Arg Phe Ala Ile Asn Pro
          35                  40                  45

Ser Leu Leu Glu Thr Ser Glu Gly Cys Arg Gln Ile Leu Gly Gln Leu
 50                  55                  60

Gln Pro Ser Leu Gln Thr Gly Ser Glu Glu Leu Lys Ser Leu Tyr Asn
 65                  70                  75                  80

Thr Ile Ala Val Leu Tyr Cys Val His Gln Arg Ile Asn Val Lys Asp
                 85                  90                  95

Thr Lys Glu Ala Leu Asp Lys Val Glu Glu Gln Asn Lys Ser Lys
             100                 105                 110

Lys Lys Ala Gln Gln Ala Ala Asp Thr Gly Asn Lys Ser Ser Gln
             115                 120                 125

Val Ser Gln Asn Tyr
         130

<210> SEQ ID NO 57
<211> LENGTH: 133
<212> TYPE: PRT
<213> ORGANISM: HIV-1

<400> SEQUENCE: 57

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
             20                  25                  30

His Ile Val Trp Ala Ser Arg Glu Leu Glu Arg Phe Ala Ile Asn Pro
          35                  40                  45

Ser Leu Leu Glu Thr Ser Glu Gly Cys Arg Gln Ile Leu Gly Gln Leu
 50                  55                  60

Gln Pro Ser Leu Gln Thr Gly Ser Glu Glu Leu Lys Ser Leu Tyr Asn
 65                  70                  75                  80

Thr Ile Ala Val Leu Tyr Cys Val His Gln Arg Ile Asn Val Lys Asp
                 85                  90                  95

Thr Lys Glu Ala Leu Asp Lys Val Glu Glu Gln Asn Lys Ser Lys
             100                 105                 110

Lys Lys Ala Gln Gln Ala Ala Asp Thr Gly Asn Lys Ser Ser Gln
             115                 120                 125

Val Ser Gln Asn Tyr
         130

<210> SEQ ID NO 58
<211> LENGTH: 133
<212> TYPE: PRT
<213> ORGANISM: HIV-1

<400> SEQUENCE: 58

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
             20                  25                  30

His Ile Val Trp Ala Ser Arg Glu Leu Glu Arg Phe Ala Ile Asn Pro
          35                  40                  45

Ser Leu Leu Glu Thr Ser Glu Gly Cys Arg Gln Ile Leu Gly Gln Leu
 50                  55                  60

Gln Pro Ser Leu Gln Thr Gly Ser Glu Glu Leu Lys Ser Leu Tyr Asn
 65                  70                  75                  80

```
Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110

Lys Lys Ala Gln Gln Ala Ala Asp Thr Gly Asn Lys Ser Ser Gln
        115                 120                 125

Val Ser Gln Asn Tyr
    130

<210> SEQ ID NO 59
<211> LENGTH: 133
<212> TYPE: PRT
<213> ORGANISM: HIV-1

<400> SEQUENCE: 59

Met Gly Ala Arg Ala Ser Val Leu Ser Gly Gly Glu Leu Asp Lys Trp
1               5                   10                  15

Glu Lys Ile Arg Leu Arg Pro Gly Arg Lys Lys Gln Tyr Lys Leu Lys
            20                  25                  30

His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
    50                  55                  60

Gln Pro Ser Leu Gln Thr Gly Ser Glu Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110

Lys Lys Ala Gln Gln Ala Ala Asp Thr Gly Asn Lys Ser Ser Gln
        115                 120                 125

Val Ser Gln Asn Tyr
    130

<210> SEQ ID NO 60
<211> LENGTH: 133
<212> TYPE: PRT
<213> ORGANISM: HIV-1

<400> SEQUENCE: 60

Met Gly Ala Arg Ala Ser Val Leu Ser Gly Gly Glu Leu Asp Lys Trp
1               5                   10                  15

Glu Lys Ile Arg Leu Arg Pro Gly Arg Lys Lys Gln Tyr Lys Leu Lys
            20                  25                  30

His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
    50                  55                  60

Gln Pro Ser Leu Gln Thr Gly Ser Glu Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110
```

```
Lys Lys Ala Gln Gln Ala Ala Ala Asp Thr Gly Asn Lys Ser Ser Gln
        115                 120                 125

Val Ser Gln Asn Tyr
    130

<210> SEQ ID NO 61
<211> LENGTH: 133
<212> TYPE: PRT
<213> ORGANISM: HIV-1

<400> SEQUENCE: 61

Met Gly Ala Arg Ala Ser Val Leu Ser Gly Gly Glu Leu Asp Lys Trp
  1               5                  10                  15

Glu Lys Ile Arg Leu Arg Pro Gly Arg Lys Lys Gln Tyr Lys Leu Lys
             20                  25                  30

His Ile Val Trp Ala Ser Arg Glu Leu Glu Arg Phe Ala Ile Asn Pro
         35                  40                  45

Ser Leu Leu Glu Thr Ser Glu Gly Cys Arg Gln Ile Leu Gly Gln Leu
     50                  55                  60

Gln Pro Ser Leu Gln Thr Gly Ser Glu Glu Leu Lys Ser Leu Tyr Asn
 65                  70                  75                  80

Thr Ile Ala Val Leu Tyr Cys Val His Gln Arg Ile Asn Val Lys Asp
                 85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
        115                 120                 125

Val Ser Gln Asn Tyr
    130

<210> SEQ ID NO 62
<211> LENGTH: 133
<212> TYPE: PRT
<213> ORGANISM: HIV-1

<400> SEQUENCE: 62

Met Gly Ala Arg Ala Ser Val Leu Ser Gly Gly Glu Leu Asp Lys Trp
  1               5                  10                  15

Glu Lys Ile Arg Leu Arg Pro Gly Arg Lys Lys Gln Tyr Lys Leu Lys
             20                  25                  30

His Ile Val Trp Ala Ser Arg Glu Leu Glu Arg Phe Ala Ile Asn Pro
         35                  40                  45

Ser Leu Leu Glu Thr Ser Glu Gly Cys Arg Gln Ile Leu Gly Gln Leu
     50                  55                  60

Gln Pro Ser Leu Gln Thr Gly Ser Glu Glu Leu Lys Ser Leu Tyr Asn
 65                  70                  75                  80

Thr Ile Ala Val Leu Tyr Cys Val His Gln Arg Ile Asn Val Lys Asp
                 85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
        115                 120                 125

Val Ser Gln Asn Tyr
    130
```

```
<210> SEQ ID NO 63
<211> LENGTH: 133
<212> TYPE: PRT
<213> ORGANISM: HIV-1

<400> SEQUENCE: 63

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
                20                  25                  30

His Ile Val Trp Ala Ser Arg Glu Leu Glu Arg Phe Ala Ile Asn Pro
            35                  40                  45

Ser Leu Leu Glu Thr Ser Glu Gly Cys Arg Gln Ile Leu Gly Gln Leu
        50                  55                  60

Gln Pro Ser Leu Gln Thr Gly Ser Glu Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
                100                 105                 110

Lys Lys Ala Gln Gln Ala Ala Ala Asp Thr Gly Asn Lys Ser Ser Gln
        115                 120                 125

Val Ser Gln Asn Tyr
    130

<210> SEQ ID NO 64
<211> LENGTH: 133
<212> TYPE: PRT
<213> ORGANISM: HIV-1

<400> SEQUENCE: 64

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
                20                  25                  30

His Ile Val Trp Ala Ser Arg Glu Leu Glu Arg Phe Ala Ile Asn Pro
            35                  40                  45

Ser Leu Leu Glu Thr Ser Glu Gly Cys Arg Gln Ile Leu Gly Gln Leu
        50                  55                  60

Gln Pro Ser Leu Gln Thr Gly Ser Glu Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
                100                 105                 110

Lys Lys Ala Gln Gln Ala Ala Ala Asp Thr Gly Asn Lys Ser Ser Gln
        115                 120                 125

Val Ser Gln Asn Tyr
    130

<210> SEQ ID NO 65
<211> LENGTH: 133
<212> TYPE: PRT
<213> ORGANISM: HIV-1
```

<400> SEQUENCE: 65

Met Gly Ala Arg Ala Ser Val Leu Ser Gly Gly Glu Leu Asp Lys Trp
1               5                   10                  15

Glu Lys Ile Arg Leu Arg Pro Gly Arg Lys Lys Gln Tyr Lys Leu Lys
            20                  25                  30

His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
    50                  55                  60

Gln Pro Ser Leu Gln Thr Gly Ser Glu Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
            115                 120                 125

Val Ser Gln Asn Tyr
    130

<210> SEQ ID NO 66
<211> LENGTH: 133
<212> TYPE: PRT
<213> ORGANISM: HIV-1

<400> SEQUENCE: 66

Met Gly Ala Arg Ala Ser Val Leu Ser Gly Gly Glu Leu Asp Lys Trp
1               5                   10                  15

Glu Lys Ile Arg Leu Arg Pro Gly Arg Lys Lys Gln Tyr Lys Leu Lys
            20                  25                  30

His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
    50                  55                  60

Gln Pro Ser Leu Gln Thr Gly Ser Glu Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
            115                 120                 125

Val Ser Gln Asn Tyr
    130

<210> SEQ ID NO 67
<211> LENGTH: 133
<212> TYPE: PRT
<213> ORGANISM: HIV-1

<400> SEQUENCE: 67

Met Gly Ala Arg Ala Ser Val Leu Ser Gly Gly Glu Leu Asp Lys Trp
1               5                   10                  15

Glu Lys Ile Arg Leu Arg Pro Gly Arg Lys Lys Gln Tyr Lys Leu Lys
            20                  25                  30

```
His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
 50                  55                  60

Gln Pro Ser Leu Gln Thr Gly Ser Glu Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Glu Gln Asn Lys Ser Lys
            100                 105                 110

Lys Lys Ala Gln Gln Ala Ala Ala Asp Thr Gly Asn Lys Ser Ser Gln
            115                 120                 125

Val Ser Gln Asn Tyr
        130

<210> SEQ ID NO 68
<211> LENGTH: 133
<212> TYPE: PRT
<213> ORGANISM: HIV-1

<400> SEQUENCE: 68

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
            20                  25                  30

His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
 50                  55                  60

Gln Pro Ser Leu Gln Thr Gly Ser Glu Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Glu Gln Asn Lys Ser Lys
            100                 105                 110

Lys Lys Ala Gln Gln Ala Ala Ala Asp Thr Gly Asn Lys Ser Ser Gln
            115                 120                 125

Val Ser Gln Asn Tyr
        130

<210> SEQ ID NO 69
<211> LENGTH: 133
<212> TYPE: PRT
<213> ORGANISM: HIV-1

<400> SEQUENCE: 69

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
            20                  25                  30

His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
 50                  55                  60

Gln Pro Ser Leu Gln Thr Gly Ser Glu Glu Leu Lys Ser Leu Tyr Asn
65                  70                  75                  80
```

```
Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110

Lys Lys Ala Gln Gln Ala Ala Asp Thr Gly Asn Lys Ser Ser Gln
            115                 120                 125

Val Ser Gln Asn Tyr
    130

<210> SEQ ID NO 70
<211> LENGTH: 133
<212> TYPE: PRT
<213> ORGANISM: HIV-1

<400> SEQUENCE: 70

Met Gly Ala Arg Ala Ser Val Leu Ser Gly Gly Glu Leu Asp Lys Trp
1               5                   10                  15

Glu Lys Ile Arg Leu Arg Pro Gly Arg Lys Lys Gln Tyr Lys Leu Lys
            20                  25                  30

His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
    50                  55                  60

Gln Pro Ser Leu Gln Thr Gly Ser Glu Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110

Lys Lys Ala Gln Gln Ala Ala Asp Thr Gly Asn Lys Ser Ser Gln
            115                 120                 125

Val Ser Gln Asn Tyr
    130

<210> SEQ ID NO 71
<211> LENGTH: 133
<212> TYPE: PRT
<213> ORGANISM: HIV-1

<400> SEQUENCE: 71

Met Gly Ala Arg Ala Ser Val Leu Ser Gly Gly Glu Leu Asp Lys Trp
1               5                   10                  15

Glu Lys Ile Arg Leu Arg Pro Gly Arg Lys Lys Gln Tyr Lys Leu Lys
            20                  25                  30

His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
    50                  55                  60

Gln Pro Ser Leu Gln Thr Gly Ser Glu Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110
```

-continued

Lys Lys Ala Gln Gln Ala Ala Ala Asp Thr Gly Asn Lys Ser Ser Gln
         115                 120                 125

Val Ser Gln Asn Tyr
    130

<210> SEQ ID NO 72
<211> LENGTH: 133
<212> TYPE: PRT
<213> ORGANISM: HIV-1

<400> SEQUENCE: 72

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
                20                  25                  30

His Ile Val Trp Ala Ser Arg Glu Leu Glu Arg Phe Ala Ile Asn Pro
            35                  40                  45

Ser Leu Leu Glu Thr Ser Glu Gly Cys Arg Gln Ile Leu Gly Gln Leu
        50                  55                  60

Gln Pro Ser Leu Gln Thr Gly Ser Glu Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
                100                 105                 110

Lys Lys Ala Gln Gln Ala Ala Ala Asp Thr Gly Asn Lys Ser Ser Gln
         115                 120                 125

Val Ser Gln Asn Tyr
    130

<210> SEQ ID NO 73
<211> LENGTH: 133
<212> TYPE: PRT
<213> ORGANISM: HIV-1

<400> SEQUENCE: 73

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
                20                  25                  30

His Ile Val Trp Ala Ser Arg Glu Leu Glu Arg Phe Ala Ile Asn Pro
            35                  40                  45

Ser Leu Leu Glu Thr Ser Glu Gly Cys Arg Gln Ile Leu Gly Gln Leu
        50                  55                  60

Gln Pro Ser Leu Gln Thr Gly Ser Glu Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
                100                 105                 110

Lys Lys Ala Gln Gln Ala Ala Ala Asp Thr Gly Asn Lys Ser Ser Gln
         115                 120                 125

Val Ser Gln Asn Tyr
    130

-continued

<210> SEQ ID NO 74
<211> LENGTH: 133
<212> TYPE: PRT
<213> ORGANISM: HIV-1

<400> SEQUENCE: 74

Met Gly Ala Arg Ala Ser Val Leu Ser Gly Gly Glu Leu Asp Lys Trp
1               5                   10                  15

Glu Lys Ile Arg Leu Arg Pro Gly Arg Lys Lys Gln Tyr Lys Leu Lys
            20                  25                  30

His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
    50                  55                  60

Gln Pro Ser Leu Gln Thr Gly Ser Glu Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
        115                 120                 125

Val Ser Gln Asn Tyr
    130

<210> SEQ ID NO 75
<211> LENGTH: 133
<212> TYPE: PRT
<213> ORGANISM: HIV-1

<400> SEQUENCE: 75

Met Gly Ala Arg Ala Ser Val Leu Ser Gly Gly Glu Leu Asp Lys Trp
1               5                   10                  15

Glu Lys Ile Arg Leu Arg Pro Gly Arg Lys Lys Gln Tyr Lys Leu Lys
            20                  25                  30

His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
    50                  55                  60

Gln Pro Ser Leu Gln Thr Gly Ser Glu Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
        115                 120                 125

Val Ser Gln Asn Tyr
    130

<210> SEQ ID NO 76
<211> LENGTH: 133
<212> TYPE: PRT
<213> ORGANISM: HIV-1

-continued

```
<400> SEQUENCE: 76

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
             20                  25                  30

His Ile Val Trp Ala Ser Arg Glu Leu Glu Arg Phe Ala Ile Asn Pro
         35                  40                  45

Ser Leu Leu Glu Thr Ser Glu Gly Cys Arg Gln Ile Leu Gly Gln Leu
     50                  55                  60

Gln Pro Ser Leu Gln Thr Gly Ser Glu Leu Lys Ser Leu Tyr Asn
 65                  70                  75                  80

Thr Ile Ala Val Leu Tyr Cys Val His Gln Arg Ile Asn Val Lys Asp
                 85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
            115                 120                 125

Val Ser Gln Asn Tyr
        130

<210> SEQ ID NO 77
<211> LENGTH: 133
<212> TYPE: PRT
<213> ORGANISM: HIV-1

<400> SEQUENCE: 77

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
             20                  25                  30

His Ile Val Trp Ala Ser Arg Glu Leu Glu Arg Phe Ala Ile Asn Pro
         35                  40                  45

Ser Leu Leu Glu Thr Ser Glu Gly Cys Arg Gln Ile Leu Gly Gln Leu
     50                  55                  60

Gln Pro Ser Leu Gln Thr Gly Ser Glu Leu Lys Ser Leu Tyr Asn
 65                  70                  75                  80

Thr Ile Ala Val Leu Tyr Cys Val His Gln Arg Ile Asn Val Lys Asp
                 85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
            115                 120                 125

Val Ser Gln Asn Tyr
        130

<210> SEQ ID NO 78
<211> LENGTH: 133
<212> TYPE: PRT
<213> ORGANISM: HIV-1

<400> SEQUENCE: 78

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
             20                  25                  30
```

```
His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
 50                  55                  60

Gln Pro Ser Leu Gln Thr Gly Ser Glu Glu Leu Lys Ser Leu Tyr Asn
 65                  70                  75                  80

Thr Ile Ala Val Leu Tyr Cys Val His Gln Arg Ile Asn Val Lys Asp
                 85                  90                  95

Thr Lys Glu Ala Leu Asp Lys Val Glu Glu Glu Gln Asn Lys Ser Lys
            100                 105                 110

Lys Lys Ala Gln Gln Ala Ala Ala Asp Thr Gly Asn Lys Ser Ser Gln
            115                 120                 125

Val Ser Gln Asn Tyr
        130

<210> SEQ ID NO 79
<211> LENGTH: 133
<212> TYPE: PRT
<213> ORGANISM: HIV-1

<400> SEQUENCE: 79

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
                20                  25                  30

His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
 50                  55                  60

Gln Pro Ser Leu Gln Thr Gly Ser Glu Glu Leu Lys Ser Leu Tyr Asn
 65                  70                  75                  80

Thr Ile Ala Val Leu Tyr Cys Val His Gln Arg Ile Asn Val Lys Asp
                 85                  90                  95

Thr Lys Glu Ala Leu Asp Lys Val Glu Glu Glu Gln Asn Lys Ser Lys
            100                 105                 110

Lys Lys Ala Gln Gln Ala Ala Ala Asp Thr Gly Asn Lys Ser Ser Gln
            115                 120                 125

Val Ser Gln Asn Tyr
        130

<210> SEQ ID NO 80
<211> LENGTH: 133
<212> TYPE: PRT
<213> ORGANISM: HIV-1

<400> SEQUENCE: 80

Met Gly Ala Arg Ala Ser Val Leu Ser Gly Gly Glu Leu Asp Lys Trp
 1               5                  10                  15

Glu Lys Ile Arg Leu Arg Pro Gly Arg Lys Lys Gln Tyr Lys Leu Lys
                20                  25                  30

His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
 50                  55                  60

Gln Pro Ser Leu Gln Thr Gly Ser Glu Glu Leu Lys Ser Leu Tyr Asn
 65                  70                  75                  80
```

-continued

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
        115                 120                 125

Val Ser Gln Asn Tyr
    130

<210> SEQ ID NO 81
<211> LENGTH: 133
<212> TYPE: PRT
<213> ORGANISM: HIV-1

<400> SEQUENCE: 81

Met Gly Ala Arg Ala Ser Val Leu Ser Gly Gly Glu Leu Asp Lys Trp
1               5                   10                  15

Glu Lys Ile Arg Leu Arg Pro Gly Arg Lys Lys Gln Tyr Lys Leu Lys
            20                  25                  30

His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
    50                  55                  60

Gln Pro Ser Leu Gln Thr Gly Ser Glu Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
        115                 120                 125

Val Ser Gln Asn Tyr
    130

<210> SEQ ID NO 82
<211> LENGTH: 133
<212> TYPE: PRT
<213> ORGANISM: HIV-1

<400> SEQUENCE: 82

Met Gly Ala Arg Ala Ser Val Leu Ser Gly Gly Glu Leu Asp Lys Trp
1               5                   10                  15

Glu Lys Ile Arg Leu Arg Pro Gly Arg Lys Lys Gln Tyr Lys Leu Lys
            20                  25                  30

His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
    50                  55                  60

Gln Pro Ser Leu Gln Thr Gly Ser Glu Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110

```
Lys Lys Ala Gln Gln Ala Ala Ala Asp Thr Gly Asn Lys Ser Ser Gln
        115                 120                 125

Val Ser Gln Asn Tyr
    130

<210> SEQ ID NO 83
<211> LENGTH: 133
<212> TYPE: PRT
<213> ORGANISM: HIV-1

<400> SEQUENCE: 83

Met Gly Ala Arg Ala Ser Val Leu Ser Gly Gly Glu Leu Asp Lys Trp
  1               5                  10                  15

Glu Lys Ile Arg Leu Arg Pro Gly Arg Lys Lys Gln Tyr Lys Leu Lys
             20                  25                  30

His Ile Val Trp Ala Ser Arg Glu Leu Glu Arg Phe Ala Ile Asn Pro
         35                  40                  45

Ser Leu Leu Glu Thr Ser Glu Gly Cys Arg Gln Ile Leu Gly Gln Leu
     50                  55                  60

Gln Pro Ser Leu Gln Thr Gly Ser Glu Glu Leu Lys Ser Leu Tyr Asn
 65                  70                  75                  80

Thr Ile Ala Val Leu Tyr Cys Val His Gln Arg Ile Asn Val Lys Asp
                 85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
        115                 120                 125

Val Ser Gln Asn Tyr
    130

<210> SEQ ID NO 84
<211> LENGTH: 133
<212> TYPE: PRT
<213> ORGANISM: HIV-1

<400> SEQUENCE: 84

Met Gly Ala Arg Ala Ser Val Leu Ser Gly Gly Glu Leu Asp Lys Trp
  1               5                  10                  15

Glu Lys Ile Arg Leu Arg Pro Gly Arg Lys Lys Gln Tyr Lys Leu Lys
             20                  25                  30

His Ile Val Trp Ala Ser Arg Glu Leu Glu Arg Phe Ala Ile Asn Pro
         35                  40                  45

Ser Leu Leu Glu Thr Ser Glu Gly Cys Arg Gln Ile Leu Gly Gln Leu
     50                  55                  60

Gln Pro Ser Leu Gln Thr Gly Ser Glu Glu Leu Lys Ser Leu Tyr Asn
 65                  70                  75                  80

Thr Ile Ala Val Leu Tyr Cys Val His Gln Arg Ile Asn Val Lys Asp
                 85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
        115                 120                 125

Val Ser Gln Asn Tyr
    130
```

```
<210> SEQ ID NO 85
<211> LENGTH: 133
<212> TYPE: PRT
<213> ORGANISM: HIV-1

<400> SEQUENCE: 85

Met Gly Ala Arg Ala Ser Val Leu Ser Gly Gly Glu Leu Asp Lys Trp
 1               5                  10                  15
Glu Lys Ile Arg Leu Arg Pro Gly Arg Lys Lys Gln Tyr Lys Leu Lys
             20                  25                  30
His Ile Val Trp Ala Ser Arg Glu Leu Glu Arg Phe Ala Ile Asn Pro
         35                  40                  45
Ser Leu Leu Glu Thr Ser Glu Gly Cys Arg Gln Ile Leu Gly Gln Leu
     50                  55                  60
Gln Pro Ser Leu Gln Thr Gly Ser Glu Glu Leu Lys Ser Leu Tyr Asn
 65                  70                  75                  80
Thr Ile Ala Val Leu Tyr Cys Val His Gln Arg Ile Asn Val Lys Asp
                 85                  90                  95
Thr Lys Glu Ala Leu Asp Lys Val Glu Glu Gln Asn Lys Ser Lys
            100                 105                 110
Lys Lys Ala Gln Gln Ala Ala Ala Asp Thr Gly Asn Lys Ser Ser Gln
        115                 120                 125
Val Ser Gln Asn Tyr
    130

<210> SEQ ID NO 86
<211> LENGTH: 133
<212> TYPE: PRT
<213> ORGANISM: HIV-1

<400> SEQUENCE: 86

Met Gly Ala Arg Ala Ser Val Leu Ser Gly Gly Glu Leu Asp Lys Trp
 1               5                  10                  15
Glu Lys Ile Arg Leu Arg Pro Gly Arg Lys Lys Gln Tyr Lys Leu Lys
             20                  25                  30
His Ile Val Trp Ala Ser Arg Glu Leu Glu Arg Phe Ala Ile Asn Pro
         35                  40                  45
Ser Leu Leu Glu Thr Ser Glu Gly Cys Arg Gln Ile Leu Gly Gln Leu
     50                  55                  60
Gln Pro Ser Leu Gln Thr Gly Ser Glu Glu Leu Lys Ser Leu Tyr Asn
 65                  70                  75                  80
Thr Ile Ala Val Leu Tyr Cys Val His Gln Arg Ile Asn Val Lys Asp
                 85                  90                  95
Thr Lys Glu Ala Leu Asp Lys Val Glu Glu Gln Asn Lys Ser Asn
            100                 105                 110
Lys Lys Ala Gln Gln Ala Ala Ala Asp Thr Gly Asn Lys Ser Ser Gln
        115                 120                 125
Val Ser Gln Asn Tyr
    130

<210> SEQ ID NO 87
<211> LENGTH: 133
<212> TYPE: PRT
<213> ORGANISM: HIV-1
```

<400> SEQUENCE: 87

Met Gly Ala Arg Ala Ser Val Leu Ser Gly Gly Glu Leu Asp Lys Trp
1               5                   10                  15

Glu Lys Ile Arg Leu Arg Pro Gly Arg Lys Lys Gln Tyr Lys Leu Lys
            20                  25                  30

His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
    50                  55                  60

Gln Pro Ser Leu Gln Thr Gly Ser Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
            115                 120                 125

Val Ser Gln Asn Tyr
        130

<210> SEQ ID NO 88
<211> LENGTH: 133
<212> TYPE: PRT
<213> ORGANISM: HIV-1

<400> SEQUENCE: 88

Met Gly Ala Arg Ala Ser Val Leu Ser Gly Gly Glu Leu Asp Lys Trp
1               5                   10                  15

Glu Lys Ile Arg Leu Arg Pro Gly Arg Lys Lys Gln Tyr Lys Leu Lys
            20                  25                  30

His Ile Val Trp Ala Ser Arg Glu Leu Glu Arg Phe Ala Ile Asn Pro
        35                  40                  45

Ser Leu Leu Glu Thr Ser Glu Gly Cys Arg Gln Ile Leu Gly Gln Leu
    50                  55                  60

Gln Pro Ser Leu Gln Thr Gly Ser Glu Leu Lys Ser Leu Tyr Asn
65                  70                  75                  80

Thr Ile Ala Val Leu Tyr Cys Val His Gln Arg Ile Asn Val Lys Asp
                85                  90                  95

Thr Lys Glu Ala Leu Asp Lys Val Glu Glu Gln Asn Lys Ser Lys
            100                 105                 110

Lys Lys Ala Gln Gln Ala Ala Ala Asp Thr Gly Asn Lys Ser Ser Gln
            115                 120                 125

Val Ser Gln Asn Tyr
        130

<210> SEQ ID NO 89
<211> LENGTH: 131
<212> TYPE: PRT
<213> ORGANISM: HIV-1

<400> SEQUENCE: 89

Met Gly Ala Arg Ala Ser Val Leu Ser Gly Gly Lys Leu Asp Lys Trp
1               5                   10                  15

Glu Lys Thr Arg Leu Arg Pro Gly Gly Lys Lys Lys Tyr Gln Leu Lys
            20                  25                  30

```
His Ile Val Trp Ala Ser Arg Glu Leu Gly Arg Phe Ala Val Asn Pro
        35                  40                  45

Gly Leu Leu Glu Thr Ala Asp Gly Cys Arg Gln Ile Leu Gly Gln Leu
    50                  55                  60

Gln Pro Ser Leu Gln Thr Gly Ser Glu Glu Leu Lys Ser Leu Phe Asn
65                  70                  75                  80

Thr Val Ala Thr Leu Tyr Cys Val His Gln Asn Ile Glu Val Lys Asp
                85                  90                  95

Thr Lys Glu Ala Leu Asp Lys Val Glu Glu Glu Gln Asn Lys Ser Lys
                100                 105                 110

Lys Asn Ala Gln Gln Ala Ala Ala Asp Thr Arg Asn Ser Gln Val Ser
            115                 120                 125

Gln Asn Tyr
    130

<210> SEQ ID NO 90
<211> LENGTH: 131
<212> TYPE: PRT
<213> ORGANISM: HIV-1

<400> SEQUENCE: 90

Met Gly Ala Arg Ala Ser Val Leu Ser Gly Gly Lys Leu Asp Lys Trp
1               5                   10                  15

Glu Lys Thr Arg Leu Arg Pro Gly Gly Lys Lys Lys Tyr Gln Leu Lys
                20                  25                  30

His Ile Val Trp Ala Ser Arg Glu Leu Glu Arg Ser Ala Val Asn Pro
        35                  40                  45

Gly Leu Leu Glu Thr Ala Asp Gly Cys Arg Gln Ile Leu Gly Gln Leu
    50                  55                  60

Gln Pro Ser Leu Gln Thr Gly Ser Glu Glu Leu Lys Ser Leu Phe Asn
65                  70                  75                  80

Thr Ile Ala Thr Leu Tyr Cys Val His Gln Asn Ile Glu Val Lys Asp
                85                  90                  95

Thr Lys Glu Ala Leu Asp Lys Val Glu Glu Glu Gln Asn Lys Ser Lys
                100                 105                 110

Lys Asn Ala Gln Gln Ala Ala Ala Asp Thr Arg Asn Ser Gln Val Ser
            115                 120                 125

Gln Asn Tyr
    130

<210> SEQ ID NO 91
<211> LENGTH: 131
<212> TYPE: PRT
<213> ORGANISM: HIV-1

<400> SEQUENCE: 91

Met Gly Ala Arg Ala Ser Val Leu Ser Gly Gly Lys Leu Asp Lys Trp
1               5                   10                  15

Glu Lys Thr Arg Leu Arg Pro Gly Gly Lys Lys Lys Tyr Gln Leu Lys
                20                  25                  30

His Ile Val Trp Ala Ser Arg Glu Leu Glu Arg Phe Ala Val Asn Pro
        35                  40                  45

Gly Leu Leu Glu Thr Ala Asp Gly Cys Arg Gln Ile Leu Gly Gln Leu
    50                  55                  60

Gln Pro Ser Leu Gln Thr Gly Ser Glu Glu Leu Lys Ser Leu Phe Asn
65                  70                  75                  80
```

```
Thr Ile Ala Thr Leu Tyr Cys Val His Gln Asn Ile Glu Val Lys Asp
                85                  90                  95

Thr Lys Glu Ala Leu Asp Lys Val Glu Glu Gln Asn Lys Ser Lys
            100                 105                 110

Lys Asn Ala Gln Gln Ala Ala Asp Thr Arg Asn Ser Gln Val Ser
        115                 120                 125

Gln Asn Tyr
    130

<210> SEQ ID NO 92
<211> LENGTH: 131
<212> TYPE: PRT
<213> ORGANISM: HIV-1

<400> SEQUENCE: 92

Met Gly Ala Arg Ala Ser Val Leu Ser Gly Gly Lys Leu Asp Lys Trp
1               5                   10                  15

Glu Lys Thr Arg Leu Arg Pro Gly Gly Lys Lys Tyr Gln Leu Lys
            20                  25                  30

His Ile Val Trp Ala Ser Arg Glu Leu Glu Arg Phe Ala Val Asn Pro
            35                  40                  45

Gly Leu Leu Glu Thr Ala Asp Gly Cys Arg Gln Ile Leu Gly Gln Leu
    50                  55                  60

Gln Pro Ser Leu Gln Thr Gly Ser Glu Glu Leu Lys Ser Leu Phe Asn
65                  70                  75                  80

Thr Val Ala Thr Leu Tyr Cys Val His Gln Asn Ile Glu Val Lys Asp
                85                  90                  95

Thr Lys Glu Ala Leu Asp Lys Val Glu Glu Gln Asn Lys Ser Lys
            100                 105                 110

Lys Asn Ala Gln Gln Ala Ala Asp Thr Arg Asn Ser Gln Val Ser
        115                 120                 125

Gln Asn Tyr
    130

<210> SEQ ID NO 93
<211> LENGTH: 131
<212> TYPE: PRT
<213> ORGANISM: HIV-1

<400> SEQUENCE: 93

Met Gly Ala Arg Ala Ser Val Leu Ser Gly Gly Lys Leu Asp Lys Trp
1               5                   10                  15

Glu Lys Thr Arg Leu Arg Pro Gly Gly Lys Lys Tyr Gln Leu Lys
            20                  25                  30

His Ile Val Trp Ala Ser Arg Glu Leu Glu Arg Phe Ala Val Asn Pro
            35                  40                  45

Gly Leu Leu Glu Thr Ala Asp Gly Cys Arg Gln Ile Leu Gly Gln Leu
    50                  55                  60

Gln Pro Ser Leu Gln Thr Gly Ser Glu Glu Leu Lys Ser Leu Phe Asn
65                  70                  75                  80

Thr Ile Ala Thr Leu Tyr Cys Val His Gln Asn Ile Glu Val Lys Asp
                85                  90                  95

Thr Lys Glu Ala Leu Asp Lys Val Glu Glu Gln Asn Lys Ser Lys
            100                 105                 110
```

Lys Asn Ala Gln Gln Ala Ala Ala Asp Thr Arg Asn Ser Gln Val Ser
        115                 120                 125

Gln Asn Tyr
    130

<210> SEQ ID NO 94
<211> LENGTH: 131
<212> TYPE: PRT
<213> ORGANISM: HIV-1

<400> SEQUENCE: 94

Met Gly Ala Arg Ala Ser Val Leu Ser Gly Gly Lys Leu Asp Lys Trp
1               5                   10                  15

Glu Lys Thr Arg Leu Arg Pro Gly Gly Lys Lys Tyr Gln Leu Lys
            20                  25                  30

His Ile Val Trp Ala Ser Arg Glu Leu Glu Arg Phe Ala Val Asn Pro
            35                  40                  45

Gly Leu Leu Glu Thr Ala Asp Gly Cys Arg Gln Ile Leu Gly Gln Leu
    50                  55                  60

Gln Pro Ser Leu Gln Thr Gly Ser Glu Glu Leu Lys Ser Leu Phe Asn
65                  70                  75                  80

Thr Ile Ala Thr Leu Tyr Cys Val His Gln Asn Ile Glu Val Lys Asp
                85                  90                  95

Thr Lys Glu Ala Leu Asp Lys Val Glu Glu Gln Asn Lys Ser Lys
            100                 105                 110

Lys Asn Ala Gln Gln Ala Ala Ala Asp Thr Arg Asn Ser Gln Val Ser
        115                 120                 125

Gln Asn Tyr
    130

<210> SEQ ID NO 95
<211> LENGTH: 131
<212> TYPE: PRT
<213> ORGANISM: HIV-1

<400> SEQUENCE: 95

Met Gly Ala Arg Ala Ser Val Leu Ser Gly Gly Lys Leu Asp Lys Trp
1               5                   10                  15

Glu Lys Thr Arg Leu Arg Pro Gly Gly Lys Lys Tyr Gln Leu Lys
            20                  25                  30

His Ile Val Trp Ala Ser Arg Glu Leu Glu Arg Phe Ala Val Asn Pro
            35                  40                  45

Gly Leu Leu Glu Thr Ala Asp Gly Cys Arg Gln Ile Leu Gly Gln Leu
    50                  55                  60

Gln Pro Ser Leu Gln Thr Gly Ser Glu Glu Leu Lys Ser Leu Phe Asn
65                  70                  75                  80

Thr Ile Ala Thr Leu Tyr Cys Val His Gln Asn Ile Glu Val Lys Asp
                85                  90                  95

Thr Lys Glu Ala Leu Asp Lys Val Glu Glu Gln Asn Lys Ser Lys
            100                 105                 110

Lys Asn Ala Gln Gln Ala Ala Ala Asp Thr Arg Asn Ser Gln Val Ser
        115                 120                 125

Gln Asn Tyr
    130

```
<210> SEQ ID NO 96
<211> LENGTH: 131
<212> TYPE: PRT
<213> ORGANISM: HIV-1

<400> SEQUENCE: 96

Met Gly Ala Arg Ala Ser Val Leu Ser Gly Gly Lys Leu Asp Lys Trp
  1               5                  10                  15

Glu Lys Thr Arg Leu Arg Pro Gly Gly Arg Lys Lys Tyr Gln Leu Lys
                 20                  25                  30

His Ile Val Trp Ala Ser Arg Glu Leu Glu Arg Phe Ala Val Asn Pro
             35                  40                  45

Gly Leu Leu Glu Thr Ala Asp Gly Cys Arg Gln Ile Leu Gly Gln Leu
     50                  55                  60

Gln Pro Ser Leu Gln Thr Gly Ser Glu Glu Leu Lys Ser Leu Phe Asn
 65                  70                  75                  80

Thr Ile Ala Thr Leu Tyr Cys Val His Gln Asn Ile Glu Val Lys Asp
                 85                  90                  95

Thr Lys Glu Ala Leu Asp Lys Val Glu Glu Gln Asn Lys Ser Lys
                100                 105                 110

Lys Asn Ala Gln Gln Ala Ala Ala Asp Thr Arg Asn Ser Gln Val Ser
            115                 120                 125

Gln Asn Tyr
    130

<210> SEQ ID NO 97
<211> LENGTH: 131
<212> TYPE: PRT
<213> ORGANISM: HIV-1

<400> SEQUENCE: 97

Met Gly Ala Arg Ala Ser Val Leu Ser Gly Gly Lys Leu Asp Lys Trp
  1               5                  10                  15

Glu Lys Thr Arg Leu Arg Pro Gly Arg Lys Lys Lys Tyr Gln Leu Lys
                 20                  25                  30

His Ile Val Trp Ala Ser Arg Glu Leu Glu Arg Phe Ala Val Asn Pro
             35                  40                  45

Gly Leu Leu Glu Thr Ala Asp Gly Cys Arg Gln Ile Leu Gly Gln Leu
     50                  55                  60

Gln Pro Ser Leu Gln Thr Gly Ser Glu Glu Leu Lys Ser Leu Phe Asn
 65                  70                  75                  80

Thr Ile Ala Thr Leu Tyr Cys Val His Gln Asn Ile Glu Val Lys Asp
                 85                  90                  95

Thr Lys Glu Ala Leu Asp Lys Val Glu Glu Gln Asn Lys Ser Lys
                100                 105                 110

Lys Asn Ala Gln Gln Ala Ala Ala Asp Thr Arg Asn Ser Gln Val Ser
            115                 120                 125

Gln Asn Tyr
    130

<210> SEQ ID NO 98
<211> LENGTH: 132
<212> TYPE: PRT
<213> ORGANISM: HIV-1
```

-continued

```
<400> SEQUENCE: 98

Met Gly Ala Arg Ala Ser Val Leu Ser Gly Gly Lys Leu Asp Gln Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ala Glu Gly Cys Arg Gln Ile Leu Gly Gln Leu
    50                  55                  60

Gln Pro Ala Leu Gln Thr Gly Ser Glu Glu Leu Lys Ser Leu Tyr Asn
65                  70                  75                  80

Thr Val Ala Thr Leu Tyr Cys Val His Gln Arg Ile Asp Ile Lys Asp
                85                  90                  95

Thr Lys Glu Ala Leu Asp Lys Ile Glu Glu Glu Gln Asn Gln Ser Lys
            100                 105                 110

Lys Lys Ala Gln Gln Ala Ala Ala Asp Thr Gly Asn Ser Asn Gln Val
        115                 120                 125

Ser Gln Asn Tyr
    130

<210> SEQ ID NO 99
<211> LENGTH: 494
<212> TYPE: PRT
<213> ORGANISM: HIV-1
<220> FEATURE:
<221> NAME/KEY: VARIANT
<222> LOCATION: 69
<223> OTHER INFORMATION: Xaa = Any Amino Acid

<400> SEQUENCE: 99

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Lys Tyr Arg Met Lys
            20                  25                  30

His Leu Val Trp Ala Ser Arg Glu Leu Glu Arg Phe Ala Leu Asn Pro
        35                  40                  45

Asp Leu Leu Glu Thr Thr Glu Gly Cys Gln Gln Ile Met Gly Gln Leu
    50                  55                  60

Gln Pro Ala Leu Xaa Thr Gly Thr Glu Glu Ile Arg Ser Leu Phe Asn
65                  70                  75                  80

Thr Val Ala Thr Leu Tyr Cys Val His Gln Lys Ile Glu Val Lys Asp
                85                  90                  95

Thr Lys Glu Ala Leu Glu Glu Val Glu Lys Ala Gln Lys Lys Ser Gln
            100                 105                 110

Lys Asn Gln Gln Ala Ala Met Asp Glu Gly Asn Asn Ser Gln Val Ser
        115                 120                 125

Gln Asn Tyr Pro Ile Val Gln Asn Ala Gln Gly Gln Met Val His Gln
    130                 135                 140

Ala Ile Ser Pro Arg Thr Leu Asn Ala Trp Val Lys Val Val Glu Glu
145                 150                 155                 160

Lys Ala Phe Ser Pro Glu Val Ile Pro Met Phe Ser Ala Leu Ser Glu
                165                 170                 175

Gly Ala Thr Pro Gln Asp Leu Asn Thr Met Leu Asn Thr Val Gly Gly
            180                 185                 190

His Gln Ala Ala Met Gln Met Leu Lys Asp Thr Ile Asn Glu Glu Ala
        195                 200                 205
```

-continued

```
Ala Glu Trp Asp Arg Met His Pro Pro Gln Ala Gly Pro Ile Pro Pro
    210                 215                 220
Gly Gln Ile Arg Glu Pro Arg Gly Ser Asp Ile Ala Gly Thr Thr Ser
225                 230                 235                 240
Thr Leu Gln Glu Gln Ile Arg Trp Met Thr Ser Asn Pro Pro Ile Pro
                245                 250                 255
Val Gly Glu Ile Tyr Lys Arg Trp Ile Ile Leu Gly Leu Asn Lys Ile
            260                 265                 270
Val Arg Met Tyr Ser Pro Val Ser Ile Leu Asp Ile Arg Gln Gly Pro
        275                 280                 285
Lys Glu Pro Phe Arg Asp Tyr Val Asp Arg Phe Phe Lys Thr Leu Arg
    290                 295                 300
Ala Glu Gln Ala Thr Gln Glu Val Lys Gly Trp Met Thr Asp Thr Leu
305                 310                 315                 320
Leu Val Gln Asn Ala Asn Pro Asp Cys Lys Thr Ile Leu Arg Ala Leu
                325                 330                 335
Gly Pro Gly Ala Thr Leu Glu Glu Met Met Thr Ala Cys Gln Gly Val
            340                 345                 350
Gly Gly Pro Ser His Lys Ala Arg Val Leu Ala Glu Ala Met Ser Gln
        355                 360                 365
Ala Ser Gly Ala Thr Val Met Met Gln Lys Ser Asn Phe Lys Gly Pro
    370                 375                 380
Arg Arg Asn Ile Lys Cys Phe Asn Cys Gly Lys Glu Gly His Leu Ala
385                 390                 395                 400
Arg Asn Cys Arg Ala Pro Arg Lys Arg Gly Cys Trp Lys Cys Gly Lys
                405                 410                 415
Glu Gly His Gln Met Lys Asp Cys Thr Glu Ser Lys Ala Asn Phe Leu
            420                 425                 430
Gly Lys Ile Trp Pro Ser Asn Lys Gly Arg Pro Gly Asn Phe Leu Gln
        435                 440                 445
Asn Arg Pro Glu Pro Thr Ala Pro Pro Ala Glu Ser Phe Gly Phe Gly
    450                 455                 460
Glu Glu Ile Ala Pro Ser Pro Lys Pro Glu Pro Lys Glu Lys Glu Met
465                 470                 475                 480
Tyr Pro Leu Ala Ser Leu Lys Ser Leu Phe Gly Ser Asp Pro
                485                 490

<210> SEQ ID NO 100
<211> LENGTH: 494
<212> TYPE: PRT
<213> ORGANISM: HIV-1
<220> FEATURE:
<221> NAME/KEY: VARIANT
<222> LOCATION: 31
<223> OTHER INFORMATION: Xaa = Any Amino Acid

<400> SEQUENCE: 100

Met Gly Ala Arg Ala Ser Val Leu Ser Gly Gly Lys Leu Asp Ala Trp
1               5                   10                  15
Glu Lys Ile Arg Leu Arg Pro Gly Gly Lys Lys Lys Tyr Arg Xaa Lys
            20                  25                  30
His Leu Val Trp Ala Ser Arg Glu Leu Glu Arg Phe Ala Leu Asn Pro
        35                  40                  45
Gly Leu Leu Glu Thr Ala Glu Gly Cys Gln Gln Ile Met Gly Gln Leu
    50                  55                  60
```

-continued

```
Gln Pro Ala Leu Gln Thr Gly Thr Glu Glu Ile Arg Ser Leu Phe Asn
 65                  70                  75                  80

Thr Val Ala Thr Leu Tyr Cys Val His Gln Lys Ile Glu Val Lys Asp
                 85                  90                  95

Thr Lys Glu Ala Leu Glu Val Glu Lys Ala Gln Lys Lys Ser Gln
            100                 105                 110

Lys Lys Gln Gln Ala Ala Met Asp Glu Gly Asn Asn Ser Gln Ala Ser
            115                 120                 125

Gln Asn Tyr Pro Ile Val Gln Asn Ala Gln Gly Gln Met Val His Gln
        130                 135                 140

Ala Ile Ser Pro Arg Thr Leu Asn Ala Trp Val Lys Val Glu Glu
145                 150                 155                 160

Lys Ala Phe Ser Pro Glu Val Ile Pro Met Phe Ser Ala Leu Ser Glu
                165                 170                 175

Gly Ala Thr Pro Gln Asp Leu Asn Thr Met Leu Asn Thr Val Gly Gly
                180                 185                 190

His Gln Ala Ala Met Gln Met Leu Lys Asp Thr Ile Asn Glu Glu Ala
                195                 200                 205

Ala Glu Trp Asp Arg Met His Pro Gln Gln Ala Gly Pro Ile Pro Pro
210                 215                 220

Gly Gln Ile Arg Glu Pro Arg Gly Ser Asp Ile Ala Gly Thr Thr Ser
225                 230                 235                 240

Thr Leu Gln Glu Gln Ile Arg Trp Met Thr Ser Asn Pro Pro Ile Pro
                245                 250                 255

Val Gly Glu Ile Tyr Lys Arg Trp Ile Ile Leu Gly Leu Asn Lys Ile
                260                 265                 270

Val Arg Met Tyr Ser Pro Val Ser Ile Leu Asp Ile Arg Gln Gly Pro
                275                 280                 285

Lys Glu Pro Phe Arg Asp Tyr Val Asp Arg Phe Phe Lys Thr Leu Arg
            290                 295                 300

Ala Glu Gln Ala Thr Gln Glu Val Lys Gly Trp Met Thr Asp Thr Leu
305                 310                 315                 320

Leu Val Gln Asn Ala Asn Pro Asp Cys Lys Thr Ile Leu Arg Ala Leu
                325                 330                 335

Gly Pro Gly Ala Thr Leu Glu Glu Met Met Thr Ala Cys Gln Gly Val
                340                 345                 350

Gly Gly Pro Ser His Lys Ala Arg Val Leu Ala Glu Ala Met Ser Leu
            355                 360                 365

Ala Ser Gly Ala Thr Val Met Met Gln Lys Ser Asn Phe Lys Gly Pro
370                 375                 380

Arg Arg Asn Ile Lys Cys Phe Asn Cys Gly Lys Glu Gly His Leu Ala
385                 390                 395                 400

Arg Asn Cys Arg Ala Pro Arg Lys Lys Gly Cys Trp Lys Cys Gly Lys
                405                 410                 415

Glu Gly His Gln Met Lys Asp Cys Thr Glu Ser Lys Ala Asn Phe Leu
                420                 425                 430

Gly Lys Ile Trp Pro Ser Asn Lys Gly Arg Pro Gly Asn Phe Leu Gln
            435                 440                 445

Asn Arg Pro Glu Pro Thr Ala Pro Pro Ala Glu Ser Phe Gly Phe Gly
450                 455                 460
```

-continued

```
Glu Glu Ile Ala Pro Ser Pro Lys Pro Glu Pro Lys Glu Lys Glu Met
465                 470                 475                 480

Tyr Pro Leu Ala Ser Leu Lys Ser Leu Phe Gly Ser Asp Pro
                485                 490
```

<210> SEQ ID NO 101
<211> LENGTH: 494
<212> TYPE: PRT
<213> ORGANISM: HIV-1
<220> FEATURE:
<221> NAME/KEY: VARIANT
<222> LOCATION: 67, 103
<223> OTHER INFORMATION: Xaa = Any Amino Acid

<400> SEQUENCE: 101

```
Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Lys Tyr Arg Met Lys
                20                  25                  30

His Leu Val Trp Ala Ser Arg Glu Leu Glu Arg Phe Ala Leu Asn Pro
            35                  40                  45

Asp Leu Leu Glu Thr Ala Asp Gly Cys Gln Gln Ile Met Gly Gln Leu
50                  55                  60

Gln Pro Xaa Leu Gln Thr Gly Thr Glu Glu Ile Arg Ser Leu Phe Asn
65                  70                  75                  80

Thr Val Ala Thr Leu Tyr Cys Val His Gln Lys Ile Glu Val Lys Asp
                85                  90                  95

Thr Lys Glu Ala Leu Glu Xaa Val Glu Lys Ala Gln Lys Lys Ser Gln
                100                 105                 110

Lys Gln Gln Gln Ala Ala Met Asp Glu Gly Asn Asn Ser Gln Ala Ser
            115                 120                 125

Gln Asn Tyr Pro Ile Val Gln Asn Ala Gln Gly Gln Met Val His Gln
130                 135                 140

Pro Ile Ser Pro Arg Thr Leu Asn Ala Trp Val Lys Val Val Glu Glu
145                 150                 155                 160

Lys Ala Phe Ser Pro Glu Val Ile Pro Met Phe Ser Ala Leu Ser Glu
                165                 170                 175

Gly Ala Thr Pro Gln Asp Leu Asn Thr Met Leu Asn Thr Val Gly Gly
            180                 185                 190

His Gln Ala Ala Met Gln Met Leu Lys Asp Thr Ile Asn Glu Glu Ala
        195                 200                 205

Ala Glu Trp Asp Arg Ile His Pro Gln Gln Ala Gly Pro Ile Pro Pro
210                 215                 220

Gly Gln Ile Arg Glu Pro Arg Gly Ser Asp Ile Ala Gly Thr Thr Ser
225                 230                 235                 240

Thr Leu Gln Glu Gln Ile Arg Trp Met Thr Ser Asn Pro Pro Ile Pro
                245                 250                 255

Val Gly Glu Ile Tyr Lys Arg Trp Ile Ile Leu Gly Leu Asn Lys Ile
            260                 265                 270

Val Arg Met Tyr Ser Pro Val Ser Ile Leu Asp Ile Arg Gln Gly Pro
        275                 280                 285

Lys Glu Pro Phe Arg Asp Tyr Val Asp Arg Phe Phe Lys Thr Leu Arg
290                 295                 300

Ala Glu Gln Ala Thr Gln Glu Val Lys Gly Trp Met Thr Asp Thr Leu
305                 310                 315                 320
```

-continued

```
Leu Val Gln Asn Ala Asn Pro Asp Cys Lys Thr Ile Leu Arg Ala Leu
                325                 330                 335

Gly Pro Gly Ala Thr Leu Glu Glu Met Met Thr Ala Cys Gln Gly Val
            340                 345                 350

Gly Gly Pro Ser His Lys Ala Arg Val Leu Ala Glu Ala Met Ser Leu
        355                 360                 365

Ala Ser Gly Ala Thr Ile Met Met Gln Lys Ser Asn Phe Lys Gly Pro
    370                 375                 380

Arg Arg Asn Ile Lys Cys Phe Asn Cys Gly Lys Glu Gly His Leu Ala
385                 390                 395                 400

Arg Asn Cys Arg Ala Pro Arg Lys Lys Gly Cys Trp Lys Cys Gly Lys
                405                 410                 415

Glu Gly His Gln Met Lys Asp Cys Thr Glu Ser Lys Ala Asn Phe Leu
            420                 425                 430

Gly Lys Ile Trp Pro Ser Asn Lys Gly Arg Pro Gly Asn Phe Leu Gln
        435                 440                 445

Asn Arg Pro Glu Pro Thr Ala Pro Ala Glu Ser Phe Gly Phe Gly
    450                 455                 460

Glu Glu Ile Ala Pro Ser Pro Lys Gln Glu Pro Lys Glu Lys Glu Ile
465                 470                 475                 480

Tyr Pro Leu Ala Ser Leu Lys Ser Leu Phe Gly Ser Asp Pro
                485                 490

<210> SEQ ID NO 102
<211> LENGTH: 215
<212> TYPE: PRT
<213> ORGANISM: HIV-1

<400> SEQUENCE: 102

Gln Gly Arg Glu Leu Glu Arg Phe Ala Leu Asn Pro Gly Leu Leu Glu
1               5                   10                  15

Thr Ala Glu Gly Cys Gln Gln Leu Ile Glu Gln Leu Gln Ser Thr Leu
            20                  25                  30

Thr Thr Gly Ser Glu Glu Leu Lys Ser Leu Phe Asn Thr Ile Ala Thr
        35                  40                  45

Leu Trp Cys Val His Gln Lys Ile Glu Val Lys Asp Thr Lys Glu Ala
    50                  55                  60

Leu Asp Lys Val Glu Glu Ala Gln Lys Arg Ser Gln Gln Lys Thr Gln
65                  70                  75                  80

Gln Ala Ala Ala Gly Thr Gly Ser Ser Ser Lys Val Ser Gln Asn Tyr
                85                  90                  95

Pro Ile Val Gln Asn Ala Gln Gly Gln Met Val His Gln Pro Val Ser
            100                 105                 110

Pro Arg Thr Leu Asn Ala Trp Val Lys Val Val Glu Glu Lys Gly Phe
        115                 120                 125

Asn Pro Glu Val Ile Pro Met Phe Ser Ala Leu Ser Glu Gly Ala Thr
    130                 135                 140

Pro Gln Asp Leu Asn Met Met Leu Asn Ile Val Gly Gly His Gln Ala
145                 150                 155                 160

Ala Met Gln Met Leu Lys Asp Thr Ile Asn Glu Glu Ala Ala Asp Trp
                165                 170                 175

Asp Arg Val His Pro Val His Ala Gly Pro Ile Pro Pro Gly Gln Met
            180                 185                 190
```

-continued

```
Arg Glu Pro Arg Gly Ser Asp Ile Ala Gly Thr Thr Ser Thr Leu Gln
        195                 200                 205

Glu Gln Ile Gly Trp Met Thr
    210                 215
```

<210> SEQ ID NO 103
<211> LENGTH: 201
<212> TYPE: PRT
<213> ORGANISM: HIV-1

<400> SEQUENCE: 103

```
Arg Phe Ala Leu Asn Pro Gly Leu Leu Glu Thr Ser Glu Gly Cys Lys
  1               5                  10                  15

Gln Ile Ile Lys Gln Leu Gln Pro Ala Leu Gln Thr Gly Thr Glu Glu
            20                  25                  30

Leu Arg Ser Leu Tyr Asn Thr Val Ala Thr Leu Tyr Cys Val His Lys
        35                  40                  45

Arg Ile Glu Val Lys Asp Thr Lys Glu Ala Leu Asp Lys Val Glu Glu
 50                  55                  60

Glu Gln Asn Lys Ile Gln Gln Lys Thr Gln Gln Ala Lys Glu Ala Asp
 65                  70                  75                  80

Gly Lys Val Ser Gln Asn Tyr Pro Ile Val Gln Asn Leu Gln Gly Gln
                85                  90                  95

Met Val His Gln Ala Ile Ser Pro Arg Thr Leu Asn Ala Trp Val Lys
            100                 105                 110

Val Ile Glu Glu Lys Ala Phe Ser Pro Glu Ile Ile Pro Met Phe Thr
        115                 120                 125

Ala Leu Ser Glu Gly Ala Thr Pro Gln Asp Leu Asn Thr Met Leu Asn
    130                 135                 140

Thr Val Gly Gly His Gln Ala Ala Met Gln Met Leu Lys Asp Thr Ile
145                 150                 155                 160

Asn Glu Glu Ala Ala Asp Trp Asp Arg Leu His Pro Val His Ala Gly
                165                 170                 175

Pro Ile Ala Pro Gly Gln Met Arg Glu Pro Arg Gly Ser Asp Ile Ala
            180                 185                 190

Gly Thr Thr Ser Ser Leu Gln Glu Gln
        195                 200
```

<210> SEQ ID NO 104
<211> LENGTH: 491
<212> TYPE: PRT
<213> ORGANISM: HIV-1

<400> SEQUENCE: 104

```
Met Gly Ala Arg Ala Ser Ile Leu Arg Gly Glu Lys Leu Asp Lys Trp
  1               5                  10                  15

Glu Lys Ile Arg Leu Arg Pro Gly Gly Arg Lys His Tyr Met Leu Lys
            20                  25                  30

His Leu Val Trp Ala Ser Arg Glu Leu Glu Arg Phe Ala Leu Asn Pro
        35                  40                  45

Gly Leu Leu Glu Thr Ser Gln Gly Cys Lys Gln Ile Ile Lys Gln Leu
    50                  55                  60

His Pro Ala Leu Lys Thr Gly Thr Glu Glu Leu Arg Ser Leu Tyr Asn
 65                  70                  75                  80

Thr Val Ala Thr Leu Tyr Cys Val His Glu Asn Ile Glu Val Arg Asp
                85                  90                  95
```

-continued

```
Thr Lys Glu Ala Leu Asp Lys Ile Glu Glu Gln Asn Lys Ser Gln
            100                 105                 110

Gln Lys Thr Gln Gln Ala Lys Ala Ala Asp Glu Gly Val Ser Gln Asn
        115                 120                 125

Tyr Pro Ile Val Gln Asn Leu Gln Gly Gln Met Val His Gln Ala Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Ala Ala Pro Gly Gln
    210                 215                 220

Met Arg Glu Pro Arg Gly Ser Asp Ile Ala Gly Thr Thr Ser Thr Leu
225                 230                 235                 240

Gln Glu Gln Ile Ala Trp Met Thr Gly Asn Pro Pro Val Pro Val Gly
                245                 250                 255

Asp Ile Tyr Lys Arg Trp Ile Ile Leu Gly Leu Asn Lys Ile Val Arg
            260                 265                 270

Met Tyr Ser Pro Val Ser Ile Leu Asp Ile Lys Gln Gly Pro Lys Glu
        275                 280                 285

Pro Phe Arg Asp Tyr Val Asp Arg Phe Phe Lys Val Leu Arg Ala Glu
    290                 295                 300

Gln Ala Thr Gln Asp Val Lys Asn Trp Met Thr Asp Thr Leu Leu Ile
305                 310                 315                 320

Gln Asn Ala Asn Pro Asp Cys Lys Thr Ile Leu Lys Ala Leu Gly Pro
                325                 330                 335

Ala Ala Ser Leu Glu Glu Met Met Thr Ala Cys Gln Gly Val Gly Gly
            340                 345                 350

Pro Gly His Lys Ala Arg Val Leu Ala Glu Ala Met Ser Gln Ala Asn
        355                 360                 365

Ser Asn Ile Met Met Gln Arg Ser Asn Phe Lys Gly Ser Lys Arg Ile
    370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Gln Glu Gly His
                405                 410                 415

Gln Met Lys Asp Cys Thr Glu Arg Gln Ala Asn Phe Leu Gly Lys Ile
            420                 425                 430

Trp Pro Ser His Lys Gly Arg Pro Gly Asn Phe Leu Gln Ser Arg Pro
        435                 440                 445

Glu Pro Thr Ala Pro Ala Glu Ser Phe Arg Phe Glu Glu Thr Thr
    450                 455                 460

Pro Ala Pro Lys Gln Glu Ser Lys Asp Arg Glu Pro Leu Ile Ser Leu
465                 470                 475                 480

Lys Ser Leu Phe Gly Ser Asp Pro Ser Ser Gln
                485                 490
```

```
<210> SEQ ID NO 105
<211> LENGTH: 508
<212> TYPE: PRT
<213> ORGANISM: HIV-1

<400> SEQUENCE: 105

Met Gly Ala Arg Ala Ser Ile Leu Arg Gly Thr Lys Leu Asp Ala Trp
 1               5                  10                  15

Glu Lys Ile Arg Leu Arg Pro Gly Gly Lys Lys His Tyr Met Leu Lys
             20                  25                  30

His Leu Val Trp Ala Ser Arg Glu Leu Glu Arg Phe Ala Leu Asn Pro
         35                  40                  45

Gly Leu Leu Glu Thr Ser Glu Gly Cys Lys Gln Ile Met Lys Gln Leu
     50                  55                  60

His Pro Ala Leu Gln Thr Gly Thr Glu Glu Leu Lys Ser Leu Tyr Asn
 65                  70                  75                  80

Thr Val Ala Thr Leu Tyr Cys Val His Glu Asn Ile Lys Val Arg Asp
                 85                  90                  95

Thr Lys Glu Ala Leu Asp Lys Ile Glu Glu Gln Asn Lys Ile Lys
             100                 105                 110

Ser Gln Gln Lys Thr Gln Gln Ala Lys Ala Ala Asp Glu Lys Val Ser
         115                 120                 125

Gln Asn Tyr Pro Ile Val Gln Asn Leu Gln Gly Gln Met Val His Gln
     130                 135                 140

Asn Leu Ser Pro Arg Thr Leu Asn Ala Trp Val Lys Val Ile Glu Glu
145                 150                 155                 160

Lys Ala Phe Ser Pro Glu Val Ile Pro Met Phe Thr Ala Leu Ser Glu
                165                 170                 175

Gly Ala Thr Pro Gln Asp Leu Ser Thr Met Leu Asn Thr Val Gly Gly
            180                 185                 190

His Gln Ala Ala Met Gln Met Leu Lys Asp Thr Ile Asn Glu Glu Ala
        195                 200                 205

Ala Glu Trp Asp Arg Leu His Pro Val His Ala Gly Pro Met Ala Pro
    210                 215                 220

Gly Gln Leu Arg Glu Pro Arg Gly Ser Asp Ile Ala Gly Thr Thr Ser
225                 230                 235                 240

Thr Leu Arg Glu Gln Ile Ala Trp Met Thr Ser Asn Pro Pro Ile Pro
                245                 250                 255

Val Gly Asp Ile Tyr Lys Arg Trp Ile Ile Leu Gly Leu Asn Lys Ile
            260                 265                 270

Val Arg Met Tyr Ser Pro Val Ser Ile Leu Asp Ile Arg Gln Gly Pro
        275                 280                 285

Lys Glu Pro Phe Arg Asp Tyr Val Asp Arg Phe Phe Lys Ala Leu Arg
    290                 295                 300

Ala Glu Gln Ala Thr Gln Asp Val Lys Asn Trp Met Thr Glu Thr Leu
305                 310                 315                 320

Leu Val Gln Asn Ala Asn Pro Asp Cys Lys Thr Ile Leu Lys Ala Leu
                325                 330                 335

Gly Ile Gly Ala Thr Leu Glu Glu Met Met Thr Ala Cys Gln Gly Val
            340                 345                 350

Gly Gly Pro Ser His Lys Ala Arg Val Leu Ala Glu Ala Met Ser Gln
        355                 360                 365

Ala Asn Asn Thr Asn Ile Met Met Gln Arg Ser Asn Phe Lys Ser Ser
    370                 375                 380
```

```
Lys Arg Ile Val Lys Cys Ser Asn Cys Gly Lys Glu Gly His Ile Ala
385                 390                 395                 400

Arg Asn Cys Arg Ala Pro Arg Lys Lys Gly Cys Trp Lys Cys Gly Lys
            405                 410                 415

Glu Gly His Gln Met Lys Asp Cys Thr Glu Arg Gln Ala Asn Phe Leu
        420                 425                 430

Gly Lys Ile Trp Pro Ser His Lys Gly Arg Pro Gly Asn Phe Leu Gln
        435                 440                 445

Asn Arg Pro Glu Pro Thr Ala Pro Pro Ala Glu Ser Phe Arg Asn Arg
    450                 455                 460

Pro Glu Pro Thr Ala Pro Pro Ala Glu Ser Phe Arg Phe Glu Glu Thr
465                 470                 475                 480

Thr Pro Thr Pro Lys Gln Glu Pro Lys Asp Arg Asp Pro Leu Thr Ser
                485                 490                 495

Leu Lys Ser Leu Phe Gly Ser Asp Pro Ser Ser Gln
            500                 505

<210> SEQ ID NO 106
<211> LENGTH: 487
<212> TYPE: PRT
<213> ORGANISM: HIV-1

<400> SEQUENCE: 106

Met Gly Ala Arg Ala Ser Val Leu Lys Gly Lys Lys Leu Asp Thr Trp
1               5                   10                  15

Glu Arg Ile Arg Leu Arg Pro Gly Gly Lys Lys His Tyr Met Leu Lys
            20                  25                  30

His Leu Val Trp Ala Ser Arg Glu Leu Glu Arg Phe Ala Leu Asn Pro
        35                  40                  45

Gly Leu Leu Glu Thr Ala Glu Gly Cys Lys Gln Ile Met Gln Gln Leu
    50                  55                  60

Gln Ser Ala Leu Gln Thr Gly Thr Glu Glu Leu Arg Ser Leu Tyr Asn
65                  70                  75                  80

Thr Val Ala Thr Leu Tyr Cys Val His Lys Glu Ile Asp Val Arg Asp
                85                  90                  95

Thr Lys Glu Ala Leu Asp Lys Ile Glu Glu Glu Gln Asn Lys Ser Gln
            100                 105                 110

Gln Lys Thr Gln Gln Ala Glu Ala Ala Asp Lys Gly Lys Val Ser Gln
        115                 120                 125

Asn Tyr Pro Ile Val Gln Asn Leu Gln Gly Gln Met Val His Gln Ala
    130                 135                 140

Ile Ser Pro Arg Thr Leu Asn Ala Trp Val Lys Val Ile Glu Glu Lys
145                 150                 155                 160

Ala Phe Ser Pro Glu Val Ile Pro Met Phe Thr Ala Leu Ser Glu Gly
                165                 170                 175

Ala Thr Pro Gln Asp Leu Asn Thr Met Leu Asn Thr Val Gly Gly His
            180                 185                 190

Gln Ala Ala Met Gln Met Leu Lys Asp Thr Ile Asn Glu Glu Ala Ala
        195                 200                 205

Glu Trp Asp Arg Leu His Pro Val His Ala Gly Pro Ile Ala Pro Gly
    210                 215                 220

Gln Met Arg Glu Pro Arg Gly Ser Asp Ile Ala Gly Thr Thr Ser Thr
225                 230                 235                 240

Leu Gln Glu Gln Ile Ala Trp Met Thr Ser Asn Pro Pro Ile Pro Val
                245                 250                 255
```

```
Gly Asp Ile Tyr Lys Arg Trp Ile Ile Leu Gly Leu Asn Lys Ile Val
            260                 265                 270

Arg Met Tyr Ser Pro Val Ser Ile Leu Asp Ile Lys Gln Gly Pro Lys
            275                 280                 285

Glu Pro Phe Arg Asp Tyr Val Asp Arg Phe Phe Lys Thr Leu Arg Ala
            290                 295                 300

Glu Gln Ser Ser Gln Glu Val Lys Asn Trp Met Thr Asp Thr Leu Leu
305                 310                 315                 320

Val Gln Asn Ala Asn Pro Asp Cys Lys Thr Ile Leu Arg Ala Leu Gly
                325                 330                 335

Pro Gly Ala Thr Leu Glu Glu Met Met Thr Ala Cys Gln Gly Val Gly
            340                 345                 350

Gly Pro Gly His Lys Ala Arg Val Leu Ala Glu Ala Met Ser Gln Ala
            355                 360                 365

Asn Thr Asn Ile Met Met Gln Lys Ser Asn Phe Lys Gly Pro Lys Arg
    370                 375                 380

Thr Val Lys Cys Phe Asn Cys Gly Lys Glu Gly His Ile Ala Arg Asn
385                 390                 395                 400

Cys Arg Ala Pro Arg Lys Lys Gly Cys Trp Lys Cys Gly Lys Glu Gly
            405                 410                 415

His Gln Met Lys Asp Cys Thr Glu Arg Gln Ala Asn Phe Leu Gly Lys
            420                 425                 430

Ile Trp Pro Ser Tyr Lys Gly Arg Ser Gly Asn Phe Leu Gln Ser Arg
            435                 440                 445

Pro Glu Pro Ser Ala Pro Pro Ala Glu Ser Phe Arg Phe Glu Glu Arg
            450                 455                 460

Glu Pro Lys Asp Lys Glu Pro Pro Leu Thr Ser Leu Lys Ser Leu Phe
465                 470                 475                 480

Gly Ser Asp Pro Ser Ser Gln
                485

<210> SEQ ID NO 107
<211> LENGTH: 497
<212> TYPE: PRT
<213> ORGANISM: HIV-1

<400> SEQUENCE: 107

Met Gly Ala Arg Ala Ser Ile Leu Ser Gly Gly Lys Leu Asp Lys Trp
1               5                   10                  15

Glu Arg Ile Arg Leu Arg Pro Gly Gly Lys Lys His Tyr Met Leu Lys
            20                  25                  30

His Leu Val Trp Ala Ser Arg Glu Leu Glu Arg Phe Ala Leu Asn Pro
        35                  40                  45

Gly Leu Leu Glu Thr Ala Glu Gly Cys Lys Gln Ile Ile Lys Gln Leu
    50                  55                  60

Gln Pro Ala Leu Gln Thr Gly Thr Glu Glu Leu Arg Ser Leu Phe Asn
65                  70                  75                  80

Thr Val Ala Thr Leu Tyr Cys Val His Lys Gly Ile Glu Val Arg Asp
                85                  90                  95

Thr Lys Glu Ala Leu Asp Lys Ile Glu Glu Gln Asn Lys Cys Gln Gln
            100                 105                 110

Gln Lys Ala Gln Gln Ala Lys Ala Ala Asp Glu Lys Val Ser Gln Asn
        115                 120                 125

Tyr Pro Ile Val Gln Asn Ala Gln Gly Gln Met Val His Gln Ala Ile
    130                 135                 140
```

```
Ser Pro Arg Thr Leu Asn Ala Trp Val Lys Val Ile Glu Glu Lys Ala
145                 150                 155                 160

Phe Asn Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Thr His Pro Val His Ala Gly Pro Val Ala Pro Gly Gln
    210                 215                 220

Met Arg Glu Pro Arg Gly Ser Asp Ile Ala Gly Thr Thr Ser Thr Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
                260                 265                 270

Met Tyr Ser Pro Val Ser Ile Leu Asp Ile Lys Gln Gly Pro Lys Glu
            275                 280                 285

Pro Phe Arg Asp Tyr Val Asp Arg Phe Phe Lys Thr Leu Arg Ala Glu
290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Ser Leu Glu Glu Met Met Thr Ala Cys Gln Gly Val Gly Gly
                340                 345                 350

Pro Ser His Lys Ala Arg Val Leu Ala Glu Ala Met Ser Gln Thr Asn
            355                 360                 365

Ser Asn Ile Leu Val Gln Arg Ser Asn Phe Lys Gly Ser Asn Arg Ile
370                 375                 380

Val Lys Cys Phe Asn Cys Gly Lys Val Gly His Ile Val Arg Asn Cys
385                 390                 395                 400

Arg Ala Pro Arg Lys Lys Gly Cys Trp Lys Cys Gly Gln Glu Gly His
                405                 410                 415

Gln Met Lys Asp Cys Thr Glu Arg Gln Ala Asn Phe Leu Gly Lys Ile
            420                 425                 430

Trp Pro Ser His Lys Gly Arg Pro Gly Asn Phe Leu Gln Asn Arg Pro
            435                 440                 445

Glu Pro Thr Ala Pro Pro Ala Glu Pro Thr Ala Pro Pro Ala Glu Ser
            450                 455                 460

Phe Arg Phe Glu Glu Thr Thr Pro Val Pro Lys Arg Glu Lys Glu Arg
465                 470                 475                 480

Glu Pro Leu Thr Ser Leu Lys Ser Leu Phe Gly Asn Asp Pro Ser Ser
                485                 490                 495

Gln

<210> SEQ ID NO 108
<211> LENGTH: 496
<212> TYPE: PRT
<213> ORGANISM: HIV-1
```

```
<400> SEQUENCE: 108

Met Gly Ala Arg Ala Ser Ile Leu Arg Gly Gly Lys Leu Asp Lys Trp
 1               5                  10                  15

Glu Lys Ile Arg Leu Arg Pro Gly Gly Lys Lys Lys Tyr Met Leu Lys
             20                  25                  30

His Leu Val Trp Ala Ser Arg Glu Leu Glu Arg Phe Ala Leu Asn Ser
         35                  40                  45

Gly Leu Leu Glu Thr Ser Asp Gly Cys Lys Gln Ile Ile Gln Gln Leu
     50                  55                  60

Gln Pro Ala Leu Lys Thr Gly Thr Glu Glu Leu Arg Ser Leu Tyr Asn
 65                  70                  75                  80

Thr Val Ala Thr Leu Tyr Cys Val His Asn Asn Ile Glu Ile Arg Asp
                 85                  90                  95

Thr Lys Glu Ala Leu Asp Arg Ile Glu Glu Gln Lys Lys Cys Gln
            100                 105                 110

Gln Lys Thr Gln Gln Lys Thr Gln Gln Val Glu Ala Ala Asp Gly
            115                 120                 125

Lys Val Ser Gln Asn Tyr Pro Ile Val Gln Asn Leu Gln Gly Gln Met
130                 135                 140

Val His Gln Ser Leu Ser Pro Arg Thr Leu Asn Ala Trp Val Lys Val
145                 150                 155                 160

Ile Glu Glu Lys Ala Phe Ser Pro Glu Ile Ile Pro Met Phe Thr Ala
                165                 170                 175

Leu Ser Glu Gly Ala Thr Pro Gln Asp Leu Asn Thr Met Leu Asn Thr
            180                 185                 190

Val Gly Gly His Gln Ala Ala Met Gln Met Leu Lys Asp Thr Ile Asn
        195                 200                 205

Glu Glu Ala Ala Glu Trp Asp Arg Leu His Pro Val His Ala Gly Pro
210                 215                 220

Val Ala Pro Gly Gln Met Arg Glu Pro Arg Gly Ser Asp Ile Ala Gly
225                 230                 235                 240

Thr Thr Ser Asn Leu Gln Glu Gln Ile Asn Trp Met Thr Ala Asn Pro
                245                 250                 255

Pro Ile Pro Val Gly Asp Ile Tyr Lys Arg Trp Ile Ile Leu Gly Leu
            260                 265                 270

Asn Lys Ile Val Arg Met Tyr Ser Pro Val Ser Ile Leu Asp Ile Lys
        275                 280                 285

Gln Gly Pro Lys Glu Pro Phe Arg Asp Tyr Val Asp Arg Phe Phe Lys
290                 295                 300

Thr Leu Arg Ala Glu Gln Ala Thr Gln Asp Val Lys Asn Trp Met Thr
305                 310                 315                 320

Asp Thr Leu Leu Val Gln Asn Ala Asn Pro Asp Cys Lys Thr Ile Leu
                325                 330                 335

Arg Ala Leu Gly Pro Gly Ala Thr Leu Glu Glu Met Met Thr Ala Cys
            340                 345                 350

Gln Gly Val Gly Pro Ser His Lys Ala Arg Val Leu Ala Glu Ala
        355                 360                 365

Met Ser Gln Thr Asn Ser Asn Ile Met Met Gln Asn Ser Asn Phe Lys
370                 375                 380

Gly Ser Arg Arg Ile Val Lys Cys Phe Asn Cys Gly Lys Val Gly His
385                 390                 395                 400

Ile Ala Arg Asn Cys Arg Ala Pro Arg Lys Lys Gly Cys Trp Lys Cys
                405                 410                 415
```

-continued

```
Gly Lys Glu Gly His Gln Met Lys Asp Cys Thr Glu Arg Gln Ala Asn
            420                 425                 430

Phe Leu Gly Arg Ile Trp Pro Ser His Lys Gly Arg Pro Gly Asn Phe
            435                 440                 445

Leu Gln Ser Arg Pro Glu Pro Thr Ala Pro Pro Ala Glu Ser Phe Arg
        450                 455                 460

Phe Glu Glu Ile Thr Pro Val Pro Lys Gln Glu Pro Lys Asp Arg Glu
465                 470                 475                 480

Pro Leu Thr Ser Leu Lys Ser Leu Phe Gly Ser Asp Pro Leu Ser Gln
                485                 490                 495

<210> SEQ ID NO 109
<211> LENGTH: 492
<212> TYPE: PRT
<213> ORGANISM: HIV-1

<400> SEQUENCE: 109

Met Gly Ala Ser Ala Ser Ile Leu Arg Gly Gly Lys Leu Asp Lys Trp
  1               5                  10                  15

Glu Lys Ile Arg Leu Arg Pro Gly Gly Lys Lys Lys Tyr Arg Leu Lys
             20                  25                  30

His Leu Val Trp Ala Ser Arg Glu Leu Glu Arg Phe Ala Leu Asn Ser
         35                  40                  45

Gly Leu Leu Glu Thr Ala Glu Gly Cys Lys Gln Ile Ile Lys Gln Leu
     50                  55                  60

Gln Pro Ala Leu Gln Thr Gly Thr Glu Glu Leu Lys Ser Leu Tyr Asn
 65                  70                  75                  80

Thr Val Ala Thr Leu Tyr Cys Val His Ala Gly Ile Glu Val Arg Asp
                 85                  90                  95

Thr Lys Glu Ala Leu Asp Lys Ile Glu Glu Glu Gln Asn Lys Cys Gln
            100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Pro Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Val Ala Pro Gly Gln
    210                 215                 220

Met Arg Glu Pro Arg Gly Ser Asp Ile Ala Gly Thr Thr Ser Thr Leu
225                 230                 235                 240

Gln Glu Gln Ile Thr Trp Met Thr Ser Asn Pro Pro Val Pro Val Gly
                245                 250                 255

Asp Ile Tyr Lys Arg Trp Ile Ile Leu Gly Leu Asn Lys Ile Val Arg
            260                 265                 270

Met Tyr Ser Pro Val Ser Ile Leu Asp Ile Lys Gln Gly Pro Lys Glu
        275                 280                 285

Pro Phe Arg Asp Tyr Val Asp Arg Phe Phe Lys Val Leu Arg Ala Glu
    290                 295                 300
```

```
Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
            325                 330                 335

Ala Ala Ser Leu Glu Glu Met Met Thr Ala Cys Gln Gly Val Gly Gly
        340                 345                 350

Pro Ser His Lys Ala Arg Val Leu Ala Glu Ala Met Ser Gln Ala Asn
    355                 360                 365

Thr Thr Asn Ile Met Met Gln Lys Ser Asn Phe Lys Gly Pro Arg Arg
370                 375                 380

Thr Val Lys Cys Phe Asn Cys Gly Lys Glu Gly His Ile Ala Lys Asn
385                 390                 395                 400

Cys Arg Ala Pro Arg Lys Lys Gly Cys Trp Lys Cys Gly Lys Glu Gly
                405                 410                 415

His Gln Met Lys Asp Cys Thr Glu Arg Gln Ala Asn Phe Leu Gly Lys
            420                 425                 430

Ile Trp Pro Ser His Lys Gly Arg Pro Gly Asn Phe Leu Gln Ser Arg
        435                 440                 445

Pro Glu Pro Thr Ala Pro Pro Ala Glu Ser Phe Arg Phe Glu Glu Thr
    450                 455                 460

Thr Pro Ala Pro Lys Gln Glu Pro Lys Asp Arg Glu Pro Leu Thr Ser
465                 470                 475                 480

Leu Lys Ser Leu Phe Gly Ser Asp Pro Leu Ser Gln
                485                 490

<210> SEQ ID NO 110
<211> LENGTH: 492
<212> TYPE: PRT
<213> ORGANISM: HIV-1

<400> SEQUENCE: 110

Met Gly Ala Arg Ala Ser Ile Leu Arg Gly Glu Lys Leu Asp Thr Trp
1               5                   10                  15

Glu Lys Ile Arg Leu Arg Pro Gly Gly Lys Lys Cys Tyr Met Leu Lys
            20                  25                  30

His Ile Val Trp Ala Ser Arg Glu Leu Glu Arg Phe Ser Leu Asn Pro
        35                  40                  45

Gly Leu Leu Glu Thr Ser Glu Gly Cys Lys Gln Ile Met Lys Gln Leu
    50                  55                  60

Gln Pro Ala Leu Gln Thr Gly Thr Glu Glu Leu Lys Ser Leu Tyr Asn
65                  70                  75                  80

Thr Val Ala Thr Leu Phe Cys Val His Glu Lys Ile Ala Val Arg Asp
                85                  90                  95

Thr Lys Glu Ala Leu Asp Lys Ile Glu Glu Gln Asn Lys Ser Gln
            100                 105                 110

Gln Lys Thr Gln Gln Ala Lys Ala Ala Asp Gly Thr Val Ser Gln Asn
        115                 120                 125

Tyr Pro Ile Val Gln Asn Leu Gln Gly Gln Met Val His Gln Ala Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190
```

```
Ala Ala Met Gln Met Leu Lys Asp Thr Ile Asn Glu Glu Ala Ala Glu
            195                 200                 205

Trp Asp Arg Leu His Pro Val His Ala Gly Pro Ile Ala Pro Gly Gln
        210                 215                 220

Met Arg Glu Pro Arg Gly Ser Asp Ile Ala Gly Thr Thr Ser Thr Leu
225                 230                 235                 240

Gln Glu Gln Ile Ala Trp Met Thr Asn Asn Pro Pro Val Pro Val Gly
                245                 250                 255

Asp Ile Tyr Lys Arg Trp Ile Ile Leu Gly Leu Asn Lys Ile Val Arg
            260                 265                 270

Met Tyr Ser Pro Val Ser Ile Leu Asp Ile Arg Gln Gly Pro Lys Glu
        275                 280                 285

Pro Phe Arg Asp Tyr Val Asp Arg Phe Phe Lys Thr Leu Arg Ala Glu
290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
            340                 345                 350

Pro Ser His Lys Ala Arg Val Leu Ala Glu Ala Met Ser Gln Thr Asn
        355                 360                 365

Asn Ala Asn Ile Met Met Gln Arg Ser Asn Phe Lys Gly Pro Arg Arg
370                 375                 380

Ile Ile Lys Cys Phe Asn Cys Gly Lys Glu Gly His Leu Ala Arg Asn
385                 390                 395                 400

Cys Arg Ala Pro Arg Lys Lys Gly Cys Trp Lys Cys Gly Lys Glu Gly
                405                 410                 415

His Gln Met Lys Asp Cys Thr Glu Arg Gln Ala Asn Phe Leu Gly Lys
            420                 425                 430

Ile Trp Pro Ser His Lys Gly Arg Pro Gly Asn Phe Leu Gln Asn Arg
        435                 440                 445

Pro Glu Pro Thr Ala Pro Ala Glu Ser Phe Arg Phe Glu Glu Thr
450                 455                 460

Thr Pro Ala Pro Lys Gln Glu Pro Arg Glu Arg Glu Pro Leu Thr Ser
465                 470                 475                 480

Leu Lys Ser Leu Phe Gly Ser Asp Pro Leu Ser Gln
                485                 490

<210> SEQ ID NO 111
<211> LENGTH: 493
<212> TYPE: PRT
<213> ORGANISM: HIV-1

<400> SEQUENCE: 111

Ser Arg Ala Ser Ile Leu Ser Gly Gly Lys Leu Asp Lys Trp Glu Lys
1               5                   10                  15

Ile Arg Leu Arg Pro Gly Gly Lys Lys Arg Tyr Lys Leu Lys His Ile
            20                  25                  30

Val Trp Ala Ser Arg Glu Leu Glu Arg Phe Ala Val Asn Pro Gly Leu
        35                  40                  45

Leu Glu Thr Thr Glu Gly Cys Gln Lys Ile Ile Ala Gln Leu Gln Pro
    50                  55                  60

Ser Ile Gln Thr Gly Ser Glu Glu Leu Lys Ser Leu Tyr Asn Thr Val
65                  70                  75                  80
```

```
Ala Val Leu Tyr Phe Val His Gln Glu Val Asp Val Lys Asp Thr Lys
                85                  90                  95
Glu Ala Leu Asp Lys Leu Glu Glu Gln Asn Ser Lys Lys Lys Ala
            100                 105                 110
Gln Gln Ala Ala Ala Gly Thr Gly Asn Ser Ser Gln Thr Ser Gln Asn
            115                 120                 125
Phe Pro Ile Val Gln Asn Ile Gln Gly Gln Met Val His Gln Ala Leu
130                 135                 140
Ser Pro Arg Thr Leu Asn Ala Trp Val Lys Val Glu Glu Lys Ala
145                 150                 155                 160
Phe Ser Pro Glu Val Ile Pro Met Phe Ser Ala Leu Ser Glu Gly Ala
                165                 170                 175
Thr Pro Gln Asp Leu Asn Thr Met Leu Asn Thr Val Gly Gly His Gln
            180                 185                 190
Ala Ala Met Gln Met Leu Lys Asp Thr Ile Asn Glu Glu Ala Ala Glu
            195                 200                 205
Trp Asp Arg Val His Pro Val His Ala Gly Pro Ile Pro Pro Gly Gln
    210                 215                 220
Met Arg Glu Pro Arg Gly Ser Asp Ile Ala Gly Thr Thr Ser Thr Leu
225                 230                 235                 240
Gln Glu Gln Ile Gln Trp Met Thr Ser Asn Pro Pro Val Pro Val Gly
                245                 250                 255
Glu Ile Tyr Lys Arg Trp Ile Ile Leu Gly Leu Asn Lys Ile Val Arg
                260                 265                 270
Met Tyr Ser Pro Val Ser Ile Leu Asp Ile Arg Gln Gly Pro Lys Glu
            275                 280                 285
Pro Phe Arg Asp Tyr Val Asp Arg Phe Phe Lys Thr Leu Arg Ala Glu
    290                 295                 300
Gln Ala Thr Gln Glu Val Lys Asn Trp Met Thr Asp Thr Leu Leu Ile
305                 310                 315                 320
Gln Asn Ala Asn Pro Asp Cys Lys Thr Ile Leu Lys Ala Leu Gly Pro
                325                 330                 335
Gly Ala Ser Leu Glu Glu Met Met Thr Ala Cys Gln Gly Val Gly Gly
            340                 345                 350
Pro Gly His Lys Ala Arg Val Leu Ala Glu Ala Met Ser Gln Ala Thr
        355                 360                 365
Asn Thr Thr Val Met Met Gln Arg Gly Asn Phe Lys Gly Gln Arg Arg
    370                 375                 380
Ile Val Lys Cys Phe Asn Cys Gly Lys Glu Gly His Ile Ala Lys Asn
385                 390                 395                 400
Cys Arg Ala Pro Arg Lys Lys Gly Cys Trp Lys Cys Gly Lys Glu Gly
                405                 410                 415
His Gln Met Lys Asp Cys Thr Glu Arg Gln Ala Asn Phe Leu Gly Lys
            420                 425                 430
Ile Trp Pro Ser His Lys Gly Arg Pro Gly Asn Phe Leu Gln Asn Arg
        435                 440                 445
Pro Glu Pro Thr Ala Pro Ala Glu Ser Phe Gly Phe Gly Glu Glu
    450                 455                 460
Met Thr Pro Ser Pro Lys Gln Glu Gln Lys Glu Glu Gly Leu Tyr Pro
465                 470                 475                 480
Pro Leu Ala Ser Leu Arg Ser Leu Phe Gly Asn Asp His
            485                 490
```

```
<210> SEQ ID NO 112
<211> LENGTH: 140
<212> TYPE: PRT
<213> ORGANISM: HIV-1

<400> SEQUENCE: 112

Gly Gly Lys Lys Lys Tyr Lys Leu Lys His Ile Val Trp Ala Ser Arg
 1               5                  10                  15

Glu Leu Glu Arg Phe Ala Val Asn Pro Gly Leu Leu Glu Thr Ser Glu
            20                  25                  30

Gly Cys Arg Gln Ile Leu Glu Gln Leu Gln Pro Ser Leu Lys Thr Gly
        35                  40                  45

Ser Glu Glu Leu Lys Ser Leu Phe Asn Thr Val Ala Thr Leu Tyr Cys
50                  55                  60

Val His Arg Arg Ile Glu Val Lys Asp Thr Lys Glu Ala Leu Asp Lys
65                  70                  75                  80

Ile Glu Glu Glu Gln Asn Lys Ser Lys Lys Ala Gln Gln Ala Ala
                85                  90                  95

Ala Asp Thr Gly Asn Asn Ser Gln Ala Ala Gly Thr Gly Asp Ser
            100                 105                 110

Ser Gln Ile Ser Gln Asp Tyr Pro Val Val Arg Asn Leu Gln Gly Gln
        115                 120                 125

Met Val His Gln Ala Ile Ser Pro Arg Thr Leu Asn
130                 135                 140

<210> SEQ ID NO 113
<211> LENGTH: 130
<212> TYPE: PRT
<213> ORGANISM: HIV-1

<400> SEQUENCE: 113

Gly Gly Lys Lys Lys Tyr Arg Leu Arg His Ile Val Trp Ala Ser Arg
 1               5                  10                  15

Glu Leu Glu Arg Phe Ala Val Asn Pro Gly Leu Leu Glu Thr Ser Glu
            20                  25                  30

Gly Cys Arg Gln Leu Leu Glu Gln Leu Gln Pro Ser Leu Lys Thr Gly
        35                  40                  45

Ser Glu Glu Leu Arg Ser Leu Phe Asn Thr Val Ala Thr Leu Tyr Cys
50                  55                  60

Val His Gln Lys Ile Asp Val Lys Asp Thr Lys Glu Ala Leu Asp Lys
65                  70                  75                  80

Ile Glu Glu Glu Gln Asn Lys Ser Lys Lys Ala Gln Gln Ala Ala
                85                  90                  95

Ala Gly Thr Gly Asn Asn Ser Gln Val Ser Gln Asn Tyr Pro Ile Val
            100                 105                 110

Gln Asn Met Gln Gly Gln Met Val His Gln Ala Ile Ser Pro Arg Thr
        115                 120                 125

Leu Asn
130

<210> SEQ ID NO 114
<211> LENGTH: 130
<212> TYPE: PRT
<213> ORGANISM: HIV-1
```

```
<400> SEQUENCE: 114

Gly Gly Lys Lys Lys Tyr Leu Leu Lys His Ile Val Trp Ala Ser Arg
  1               5                  10                  15

Glu Leu Glu Arg Phe Ser Ile Asn Pro Gly Leu Leu Glu Thr Ser Glu
             20                  25                  30

Gly Cys Arg Gln Ile Leu Thr Gln Leu Gln Pro Ala Leu Lys Thr Gly
         35                  40                  45

Ser Glu Glu Leu Lys Ser Leu Tyr Asn Thr Val Ala Val Leu Tyr Cys
     50                  55                  60

Val His Gln Lys Ile Asp Val Lys Asp Thr Lys Glu Ala Leu Asp Lys
 65                  70                  75                  80

Ile Glu Glu Gln Asn Lys Ser Lys Glu Lys Ala Gln Gln Ala Ala
                 85                  90                  95

Ala Gly Thr Gly Asn Ser Ser Gln Val Ser Gln Asn Tyr Pro Ile Val
                100                 105                 110

Gln Asn Met Gln Gly Gln Met Val His Gln Ala Ile Ser Pro Arg Thr
            115                 120                 125

Leu Asn
    130

<210> SEQ ID NO 115
<211> LENGTH: 130
<212> TYPE: PRT
<213> ORGANISM: HIV-1

<400> SEQUENCE: 115

Gly Gly Lys Lys Lys Tyr Lys Leu Lys His Val Ala Trp Ala Ser Arg
  1               5                  10                  15

Glu Leu Glu Arg Phe Ser Ile Asn Pro Gly Leu Leu Glu Thr Ser Glu
             20                  25                  30

Gly Cys Arg Gln Ile Leu Thr Gln Leu Gln Pro Ala Leu Lys Thr Gly
         35                  40                  45

Ser Glu Glu Leu Lys Ser Leu Tyr Asn Thr Val Ala Val Leu Tyr Cys
     50                  55                  60

Val His Gln Lys Ile Asp Val Lys Asp Thr Lys Glu Ala Leu Asp Lys
 65                  70                  75                  80

Ile Glu Glu Gln Asn Lys Ser Lys Glu Lys Ala Gln Gln Ala Ala
                 85                  90                  95

Ala Gly Thr Gly Asn Ser Ser Gln Val Ser Gln Asn Tyr Pro Ile Val
                100                 105                 110

Gln Asn Ile Gln Gly Gln Met Val His Gln Ala Ile Ser Pro Arg Thr
            115                 120                 125

Leu Asn
    130

<210> SEQ ID NO 116
<211> LENGTH: 130
<212> TYPE: PRT
<213> ORGANISM: HIV-1

<400> SEQUENCE: 116

Gly Gly Lys Lys Lys Tyr Arg Leu Lys His Ile Ala Trp Ala Ser Arg
  1               5                  10                  15

Glu Leu Glu Arg Phe Ala Val Asn Pro Gly Leu Leu Glu Thr Ser Gly
             20                  25                  30
```

```
Gly Cys Lys Gln Ile Leu Glu Gln Leu Gln Pro Ser Leu Gln Thr Gly
            35                  40                  45

Ser Glu Glu Leu Arg Ser Leu Tyr Asn Thr Val Ala Thr Leu Tyr Cys
 50                  55                  60

Val His Gln Lys Ile Asp Val Lys Asp Thr Lys Glu Ala Leu Asp Lys
 65                  70                  75                  80

Ile Glu Glu Gln Asn Lys Ser Lys Lys Ala Gln Gln Ala Ala
                 85                  90                  95

Ala Gly Thr Gly Asn Ser Ser Gln Val Ser Gln Asn Tyr Pro Ile Val
            100                 105                 110

Gln Asn Met Gln Gly Gln Met Val His Gln Ala Ile Ser Pro Arg Thr
            115                 120                 125

Leu Asn
    130

<210> SEQ ID NO 117
<211> LENGTH: 237
<212> TYPE: PRT
<213> ORGANISM: HIV-1

<400> SEQUENCE: 117

Met Gly Ala Arg Ala Ser Val Leu Ser Gly Gly Lys Leu Asp Ala Trp
  1               5                  10                  15

Glu Lys Ile Arg Leu Arg Pro Gly Gly Lys Lys Tyr Arg Met Lys
                 20                  25                  30

His Leu Val Trp Ala Ser Arg Glu Leu Glu Arg Phe Ala Leu Asn Pro
             35                  40                  45

Ser Leu Leu Glu Thr Ala Glu Gly Cys Gln Gln Ile Met Glu Gln Ile
 50                  55                  60

Gln Pro Ala Leu Lys Thr Gly Ser Glu Glu Leu Arg Ser Leu Phe Asn
 65                  70                  75                  80

Thr Val Ala Thr Leu Tyr Cys Val His Gln Arg Ile Asp Val Lys Asp
                 85                  90                  95

Thr Lys Glu Ala Leu Asp Lys Ile Glu Glu Ile Gln Asn Lys Ser Lys
            100                 105                 110

Gln Lys Thr Gln Gln Ala Ala Ala Asp Thr Gly Asn Ser Ser Lys Val
            115                 120                 125

Ser Gln Asn Tyr Pro Ile Val Gln Asn Ala Gln Gly Gln Met Ile His
            130                 135                 140

Gln Asn Leu Ser Pro Arg Thr Leu Asn Ala Trp Val Lys Val Ile Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Val Met Leu Asn Ile Val Gly
            180                 185                 190

Gly His Gln Ala Ala Met Gln Met Leu Lys Asp Thr Ile Asn Glu Glu
            195                 200                 205

Ala Ala Glu Trp Asn Arg Met His Pro Val His Ala Gly Pro Ile Pro
            210                 215                 220

Pro Gly Gln Ile Arg Glu Pro Arg Gly Thr Asp Ile Ala
225                 230                 235

<210> SEQ ID NO 118
<211> LENGTH: 78
<212> TYPE: PRT
<213> ORGANISM: HIV-1
```

```
<400> SEQUENCE: 118

Met Lys Val Cys Thr Glu Arg Gln Ala Asn Phe Leu Gly Lys Ile Trp
  1               5                  10                  15

Pro Ser His Lys Gly Arg Pro Gly Asn Phe Leu Gln Asn Arg Pro Glu
             20                  25                  30

Pro Thr Ala Pro Pro Glu Glu Ser Phe Lys Phe Gly Glu Glu Thr Thr
             35                  40                  45

Ala Pro Ser Gln Lys Gln Glu Pro Ile Asp Lys Glu Leu Tyr Pro Leu
     50                  55                  60

Thr Ser Pro Gln Ile Thr Leu Gly Asn Asp Pro Ser Ser Gln
 65                  70                  75

<210> SEQ ID NO 119
<211> LENGTH: 138
<212> TYPE: PRT
<213> ORGANISM: HIV-1
<220> FEATURE:
<221> NAME/KEY: VARIANT
<222> LOCATION: 113
<223> OTHER INFORMATION: Xaa = Any Amino Acid

<400> SEQUENCE: 119

Gly Gly Lys Lys Lys Tyr Lys Leu Lys His Ile Val Trp Ala Ser Arg
  1               5                  10                  15

Val Leu Glu Arg Phe Ala Val Asn Pro Gly Leu Leu Glu Thr Ser Glu
             20                  25                  30

Gly Cys Arg Gln Ile Leu Glu Gln Leu Gln Pro Ser Leu Lys Thr Gly
             35                  40                  45

Ser Glu Glu Leu Lys Ser Leu Phe Asn Thr Val Ala Thr Leu Tyr Cys
     50                  55                  60

Val His Arg Arg Ile Glu Val Lys Asp Thr Lys Glu Ala Leu Asp Lys
 65                  70                  75                  80

Ile Glu Glu Glu Gln Asn Lys Ser Lys Lys Ala Gln Gln Ala Ala
                 85                  90                  95

Ala Asp Thr Gly Asn Asn Ser Gln Ala Ala Ala Gly Thr Gly Asn Ser
             100                 105                 110

Xaa Gln Val Ser Gln Asn Tyr Pro Ile Val Arg Asn Leu Gln Gly Gln
         115                 120                 125

Met Val His Gln Ala Ile Ser Pro Arg Thr
         130                 135

<210> SEQ ID NO 120
<211> LENGTH: 123
<212> TYPE: PRT
<213> ORGANISM: HIV-1

<400> SEQUENCE: 120

Gly Gly Lys Lys His Tyr Met Leu Lys His Ile Val Trp Ala Ser Arg
  1               5                  10                  15

Glu Leu Asp Arg Phe Ala Leu Asn Pro Gly Leu Leu Glu Thr Ser Glu
             20                  25                  30

Gly Cys Lys Gln Ile Met Gln Leu Gln Pro Ala Leu Gln Thr Gly
             35                  40                  45

Thr Glu Glu Leu Arg Ser Leu Phe Asn Thr Val Ala Thr Leu Tyr Cys
     50                  55                  60

Val His Ala Gly Ile Glu Val Arg Asp Thr Lys Glu Ala Leu Asp Lys
 65                  70                  75                  80
```

-continued

```
Ile Glu Glu Glu Gln Asn Lys Ser Gln Arg Lys Thr Gln Gln Ala Lys
                85                  90                  95

Glu Ala Asp Gly Lys Val Ser Gln Asn Tyr Pro Ile Val Gln Asn Leu
            100                 105                 110

Gln Gly Gln Met Val His Gln Ala Leu Ser Pro
        115                 120

<210> SEQ ID NO 121
<211> LENGTH: 500
<212> TYPE: PRT
<213> ORGANISM: HIV-1

<400> SEQUENCE: 121

Met Gly Ala Arg Ala Ser Val Leu Ser Gly Gly Lys Leu Asp Glu Trp
  1               5                  10                  15

Glu Lys Ile Arg Leu Arg Pro Gly Gly Lys Lys Tyr Arg Leu Lys
                20                  25                  30

His Leu Val Trp Ala Ser Arg Glu Leu Glu Arg Phe Ala Leu Asn Pro
            35                  40                  45

Gly Leu Leu Glu Thr Ser Glu Gly Cys Lys Gln Ile Ile Gly Gln Leu
        50                  55                  60

Gln Pro Ala Ile Gln Thr Gly Ser Glu Glu Ile Lys Ser Leu Tyr Asn
 65                  70                  75                  80

Thr Val Ala Thr Leu Tyr Cys Val His Glu Arg Ile Gln Val Lys Asp
                85                  90                  95

Thr Lys Glu Ala Leu Asp Lys Ile Gly Glu Glu Gln Thr Lys Ser Lys
            100                 105                 110

Lys Lys Ala Gln Gln Ala Thr Ala Asp Thr Arg Asn Ser Ser Gln Val
        115                 120                 125

Ser Gln Asn Tyr Pro Ile Val Gln Asn Thr Gln Gly Gln Met Val Tyr
    130                 135                 140

Gln Ser Ile Ser Pro Arg Thr Leu Asn Ala Trp Val Lys Val Ile Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Gly Ala Met Gln Met Leu Lys Glu Thr Ile Asn Glu Glu
        195                 200                 205

Ala Ala Glu Trp Asp Arg Leu His Pro Val His Ala Gly Pro Val Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Gly Asn Pro Val Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Ile Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335
```

-continued

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Ala Thr Lys Gly Asn Ala Ile Met Met Gln Arg Gly Asn Phe Lys
    370                 375                 380

Gly Pro Lys Arg Ile Ile Lys Cys Phe Asn Cys Gly Lys Gly Gly His
385                 390                 395                 400

Ile Ala Lys Asn Cys Arg Ala Pro Arg Lys Lys Gly Cys Trp Lys Cys
                405                 410                 415

Gly Arg Glu Gly His Gln Met Lys Asp Cys Thr Glu Arg Gln Ala Asn
            420                 425                 430

Phe Leu Gly Lys Ile Trp Pro Ser His Lys Gly Arg Pro Gly Asn Phe
        435                 440                 445

Leu Gln Ser Arg Pro Glu Pro Thr Ala Pro Ala Glu Ser Phe Gly
    450                 455                 460

Phe Gly Glu Glu Met Thr Pro Phe Gln Lys Gln Glu Gln Lys Asp Lys
465                 470                 475                 480

Glu Glu Leu Tyr Leu Leu Ala Ser Leu Lys Ser Leu Phe Gly Asn Asp
                485                 490                 495

Pro Leu Ser Gln
            500

<210> SEQ ID NO 122
<211> LENGTH: 500
<212> TYPE: PRT
<213> ORGANISM: HIV-1

<400> SEQUENCE: 122

Met Gly Ala Arg Ala Ser Val Leu Ser Gly Gly Lys Leu Asp Glu Trp
1               5                   10                  15

Glu Lys Ile Arg Leu Arg Pro Gly Gly Lys Lys Gln Tyr Lys Leu Lys
            20                  25                  30

His Leu Val Trp Ala Ser Arg Glu Leu Asp Arg Phe Ala Ile Asn Pro
        35                  40                  45

Gly Leu Leu Glu Thr Ser Glu Gly Cys Lys Gln Ile Ile Gly Gln Leu
    50                  55                  60

Gln Pro Ala Ile Gln Thr Gly Ser Glu Glu Ile Lys Ser Leu Tyr Asn
65                  70                  75                  80

Thr Val Ala Thr Leu Tyr Cys Val His Glu Arg Ile Lys Val Ala Asp
                85                  90                  95

Thr Lys Glu Ala Leu Asp Lys Ile Glu Glu Glu Gln Thr Lys Ser Lys
            100                 105                 110

Lys Lys Ala Gln Gln Ala Thr Ala Asp Thr Gly Asn Ser Ser Gln Val
        115                 120                 125

Ser Gln Asn Tyr Pro Ile Val Gln Asn Leu Gln Gly Gln Met Val His
    130                 135                 140

Gln Pro Leu Thr Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

```
Ala Ala Glu Trp Asp Arg Leu His Pro Val Gln Ala Gly Pro Val Ala
    210                 215                 220

Pro Gly Gln Ile Arg Glu Pro Arg Gly Ser Asp Ile Ala Gly Thr Thr
225                 230                 235                 240

Ser Thr Leu Gln Glu Gln Ile Arg Trp Met Thr Ser Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
        275                 280                 285

Pro Lys Glu Pro Phe Arg Asp Tyr Val Asp Arg Phe Tyr Lys Thr Leu
290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Ser His Lys Ala Arg Val Leu Ala Glu Ala Met Ser
        355                 360                 365

Gln Ala Thr Gly Gly Asn Thr Ile Met Met Gln Arg Gly Asn Phe Lys
370                 375                 380

Gly Pro Lys Lys Ser Ile Lys Cys Phe Asn Cys Gly Lys Glu Gly His
385                 390                 395                 400

Thr Ala Lys Asn Cys Arg Ala Pro Arg Arg Arg Gly Cys Trp Lys Cys
                405                 410                 415

Gly Arg Glu Gly His Gln Leu Lys Asp Cys Pro Glu Arg Arg Gln Ala
            420                 425                 430

Asn Phe Leu Gly Lys Ile Trp Pro Ser Asn Lys Gly Arg Pro Gly Asn
        435                 440                 445

Phe Leu Gln Ser Arg Pro Glu Pro Thr Ala Pro Pro Ala Glu Ser Phe
450                 455                 460

Gly Phe Gly Glu Glu Ile Thr Pro Ser Gln Lys Gln Glu Gln Lys Asp
465                 470                 475                 480

Lys Glu Pro His Pro Leu Ala Ser Leu Lys Ser Leu Phe Gly Asn Asp
                485                 490                 495

Pro Leu Ser Gln
            500

<210> SEQ ID NO 123
<211> LENGTH: 273
<212> TYPE: PRT
<213> ORGANISM: HIV-1
<220> FEATURE:
<221> NAME/KEY: VARIANT
<222> LOCATION: 54, 214, 254
<223> OTHER INFORMATION: Xaa = Any Amino Acid

<400> SEQUENCE: 123

Gly Ala Arg Ala Ser Val Leu Ser Gly Gly Lys Leu Asp Ala Trp Glu
  1               5                  10                  15

Lys Ile Arg Leu Arg Pro Gly Gly Lys Lys Tyr Arg Leu Lys His
                20                  25                  30

Leu Val Trp Ala Ser Arg Glu Leu Glu Arg Phe Ala Leu Asn Pro Gly
            35                  40                  45
```

```
Leu Leu Glu Ser Ala Xaa Gly Cys Gln Gln Leu Ile Glu Gln Leu Gln
 50                  55                  60
Ser Thr Leu Lys Thr Gly Ser Glu Glu Leu Lys Ser Leu Phe Asn Thr
 65                  70                  75                  80
Ile Ala Thr Leu Trp Cys Val His Gln Arg Ile Glu Val Lys Asp Thr
                 85                  90                  95
Lys Glu Ala Leu Asp Lys Leu Glu Glu Val Gln Lys Lys Ser Gln Gln
            100                 105                 110
Lys Thr Gln Gln Ala Ala Gly Pro Gly Ser Ser Ser Lys Val Ser
            115                 120                 125
Gln Asn Tyr Pro Ile Val Gln Asn Ala Gln Gly Gln Met Val His Gln
            130                 135                 140
Pro Val Ser Pro Arg Thr Leu Asn Ala Trp Val Lys Val Val Glu Glu
145                 150                 155                 160
Lys Gly Phe Asn Pro Glu Val Ile Pro Met Phe Ser Ala Leu Ser Glu
                165                 170                 175
Gly Ala Thr Pro Gln Asp Leu Asn Met Met Leu Asn Ile Val Gly Gly
            180                 185                 190
His Gln Ala Ala Met Gln Met Leu Lys Glu Thr Ile Asn Glu Glu Ala
            195                 200                 205
Ala Glu Trp Asp Arg Xaa His Pro Val His Ala Gly Pro Ile Pro Pro
210                 215                 220
Gly Gln Met Arg Glu Pro Arg Gly Ser Asp Ile Ala Gly Thr Thr Ser
225                 230                 235                 240
Thr Leu Gln Glu Gln Ile Gly Trp Met Thr Ser Asn Pro Xaa Ile Pro
                245                 250                 255
Val Gly Asp Ile Tyr Lys Arg Trp Ile Ile Leu Gly Leu Asn Lys Ile
            260                 265                 270
Val

<210> SEQ ID NO 124
<211> LENGTH: 276
<212> TYPE: PRT
<213> ORGANISM: HIV-1
<220> FEATURE:
<221> NAME/KEY: VARIANT
<222> LOCATION: 17, 53, 65, 66, 94, 103, 108, 253
<223> OTHER INFORMATION: Xaa = Any Amino Acid

<400> SEQUENCE: 124

Gly Ala Arg Ala Ser Val Leu Ser Gly Gly Lys Leu Asp Ala Trp Glu
 1                5                  10                  15
Xaa Ile Arg Leu Arg Pro Gly Gly Lys Lys Lys Tyr Lys Met Lys His
             20                  25                  30
Leu Val Trp Ala Ser Arg Glu Leu Glu Arg Phe Ala Val Asn Pro Gly
         35                  40                  45
Leu Leu Glu Ser Xaa Glu Gly Cys Gln Gln Ile Ile Glu Gln Leu Gln
 50                  55                  60
Xaa Xaa Leu Lys Thr Gly Ser Glu Glu Leu Lys Ser Leu Tyr Asn Thr
65                  70                  75                  80
Val Val Thr Leu Trp Cys Val His Gln Arg Ile Glu Ile Xaa Asp Thr
                 85                  90                  95
Lys Glu Ala Leu Asp Lys Xaa Glu Glu Val Gln Xaa Lys Ser Gln Gln
            100                 105                 110
Lys Thr Gln Gln Ala Ala Gly Thr Gly Ser Ser Gly Lys Val Ser
            115                 120                 125
```

```
Gln Asn Tyr Pro Ile Val Gln Asn Ala Gln Gly Gln Met Val His Gln
            130                 135                 140

Ala Leu Ser Pro Arg Thr Leu Asn Ala Trp Val Lys Val Val Glu Glu
145                 150                 155                 160

Lys Gly Phe Asn Pro Glu Val Ile Pro Met Phe Ser Ala Leu Ser Glu
                165                 170                 175

Gly Ala Thr Pro Gln Asp Leu Asn Met Met Leu Asn Ile Val Gly Gly
            180                 185                 190

His Gln Ala Ala Met Gln Met Leu Lys Glu Thr Ile Asn Glu Glu Ala
            195                 200                 205

Ala Glu Trp Asp Arg Val His Pro Val His Ala Gly Pro Ile Pro Pro
210                 215                 220

Gly Gln Met Arg Glu Pro Arg Gly Ser Asp Ile Ala Gly Thr Thr Ser
225                 230                 235                 240

Thr Leu Gln Glu Gln Ile Gly Trp Met Thr Asn Asn Xaa Pro Ile Pro
                245                 250                 255

Val Gly Asp Ile Tyr Lys Arg Trp Ile Ile Leu Gly Leu Asn Lys Ile
            260                 265                 270

Val Arg Met Tyr
            275

<210> SEQ ID NO 125
<211> LENGTH: 277
<212> TYPE: PRT
<213> ORGANISM: HIV-1
<220> FEATURE:
<221> NAME/KEY: VARIANT
<222> LOCATION: 8
<223> OTHER INFORMATION: Xaa = Any Amino Acid

<400> SEQUENCE: 125

Gly Ala Arg Ala Ser Val Leu Xaa Gly Gly Lys Leu Asp Ala Trp Glu
  1               5                  10                  15

Lys Ile Arg Leu Arg Pro Gly Gly Lys Lys Tyr Arg Met Lys His
             20                  25                  30

Leu Val Trp Ala Ser Arg Glu Leu Glu Arg Phe Ala Leu Asn Pro Gly
             35                  40                  45

Leu Leu Glu Thr Ala Glu Gly Cys Gln Gln Ile Leu Glu Gln Leu Gln
 50                  55                  60

Ser Thr Leu Lys Thr Gly Ser Glu Glu Leu Lys Ser Leu Phe Asn Thr
 65                  70                  75                  80

Val Ala Thr Leu Trp Cys Val His Gln Arg Ile Glu Val Lys Asp Thr
                 85                  90                  95

Lys Glu Ala Leu Asp Lys Ile Glu Glu Val Gln Asn Lys Ser Gln Gln
                100                 105                 110

Lys Thr Gln Gln Ala Ala Gly Thr Gly Ser Ser Ser Lys Val Ser
            115                 120                 125

Gln Asn Tyr Pro Ile Val Gln Asn Ala Gln Gly Gln Met Ala His Gln
            130                 135                 140

Pro Leu Ser Pro Arg Thr Leu Asn Ala Trp Val Lys Val Val Glu Glu
145                 150                 155                 160

Lys Gly Phe Asn Pro Glu Val Ile Pro Met Phe Ser Ala Leu Ser Glu
                165                 170                 175

Gly Ala Thr Pro Gln Asp Leu Asn Met Met Leu Asn Ile Val Gly Gly
            180                 185                 190
```

```
His Gln Ala Ala Met Gln Met Leu Lys Glu Thr Ile Asn Glu Glu Ala
            195                 200                 205
Ala Glu Trp Asp Arg Val His Pro Val His Ala Gly Pro Ile Pro Pro
210                 215                 220
Gly Gln Met Arg Glu Pro Arg Gly Ser Asp Ile Ala Gly Thr Thr Ser
225                 230                 235                 240
Thr Leu Gln Glu Gln Ile Gly Trp Met Thr Asn Asn Pro Pro Ile Pro
            245                 250                 255
Val Gly Asp Ile Tyr Lys Arg Trp Ile Ile Leu Gly Leu Asn Lys Ile
            260                 265                 270
Val Arg Met Tyr Ser
            275

<210> SEQ ID NO 126
<211> LENGTH: 494
<212> TYPE: PRT
<213> ORGANISM: HIV-1

<400> SEQUENCE: 126

Gly Ala Arg Ala Ser Val Leu Ser Gly Gly Lys Leu Asp Ala Trp Glu
1               5                   10                  15
Lys Ile Arg Leu Arg Pro Gly Gly Lys Lys Tyr Lys Leu Lys His
            20                  25                  30
Leu Val Trp Ala Ser Arg Glu Leu Glu Arg Phe Ala Leu Asn Pro Gly
            35                  40                  45
Leu Leu Glu Thr Thr Glu Gly Cys Arg Gln Ile Ile Thr Gln Ile Gln
    50                  55                  60
Pro Ser Ile Gln Thr Gly Ser Glu Glu Ile Lys Ser Leu Tyr Asn Thr
65                  70                  75                  80
Ile Ala Val Leu Tyr Phe Val His Gln Lys Ile Glu Val Lys Asp Thr
                85                  90                  95
Lys Glu Ala Leu Asp Lys Leu Glu Glu Gln Asn Lys Ser Gln Arg
            100                 105                 110
Lys Thr Gln Gln Glu Ala Ala Asp Lys Gly Val Ser Gln Asn Tyr Pro
            115                 120                 125
Ile Val Gln Asn Leu Gln Gly Gln Met Val His Gln Ala Leu Ser Pro
130                 135                 140
Arg Thr Leu Asn Ala Trp Val Lys Val Ile Glu Glu Lys Ala Phe Ser
145                 150                 155                 160
Pro Glu Val Ile Pro Met Phe Thr Ala Leu Ser Glu Gly Ala Thr Pro
                165                 170                 175
Gln Asp Leu Asn Thr Met Leu Asn Thr Val Gly Gly His Gln Ala Ala
            180                 185                 190
Met Gln Met Leu Lys Asp Thr Ile Asn Asp Glu Ala Ala Glu Trp Asp
            195                 200                 205
Arg Leu His Pro Val His Ala Gly Pro Ile Pro Pro Gly Gln Met Arg
    210                 215                 220
Glu Pro Arg Gly Ser Asp Ile Ala Gly Thr Thr Ser Thr Leu Gln Glu
225                 230                 235                 240
Gln Ile Ala Trp Met Thr Ser Asn Pro Pro Val Pro Val Gly Glu Ile
                245                 250                 255
Tyr Lys Arg Trp Ile Ile Leu Gly Leu Asn Lys Ile Val Arg Met Tyr
            260                 265                 270
Ser Pro Val Ser Ile Leu Asp Ile Arg Gln Gly Pro Lys Glu Pro Phe
            275                 280                 285
```

```
Arg Asp Tyr Val Asp Arg Phe Phe Lys Thr Leu Arg Ala Glu Gln Ala
    290                 295                 300

Thr Gln Glu Val Lys Asn Trp Met Thr Asp Thr Leu Leu Val Gln Asn
305                 310                 315                 320

Ala Asn Pro Asp Cys Lys Thr Ile Leu Lys Ala Leu Gly Pro Gly Ala
                325                 330                 335

Ser Leu Glu Glu Met Met Thr Ala Cys Gln Gly Val Gly Gly Pro Ser
            340                 345                 350

His Lys Ala Arg Ile Leu Ala Glu Ala Met Ser Gln Val Thr Asn Pro
        355                 360                 365

Val Val Met Met Gln Lys Gly Asn Phe Lys Gly His Arg Lys Ile Val
    370                 375                 380

Lys Cys Phe Asn Cys Gly Lys Glu Gly His Ile Ala Arg Asn Cys Arg
385                 390                 395                 400

Ala Pro Arg Lys Lys Gly Cys Trp Lys Cys Gly Lys Glu Gly His Gln
                405                 410                 415

Met Lys Asp Cys Thr Glu Arg Gln Ala Asn Phe Leu Gly Lys Ile Trp
            420                 425                 430

Pro Ser His Lys Gly Arg Pro Gly Asn Phe Leu Gln Ser Arg Pro Glu
        435                 440                 445

Pro Thr Ala Pro Pro Ala Glu Ser Phe Gly Phe Gly Glu Glu Ile Thr
    450                 455                 460

Pro Ser Pro Arg Gln Glu Thr Lys Asp Lys Glu Gln Ser Pro Pro Leu
465                 470                 475                 480

Thr Ser Leu Lys Ser Leu Phe Gly Asn Asp Pro Leu Ser Gln
                485                 490

<210> SEQ ID NO 127
<211> LENGTH: 503
<212> TYPE: PRT
<213> ORGANISM: HIV-1

<400> SEQUENCE: 127

Met Gly Ala Arg Ala Ser Ile Leu Ser Gly Gly Leu Asp Arg Trp
1               5                   10                  15

Glu Lys Ile Arg Leu Arg Pro Gly Gly Lys Lys Lys Tyr Arg Leu Lys
            20                  25                  30

His Leu Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Lys Ile Asp Val Lys Asp
                85                  90                  95

Thr Lys Glu Ala Leu Asp Lys Ile Glu Glu Gln Asn Lys Ser Lys
            100                 105                 110

Lys Lys Ala Gln Gln Ala Ala Ala Asp Thr Gly Asn Ser Ser Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175
```

```
Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Leu His Pro Val His Ala Gly Pro Asn Pro
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Ala Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Lys Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ser Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Lys Gly Asn Phe Arg
    370                 375                 380

Asn Gln Arg Lys Ile Val Lys Cys Phe Asn Cys Gly Lys Glu Gly His
385                 390                 395                 400

Ile Ala Lys Asn Cys Arg Ala Pro Arg Lys Arg Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser His Arg Gly Arg Pro Gly Asn Phe
        435                 440                 445

Pro Gln Asn Arg Leu Glu Pro Thr Ala Pro Ala Pro Pro Glu Glu
    450                 455                 460

Ile Phe Arg Phe Gly Glu Glu Thr Thr Thr Pro Ser Gln Lys Gln Glu
465                 470                 475                 480

Met Ile Asp Lys Glu Leu Tyr Pro Ser Ala Ser Leu Lys Ser Leu Phe
                485                 490                 495

Gly Asn Asp Pro Leu Ser Gln
            500

<210> SEQ ID NO 128
<211> LENGTH: 472
<212> TYPE: PRT
<213> ORGANISM: HIV-1

<400> SEQUENCE: 128

Gly Gly Lys Lys Gln Tyr Lys Met Lys His Leu Ile Trp Ala Ser Arg
  1               5                  10                  15

Glu Leu Glu Arg Phe Ala Leu Asn Pro Ser Leu Leu Glu Thr Gly Glu
             20                  25                  30

Gly Cys Gln Gln Ile Met Glu Gln Leu Gln Ser Ala Leu Arg Thr Gly
         35                  40                  45
```

```
Ser Glu Glu Phe Lys Ser Leu Tyr Asn Thr Val Ala Thr Leu Tyr Cys
 50                  55                  60

Val His Gln Arg Ile Ala Val Lys Asp Thr Lys Glu Ala Leu Asp Lys
 65                  70                  75                  80

Ile Glu Glu Ile Gln Ser Lys Ser Lys Gln Lys Ala Gln Gln Ala Ala
                 85                  90                  95

Ala Ala Thr Gly Asn Ser Ser Asn Leu Ser Gln Asn Tyr Pro Ile Val
            100                 105                 110

Gln Asn Ala Gln Gly Gln Met Val His Gln Pro Ile Ser Pro Arg Thr
        115                 120                 125

Leu Asn Ala Trp Val Lys Val Val Glu Glu Lys Ala Phe Ser Pro Glu
    130                 135                 140

Val Ile Pro Met Phe Ser Ala Leu Ser Glu Gly Ala Thr Pro Gln Asp
145                 150                 155                 160

Leu Asn Met Met Leu Asn Ile Val Gly Gly His Gln Ala Ala Met Gln
                165                 170                 175

Met Leu Lys Asp Thr Ile Asn Glu Glu Ala Ala Asp Trp Asp Arg Thr
            180                 185                 190

His Pro Val Gln Ala Gly Pro Ile Pro Pro Gly Gln Ile Arg Glu Pro
        195                 200                 205

Arg Gly Ser Asp Ile Ala Gly Thr Thr Ser Asn Leu Gln Glu Gln Ile
    210                 215                 220

Arg Trp Met Thr Ser Asn Pro Pro Asn Pro Val Gly Glu Ile Tyr Lys
225                 230                 235                 240

Arg Trp Ile Ile Leu Gly Leu Asn Lys Ile Val Arg Met Tyr Ser Pro
                245                 250                 255

Val Ser Ile Leu Asp Ile Arg Gln Gly Pro Lys Glu Pro Phe Arg Asp
            260                 265                 270

Tyr Val Asp Arg Phe Phe Lys Thr Leu Arg Ala Glu Gln Ala Thr Gln
        275                 280                 285

Glu Val Lys Gly Trp Met Thr Asp Thr Leu Leu Val Gln Asn Ala Asn
    290                 295                 300

Pro Asp Cys Lys Thr Ile Leu Lys Ala Leu Gly Pro Gly Ala Thr Leu
305                 310                 315                 320

Glu Glu Met Met Thr Ala Cys Gln Gly Val Gly Gly Pro Ser His Lys
                325                 330                 335

Ala Arg Val Leu Ala Glu Ala Met Asn Gln Ala Ser Gly Arg Ala Ile
            340                 345                 350

Met Met Gln Lys Ser Asn Phe Lys Gly Pro Arg Arg Ser Ile Lys Cys
        355                 360                 365

Phe Asn Cys Gly Lys Glu Gly His Leu Ala Arg Asn Cys Arg Ala Pro
    370                 375                 380

Arg Lys Lys Gly Cys Trp Lys Cys Gly Lys Glu Gly His Gln Met Lys
385                 390                 395                 400

Asp Cys Thr Glu Arg Gln Ala Asn Phe Leu Gly Lys Ile Trp Pro Ser
                405                 410                 415

Asn Lys Gly Arg Pro Gly Asn Phe Leu Gln Asn Arg Pro Glu Pro Thr
            420                 425                 430

Ala Pro Pro Ala Glu Ser Phe Gly Phe Gly Glu Glu Ile Ala Ser Ser
        435                 440                 445
```

```
Pro Lys Gln Glu Pro Lys Lys Lys Glu Leu Tyr Pro Leu Ala Ser Leu
            450                 455                 460
Lys Ser Leu Phe Gly Asn Asp Pro
465                 470

<210> SEQ ID NO 129
<211> LENGTH: 497
<212> TYPE: PRT
<213> ORGANISM: HIV-1

<400> SEQUENCE: 129

Ala Arg Ala Ser Val Leu Ser Gly Gly Lys Leu Asp Ala Trp Glu Lys
  1               5                  10                  15
Ile Arg Leu Arg Pro Gly Gly Lys Lys Lys Tyr Arg Met Lys His Leu
             20                  25                  30
Val Trp Ala Ser Arg Glu Leu Glu Arg Phe Ala Leu Asn Pro Ser Leu
         35                  40                  45
Leu Glu Thr Thr Glu Gly Cys Gln Gln Ile Met Glu Gln Leu Gln Ser
     50                  55                  60
Ala Leu Lys Thr Gly Thr Glu Glu Leu Arg Ser Leu Phe Asn Thr Val
 65                  70                  75                  80
Ala Val Leu Tyr Cys Val His Gln Arg Ile Glu Ile Lys Asp Thr Lys
                 85                  90                  95
Glu Ala Leu Asp Lys Ile Glu Glu Ile Gln Lys Lys Ser Lys Gln Lys
            100                 105                 110
Ala Gln Gln Ala Ala Ala Asp Thr Gly Asn Ser Ser Lys Val Ser Gln
        115                 120                 125
Asn Tyr Pro Ile Val Gln Asn Ala Gln Gly Gln Met Val His Gln Ser
    130                 135                 140
Leu Ser Pro Arg Thr Leu Asn Ala Trp Val Lys Val Ile Glu Glu Lys
145                 150                 155                 160
Ala Phe Ser Pro Glu Val Ile Pro Val Phe Ser Ala Leu Ser Glu Gly
                165                 170                 175
Ala Thr Pro Gln Asp Leu Asn Met Met Leu Asn Ile Val Gly Gly His
            180                 185                 190
Gln Ala Ala Met Gln Met Leu Lys Asp Thr Ile Asn Glu Glu Ala Ala
        195                 200                 205
Glu Trp Asp Arg Leu His Pro Ala His Ala Gly Pro Val Ala Pro Gly
    210                 215                 220
Gln Met Arg Glu Pro Arg Gly Ser Asp Ile Ala Gly Thr Thr Ser Thr
225                 230                 235                 240
Pro Gln Glu Gln Ile Gly Trp Met Thr Gly Asn Pro Pro Ile Pro Val
                245                 250                 255
Gly Asp Ile Tyr Lys Arg Trp Ile Ile Leu Gly Leu Asn Lys Ile Val
            260                 265                 270
Arg Met Tyr Ser Pro Val Ser Ile Leu Asp Ile Lys Gln Gly Pro Lys
        275                 280                 285
Glu Pro Phe Arg Asp Tyr Val Asp Arg Phe Phe Lys Thr Leu Arg Ala
    290                 295                 300
Glu Gln Ala Thr Gln Asp Val Lys Asn Trp Met Thr Glu Thr Leu Leu
305                 310                 315                 320
Val Gln Asn Ala Asn Pro Asp Cys Lys Ser Ile Leu Arg Ala Leu Gly
                325                 330                 335
Ala Gly Ala Thr Leu Glu Glu Met Met Ser Ala Cys Gln Gly Val Gly
            340                 345                 350
```

-continued

```
Gly Pro Ser His Lys Ala Arg Val Leu Ala Glu Ala Met Ser Gln Ala
            355                 360                 365
Gln Gln His Thr Thr Val Met Met Gln Arg Ala Asn Phe Arg Gly Gln
        370                 375                 380
Lys Arg Ile Lys Cys Phe Asn Cys Gly Lys Glu Gly His Leu Ala Arg
385                 390                 395                 400
Asn Cys Arg Ala Pro Arg Lys Lys Gly Cys Trp Lys Cys Gly Lys Glu
                405                 410                 415
Gly His Gln Met Lys Asp Cys Thr Glu Arg Gln Ala Asn Phe Leu Gly
            420                 425                 430
Lys Met Trp Pro Ser Ser Lys Gly Arg Pro Gly Asn Phe Pro Gln Ser
        435                 440                 445
Arg Pro Glu Pro Thr Ala Pro Ala Glu Leu Phe Gly Met Gly Glu
    450                 455                 460
Glu Ile Ala Ser Pro Pro Lys Gln Glu Gln Lys Asp Arg Glu Gln Asn
465                 470                 475                 480
Ser Pro Ser Val Ser Leu Lys Ser Leu Phe Gly Asn Asp Leu Leu Ser
                485                 490                 495
Gln

<210> SEQ ID NO 130
<211> LENGTH: 496
<212> TYPE: PRT
<213> ORGANISM: HIV-1

<400> SEQUENCE: 130

Ala Arg Ala Ser Val Leu Ser Gly Gly Arg Leu Asp Ala Trp Glu Lys
1               5                   10                  15
Ile Arg Leu Arg Pro Gly Gly Lys Lys Lys Tyr Arg Met Lys His Leu
            20                  25                  30
Val Trp Ala Ser Arg Glu Leu Asp Arg Phe Ala Leu Asn Pro Ser Leu
        35                  40                  45
Leu Glu Thr Thr Glu Gly Cys Gln Gln Ile Ile Gly Gln Leu Gln Pro
    50                  55                  60
Ala Phe Lys Thr Gly Thr Glu Glu Leu Lys Ser Leu Tyr Asn Thr Val
65                  70                  75                  80
Ala Thr Leu Trp Cys Val His Gln Arg Ile Asp Val Lys Asp Thr Lys
                85                  90                  95
Glu Ala Leu Asp Lys Leu Glu Glu Ile Gln Lys Lys Ser Lys Gln Lys
            100                 105                 110
Thr Gln Gln Ala Val Ala Asp Thr Gly Ser Ser Ser Lys Val Ser His
        115                 120                 125
Asn Tyr Pro Val Val Gln Asn Ala Gln Gly Gln Met Ile His Gln Asn
    130                 135                 140
Leu Ser Pro Arg Thr Leu Asn Ala Trp Val Lys Val Ile Glu Glu Lys
145                 150                 155                 160
Gly Phe Asn Pro Glu Val Ile Pro Met Phe Ser Ala Leu Ser Glu Gly
                165                 170                 175
Ala Thr Pro Gln Asp Leu Asn Thr Met Leu Asn Ile Val Gly Gly His
            180                 185                 190
Gln Ala Ala Met Gln Met Leu Lys Asp Thr Ile Asn Glu Glu Ala Ala
        195                 200                 205
Glu Trp Asp Arg Leu His Pro Val His Ala Gly Pro Ile Pro Pro Gly
    210                 215                 220
```

-continued

```
Gln Met Arg Glu Pro Arg Gly Ser Asp Ile Ala Gly Thr Thr Ser Thr
225                 230                 235                 240

Pro Gln Glu Gln Leu Gln Trp Met Thr Ser Asn Pro Pro Ile Pro Val
            245                 250                 255

Gly Asp Ile Tyr Lys Arg Trp Ile Ile Leu Gly Leu Asn Lys Ile Val
                260                 265                 270

Arg Met Tyr Ser Pro Val Ser Ile Leu Asp Ile Arg Gln Gly Pro Lys
            275                 280                 285

Glu Pro Phe Arg Asp Tyr Val Asp Arg Phe Phe Lys Ala Leu Arg Ala
    290                 295                 300

Glu Gln Ala Thr Gln Glu Val Lys Gly Trp Met Thr Glu Thr Leu Leu
305                 310                 315                 320

Val Gln Asn Ala Asn Pro Asp Cys Lys Ser Ile Leu Lys Ala Leu Gly
                325                 330                 335

Thr Gly Ala Thr Leu Glu Glu Met Met Thr Ala Cys Gln Gly Val Gly
            340                 345                 350

Gly Pro Gly His Lys Ala Arg Val Leu Ala Glu Ala Met Ser Gln Val
        355                 360                 365

Gln Gln Pro Asn Ile Met Met Gln Arg Gly Asn Phe Arg Gly Gln Arg
    370                 375                 380

Arg Ile Lys Cys Phe Asn Cys Gly Lys Glu Gly His Leu Ala Lys Asn
385                 390                 395                 400

Cys Arg Ala Pro Arg Lys Lys Gly Cys Trp Lys Cys Gly Lys Glu Gly
                405                 410                 415

His Gln Met Lys Asp Cys Thr Glu Arg Gln Ala Asn Phe Leu Gly Lys
            420                 425                 430

Ile Trp Pro Ser Ser Lys Gly Arg Pro Gly Asn Phe Pro Gln Ser Arg
        435                 440                 445

Pro Glu Pro Thr Ala Pro Pro Ala Glu Ile Phe Gly Met Gly Glu Val
    450                 455                 460

Ile Thr Ser Pro Pro Lys Gln Glu Gln Lys Asp Lys Glu Gln Val Pro
465                 470                 475                 480

Pro Leu Val Ser Leu Lys Ser Leu Phe Gly Asn Asp Pro Leu Ser Gln
                485                 490                 495

<210> SEQ ID NO 131
<211> LENGTH: 241
<212> TYPE: PRT
<213> ORGANISM: HIV-1

<400> SEQUENCE: 131

Gly Gly Lys Lys Cys Tyr Met Met Lys His Ile Val Trp Ala Ser Arg
1               5                   10                  15

Glu Leu Glu Arg Phe Ala Leu Asp Pro Gly Leu Leu Glu Thr Ser Glu
            20                  25                  30

Gly Cys Lys Gln Ile Leu Lys Gln Leu Gln Pro Ala Leu Pro Thr Gly
        35                  40                  45

Thr Lys Glu Leu Ile Ser Leu Tyr Asn Thr Val Ala Thr Leu Tyr Cys
    50                  55                  60

Val His Glu Lys Ile Glu Val Arg Asp Thr Lys Glu Ala Leu Asp Lys
65                  70                  75                  80

Leu Lys Glu Glu Gln Asn Lys Ser Gln Gln Thr Gln Gln Ala Ala
                85                  90                  95

Met Ala Asp Lys Gly Lys Val Ser Gln Asn Tyr Pro Ile Val Gln Asn
            100                 105                 110
```

-continued

```
Leu Gln Gly Gln Met Val His Gln Ala Ile Ser Pro Arg Thr Leu Asn
        115                 120                 125
Ala Trp Val Lys Val Ile Glu Glu Lys Ala Phe Ser Pro Glu Val Ile
130                 135                 140
Pro Met Phe Thr Ala Leu Ser Glu Gly Ala Thr Pro Gln Asp Leu Asn
145                 150                 155                 160
Thr Met Leu Asn Thr Val Gly Gly His Gln Ala Ala Met Gln Met Leu
                165                 170                 175
Lys Asp Thr Ile Asn Glu Glu Ala Ala Glu Trp Asp Arg Leu His Pro
            180                 185                 190
Val Gln Ala Gly Pro Val Ala Pro Gly Gln Val Arg Glu Pro Arg Gly
        195                 200                 205
Ser Asp Ile Ala Gly Thr Thr Ser Thr Leu Gln Glu Gln Ile Ala Trp
    210                 215                 220
Met Thr Ser Asn Pro Pro Ile Pro Val Gly Glu Ile Tyr Lys Arg Trp
225                 230                 235                 240
Ile

<210> SEQ ID NO 132
<211> LENGTH: 509
<212> TYPE: PRT
<213> ORGANISM: HIV-1
<220> FEATURE:
<221> NAME/KEY: VARIANT
<222> LOCATION: 213, 229, 355, 497
<223> OTHER INFORMATION: Xaa = Any Amino Acid

<400> SEQUENCE: 132

Met Gly Ala Arg Ser Ser Val Leu Ser Gly Lys Lys Ala Asp Glu Leu
1               5                   10                  15
Glu Lys Val Arg Leu Arg Pro Gly Gly Lys Lys Lys Tyr Met Leu Lys
            20                  25                  30
His Val Val Trp Ala Ala Asn Glu Leu Asp Arg Phe Gly Leu Ala Glu
        35                  40                  45
Ser Leu Leu Glu Ser Lys Glu Gly Cys Gln Lys Ile Leu Ser Val Leu
    50                  55                  60
Ala Pro Leu Val Pro Thr Gly Ser Glu Asn Leu Lys Ser Leu Tyr Asn
65                  70                  75                  80
Thr Val Cys Val Ile Trp Cys Leu His Ala Glu Gln Lys Val Lys His
                85                  90                  95
Thr Glu Glu Ala Lys Gln Val Val Gln Arg His Leu Val Val Glu Thr
            100                 105                 110
Gly Thr Thr Glu Lys Val Pro Ala Thr Ser Arg Pro Ile Ala Pro Pro
        115                 120                 125
Ser Gly Arg Gly Gly Asn Tyr Pro Val Gln Gln Val Gly Gly Asn Tyr
    130                 135                 140
Val His Leu Pro Leu Ser Pro Arg Thr Leu Asn Ala Trp Val Lys Leu
145                 150                 155                 160
Val Glu Glu Lys Lys Phe Gly Ala Glu Val Pro Gly Phe Gln Ala
                165                 170                 175
Leu Ser Glu Gly Cys Leu Pro Tyr Asp Ile Asn Gln Met Leu Asn Cys
            180                 185                 190
Val Gly Glu His Gln Ala Ala Met Gln Ile Ile Arg Glu Ile Ile Asn
        195                 200                 205
Glu Glu Ala Ala Xaa Trp Asp Leu Gln His Pro Gln Gln Gly Pro Pro
    210                 215                 220
```

```
Pro Ala Gly Gln Xaa Arg Glu Pro Thr Gly Ser Asp Ile Ala Gly Thr
225                 230                 235                 240

Thr Ser Thr Ile Glu Glu Gln Ile Gln Trp Thr His Arg Gln Gln Asn
            245                 250                 255

Pro Ile Pro Val Gly Asn Ile Tyr Arg Arg Trp Ile Gln Leu Gly Leu
        260                 265                 270

Gln Lys Cys Val Arg Met Tyr Asn Pro Thr Asn Ile Leu Asp Val Lys
    275                 280                 285

Gln Gly Pro Lys Glu Pro Phe Gln Ser Tyr Val Asp Arg Phe Tyr Lys
290                 295                 300

Ser Leu Arg Ala Glu Gln Thr Asp Pro Ala Val Lys Asn Trp Met Thr
305                 310                 315                 320

Gln Thr Leu Leu Ile Gln Asn Ala Asn Pro Asp Cys Lys Leu Val Leu
            325                 330                 335

Lys Gly Leu Gly Met Asn Pro Thr Leu Glu Glu Met Leu Thr Ala Cys
        340                 345                 350

Gln Gly Xaa Gly Gly Pro Gly Gln Lys Ala Arg Leu Met Ala Glu Ala
    355                 360                 365

Leu Lys Glu Ala Leu Asn Pro Thr Ala Leu Pro Phe Ala Ala Ala Gln
370                 375                 380

Gln Lys Thr Gly Gly Lys Arg Ser Thr Ile Lys Cys Trp Asn Cys Gly
385                 390                 395                 400

Lys Glu Gly His Thr Val Arg Gln Cys Arg Ala Pro Arg Arg Gln Gly
            405                 410                 415

Cys Trp Lys Cys Gly Lys Pro Gly His Ile Met Ala Lys Cys Pro Glu
        420                 425                 430

Arg Gln Ala Gly Phe Leu Gly Phe Gly Pro Trp Gly Lys Lys Pro Arg
    435                 440                 445

Asn Phe Pro Met Thr Gln Val Pro Gln Gly Leu Thr Pro Ser Ala Pro
450                 455                 460

Pro Met Asp Pro Ala Val Asp Leu Leu Lys Asn Tyr Met Gln Leu Gly
465                 470                 475                 480

Arg Lys Gln Lys Glu Gln Arg Asn Lys Pro Tyr Lys Glu Val Thr Glu
            485                 490                 495

Xaa Leu Leu His Leu Ser Ser Leu Phe Gly Asp Asp Gln
        500                 505

<210> SEQ ID NO 133
<211> LENGTH: 75
<212> TYPE: PRT
<213> ORGANISM: HIV-1

<400> SEQUENCE: 133

Glu Leu Glu Arg Phe Ala Leu Asn Pro Asp Leu Leu Glu Thr Thr Glu
1               5                   10                  15

Gly Cys Gln Gln Ala Leu Ile Gln Leu Gln Pro Ala Leu Lys Ile Gly
            20                  25                  30

Ile Glu Glu Leu Lys Ser Leu Tyr Asn Thr Val Ala Thr Leu Tyr Cys
        35                  40                  45

Val His Arg Gly Ile Asp Val Lys Asp Thr Lys Glu Ala Leu Asp Lys
    50                  55                  60

Ile Glu Glu Ile Gln Ile Lys Ser Lys Asn Ser
65                  70                  75
```

```
<210> SEQ ID NO 134
<211> LENGTH: 239
<212> TYPE: PRT
<213> ORGANISM: HIV-1
<220> FEATURE:
<221> NAME/KEY: VARIANT
<222> LOCATION: 19, 145, 217
<223> OTHER INFORMATION: Xaa = Any Amino Acid

<400> SEQUENCE: 134

Gly Gly Lys Lys Lys Tyr Arg Met Lys His Leu Val Trp Ala Ser Arg
 1               5                  10                  15

Glu Leu Xaa Arg Phe Ala Val Asp Pro Gly Leu Leu Glu Thr Pro Glu
            20                  25                  30

Gly Cys Arg Lys Ile Ile Gly Gln Leu Gln Pro Ser Leu Gln Thr Gly
        35                  40                  45

Ser Asp Glu Leu Arg Ser Leu Tyr Asn Ala Val Val Leu Tyr Tyr
 50                  55                  60

Val His Gln Lys Ile Asp Val Lys Asp Thr Lys Glu Ala Leu Glu Lys
65                  70                  75                  80

Leu Glu Glu Glu Gln His Arg Ser Gln Gln Lys Thr Gln Gln Ala Ala
                85                  90                  95

Ala Asp Lys Gly Val Ser Gln Asn Tyr Pro Ile Val Gln Asn Leu Gln
            100                 105                 110

Gly Gln Met Val His Gln Ala Leu Ser Pro Arg Thr Leu Asn Ala Trp
        115                 120                 125

Val Lys Val Ile Glu Glu Lys Ala Phe Ser Pro Glu Val Ile Pro Met
    130                 135                 140

Xaa Ser Ala Leu Ser Glu Gly Ala Thr Pro Gln Asp Leu Asn Thr Met
145                 150                 155                 160

Leu Asn Thr Val Gly Gly His Gln Ala Ala Met Gln Ile Leu Lys Asp
                165                 170                 175

Thr Ile Asn Glu Glu Ala Ala Asp Trp Asp Arg Leu His Pro Val His
            180                 185                 190

Ala Gly Pro Ile Pro Pro Gly Gln Met Arg Glu Pro Arg Gly Ser Asp
        195                 200                 205

Ile Ala Gly Thr Thr Ser Thr Leu Xaa Glu Gln Ile Gln Trp Met Thr
    210                 215                 220

Ser Asn Pro Pro Val Pro Val Gly Asp Ile Tyr Lys Arg Trp Ile
225                 230                 235

<210> SEQ ID NO 135
<211> LENGTH: 420
<212> TYPE: PRT
<213> ORGANISM: HIV-1

<400> SEQUENCE: 135

Gly Gly Lys Lys Lys Tyr Arg Leu Lys His Leu Val Trp Ala Ser Arg
 1               5                  10                  15

Glu Leu Glu Arg Phe Ala Leu Asn Pro Gly Leu Leu Glu Thr Thr Glu
            20                  25                  30

Gly Cys Lys Gln Ile Ile Gly Gln Leu Gln Pro Ser Leu Gln Thr Gly
        35                  40                  45

Thr Glu Glu Leu Lys Ser Leu Tyr Asn Leu Val Val Leu Tyr Cys
 50                  55                  60

Val His Arg Lys Ile Asp Val Arg Asp Thr Lys Glu Ala Leu Asp Lys
65                  70                  75                  80
```

```
Leu Gln Glu Glu Gln Ala Lys Cys Gln Gln Lys Thr Gln Gln Ala Thr
                85                  90                  95

Ala Asp Lys Gly Val Ser Gln Asn Tyr Pro Ile Val Gln Asn Leu Gln
            100                 105                 110

Gly Gln Met Val His Gln Ala Ile Ser Pro Arg Thr Leu Asn Ala Trp
        115                 120                 125

Val Lys Val Ile Glu Glu Lys Ala Phe Ser Pro Glu Val Ile Pro Met
130                 135                 140

Phe Ser Ala Leu Ser Glu Gly Ala Thr Pro Gln Asp Leu Asn Thr Met
145                 150                 155                 160

Leu Asn Thr Val Gly Gly His Gln Ala Ala Met Gln Met Leu Lys Asp
                165                 170                 175

Thr Ile Asn Glu Glu Ala Ala Glu Trp Asp Arg Val His Pro Val Gln
            180                 185                 190

Ala Gly Pro Asn Pro Pro Gly Gln Met Arg Glu Pro Arg Gly Ser Asp
        195                 200                 205

Ile Ala Gly Thr Thr Ser Thr Leu Gln Glu Gln Ile Ala Trp Met Thr
    210                 215                 220

Gly Asn Pro Pro Val Pro Val Gly Glu Ile Tyr Lys Arg Trp Ile Ser
225                 230                 235                 240

Leu Val Val Asn Lys Ile Val Arg Met Tyr Ser Pro Val Ser Ile Leu
                245                 250                 255

Asp Ile Arg Gln Gly Pro Lys Glu Pro Phe Arg Asp Tyr Val Asp Arg
            260                 265                 270

Phe Phe Lys Thr Leu Arg Ala Glu Gln Ala Thr Gln Glu Val Lys Gly
        275                 280                 285

Trp Met Thr Asp Thr Leu Leu Val Gln Asn Ala Asn Pro Asp Cys Lys
    290                 295                 300

Thr Ile Leu Lys Ala Leu Gly Pro Gly Ala Thr Leu Glu Glu Met Met
305                 310                 315                 320

Thr Ala Cys Gln Gly Val Gly Pro Ser His Lys Ala Arg Val Leu
                325                 330                 335

Ala Glu Ala Met Ser Arg Ala Thr Asn Thr Ser Ile Met Met Gln Lys
            340                 345                 350

Ser Asn Phe Arg Gly Gln Arg Lys Met Val Lys Cys Phe Asn Cys Gly
        355                 360                 365

Lys Glu Gly His Ile Ala Lys Asn Cys Arg Ala Pro Arg Lys Arg Gly
    370                 375                 380

Cys Trp Lys Cys Gly Lys Glu Gly His Gln Met Lys Asp Cys Thr Glu
385                 390                 395                 400

Arg Gln Ala Asn Phe Leu Gly Lys Ile Trp Pro Ser Asn Lys Gly Arg
                405                 410                 415

Pro Gly Asn Phe
            420

<210> SEQ ID NO 136
<211> LENGTH: 501
<212> TYPE: PRT
<213> ORGANISM: HIV-1

<400> SEQUENCE: 136

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Tyr Arg Leu Lys
            20                  25                  30
```

-continued

```
His Ile Val Trp Ala Ser Arg Glu Leu Glu Arg Phe Ala Ile Asn Pro
        35                  40                  45
Gly Leu Leu Glu Thr Ser Glu Gly Cys Lys Gln Ile Ile Ala Gln Leu
        50                  55                  60
Gln Pro Ala Ile Gln Thr Gly Ser Glu Glu Leu Arg Ser Leu Tyr Asn
65                  70                  75                  80
Thr Val Ala Thr Leu Tyr Cys Val His Glu Lys Ile Glu Val Lys Asp
                85                  90                  95
Thr Lys Glu Ala Leu Glu Lys Ile Glu Glu Gln Asn Lys Ser Lys
            100                 105                 110
Ser Lys Arg Ala Gln Ala Glu Ala Gly Thr Lys Asn Ser Gly Pro
        115                 120                 125
Val Ser Gln Asn Phe Pro Ile Val Gln Asn Leu Gln Gly Gln Met Val
    130                 135                 140
His Gln Ala Leu Ser Pro Arg Thr Leu Asn Ala Trp Val Lys Val Ile
145                 150                 155                 160
Glu Glu Lys Ala Phe Ser Pro Glu Val Ile Pro Met Phe Thr Ala Leu
                165                 170                 175
Ser Glu Gly Ala Thr Pro Gln Asp Leu Asn Thr Met Leu Asn Thr Val
            180                 185                 190
Gly Gly His Gln Ala Ala Met Gln Met Leu Lys Glu Thr Ile Asn Glu
        195                 200                 205
Glu Ala Ala Glu Trp Asp Arg Val His Pro Ala Gln Ala Gly Pro Ile
210                 215                 220
Ala Pro Gly Gln Ile Arg Glu Pro Arg Gly Ser Asp Ile Ala Gly Thr
225                 230                 235                 240
Thr Ser Thr Leu Gln Glu Gln Ile Thr Trp Met Thr Asn Asn Pro Pro
                245                 250                 255
Ile Pro Val Gly Glu Ile Tyr Lys Arg Trp Ile Ile Leu Gly Leu Asn
            260                 265                 270
Lys Ile Val Arg Met Tyr Ser Pro Val Ser Ile Leu Asp Ile Arg Gln
        275                 280                 285
Gly Pro Lys Glu Pro Phe Arg Asp Tyr Val Asp Arg Phe Tyr Lys Thr
    290                 295                 300
Leu Arg Ala Glu Gln Ala Ser Gln Asp Val Lys Asn Trp Met Thr Glu
305                 310                 315                 320
Thr Leu Leu Val Gln Asn Ala Asn Pro Asp Cys Lys Thr Ile Leu Lys
                325                 330                 335
Ala Leu Gly Pro Gln Ala Thr Leu Glu Glu Met Met Thr Ala Cys Gln
            340                 345                 350
Gly Val Gly Gly Pro Ser His Lys Ala Arg Val Leu Ala Glu Ala Met
        355                 360                 365
Ser Gln Ala Thr Gly Ser Pro Ala Val Met Met Gln Arg Gly Asn Phe
    370                 375                 380
Lys Gly Pro Arg Lys Ser Ile Lys Cys Phe Asn Cys Gly Lys Glu Gly
385                 390                 395                 400
His Thr Ala Lys Asn Cys Arg Ala Pro Arg Lys Arg Gly Cys Trp Lys
                405                 410                 415
Cys Gly Arg Glu Gly His Gln Met Lys Asp Cys Ile Glu Gly Gln Ala
            420                 425                 430
Asn Phe Leu Gly Arg Val Trp Leu Ser His Lys Gly Arg Pro Gly Asn
        435                 440                 445
```

```
Phe Leu Gln Ser Arg Pro Glu Pro Ser Ala Pro Pro Ala Glu Ser Phe
    450                 455                 460
Gly Phe Gly Glu Glu Ile Thr Pro Ser Pro Lys Gln Glu Gln Lys Asp
465                 470                 475                 480
Glu Gly Lys Tyr Pro Pro Leu Ala Ser Leu Lys Ser Leu Phe Gly Asn
                485                 490                 495
Asp Pro Leu Ser Gln
            500

<210> SEQ ID NO 137
<211> LENGTH: 258
<212> TYPE: PRT
<213> ORGANISM: HIV-1

<400> SEQUENCE: 137

Pro Met Phe Thr Ala Leu Ser Glu Gly Ala Thr Pro Gln Asp Leu Asn
  1               5                  10                  15
Thr Met Leu Asn Thr Val Gly Gly His Gln Ala Ala Met Gln Met Leu
                20                  25                  30
Lys Asp Thr Ile Asn Glu Glu Ala Ala Glu Trp Asp Arg Leu His Pro
            35                  40                  45
Val His Ala Gly Pro Val Ala Pro Gly Gln Met Arg Asp Pro Arg Gly
 50                  55                  60
Ser Asp Ile Ala Gly Thr Thr Ser Thr Leu Gln Glu Gln Ile Ala Trp
 65                  70                  75                  80
Met Thr Asn Asn Pro Pro Ile Pro Val Gly Asp Ile Tyr Lys Arg Trp
                85                  90                  95
Ile Ile Leu Gly Leu Asn Lys Ile Val Arg Met Tyr Ser Pro Val Ser
            100                 105                 110
Ile Leu Asp Ile Lys Gln Gly Pro Lys Glu Pro Phe Arg Asp Tyr Val
        115                 120                 125
Asp Arg Phe Phe Lys Thr Leu Arg Ala Glu Gln Ser Thr Gln Glu Val
130                 135                 140
Lys Asn Trp Met Thr Asp Thr Leu Leu Ile Gln Asn Ala Asn Pro Asp
145                 150                 155                 160
Cys Lys Thr Ile Leu Arg Ser Leu Gly Pro Gly Ala Thr Leu Glu Glu
                165                 170                 175
Met Met Thr Ala Cys Gln Gly Val Gly Gly Pro Gly His Lys Ala Arg
            180                 185                 190
Val Leu Ala Glu Ala Met Ser Gln Val Asn Gln Thr Asn Ile Met Met
        195                 200                 205
Gln Lys Ser Asn Phe Lys Gly Pro Arg Arg Met Val Lys Cys Phe Asn
    210                 215                 220
Cys Gly Lys Glu Gly His Ile Ala Lys Asn Cys Arg Ala Pro Arg Lys
225                 230                 235                 240
Lys Gly Cys Trp Lys Cys Gly Lys Glu Gly Tyr Gln Met Lys Asp Cys
                245                 250                 255
Thr Glu

<210> SEQ ID NO 138
<211> LENGTH: 257
<212> TYPE: PRT
<213> ORGANISM: HIV-1
```

-continued

```
<400> SEQUENCE: 138

Pro Gln Asp Leu Asn Thr Met Leu Asn Thr Val Gly Gly His Gln Ala
1               5                   10                  15

Ala Met Gln Met Leu Lys Glu Thr Ile Asn Glu Glu Ala Ala Glu Trp
            20                  25                  30

Asp Arg Met His Pro Val His Ala Gly Pro Ile Ala Pro Gly Gln Leu
        35                  40                  45

Arg Glu Pro Arg Gly Ser Asp Ile Ala Gly Thr Thr Ser Thr Leu Gln
    50                  55                  60

Glu Gln Ile Gly Trp Met Thr Asn Asn Pro Pro Ile Pro Val Gly Glu
65                  70                  75                  80

Ile Tyr Lys Arg Trp Ile Ile Leu Gly Leu Asn Lys Ile Val Arg Met
                85                  90                  95

Tyr Ser Pro Val Ser Ile Leu Asp Ile Arg Gln Gly Pro Lys Glu Pro
            100                 105                 110

Phe Arg Asp Tyr Val Asp Arg Phe Tyr Lys Thr Leu Arg Ala Glu Gln
        115                 120                 125

Ala Ser Gln Asp Val Lys Asn Trp Met Thr Glu Thr Leu Leu Val Gln
    130                 135                 140

Asn Ala Asn Pro Asp Cys Lys Thr Ile Leu Lys Ala Leu Gly Pro Gly
145                 150                 155                 160

Ala Thr Leu Glu Glu Met Met Thr Ala Cys Gln Gly Val Gly Gly Pro
                165                 170                 175

Ser His Lys Ala Arg Val Leu Ala Glu Ala Met Ser Gln Ala Thr Asn
            180                 185                 190

Asn Val Asn Ala Ala Ile Met Met Gln Arg Gly Asn Phe Lys Gly Gln
        195                 200                 205

Arg Lys Ile Ile Lys Cys Phe Asn Cys Gly Lys Glu Gly His Ile Ala
    210                 215                 220

Lys Asn Cys Arg Ala Pro Arg Lys Lys Gly Cys Trp Lys Cys Gly Lys
225                 230                 235                 240

Glu Gly His Gln Met Lys Asp Cys Thr Asp Arg Gln Ala Asn Phe Leu
                245                 250                 255

Gly

<210> SEQ ID NO 139
<211> LENGTH: 178
<212> TYPE: PRT
<213> ORGANISM: HIV-1

<400> SEQUENCE: 139

Ile Pro Val Gly Glu Ile Tyr Lys Arg Trp Ile Val Leu Gly Leu Asn
1               5                   10                  15

Lys Ile Val Arg Met Tyr Ser Pro Val Ser Ile Leu Asp Ile Arg Gln
            20                  25                  30

Gly Pro Lys Glu Pro Phe Arg Asp Tyr Val Asp Arg Phe Phe Lys Thr
        35                  40                  45

Leu Arg Ala Glu Gln Ala Thr Gln Glu Val Lys Ser Trp Met Thr Gly
    50                  55                  60

Thr Leu Leu Val Gln Asn Ala Asn Pro Asp Cys Lys Thr Ile Leu Arg
65                  70                  75                  80

Ala Leu Gly Pro Gly Ala Thr Ile Glu Glu Met Met Thr Ala Cys Gln
                85                  90                  95
```

Gly Val Gly Glu Pro Gly His Lys Ala Arg Val Leu Ala Glu Ala Met
                100                 105                 110

Ser Gln Val Gln Asn Thr Asn Ile Leu Met Gln Arg Gly Asn Phe Lys
        115                 120                 125

Gly Gln Lys Arg Ile Lys Cys Phe Asn Cys Gly Lys Glu Gly His Leu
    130                 135                 140

Ala Arg Asn Cys Arg Ala Pro Arg Lys Lys Gly Cys Trp Lys Cys Gly
145                 150                 155                 160

Lys Glu Gly His Gln Met Lys Asp Cys Thr Glu Lys Gln Ala Asn Phe
                165                 170                 175

Leu Gly

<210> SEQ ID NO 140
<211> LENGTH: 491
<212> TYPE: PRT
<213> ORGANISM: HIV-1

<400> SEQUENCE: 140

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
            20                  25                  30

His Leu Val Trp Ala Ser Arg Glu Leu Glu Arg Phe Ala Val Asn Pro
        35                  40                  45

Gly Leu Leu Glu Thr Ala Glu Gly Cys Lys Gln Ile Ile Lys Gln Leu
    50                  55                  60

Gln Pro Ala Leu Gln Thr Gly Thr Glu Glu Leu Arg Ser Leu Tyr Asn
65                  70                  75                  80

Thr Val Ala Thr Leu Tyr Cys Val His Ala Glu Ile Glu Val Arg Asp
                85                  90                  95

Thr Lys Glu Ala Leu Asp Arg Ile Glu Glu Glu Gln Asn Lys Ser Gln
            100                 105                 110

Gln Lys Thr Gln Gln Ala Asn Glu Ala Asp Gly Lys Val Ser Gln Asn
        115                 120                 125

Tyr Pro Ile Val Gln Asn Leu Gln Gly Gln Met Val His Gln Ala Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Ile Ala Pro Gly Gln
    210                 215                 220

Met Arg Glu Pro Arg Gly Ser Asp Ile Ala Gly Thr Thr Ser Ser Leu
225                 230                 235                 240

Gln Glu Gln Ile Ala Trp Met Thr Gly Asn Pro Pro Val Pro Val Gly
                245                 250                 255

Asp Ile Tyr Lys Arg Trp Ile Ile Leu Gly Leu Asn Lys Ile Val Arg
            260                 265                 270

Met Tyr Ser Pro Val Ser Ile Leu Asp Ile Lys Gln Gly Pro Lys Glu
        275                 280                 285

-continued

```
Pro Phe Arg Asp Tyr Val Asp Arg Phe Phe Lys Thr Leu Arg Ala Glu
    290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Ser Leu Glu Glu Met Met Thr Ala Cys Gln Gly Val Gly Gly
                340                 345                 350

Pro Ser His Lys Ala Arg Val Leu Ala Glu Ala Met Ser Gln Thr Asn
                355                 360                 365

Ser Thr Ile Leu Met Gln Arg Ser Asn Phe Lys Gly Pro Lys Arg Ile
370                 375                 380

Val Lys Cys Phe Asn Cys Gly Lys Glu Gly His Ile Ala Lys Asn Cys
385                 390                 395                 400

Arg Ala Pro Arg Lys Lys Gly Cys Trp Lys Cys Gly Lys Glu Gly His
                405                 410                 415

Gln Met Lys Asp Cys Thr Glu Arg Gln Ala Asn Phe Leu Gly Lys Ile
                420                 425                 430

Trp Pro Ser His Lys Gly Arg Pro Gly Asn Phe Leu Gln Ser Arg Pro
                435                 440                 445

Glu Pro Thr Ala Pro Pro Ala Glu Ser Phe Arg Phe Glu Glu Thr Thr
450                 455                 460

Pro Ala Leu Gln Gln Gly Pro Lys Asp Arg Glu Pro Leu Thr Ser Leu
465                 470                 475                 480

Arg Ser Leu Phe Gly Ser Asp Pro Leu Ser Gln
                485                 490

<210> SEQ ID NO 141
<211> LENGTH: 293
<212> TYPE: PRT
<213> ORGANISM: HIV-1

<400> SEQUENCE: 141

Asn Ser Ser Gln Val Ser Gln Asn Tyr Pro Ile Val Gln Asn Met Gln
  1               5                  10                  15

Gly Gln Met Val His Gln Ala Ile Ser Pro Arg Thr Leu Asn Ala Trp
                 20                  25                  30

Val Lys Val Ile Glu Glu Lys Ala Phe Ser Pro Glu Val Ile Pro Met
                 35                  40                  45

Phe Thr Ala Leu Ser Glu Gly Ala Thr Pro Gln Asp Leu Asn Thr Met
     50                  55                  60

Leu Asn Thr Val Gly Gly His Gln Ala Ala Met Gln Met Leu Lys Asp
 65                  70                  75                  80

Thr Ile Asn Glu Glu Ala Ala Glu Trp Asp Arg Leu His Pro Val Gln
                 85                  90                  95

Ala Gly Pro Ile Ala Pro Gly Gln Met Arg Glu Pro Arg Gly Ser Asp
                100                 105                 110

Ile Ala Gly Thr Thr Ser Thr Leu Gln Glu Gln Ile Gly Trp Met Thr
                115                 120                 125

Ser Asn Pro Pro Ile Pro Val Gly Glu Ile Tyr Lys Arg Trp Ile Ile
            130                 135                 140

Leu Gly Leu Asn Lys Ile Val Arg Met Tyr Ser Pro Thr Ser Ile Leu
145                 150                 155                 160

Asp Ile Lys Gln Gly Pro Lys Glu Pro Phe Arg Asp Tyr Val Asp Arg
                165                 170                 175
```

```
Phe Tyr Lys Thr Leu Gly Ala Glu Gln Ala Ser Gln Asp Val Lys Asn
            180                 185                 190

Trp Met Thr Glu Thr Leu Leu Val Gln Asn Ala Asn Pro Asp Cys Lys
        195                 200                 205

Thr Ile Leu Lys Ala Leu Gly Pro Ala Ala Thr Leu Glu Glu Met Met
    210                 215                 220

Thr Ala Cys Gln Gly Val Gly Gly Pro Gly His Lys Ala Arg Val Leu
225                 230                 235                 240

Ala Glu Ala Met Ser Gln Val Thr Asn Ser Thr Val Met Met Gln Lys
            245                 250                 255

Gly Asn Phe Arg Asn Gln Arg Lys Ile Val Lys Cys Phe Asn Cys Gly
        260                 265                 270

Lys Glu Gly His Ile Ala Lys Asn Cys Arg Ala Pro Arg Lys Arg Gly
    275                 280                 285

Cys Trp Lys Cys Gly
    290

<210> SEQ ID NO 142
<211> LENGTH: 294
<212> TYPE: PRT
<213> ORGANISM: HIV-1

<400> SEQUENCE: 142

Asn Ser Ser Gln Val Ser Gln Asn Tyr Pro Ile Val Gln Asn Val Gln
1               5                   10                  15

Gly Gln Met Val His Gln Ala Ile Ser Pro Arg Thr Leu Asn Ala Trp
            20                  25                  30

Val Lys Val Val Glu Glu Lys Ala Phe Ser Pro Glu Val Ile Pro Met
        35                  40                  45

Phe Ser Ala Leu Ser Glu Gly Ala Thr Pro Gln Asp Leu Asn Thr Met
    50                  55                  60

Leu Asn Thr Val Gly Gly His Gln Ala Ala Met Gln Met Leu Lys Glu
65                  70                  75                  80

Thr Ile Asn Glu Glu Ala Ala Glu Trp Asp Arg Leu His Pro Val His
            85                  90                  95

Ala Gly Pro Ile Ala Pro Gly Gln Met Arg Glu Pro Arg Gly Ser Asp
        100                 105                 110

Ile Ala Gly Thr Thr Ser Thr Leu Gln Glu Gln Ile Gly Trp Met Thr
    115                 120                 125

His Asn Pro Pro Ile Pro Val Gly Glu Ile Tyr Lys Arg Trp Ile Ile
    130                 135                 140

Leu Gly Leu Asn Lys Ile Val Arg Met Tyr Ser Pro Thr Ser Ile Leu
145                 150                 155                 160

Asp Ile Lys Gln Gly Pro Lys Glu Pro Phe Arg Asp Tyr Val Asp Arg
            165                 170                 175

Phe Tyr Lys Thr Leu Arg Ala Glu Gln Ala Ser Gln Glu Val Lys Asn
        180                 185                 190

Trp Met Thr Glu Thr Leu Leu Val Gln Asn Ala Asn Pro Asp Cys Lys
    195                 200                 205

Thr Ile Leu Lys Ala Leu Gly Pro Ala Ala Thr Leu Glu Glu Met Met
    210                 215                 220

Thr Ala Cys Gln Gly Val Gly Gly Pro Gly His Lys Ala Arg Val Leu
225                 230                 235                 240

Ala Glu Ala Met Ser Gln Val Thr Asn Ser Ala Thr Ile Met Met Gln
            245                 250                 255
```

```
Lys Gly Asn Phe Arg Ser Gln Arg Lys Ile Val Lys Cys Phe Asn Cys
            260                 265                 270
Gly Lys Glu Gly His Ile Ala Lys Asn Cys Arg Ala Pro Arg Lys Lys
        275                 280                 285
Gly Cys Trp Lys Cys Gly
        290

<210> SEQ ID NO 143
<211> LENGTH: 491
<212> TYPE: PRT
<213> ORGANISM: HIV-1

<400> SEQUENCE: 143

Met Gly Ala Arg Ala Ser Ile Leu Arg Gly Gly Lys Leu Asp Lys Trp
 1               5                  10                  15
Glu Lys Ile Arg Leu Arg Pro Gly Gly Lys His Tyr Met Ile Lys
                20                  25                  30
His Leu Val Trp Ala Ser Arg Glu Leu Glu Arg Phe Ala Leu Asn Pro
            35                  40                  45
Gly Leu Leu Glu Thr Ser Glu Gly Cys Lys Gln Ile Ile Lys Gln Leu
        50                  55                  60
Gln Pro Ala Leu Gln Thr Gly Thr Glu Glu Leu Arg Ser Leu His Asn
 65                  70                  75                  80
Thr Val Ala Thr Leu Tyr Cys Val His Ala Gly Ile Glu Ile Arg Asp
                85                  90                  95
Thr Lys Glu Ala Leu Asp Lys Ile Glu Glu Gln Glu Lys Ser Gln
            100                 105                 110
Gln Lys Thr Gln Gln Ala Lys Glu Ala Asp Gly Lys Val Ser Gln Asn
        115                 120                 125
Tyr Pro Ile Val Gln Asn Leu Gln Gly Gln Met Val His Gln Ala Leu
130                 135                 140
Ser Pro Arg Thr Leu Asn Ala Trp Val Lys Val Ile Glu Glu Lys Ala
145                 150                 155                 160
Phe Ser Pro Glu Ile Ile Pro Met Phe Thr Ala Leu Ser Glu Gly Ala
                165                 170                 175
Thr Pro Gln Asp Leu Asn Thr Met Leu Asn Thr Val Gly Gly His Gln
            180                 185                 190
Ala Ala Met Gln Met Leu Lys Asp Thr Ile Asn Glu Glu Ala Ala Glu
        195                 200                 205
Trp Asp Arg Leu His Pro Ala Gln Ala Gly Pro Ile Ala Pro Gly Gln
    210                 215                 220
Met Arg Glu Pro Arg Gly Ser Asp Ile Ala Gly Thr Thr Ser Thr Leu
225                 230                 235                 240
Gln Glu Gln Ile Ala Trp Met Thr Gly Asn Pro Pro Val Pro Val Gly
                245                 250                 255
Glu Ile Tyr Lys Arg Trp Ile Ile Leu Gly Leu Asn Lys Ile Val Arg
            260                 265                 270
Met Tyr Ser Pro Val Ser Ile Leu Asp Ile Lys Gln Gly Pro Lys Glu
        275                 280                 285
Pro Phe Arg Asp Tyr Val Asp Arg Phe Phe Lys Thr Leu Arg Ala Glu
    290                 295                 300
Gln Ala Thr Gln Asp Val Lys Asn Trp Met Thr Asp Thr Leu Leu Val
305                 310                 315                 320
Gln Asn Ala Asn Pro Asp Cys Lys Thr Ile Leu Arg Ala Leu Gly Pro
                325                 330                 335
```

-continued

```
Gly Ala Ser Leu Glu Glu Met Met Thr Ala Cys Gln Gly Val Gly Gly
            340                 345                 350

Pro Ser His Lys Ala Arg Val Leu Ala Glu Ala Met Ser Gln Thr Asn
        355                 360                 365

Asn Ser Ile Leu Met Gln Arg Ser Asn Phe Lys Gly Phe Lys Arg Thr
    370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
                405                 410                 415

Gln Met Lys Asp Cys Thr Glu Arg Gln Ala Asn Phe Leu Gly Lys Ile
            420                 425                 430

Trp Pro Ser His Lys Gly Arg Pro Gly Asn Phe Leu Gln Asn Arg Pro
        435                 440                 445

Glu Pro Thr Ala Pro Ala Glu Ser Phe Arg Phe Glu Glu Thr Thr
    450                 455                 460

Pro Ala Leu Lys Gln Glu Gln Lys Asp Arg Glu Pro Leu Thr Ser Leu
465                 470                 475                 480

Lys Ser Leu Phe Gly Ser Asp Pro Leu Ser Gln
                485                 490

<210> SEQ ID NO 144
<211> LENGTH: 557
<212> TYPE: PRT
<213> ORGANISM: HIV-1

<400> SEQUENCE: 144

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Tyr Arg Leu Lys
            20                  25                  30

His Leu Val Trp Ala Ser Arg Glu Met Glu Arg Phe Ala Leu Asn Pro
        35                  40                  45

Gly Leu Leu Glu Thr Ala Glu Gly Cys His Gln Ile Met Ser Gln Leu
    50                  55                  60

Gln Pro Ala Ile Gln Thr Gly Thr Glu Glu Ile Lys Ser Leu Phe Asn
65                  70                  75                  80

Thr Val Ala Thr Leu Tyr Cys Val His Gln Lys Ile Glu Val Lys Asp
                85                  90                  95

Thr Thr Glu Ala Leu Glu Glu Val Glu Lys Ile Gln Lys Lys Ser Gln
            100                 105                 110

Gln Lys Ile Gln Gln Ala Ala Arg Asp Glu Gly Asn Ser Ser Gln Val
        115                 120                 125

Ser Gln Asn Tyr Pro Ile Val Gln Asn Ala Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Asp Thr Ile Asn Glu Glu
        195                 200                 205

Ala Ala Glu Trp Asp Arg Met His Pro Pro Gln Ala Gly Pro Ile Pro
    210                 215                 220
```

-continued

```
Pro Gly Gln Ile Arg Glu Pro Arg Gly Ser Asp Ile Ala Gly Thr Thr
225                 230                 235                 240

Ser Asn Leu Gln Glu Gln Ile Arg Trp Met Thr Ser Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
        275                 280                 285

Pro Lys Glu Pro Phe Arg Asp Tyr Val Asp Arg Phe Phe Lys Thr Leu
    290                 295                 300

Arg Ala Glu Gln Ala Thr Gln Glu Val Lys Gly Trp Met Thr Asp Thr
305                 310                 315                 320

Leu Leu Val Gln Asn Ala Asn Pro Asp Cys Lys Thr Ile Leu Arg Ala
                325                 330                 335

Leu Gly Pro Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Ala Thr Gly Ala Ala Ala Ile Met Met Gln Lys Ser Asn Phe
    370                 375                 380

Lys Gly Pro Lys Arg Asn Ile Lys Cys Phe Asn Cys Gly Lys Glu Gly
385                 390                 395                 400

His Leu Ala Arg Asn Cys Arg Ala Pro Arg Lys Lys Gly Cys Trp Lys
                405                 410                 415

Cys Gly Lys Glu Gly His Gln Met Lys Asp Cys Thr Glu Arg Gln Ala
            420                 425                 430

Asn Phe Leu Gly Lys Ile Trp Pro Ser Asn Lys Gly Arg Pro Gly Asn
        435                 440                 445

Phe Leu Gln Asn Arg Pro Glu Pro Thr Ala Pro Pro Ala Glu Ser Phe
    450                 455                 460

Gly Phe Gly Glu Glu Ile Ala Pro Ser Pro Lys Pro Glu Pro Lys Glu
465                 470                 475                 480

Lys Glu Thr His Pro Leu Ala Ser Leu Lys Ser Leu Phe Gly Ser Asp
                485                 490                 495

Pro Thr Leu Glu Glu Met Met Thr Ala Cys Gln Gly Val Gly Gly Pro
            500                 505                 510

Gly His Lys Ala Arg Val Leu Ala Glu Ala Met Ser Gln Val Gln Asn
        515                 520                 525

Thr Asn Ile Met Met Gln Lys Gly Asn Phe Arg Gly Gln Lys Arg Ile
    530                 535                 540

Lys Cys Phe Asn Cys Gly Lys Glu Gly His Leu Ala Lys
545                 550                 555
```

METHODS FOR IDENTIFYING COMPOUNDS WHICH INHIBIT BINDING OF NUCLEOCAPSID 7 PROTEIN TO HIV-1 RNA

This application claims priority of U.S. Ser. No. 60/347,369, filed Jan. 11, 2002, which is hereby incorporated by reference in its entirety.

FIELD OF THE INVENTION

The present invention relates to the field of compound screening assays. This invention relates to biopolymer binding assays, and more particularly to methods for assaying binding between nucleic acids and the human immunodeficiency virus (HIV) nucleocapsid 7 protein (NCp7) and related protein and peptide sequences.

BACKGROUND OF THE INVENTION

It is estimated that there are greater than 30 million cases of HIV infection and AIDS worldwide. There are steep rises of new infections in Eastern Europe and Latin America. In the Caribbean region, AIDS is the primary cause of death among young men and women. In Asia, some 7 million people are living with HIV. In industrialized countries, AIDS continues to have a significant impact in minority communities where complacency in the face of a major health risk is a growing problem (Report of the Executive Director of the Joint United Nations Program on HIV/AIDS (UNAIDS)).

HIV-1 is a retrovirus and thus utilizes RNA as its genomic message. Genome packaging is directed by a gag polyprotein produced in the host cell during late stages of the infectious cycle. An element of gag that is essential for genome recognition and the packaging of infectious RNA is a 55 amino acid nucleocapsid protein, NCp7. NC proteins of all known classes of retrovirus (except spumavirus) contain one or two copies of a retroviral zinc finger (ZF) motif, $Cys(X)_2Cys(X)_4His(X)_4Cys$, where X is a variable amino acid and $Zn^{2+}$ is coordinated to the invariant cysteine and histidine residues. As part of gag, NCp7 initiates genomic RNA encapsidation by recognition of a ca. 120 nucleotide sequence (psi-site or Ψ-site) of the RNA genome that contains four stem-loop (SL) sequences in its secondary structure (e.g., SL1, SL2, SL3, and SL4). Although multidrug therapy of AIDS with inhibitors of HIV-1 reverse transcriptase and HIV-1 protease has dramatically delayed the onset of clinical disease and death due to AIDS, problems with this therapy are of increasing concern.

Currently available drugs for the treatment of HIV include six nucleoside reverse transcriptase (RT) inhibitors (zidovudine, didanosine, stavudine, lamivudine, zalcitabine and abacavir), three non-nucleoside reverse transcriptase inhibitors (nevirapine, delavirdine and efavirenz), and five peptidomimetic protease inhibitors (saquinavir, indinavir, ritonavir, nelfinavir and amprenavir). Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. many nucleoside analogs cannot be phosphorylated in resting cells, which is required for biological activity) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present Therefore, novel anti-HIV agents exhibiting distinct resistance patterns, and favorable pharmacokinetic as well as safety profiles are needed to provide more treatment options.

Currently marketed HIV-1 drugs are dominated by either nucleoside reverse transcriptase inhibitors or peptidomimetic protease inhibitors. Non-nucleoside reverse transcriptase inhibitors (NNRTIs) have recently gained an increasingly important role in the therapy of HIV infections At least 30 different classes of NNRTI have been described in the literature (De Clercq) and several NNRTIs have been evaluated in clinical trials. Dipyridodiazepinone (nevirapine), benzoxazinone (efavirenz) and bis(heteroaryl) piperazine derivatives (delavirdine) have been approved for clinical use. However, the major drawback to the development and application of NNRTIs is the propensity for rapid emergence of drug resistant strains, both in tissue cell culture and in treated individuals, particularly those subject to monotherapy.

Furthermore, although work continues to advance in the development of vaccines against HIV-1, there is currently no vaccine available with proven effectiveness in humans (Amara et al, *Science* 2001 Apr. 6; 292(5514): 69–74). In addition, it is clear that there is a need for anti-HIV drugs targeted against novel viral targets that are less prone to the development of resistant virus. These facts stress the importance of methods for the identification of new anti-HIV molecules or compounds and HIV targets that possess the following properties: 1) anti-HIV molecules or compounds against the new targets would not exert cross-resistance with current anti-HIV drugs that affect other targets, 2) structural distinctiveness of the target compared to mammalian counterparts such that new molecule or compound selectivity can be achieved toward the HIV target, and 3) target structural and functional conservation so that mutational escape toward drug-resistance is minimized.

SUMMARY OF THE INVENTION

The present invention is directed to a method for determining whether a compound inhibits formation of a complex between an HIV nucleocapsid protein 7 (NCp7) polypeptide and an HIV Ψ-site oligonucleotide comprising the steps of: (a) admixing an NCp7 polypeptide with a compound; (b) adding an HIV 1-site oligonucleotide to the admixture of step (a) under appropriate binding conditions so as to form an HIV Ψ-site oligonucleotide-NCp7 polypeptide complex; and (c) comparing the amount of complex formed in step (b) with the amount of complex formed in the absence of the compound, thereby determining whether the compound inhibits complex formation, wherein a decrease in the amount of complex formed in the presence of the compound indicates that the compound inhibits complex formation.

The present invention is directed to a method for determining whether a molecule inhibits binding of NCp7 to an oligonucleotide which comprises: (a) attaching a NCp7 polypeptide to a solid support, wherein the NCp7 polypeptide is selected from the group consisting of: SEQ ID NO:1, SEQ ID NO:2, SEQ ID NO:3, SEQ ID NO:4; SEQ ID NOS:10–17, or SEQ ID NOS:18–144 (but not limited thereto); (b) incubating the solid support with the NCp7 polypeptide linked thereto with a blocking agent; (c) incubating the solid support with the NCp7 polypeptide linked thereto with: (i) at least one labeled oligonucleotide selected from the group consisting of: SEQ ID NO:5, SEQ ID NO:6, SEQ ID NO:7, SEQ ID NO:8, SEQ ID NO:9, a portion of a HIV-1 Ψ-site RNA which binds to NCp7 polypeptide, an oligonucleotide which binds to the NCp7 polypeptide under physiological conditions, and any combination thereof, and (ii) an amount of the molecule to be tested under binding conditions; and (d) determining the amount of oligonucleotide bound to the NCp7 polypeptide, wherein a decrease in the amount of oligonucleotide bound in the presence of the molecule compared with the amount of oligonucleotide bound in the absence of the molecule indicates that the molecule inhibits binding of NCp7 polypeptide to the oligonucleotide.

The present invention is further directed to a method for determining whether a test molecule has an ability to inhibit binding of NCp7 to an oligonucleotide. The method comprises: (a) attaching to a solid support at least one labeled oligonucleotide selected from the group consisting of: SEQ ID NO:5, SEQ ID NO:6, SEQ ID NO:7, SEQ ID NO:8, SEQ ID NO:9, a portion of a HIV-1 Ψ-site RNA which binds to NCp7 polypeptide, an oligonucleotide which binds to the NCp7 polypeptide under physiological conditions, and any combination thereof, (b) incubating the solid support with the oligonucleotide linked thereto with a blocking agent; (c) incubating the solid support with the oligonucleotide linked thereto with: (i) NCp7 polypeptide wherein the NCp7 polypeptide is selected from the group consisting of: SEQ ID NO:1, SEQ ID NO:2, SEQ ID NO:3; SEQ ID NO:4; SEQ ID NOS:10–17, or SEQ ID NOS:18–144 (but not limited thereto); and (ii) an amount of the molecule to be tested under binding conditions; and (iii) determining the amount of oligonucleotide bound to the NCp7 polypeptide, wherein a decrease in the amount of oligonucleotide bound in the presence of the molecule compared with the amount of oligonucleotide bound in the absence of the molecule indicates that the molecule inhibits binding of NCp7 polypeptide to the oligonucleotide.

The present invention is further directed to screening methods for identifying a molecule from a library of molecules that inhibits binding of NCp7 polypeptide to an oligonucleotide, the method comprising: (a) attaching an NCp7 polypeptide to a solid support, such as an NCp7 zinc finger (ZF) motif having the polypeptide sequence as follows: SEQ ID NO:1, SEQ ID NO:2, SEQ ID NO:3; SEQ ID NO:4; SEQ ID NOS:10–17, or SEQ ID NOS:18–144 (but not limited thereto); (b) incubating the solid support with a blocking agent; (c) washing the solid support so as to remove unbound blocking agent; (d) incubating the solid support with at least one labeled oligonucleotide selected from the group consisting of: SEQ ID NO:5, SEQ ID NO:6, SEQ ID NO:7, SEQ ID NO:8, SEQ ID NO:9, a portion of a HIV-1 Ψ-site RNA which binds to NCp7 polypeptide, an oligonucleotide which binds to the NCp7 polypeptide under physiological conditions, and any combination thereof, and a sufficient amount of a test molecule under appropriate binding conditions; (e) washing the solid support to remove unbound oligonucleotide and test molecules; and (f) determining the amount of oligonucleotide bound to the NCp7 polypeptide, wherein a decrease in the amount of oligonucleotide bound in the presence of the test molecule compared with the amount of oligonucleotide bound in the absence of the test molecule indicates that the molecule inhibits binding of NCp7 polypeptide to the oligonucleotide.

The present invention is still further directed towards methods for identifying a molecule from a library of molecules by means of screening said library, wherein a particular compound which is a member of said library is found to inhibit association of NCp7 to an oligonucleotide. Such methods are comprised of (a) attaching to a solid support at least one labeled oligonucleotide selected from the group consisting of: SEQ ID NO:5, SEQ ID NO:6, SEQ ID NO:7, SEQ ID NO:8, SEQ ID NO:9, a portion of a HIV-1 Ψ-site RNA which binds to NCp7 polypeptide, an oligonucleotide which binds to the NCp7 polypeptide under physiological conditions, and any combination thereof, (b) incubating the solid support with the oligonucleotide linked thereto with a blocking agent; (c) incubating the solid support with the oligonucleotide linked thereto with: (i) NCp7 polypeptide wherein the NCp7 polypeptide is selected from the group consisting of: SEQ ID NO:1, SEQ ID NO:2, SEQ ID NO:3; SEQ ID NO:4; SEQ ID NOS:10–17, or SEQ ID NOS:18–144 (but not limited thereto); and (ii) an amount of the molecule to be tested under binding conditions; and (d) determining the amount of oligonucleotide bound to the NCp7 polypeptide, wherein a decrease in the amount of oligonucleotide bound in the presence of the molecule compared with the amount of oligonucleotide bound in the absence of the molecule indicates that the molecule inhibits binding of NCp7 polypeptide to the oligonucleotide.

Aspects of the present invention are directed to methods of treating a subject suffering from HIV infection which comprises administering to the subject an effective amount of a composition comprising the molecule identified by the above screening method.

In the present embodiments of the assay, the blocking agent is selected from the group consisting of: bovine serum albumin (BSA), poly-L-lysine, poly-DL-lysine, poly-L-glutamic acid, poly-DL-glutamic acid, polyethyleneimine, poly-4-vinylpyridine, poly-2-vinylpyridine, poly-3-vinylpyridine, polyethylene oxide, bacterial tRNA, yeast tRNA, casein, ovalbumin, gamma-globulin, heparin, polybrene, polyacrylic acid, polymethacrylic acid, ampholytic copolymers of acrylic acid with acrylamide, poly-N-carboxyethylacrylamide, poly-N-carboxymethylacrylamide, poly-N-carboxypropylacrylamide, poly(glycolic acid), copolymers of polyacrylic acid and poyl(glycolic acid), polylactic acid oligomers and any combination thereof.

In one embodiment, the amount of BSA comprises from about 0.25% to about 10%. In another embodiment, the amount of BSA comprises from about 0.5% to about 5%. In still another embodiment, the amount of BSA comprises from about 1% to about 3%.

In the present embodiment of the invention, the solid support is selected from the group consisting of: a solid phase column support; a silica support; a magnetic support; a gel support; a glass support; a polystyrene support; a polypropylene support; a polycarbonate surface derivatized with tetraethoxysilane; a polycarbonate surface derivatized with dimethyldiethoxysilane; a polycarbonate surface derivatized with silicon tetraacetate; a polycarbonate surface derivatized with methyltriacetoxysilane; a polycarbonate support derivatized with any di- or tri-alkoxysilane; an synthetic alumina surface, whereby hydroxyl groups upon the said surface may be optionally derivatized with tetraethoxysilane, dimethyldiethoxysilane; methyltriacetoxysilane; or with any di- or tri-alkoxysilane; a silicon monoxide surface, whereby hydroxyl groups upon the said surface may be optionally derivatized with tetraethoxysilane, dimethyldiethoxysilane; methyltriacetoxysilane; or with any di- or tri-alkoxysilane; a silicon monoxide surface upon a silicon substrate, whereby hydroxyl groups upon the said surface may be optionally derivatized with tetraethoxysilane, dimethyldiethoxysilane; methyltriacetoxysilane; or with any di- or tri-alkoxysilane , a titanium dioxide surface whereby hydroxyl groups upon the said surface may be optionally derivatized with tetraethoxysilane, dimethyldiethoxysilane; methyltriacetoxysilane; or with any di- or tri-alkoxysilane, a zirconium dioxide surface whereby hydroxyl groups upon the said surface may be optionally derivatized with tetraethoxysilane, dimethyldiethoxysilane; methyltriacetoxysilane; or with any di- or tri-alkoxysilane, a tin oxide surface of electrically conductive nature, whereby hydroxyl groups upon the said surface may be optionally derivatized with tetraethoxysilane, dimethyldiethoxysilane; methyltri-acetoxysilane; or with any di- or tri-alkoxysilane , a polycarbonate, polystyrene, or polypropylene support derivatized with streptavidin; and any combination thereof.

In one embodiment of the invention, the oligonucleotide is labeled with biotin, a fluorescent label, a radioactive label, a chemiluminescent label, a protein detectable by an antibody, an avidin, a horseradish peroxidase, a green fluorescent protein or any combination thereof.

In one embodiment of the invention, the oligonucleotide is attached to the solid support covalently or non-covalently.

In another embodiment, the molecule comprises an azodicarbonamide (ADA) or a derivative thereof. In a further aspect of the invention, the molecule comprises a 2,2'-dithiobisbenzamide (DIBA-1) or a derivative thereof.

In another aspect of the invention, the molecule has the structure

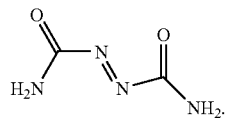

In another aspect of the invention, the molecule has the structure

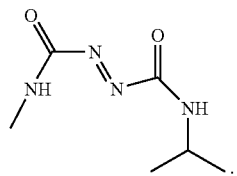

In another aspect of the invention, the molecule has the structure

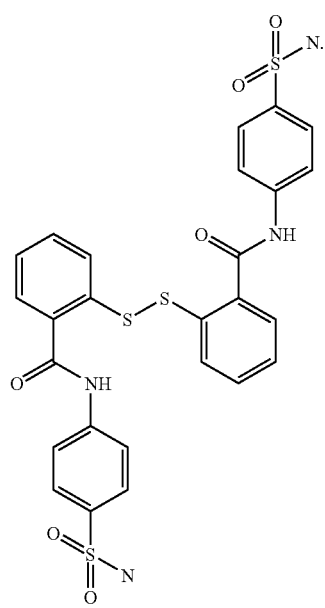

In another aspect of the invention, the molecule has the structure

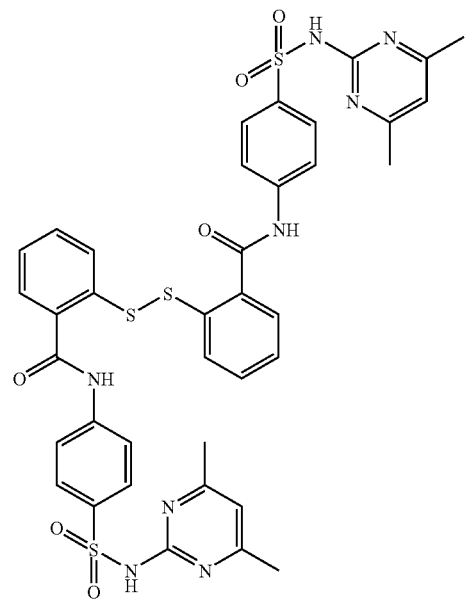

In another aspect of the invention, the molecule has the structure

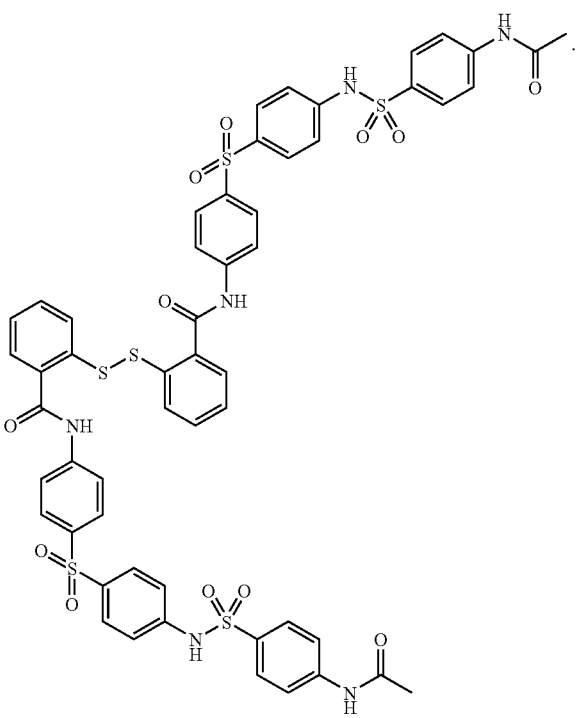

In another aspect of the invention, the molecule has the structure

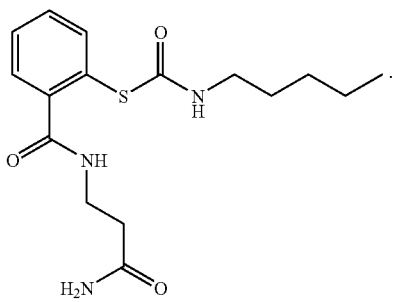

In another aspect of the invention, the molecule has the structure

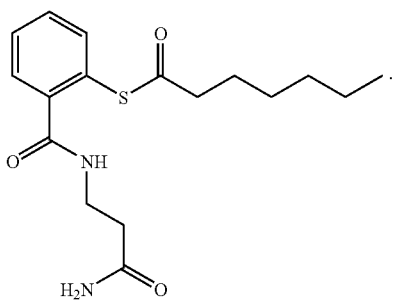

In another aspect of the invention, the molecule has the structure

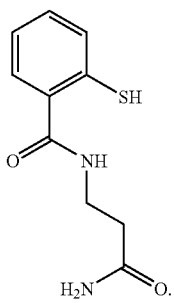

In another aspect of the invention, the molecule has the structure

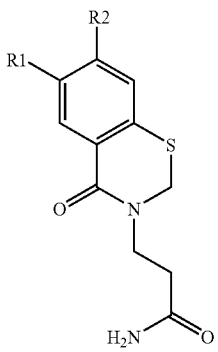

wherein R1 and R2 are independently alkyl, trifluoroalkyl, dialkylamino, nitro, trifluoroalkoxy, or any combination thereof.

In another aspect of the invention, the molecule has the structure

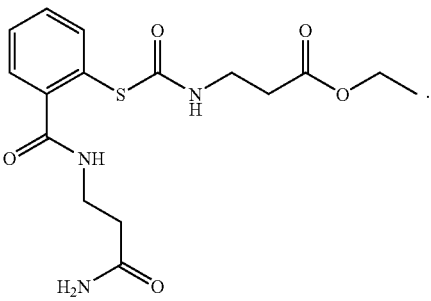

In another aspect of the invention, the molecule has the structure

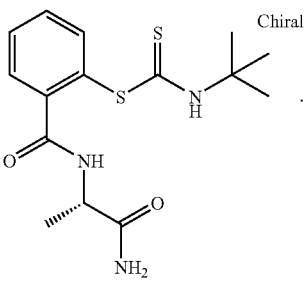

In another aspect of the invention, the molecule has the structure

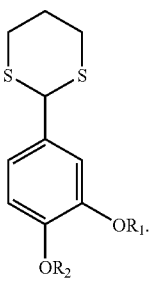

In another aspect of the invention, the molecule has the structure

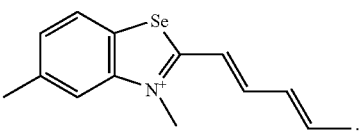

In another aspect of the invention, the molecule has the structure

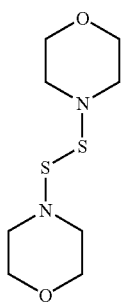

In another aspect of the invention, the binding conditions comprise from about 5 mM KCl to about 100 mM KCl and from about 5 mM MgCl$_2$ to about 100 mM MgCl$_2$.

In another aspect of the invention, the compound comprises a molecule selected from the group consisting of: tetramethylthiuram disulfide, tetraethylthiuram disulfide, tetraisopropylthiuram disulfide, tetrabutylthiuram disulfide, dicyclopentamethylenethiuram disulfide, isopropylxanthic disulfide, O,O-diethyl dithiobis-(thioformate), benzoyl disulfide, benzoylmethyl disulfide, formamidine disulfide 2HCl, 2-(diethylamino)ethyl disulfide, aldrithiol-2, aldrithiol-4,2,2-dithiobis(pyridine N-oxide), 6,6-dithiodinicotinic acid, 4-methyl-2-quinolyl disulfide, 2-quinolyl disulfide, 2,2 dithiobis(benzothiazole), 2,2-dithiobis(4-tert-butyl-1-isopropyl)-imidazole, 4-(dimethylamino)phenyl disulfide, 2-acetamidophenyl disulfide, 2,3-dimethoxyphenyl disulfide, 4-acetamidophenyl disulfide, 2-(ethoxycarboxamido)phenyl disulfide, 3-nitrophenyl disulfide, 4-nitrophenyl disulfide, 2-aminophenyl disulfide, 2,2 dithiobis(benzonitrile), p-tolyl disulfoxide, 2,4,5-trichlorophenyl disulfide, 4-methylsulfonyl-2-nitrophenyl disulfide, 4-methylsulfonyl-2-nitrophenyl disulfide, 3,3-dithiodipropionic acid, N,N-diformyl-1-cystine, trans-1,2-dithiane-4,5-diol, 2-chloro-5-nitrophenyl disulfide, 2-amino-4-chlorophenyl disulfide, 5,5-dithiobis(2-nitrobenzoic acid), 2,2-dithiobis(1-naphtylamine), 2,4-dinitrophenyl p-tolyl disulfide, 4-nitrophenyl p-tolyl disulfide, 4-chloro-3-nitrophenyl disulfideformamidine disulfide dihydrochloride and any combination thereof.

In one aspect of the invention, the molecule is in a library of test molecules.

The invention is also directed to a method for treating a subject infected with a HIV which comprises administering to the subject an effective amount of the molecule or compound identified by methods described herein. In one aspect of the invention, the administration comprises intralesional, intraperitoneal, intramuscular or intravenous injection; infusion; liposome-mediated delivery; or topical, nasal, oral, anal, ocular or otic delivery.

The invention is also directed to a method for inhibiting HIV viral replication in a subject which comprises administering to the subject an effective amount of a composition comprising the molecule identified by the methods disclosed herein, wherein the composition inhibits HIV viral replication in the subject.

The invention is also directed to a composition for inhibiting viral replication which comprises a molecule identified by the screening methods disclosed herein or a derivative thereof and a carrier. In one aspect of the invention, the carrier is an aqueous carrier, a liposome, or a lipid carrier.

DETAILED DESCRIPTION OF THE INVENTION

Definitions

Figure 1:
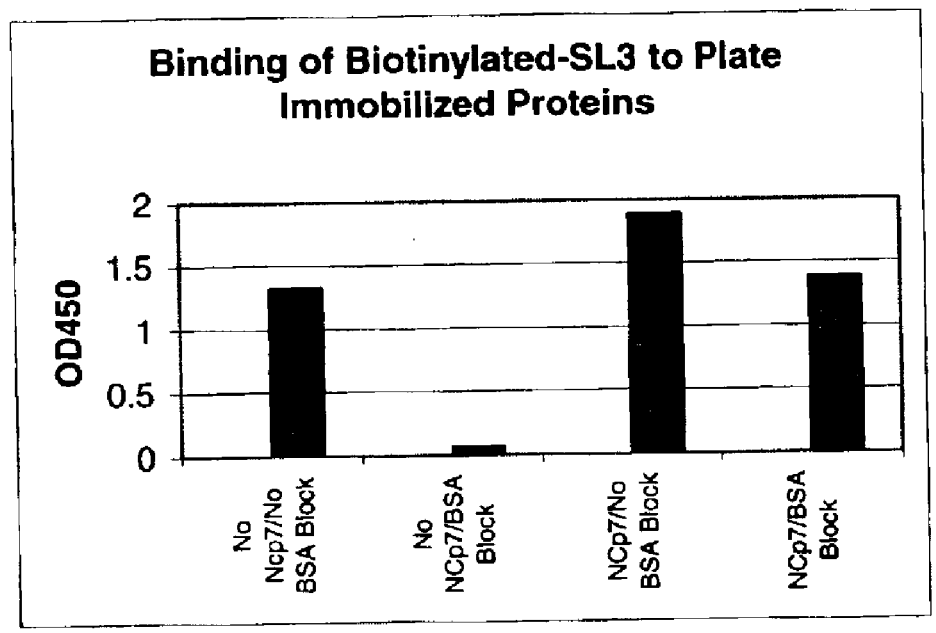
FIG. 1 illustrates results showing binding of biotinylated-SL3 to plate immobilized NCp7 proteins. The X-axis shows the conditions of the specific binding assay. The Y-axis shows the OD$_{450}$.

By "nucleic acid" or "oligonucleotide" or grammatical equivalents, herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp169–176). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occurring nucleic acids and analogs may be made.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

As used herein, the word "or" means any one member of a particular list and also includes any combination of members of that list.

Two nucleic acid or polypeptide sequences are "substantially homologous" or "substantially identical" when at least about 80% (preferably at least about 90%, and most preferably at least about 95%) of the nucleotides or amino acids match over a defined length of the molecule. Nucleic acid sequences that are substantially identical can be identified in a Southern hybridization, experiment under, for example, stringent conditions, as defined for that particular system. Defining appropriate hybridization conditions is within the skill of the art. See, e.g., Sambrook et al., supra; DNA Cloning, vols I & II, supra; Nucleic Acid Hybridization, supra. Stringent hybridization conditions are used to permit selective hybridization of nucleic acids which are from about 95% identical to about 99.9% identical. Slightly less stringent hybridization conditions can be employed to allow hybridization of nucleic acid molecules which are from about 85% identical to about 95% identical. As used herein, "homology" has the same meaning as "identity" in the context of nucleotide sequences. However, it will be appreciated that amino acid sequence "homology" includes conservative amino acid substitutions.

As used herein, the abbreviation "NCp7" refers to the nucleocapsid protein 7 of HIV-1 including the protein in the form of a polyprotein as part of the gag gene product and in the form of a mature protein, i.e., spliced away from the polyprotein and existing as an independent protein.

As used herein, "NCp7 polypeptide" encompasses any polypeptide derived from the full length and naturally occurring HIV-1 NCp7 polypeptide. This includes the polypeptides listed herein as SEQ ID NO:1, SEQ ID NO:2, SEQ ID NO:3 and SEQ ID NO:4. An NCp7 polypeptide also includes any other polypeptide or fragment derived from these polypeptides, which retains the ability to bind the psi-site of HIV-1 RNA. For example, an NCp7 polypeptide includes, and is not limited to, a truncated peptide wherein the C-terminal or N-terminal portion of the full-length NCp7 polypeptide is deleted; a peptide which includes amino acid residue substitutions or additions or deletions which do not affect the ability of the peptide to bind to the psi-site RNA, to which it would bind under normal, viral physiological conditions. The NCp7 polypeptides exemplified in this application are provided only as examples and do not limit the intent of the invention to include other polypeptides. Of course, replacement of amino acid residues which do not affect the function of the zinc-finger binding domains of the NCp7 polypeptide are considered other polypeptides encompassed by the invention.

As used herein, the term "compound" encompasses molecules, such as small organic molecules, nucleic acid molecules and polypeptides or any combination thereof. The terms "compound" and "molecule" are used interchangeably herein. The molecule of the invention can exist as a single, isolated molecule, or as a member of a population of molecules, as in a library of molecules. One example of a polypeptide is an antibody or a fragment thereof which retains binding specificity. The invention includes derivatives of such compounds and salts thereof which would be useful for preparation of a pharmaceutical composition. The invention also includes methods for using such pharmaceutical compositions or molecules or compounds in the treatment of subjects suffering from HIV infection. The present invention encompasses methods to test for the ability of a compound to inhibit the interaction between NCp7 polypeptide and an oligonucleotide which contains all or part of the psi ($\Psi$)-site of HIV-1 RNA. The genome of the HIV-1 contains a stretch of approximately 120 nucleotides known as the psi-site that is essential for RNA packaging during virus assembly. The nucleotides have been proposed to form four stem-loops (SL1–SL4) that have both independent and overlapping functions. The stem loop number 3 (SL3) within the psi-site RNA has been mapped as a major determinant for specific packaging.

"Small organic molecules," as used herein, are organic molecules which are of a molecular weight no larger than 10,000 Daltons, preferably no larger than 5,000 Daltons and most preferably no larger than 1,000 Daltons. Such small organic molecules are capable of interfering, either competitively or non-competitively with the binding interaction of NCp7 and the oligonucleotide sequence to which it normally binds. The small organic molecule which could interfere with such binding would be identifiable by the screening assays which are described herein. The small organic molecules interact by covalent or non-covalent means with the NCp protein.

As used herein, "inhibits" means reducing, slowing or interfering with a process. The term "inhibits" does not require complete reversal, but rather encompasses any detectable level of slowing or reducing a process.

As used herein, the term "alkyl" is, for example, a C1–C6 straight or branched chain alkyl group, which includes methyl, ethyl, n-propyl, isopropyl, n-butyl, isobutyl, sec-butyl, tert-butyl, n-pentyl, isopentyl, neopentyl, tert-pentyl, n-hexyl, isohexyl, and the like, n-butyl, isobutyl, and tert-butyl. The term "alkyl" here includes cycloalkyl lower alkyl. The term "cycloalkyl lower alkyl" is, for example, the above-mentioned lower alkyl group substituted with C3–C6 cycloalkyl, which includes cyclopropyl methyl, 2-cyclopropyl ethyl, 4-cyclopropyl butyl, cyclopentyl methyl, 3-cyclopentyl propyl, cyclohexyl methyl, 2-cyclohexyl ethyl, and the like.

As used herein, "alkoxy" includes O-methyl, O-ethyl, O-n-propyl, O-2-propyl, O-n-butyl, O-sec-butyl, or O-t-butyl, wherein the Si atom is optionally substituted with an additional one or two alkoxy groups, a halo group, an alkylthio group (wherein alkyl is C1 through C8), an alkyl group, a phenoxy group, a p-chlorophenoxy group, an amino group, or a straight chain or branched alkylamino group, wherein the amino group may be optionally substituted with one or two alkyl groups.

The term trifluoroalkyl refers to any of the above alkyl or alkoxy compounds in which most preferably one, but optionally more than one carbon has its hydrogens completely replaced by fluorine.

As used herein, a fluorescent label includes a composition or compound which includes any organic dye or protein which when excited by light from wavelength of 200 nm to 1000 nm efficiently emits light by virtue of decay from the singlet excited state; as typified by those reagents described in the *Handbook of Fluorescent Probes*, Richard Haughland, 1999. For example, a fluorescent label includes green fluorescent protein. Specific fluorescent dyes of interest include: xanthene dyes, e.g. fluorescein and rhodamine dyes, such as fluorescein isothiocyanate (FITC), 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G$^5$ or G$^5$), 6-carboxyrhodamine-6G (R$^6$G$^6$ or G$^6$), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. Specific fluorophores of interest that are commonly used in microbiology applications include: Pyrene, Coumarin, Diethylaminocoumarin, FAM, Fluorescein Chlorotriazinyl, Fluorescein, R110, Eosin, JOE, R6G, Tetramethylrhodamine, TAMRA, Lissamine, ROX, Napthofluorescein, Texas Red, Napthofluorescein, Cy3, and Cy5, etc. Some preferred labels include a fluorescein nucleus, an eosin nucleus, a cyanine nucleus, a pyrene nucleus, all of which are described in Haughland, supra, various chelates of europium and gadolinium as are described in *Anal. Chem.* [2001 Sep. 1; 73(17):4277–85; Long-wavelength long-lifetime luminophores. Maliwal B P, Gryczynski Z, Lakowicz J R].

As used herein, a radioactive label includes, but is not limited to $^3$H, $^{14}$C, $^{11}$C, $^{35}$S, $^{31}$P, $^{32}$P, $^{45}$Ca, $^{44}$mSc, $^{46}$Sc, $^{51}$Cr, $^{49}$V, $^{55}$Fe, $^{59}$Fe, $^{57}$Co, $^{58}$Co, $^{60}$Co, $^{65}$Zn, $^{67}$Ga, $^{90}$Sr, $^{93}$mNb, $^{97}$mTC, $^{99}$mTc, $^{114}$mIn, $^{123}$I, $^{125}$I, $^{131}$I, $^{137}$Cs, $^{145}$Sm, $^{184}$Rh, or any combination thereof. Of these, most preferable are $^3$H, $^{14}$C, $^{35}$S, and $^{32}$P.

As used herein, binding conditions include, but are not limited to Tris, phosphate, or HEPES buffer containing between 0 mM and 100 mM KCl and from about 0 mM MgCl$_2$ to about 100 mM MgCl$_2$. In addition, binding conditions include a temperature within a temperature range permissive for binding, such as about 37° C. Binding conditions also include an incubation time from about 10 minutes to about five (5) hours during which time the polypeptide and the oligonucleotide bind to each other to form a complex. In one example, the binding conditions include a time of two (2) hours. Example of buffers which are useful in the assay shown in the Table below:

| BUFFER | pH RANGE |
| --- | --- |
| MES(2-[N-Morpholino]ethanesulfonic acid) | 5.5–6.7 |
| BIS-TIS(bis[2-Hydroxyethyl]imino-tris-[hydroxymethyl]-methane) | 5.8–7.2 |
| ADA(N-[2-Acetamido]-2-iminodiacetic acid) | 6.0–7.2 |
| PIPES(Piperazine-N,N'-bis[2-ethanesulfonic acid)) | 6.1–7.5 |
| ACES(2-[(2-Amino-2-oxoethyl)-amino]ethanesulfonic acid) | 6.1–7.5 |
| BIS-TRIS PROPANE(1,3-bis[tris(Hydroxymethyl)methylamino]-propane) | 6.3–9.5 |
| MOPSO(3-[N-Morpholino]-2-hydroxy-propanesulfonic acid) | 6.2–7.6 |
| BES(N,N-bis[2-Hydroxyethyl]-2-aminoethanesulfonic acid) | 6.4–7.8 |
| MOPS(3-[N-Morpholino]propanesulfonic acid) | 6.5–7.9 |
| TES(N-tris[Hydroxymethyl]methyl-2-aminoethanesulfonic acid) | 6.8–8.2 |
| HEPES(N-2-Hydroxyethylpiperazine-N'-2-ethanesulfonic acid) | 6.8–8.2 |
| TAPSO(3-[N-tris(Hydroxymethyl) methylamino]-2-hydroxypropane-sulfonic acid) | 7.0–8.2 |
| POPSO(Piperazine-N,N'-bis[2-hydroxypropanesulfonic acid]) | 7.2–8.5 |
| EPPS(N[2-Hydroxyethyl]-piperazine-N'-3-propanesulfonic acid) | 7.3–8.7 |
| TRIS(tris[Hydroxymethyl)amino-methane) | 7.0–9.0 |
| TRICINE(N-tris[Hydroxymethyl]-methylglycine) | 7.4–8.8 |
| BICINE(N,N-bis[2-Hydroxyethyl] glycine) | 7.6–9.0 |
| TAPS(tris[Hydroxymethyl)methylamino-propanesulfonic acid) | 7.7–9.1 |

The oligonucleotides of the present invention are nucleic acid molecules that bind to the NCp7 polypeptide. In one example, the oligonucleotide has a nucleotide sequence that contains the SL3 stem loop sequence of the HIV-1 Ψ-site to which the NCp7 protein binds in normal HIV physiology. In another example, the oligonucleotide used in the methods of the present invention has a sequence that is capable of being bound by a zinc finger containing protein, such as the NCp7 protein.

The "polypeptides" of the present invention encompass any one or more domains in the NCp7 polypeptide. In one example, the entire 72 amino acid NCp7 is used in the assay. In another example, a smaller portion of the NCp7 protein is used which includes the two zinc finger binding motifs and the small amino acid region which links the two regions. In another example, the amino acid sequence of the NCp7 polypeptide consisting essentially of two zinc finger binding domains and amino acids which link the two zinc finger binding domains is used in the method of the invention. In one example, the polypeptide of the present invention contains a single zinc finger-binding motif.

As used herein, a percent "sequence identity" refers to a calculation of "homology" or "identity" between two different nucleic acid or amino acid sequences when the sequences are aligned and compared. The percent sequence identity between the two sequences is a function of the number of identical positions shared by the sequences, taking into account the number of gaps, and the length of each gap, which need to be introduced for optimal alignment of the two sequences. Percent identity between two given sequences can be calculated using an algorithm such as BLAST (Altschul, et al. (1990) *J. Mol. Biol.* 215:403–410). For sequences no longer than 250 nucleotides or about 80 amino acids ("short queries"), when using BLAST the search parameters can be as follows: the filter is off, the scoring matrix is PAM30, the word size is 3 or 2, the E value is 1000 or more, and the gap costs are 11, 1. The BLAST web site provides advice for special circumstances and it is expected that one would follow such advice in the given circumstance. For sequences longer than 250 nucleotides or 80 amino acid residues, the default search parameters can be used. Any other sequence comparison algorithm can be used to determine percent identity.

As used herein, "label" encompasses any method or type of label which can be used to detect the presence of a molecule. Some examples of such a label are a fluorescent label, a calorimetric label, an enzymatic label or a radioactive label. The present invention encompasses one or more of these labels and is not limited to the types of labels, which are disclosed herein. Any label which serves the purpose of allowing the oligonucleotide to be detected in the screening assay is encompassed by the present invention. Some examples of labels used are the following: $^{32}$P-dATP, Texas Red, or a biotin-labeled oligonucleotide binding to a streptavidin partner with horseradish peroxidase detection.

The binding conditions of the present invention encompass normal buffer conditions, temperature and time that allows for the hybridization of the oligonucleotide to the NCp7 polypeptide. For example, an example of a buffer which is used in the examples provided herein which is preferred is 50 mM Tris-HCl, pH 7.5, 50 mM KCl, 10 mM MgCl$_2$, which contains 10% (w/v) glycerol and 1% (w/v) DMSO. The binding conditions encompass incubation at room temperature for two hours. It is clear to the skilled worker that the binding conditions can be varied and are not restricted to those examples that are recited in the working examples of this application. Other binding times are compatible with the features of the present invention, including between fifteen (15) minutes to thirty (30) minutes, thirty (30) minutes to three (3) hours, and three (3) hours to six (6) hours. Additional binding conditions that may be employed within the scope of the present invention include the use of additional buffers such as phosphate buffers, prepared using mixtures of potassium monohydrogen phosphate and potassium dihydrogen phosphate, at a concentration from about 0 mM HEPES to about 200 mM HEPES (hydroxypiperazine-ethylsulfate) buffers within the same general range of concentrations, concentrations of KCl within the range from about 0 mM KCl to about 200 mM KCl, concentrations of MgCl$_2$ within the range lying between about 0 mM and about 200 mM, concentrations of NaCl including the range between about 0 mM and about 150 mM, concentrations of dimethylsulfoxide (DMSO) including between about 0% DMSO to about 50%, (w/v) DMSO, concentrations of glycerol including the range lying between about 0% and about 50%. (w/v). For these solutions, a range of pH values may be employed in the range pH 6 to pH 8.

As used herein, the term "solid support" encompasses any solid structure to which the NCp7 polypeptide or oligonucleotide is affixed. Some examples include a polystyrene plate (e.g., a NUNC™ 96-well plate), a bead, a silicon support (e.g. a silicon micro-chip produced with protein attached thereto in specific, discrete and addressable locations), nitrocellulose, a plastic substrate, a glass substrate, a solid phase column support; a silica support; a magnetic support; a gel support; a glass support; a polystyrene support; a polypropylene support; a polycarbonate surface derivatized with tetraethoxysilane; a polycarbonate surface derivatized with dimethyldiethoxysilane; a polycarbonate surface derivatized with silicon tetraacetate; a polycarbonate surface derivatized with methyltriacetoxysilane; a polycarbonate support derivatized with any di- or tri-alkoxysilane; an synthetic alumina surface, whereby hydroxyl groups upon the said surface may be optionally derivatized with tetraethoxysilane, dimethyldiethoxysilane; methyltriacetoxysilane; or with any di- or tri-alkoxysilane; a silicon monoxide surface, whereby hydroxyl groups upon the said surface may be optionally derivatized with tetraethoxysilane, dimethyldiethoxysilane; methyltriacetoxysilane; or with any di- or tri-alkoxysilane; a silicon monoxide surface upon a silicon substrate, whereby hydroxyl groups upon the said surface may be optionally derivatized with tetraethoxysilane, dimethyldiethoxysilane; methyltriacetoxysilane; or with any di- or tri-alkoxysilane , a titanium dioxide surface whereby hydroxyl groups upon the said surface may be optionally derivatized with tetraethoxysilane, dimethyldiethoxysilane; methyltriacetoxysilane; or with any di- or tri-alkoxysilane, a zirconium dioxide surface whereby hydroxyl groups upon the said surface may be optionally derivatized with tetraethoxysilane, dimethyldiethoxysilane; methyltriacetoxysilane; or with any di- or tri-alkoxysilane, a tin oxide surface of electrically conductive nature, whereby hydroxyl groups upon the said surface may be optionally derivatized with tetraethoxysilane, dimethyldiethoxysilane; methyltriacetoxysilane; or with any di- or tri-alkoxysilane, a polycarbonate, polystyrene, or polypropylene support derivatized with streptavidin; and any combination thereof.

The following polypeptides and oligonucleotides are useful in the invention:

```
                                           SEQ ID NO:1
Amino acid sequence of the NCp7 protein (full-
length mature protein):
MQKGNFRNQRKTVKCFNCGKEGHIAKNCRAPRKKGCWKCGKEGHQM

KDCTERQAN

SEQ ID NO:2
Amino acid sequence of first zinc finger of NCp7:
VKCFNCGKEGHTARNCRA SEQ ID NO:3
Amino acid sequence of second zinc finger NCp7:
KGCWKCGKEGHQMKDCTE
```

SEQ ID NO:4—Amino acid sequence of first and second zinc fingers of NCp7 and the amino acids linking them: There are multiple sequences in Genbank representing the NCp7 sequence and its mutant variants which are possible in nature. A representative set of these is indicated below.

```
                                          [SEQ ID NO:10]
ARILAEAMSQVTNTAVMMQRNNFKGQRKIIKCFNCGKEGHLAKNCRAPR

KKGCWKCG
                                          [SEQ ID NO:11]
ARVLAEAMSQVSGVGAAIMMQKSNFKGPKRMIKCFNCGKEGHLARNCR

APRKRGCWKCG
                                          [SEQ ID NO:12]
ARVLAEAMSQVTQPATIMMQKGNFRNQRKTVKCFNCGKEGHIAKNCRA

PRKKGCWKCGR
                                          [SEQ ID NO:13]
ARVLAEAMSQVTGSAATIMMQRGNIRNQRKTVKCFNCGKEGHIARNCRA
```

-continued

PRKKGCWKCGK

[SEQ ID NO:14]
ARVLAEAMSQVTQSATMMMQRGNFRNQKKTVKCFNCGKEGHIAKNCR

APRKKGCWKCGR

[SEQ ID NO:15]
ARVLAEAMSQVTNSPAIMMQRGNFRNQRKIVKCFNCGKEGHIAKNCRAP

RKRGCWKCGK

[SEQ ID NO:16]
ARVLAEAMSQVTQPATIMMQRGNFRNQRKTVKCFNCGKEGHIAKNCRA

PRKKGCWKCGR

[SEQ ID NO:17]
ARVLAEAMSQVTASATIMMQRGNFKNQRKTVKCFNCGKEGHIAKNCRA

PRKKGCWKCG

These sequences are normally contained within the gag protein. Representative examples of the HIV gag protein which contains the NCp sequence from different mutant HIV samples are well known to those skilled in the prior art. Non-limiting examples are represented by sequence Ids 4-1 through 4-100 shown below, along with their Genbank numerical listings:

>gi|18073998|emb|CAC86563.1| gag protein
[Human immunodeficiency virus type 1]
MGARASVLSGGKLDAWEKIRLRPGGKKKYRLKHIVWASRELERFALNPGL [SEQ ID NO:18]

LETSEGCKQIIGQLQPAVQTGSEELKSLFNTVATLYCVHERIEVKDTKEA

LEKIEEEQAKSKKKAQQATADTRNSSQVSQNYPIVQNLQGQMIHQAISPR

TLNAWVKVIEEKAFSPEVIPMFTALSEGATPQDLNTMLNTVGGHQAAMQM

LKETINEEAAEWDRLHPPQAGPVAPGQMREPRGSDIAGTTSTLQEQIGWM

TSNPPVPVGEIYKRWIILGLNKIVRMYSPVSILDIRQGPKEPFRDYVDRF

YKTLRAEQASQDVKNWMTETLLVQNANPDCKTILKALGPGATLEEMMTAC

QGVGGPSHKARVLAEAMSQATNLNGAAMMQRSNFKGPRKIVKCFNCGKEG

HIARNCKAPRKKGCWKCGSEGHQMKDCTERQANFLGKIWPSHKGRPGNFL

QNRPEPTAPPAESFGFGEEITPSQKQEQKNQEPQPLTSLRSLFGNDPLLP

>gi|18073555|emb|CAC83671.1| gag protein
[Human immunodeficiency virus type 1]
LNKIVRMYSPVSILDIRQGPKEPFRDYVDRFFKTLRAEQATQEVKGWMTD [SEQ ID NO:19]

TLLVQNANPDCKTILRALGPGATLEEMMTACQGVGGPSPKARVFS

>gi|18073553|emb|CAC83670.1| gag protein
[Human immunodeficiency virus type 1]
LNKIVRMYSPVSILDIRQGPKEPFRDYVDRFFKTLRAEQATQEVKGWMTD [SEQ ID NO:20]

TLLVQNANPDCKTILRALGPGATLEEMMTACQGVGGPSHKARVLAEAMSQ

ASGATIMMQKSNFKGPRRMIKCFNCGKEGHLARNCRAPR

>gi|18073551|emb|CAC83669.1| gag protein
[Human immunodeficiency virus type 1]
LNKIVRMYSPVSILDIRQGPKEPFRDYVDRFFKTLRAEQATQEVKGWMTD [SEQ ID NO:21]

TLLVQNANPDCKTILRALGPGATLEEMMTACQGVGGPSHKARVFS

>gi|18073549|emb|CAC83668.1| gag protein
[Human immunodeficiency virus type 1]
LNKIVRMYSPVSILDIRQGPKEPFRDYVDRFFKTLRAGQATQEVKGWMTD [SEQ ID NO:22]

TLLVQNANPDCKTILRALGPGATLEEMMTACQGVGGPGHKARVLAEAMSQ

ATGAAMMMQKSNFKGPKRMIKCFNCGKEGHLARNCRAPR

>gi|18073547|emb|CAC83667.1| gag protein
[Human immunodeficiency virus type 1]
LNKIVRMYSPVSILDIRQGPKEPFRDYVDRFFKTLRAEQATQEVKGWMTD [SEQ ID NO:23]

TLLVQNANPDCKTILKALGSGATLEEMMTACQGVGGPGHKARVLAEAMSQ

VSGTTVMMQKSNFKGPKRTVKCFNCGKEGHLARNCRAPR

-continued

```
>gi|18073545|emb|CAC83666.1| gag protein
[Human immunodeficiency virus type 1]
LNKIVRMYSPVSILDIRQGPKEPFRDYVDRFFKTLRAEQATQEVKGWMTD     [SEQ ID NO:24]

TLLVQNANPDCKTILKALGPGATLEEMMTACQGVGGPGHKARVLAEAMSQ

VSGTTVMMQKSNFKGPKRTIKCFNCGKEGHLARNCRAPR

>gi|18073543|emb|CAC83665.1| gag protein
[Human immunodeficiency virus type 1]
LNKIVRMYSPTSILDIKQGPKESFRDYVDRFFKTLRAEQATQEVKNWMTD     [SEQ ID NO:25]

TLLVQNANPDCKTILRALGPGATLEEMMTACQGVGGPSHKARVLAEAMSQ

ASGATVMMQKGNFKGPKRMIKCFNCGKEGHLARNCRAPR

>gi|18073541|emb|CAC83664.1| gag protein
[Human immunodeficiency virus type 1]
LNKIVRMYSPVSILDIKQGPKEPFRDYVDRFFKTLRAEQCTQEVKGWMTD     [SEQ ID NO:26]

TLLVQNANPDCKTILRALGPGATLEEMMTACQGVGGPSHKARILAEAMSQ

VSGATIMMQKSNFKGPKRMIKCFNCGKEGHLARNCRAPR

>gi|18073539|emb|CAC83663.1| gag protein
[Human immunodeficiency virus type 1]
LNKIVRMYSPVSILDIRQGPKEPFRDYVDRFFKTLRAEQATQEVKNWMTD     [SEQ ID NO:27]

TLLVQNANPDCKNILRALGPGATLEEMMTACQGVGGPGHKARVLAEAMSQ

VSGPTVMMQKSNFKGPRKMIKCFNCGKEGHLARNCRAPR

>gi|18073537|emb|CAC83662.1| gag protein
[Human immunodeficiency virus type 1]
LNKIVRMYSPVSILDIRQGPKEPFRDYVDRFFKTLRAEQATQEVKGWMTD     [SEQ ID NO:28]

TLLVQNANPDCKTILRALGPGATLEEMMTACQGVGGPGHKARVLAEAMSQ

ASGAAAAIMMQKSNFKGPRRMIKCFNCGKEGHLARNCRAPR

>gi|18073535|emb|CAC83661.1| gag protein
[Human immunodeficiency virus type 1]
LNKIVRMYSPVSILDIRQGPKEPFRDYVDRFFKTLRAEQATQEVKGWMTE     [SEQ ID NO:29]

TLLVQNANPDCKTILRALGSGATLEEMMTACQGVGGPSHKARVLAEAMSQ

ASGAATAIMMQKSNFKGPRRMIKCFNCGKEGHLARNCRAPR

>gi|18073533|emb|CAC83660.1| gag protein
[Human immunodeficiency virus type 1]
LNKIVRMYSPVGILDIKQGPKEPFRDYVDRFFKTLRAEQATQEVKGWMTD     [SEQ ID NO:30]

TLLVQNANPDCKTILRALGPGATLEEMMTACQGVGGPSHKAKVLAEAMSQ

ASGAAPAIMMQKSNFKGPRRMIKCFNCGKEGHLARNCRAPR gi|18073411|emb|CAC88001.1| GAG protein
[Human immunodeficiency virus type 1]
MGARASVLSGGKLDAWEKIRLRPGGKKKYRLKHLVWASRELERFALNPSL     [SEQ ID NO:31]

LETGEGCQQIMEQLQSALRTGTEELRSLYNTVVTLYCVHQRIEVKDTKEA

LDKVEEIKNKSKQKKQQAEADTGNSNKVSQNFPIVQNAQGQMVHQAISPR

TLNAWVKVVEEKAFSPEVIPMFSALSEGATPQDLNMMLNIVGGHQAAMQM

LKETINDEAAEWDRVHPVHAGPIPPGQMREPRGSDIAGTTSTLQEQVGWM

TSNPPVPVGDIYRRWIILGLNKIVRMYSPVSILDIKQGPKEPFRDYVDRF

FKALRAEQATQEVKGWMTETLLVQNANPDCKTILRGLGQGATLEEMMTAC

QGVGGPSHKARVLAEAMSQAQQTNIMMQRSNFKGQKKIKCFNCGREGHLA

RNCRAPRKKGCWKCGQEGHQMKDCTERQANFLGKIWPSHKGRPGNFLQSR

PEPTAPPAESFGFGENTGPSPKQEQSFGIGENVAPSPKQEPKKEELYPLT

SLKSLFGNDPLLQ
```

-continued

>gi|18073401|emb|CAC87992.1| GAG protein
[Human immunodeficiency virus type 1]
MGARASVLSGGKLDSWEKIRLRPGGKKKYRLKHLVWASRELERFALNPSL [SEQ ID NO:32]

LETGEGCQQLMGQLQPALGTGTEELRSLYNTLATLYCVHHRIEIKDTKEA

LDKIEEIQNKSKQKKQQAAADTGNSSNVSQNYPIVQNAQGQMVHQPVSPR

TLNAWVKVVEEKAFSPEVIPMFSALSEGATPQDLNMMLNIVGGHQAAMQM

LKDTINEEAAEWDRLHPVQAGPIAPGQMRDPRGSDIAGTTSTLQEQIGWM

TGNPPIPVGDIYRRWIILGLNKIVRMYSPVSILDIKQGPKEPFRDYVDRF

FKALRAEQATQEVKGWMTDTLLIQNANPDCKSILRALGTGATLEEMMTAC

QGVGGPSHKARVLAEAMSQVQQTNVMMQRSNFKGQKRIKCFNCGKEGHLA

RNCRAPRKKGCWKCGREGHQMKDCTERQANFLGKIWPSSKGRPGNFLQSR

PEPTAPPAESFGFGEEIAPSPKQEPKEKEKELYPLTSLKSLFGSDP

>gi|18041988|gb|AAL57773.1| gag protein
[Human immunodeficiency virus type 1]
NYPIVQNLQGQMVHQALSPRTLNAWVKVIEEKAFSPEVIPMFTALSEGAT [SEQ ID NO:33]

PXDLNTMLNTVGGHQAAMQMLKDTINEEAAEWDRLHPVHAGPIAPGQMRE

PRGSDIAGTTSTLQEQIAWMTSNPPIPVGDIYKRWIILGLNKIVRMYSPV

SI

>gi|18041986|gb|AAL57772.1| gag protein
[Human immunodeficiency virus type 1]
SQNYPIVQNLQGQMVHQAISPRTLNAWVKVIEEKAFSPEVIPMFSALSEG [SEQ ID NO:34]

ATPQDLNTMLNTVGGHQAAMQMLKDTINEEAAEWDRTHPVHAGP

>gi|18026827|gb|AAL55638.1|AF217181_1 gag protein
[Simian-Human immunodeficiency virus]
MGVRNSVLSGKKADELEKIRLRPNGKKKYMLKHVVWAANELDRFGLAESL [SEQ ID NO:35]

LENKEGCQKILSVLAPLVPTGSENLKSLYNTVCVIWCIHAEEKVKHTEEA

KQIVQRHLVVETGTTETMPKTSRPTAPSSGRGGNYPVQQIGGNYVHLPLS

PRTLNAWVKLIEEKKFGAEVVPGFQALSEGCTPYDINQMLNCVGDHQAAM

QIIRDIINEEAADWDLQHPQPAPQQGQLREPSGSDIAGTTSSVDEQIQWM

YRQQNPIPVGNIYRRWIQLGLQKCVRMYNPTNILDVKQGPKEPFQSYVDR

FYKSLRAEQTDAAVKNWMTQTLLIQNANPDCKLVLKGLGVNPTLEEMLTA

CQGVGGPGQKARLMAEALKEALAPVPIPFAAAQQRGPRKPIKCWNCGKEG

HSARQCRAPRRQGCWKCGKMDHVMAKCPDRQAGFLGLGPWGKKPRNFPMA

QVHQGLIPTAPPEDPAVDLLKNYMQLGKQQREKQRESREKPYKEVTEDLL

HLNSLFGGDQ

>gi|17999800|gb|AAK76357.1| gag protein
[Human immunodeficiency virus type 1]
MGARASVLSGGELDKWEKIRLRPGRKKQYKLKHIVWASRELERFAINPSL [SEQ ID NO:36]

LETSEGCRQILGQLQPSLQTGSEELKSLYNTIAVLYCVHQRINVKDTKEA

LDKVEEEQNKSKKKAQQAAADTGNKSSQVSQNY

>gi|17999798|gb|AAK76356.1| gag protein
[Human immunodeficiency virus type 1]
MGARASVLSGGELDKWEKIRLRPGRKKQYKLKHIVWASRELERFAINPSL [SEQ ID NO:37]

LETSEGCRQILGQLQPSLQTGSEELKSLYNTIAVLYCVHQRINVKDTKEA

LDKVEEEQNKSKKKAQQAAADTGNKSSQVSQNY

```
>gi|17999796|gb|AAK76355.1| gag protein
[Human immunodeficiency virus type 1]
MGARASVLSGGELDKWEKIRLRPGRKKQYKLKHIVWASRELERFAINPSL    [SEQ ID NO:38]

LETTEGCRQILGQLQPSLQTGSEELKSLYNTIAVLYCVHQRINVKDTKEA

LDKVEEEQNKSKKKAQQAAADTGNKSSQVSQNY

>gi|17999794|gb|AAK76354.1| gag protein
[Human immunodeficiency virus type 1]
MGARASVLSGGELDKWEKIRLRPGRKKQYKLKHIVWASRELERFAINPSL    [SEQ ID NO:39]

LETSEGCRQILGQLQPSLQTGSEELKSLYNTIAVLYCVHQRINVKDTKEA

LDKVEEEQNKSKKKAQQAAADTGNKSSQVSQNY

>gi|17999792|gb|AAK76353.1| gag protein
[Human immunodeficiency virus type 1]
MGARASVLSGGELDKWEKIRLRPGRKKQYKLKHIVWASRELERFAINPSL    [SEQ ID NO:40]

LETSEGCRQILGQLQPSLQTGSEELKSLYNTIAVLYCVHQRINVKDTKEA

LDKVEEEQNKSKKKAQQAAADTGNKSSQVSQNY

>gi|17999790|gb|AAK76352.1| gag protein
[Human immunodeficiency virus type 1]
MGARASVLSGGELEKWEKIRLRPGRKKQYKLKHIVWASRELERFAINPSL    [SEQ ID NO:41]

LETSEGCRQILGQLQPSLQTGSEELKSLYNTIAVLYCVHQRINVKDTKEA

LDKVEEEQNKSKKKAQQAAADTGNKSSQVSQNY gi|17999788|gb|AAK76351.1| gag protein
[Human immunodeficiency virus type 1]
MGARASVLSGGELDKWEKIRLRPGRKKQYKLKHIVWASRELERFAINPSL    [SEQ ID NO:42]

LETSEGCRQILGQLQPSLQTGSEELKSLYNTIAVLYCVHQRINVKDTKEA

LDKVEEEQNKSKKKAQQAAADTGNKSSQVSQNY gi|17999786|gb|AAK76350.1| gag protein
[Human immunodeficiency virus type 1]
MGARASVLSGGELDKWEKIRLRPGRKKQYKLKHIVWASRELERFAINPSL    [SEQ ID NO:43]

LETSEGCRQILGQLQPSLQTGSEELKSLYNTIAVLYCVHQRINVKDTKEA

LDKVEEEQNKSKKKAQQAAADTGNKSSQVSQNY

>gi|17999784|gb|AAK76349.1| gag protein
MGARASVLSGGELDKWEKIRLRPGRKKQYKLKHIVWASRELERFAINPSL    [SEQ ID NO:44]

LETSEGCRQILGQLQPSLQTGSEELKSLYNTIAVLYCVHQRINVKDTKEA

LDKVEEEQNKSKKKAQQAAADTGNKSSQVSQNY

>gi|17999782|gb|AAK76348.1| gag protein
[Human immunodeficiency virus type 1]
MGARASVLSGGELDKWEKIRLRPGRKKQYKLKHIVWASRELERFAINPSL    [SEQ ID NO:45]

LETSEGCRQILGQLQPSLQTGSEELKSLYNTIAVLYCVHQRINVKDTKEA

LDKVEEEQNKSKKKAQQAAADTGNKSSQVSQNY

>gi|17999780|gb|AAK76347.1| gag protein
[Human immunodeficiency virus type 1]
MGARASVLSGGELDKWEKIRLRPGRKKQYKLKHIVWASRELERFAINPSL    [SEQ ID NO:46]

LETSEGCRQILGQLQPSLQTGSEELKSLYNTIAVLYCVHQRINVKDTKEA

LDKVEEEQNKSKKKAQQAAADTGNKSSQVSQNY

>gi|17999778|gb|AAK76346.1| gag protein
[Human immunodeficiency virus type 1]
MGARASVLSGGELDKWEKIRLRPGRKKQYKLKHIVWASRELERFAINPSL    [SEQ ID NO:47]

LETSEGCRQILGQLQPSLQTGSEELKSLYNTIAVLYCVHQRINVKDTKEA

LDKVEEEQNKSKKKAQQAAADTGNKSSQVSQNY
```

-continued

```
>gi|17999776|gb|AAK76345.1| gag protein
[Human immunodeficiency virus type 1]
MGARASVLSGGELDKWEKIRLRPGRKKQYKLKHIVWASRELERFAINPSL    [SEQ ID NO:48]

LETSEGCRQILGQLQPSLQTGSEELKSLYNTIAVLYCVHQRINVKDTKEA

LDKVEEEQNKSKKKAQQAAADTGNKSSQVSQNY

>gi|17999774|gb|AAK76344.1| gag protein
[Human immunodeficiency virus type 1]
MGARASVLSGGELDKWEKIRLRPGRKKQYKLKHIVWASRELERFAINPSL    [SEQ ID NO:49]

LETSEGCRQILGQLQPSLQTGSEELKSLYNTIAVLYCVHQRINVKDTKEA

LDKVEEEQNKSKKKAQQAAADTGNKSSQVSQNY

>gi|17999772|gb|AAK76343.1| gag protein
[Human immunodeficiency virus type 1]
MGARASVLSGGELDKWEKIRLRPGRKKQYKLKHIVWASRELERFAINPSL    [SEQ ID NO:50]

LETSEGCRQILGQLQPSLQTGSEELKSLYNTIAVLYCVHQRINVKDTKEA

LDKVEEEQNKSKKKAQQAAADTGNKSSQVSQNY

>gi|17999770|gb|AAK76342.1| gag protein
[Human immunodeficiency virus type 1]
MGARASVLSGGELDKWEKIRLRPGRKKQYKLKHIVWASRELERFAINPSL    [SEQ ID NO:51]

LETSEGCRQILGQLQPSLQTGSEELKSLYNTIAVLYCVHQRINVKDTKEA

LDKVEEEQNKSKKKAQQAAADTGNKSSQVSQNY

>gi|17999768|gb|AAK76341.1| gag protein
[Human immunodeficiency virus, type 1]
MGARASVLSGGELDKWEKIRLRPGRKKQYKLKHIVWASRELERFAINPSL    [SEQ ID NO:52]

LETSEGCRQILGQLQPSLQTGSEELKSLYNTIAVLYCVHQRINVKDTKEA

LDKVEEEQNKSKKKAQQAAADTGNKSSQVSQNY

>gi|17999766|gb|AAK76340.1| gag protein
[Human immunodeficiency virus type 1]
MGARASVLSGGELDKWEKIRLRPGRKKQYKLKHIVWASRELERFAINPSL    [SEQ ID NO:53]

LETSEGCRQILGQLQPSLQTGSEELKSLYNTIAVLYCVHQRINVKDTKEA

LDKVEEEQNKSKKKAQQAAADTGNKSSQVSQNY

>gi|17999764|gb|AAK76339.1| gag protein
[Human immunodeficiency virus type 1]
MGARASVLSGGELDKWEKIRLRPGRKKQYKLKHIVWASRELERFAINPSL    [SEQ ID NO:54]

LETSEGCRQILGQLQPSLQTGSEELKSLYNTIAVLYCVHQRINVKDTKEA

LDKVEEEQNKSKKKAQQAAADTGNKSSQVSQNY

>gi|17999762|gb|AAK76338.1| gag protein
[Human immunodeficiency virus type 1]
MGARASVLSGGELDKWEKIRLRPGRKKQYKLKHIVWASRELERFAINPSL    [SEQ ID NO:55]

LETSEGCRQILGQLQPSLQTGSEELKSLYNTIAVLYCVHQRINVKDTKEA

LDKVEEEQNKSKKKAQQAAADTGNKSSQVSQNY

>gi|17999760|gb|AAK76337.1| gag protein
[Human immunodeficiency virus type 1]
MGARASVLSGGELDKWEKIRLRPGRKKQYKLKHIVWASRELERFAINPSL    [SEQ ID NO:56]

LETSEGCRQILGQLQPSLQTGSEELKSLYNTIAVLYCVHQRINVKDTKEA

LDKVEEEQNKSKKKAQQAAADTGNKSSQVSQNY

>gi|17999758|gb|AAK76336.1| gag protein
[Human immunodeficiency virus type 1]
MGARASVLSGGELDKWEKIRLRPGRKKQYKLKHIVWASRELERFAINPSL    [SEQ ID NO:57]

LETSEGCRQILGQLQPSLQTGSEELKSLYNTIAVLYCVHQRINVKDTKEA

LDKVEEEQNKSKKKAQQAAADTGNKSSQVSQNY
```

```
>gi|17999756|gb|AAK76335.1| gag protein
[Human immunodeficiency virus type 1]
MGARASVLSGGELDKWEKIRLRPGRKKQYKLKHIVWASRELERFAINPSL   [SEQ ID NO:58]

LETSEGCRQILGQLQPSLQTGSEELKSLYNTIAVLYCVHQRINVKDTKEA

LDKVEEQNKSKKKAQQAAADTGNKSSQVSQNY

>gi|17999754|gb|AAK76334.1| gag protein
[Human immunodeficiency virus type 1]
MGARASVLSGGELDKWEKIRLRPGRKKQYKLKHIVWASRELERFAINPSL   [SEQ ID NO:59]

LETSEGCRQILGQLQPSLQTGSEELKSLYNTIAVLYCVHQRINVKDTKEA

LDKVEEQNKSKKKAQQAAADTGNKSSQVSQNY

>gi|17999752|gb|AAK76333.1| gag protein
[Human immunodeficiency virus type 1]
MGARASVLSGGELDKWEKIRLRPGRKKQYKLKHIVWASRELERFAINPSL   [SEQ ID NO:60]

LETSEGCRQILGQLQPSLQTGSEELKSLYNTIAVLYCVHQRINVKDTKEA

LDKVEEQNKSKKKAQQAAADTGNKSSQVSQNY

>gi|17999750|gb|AAK76332.1| gag protein
[Human immunodeficiency virus type 1]
MGARASVLSGGELDKWEKIRLRPGRKKQYKLKHIVWASRELERFAINPSL   SEQ ID NO:61]

LETSEGCRQILGQLQPSLQTGSEELKSLYNTIAVLYCVHQRINVKDTKEA

LDKVEEQNKSKKKAQQAAADTGNKSSQVSQNY

>gi|17999748|gb|AAK76331.1| gag protein
[Human immunodeficiency virus type 1]
MGARASVLSGGELDKWEKIRLRPGRKKQYKLKHIVWASRELERFAINPSL   [SEQ ID NO:62]

LETSEGCRQILGQLQPSLQTGSEELKSLYNTIAVLYCVHQRINVKDTKEA

LDKVEEQNKSKKKAQQAAADTGNKSSQVSQNY

>gi|17999746|gb|AAK76330.1| gag protein
[Human immunodeficiency virus type 1]
MGARASVLSGGELDKWEKIRLRPGRKKQYKLKHIVWASRELERFAINPSL   [SEQ ID NO:63]

LETSEGCRQILGQLQPSLQTGSEELKSLYNTIAVLYCVHQRINVKDTKEA

LDKVEEQNKSKKKAQQAAADTGNKSSQVSQNY

>gi|17999744|gb|AAK76329.1| gag protein
[Human immunodeficiency virus type 1]
MGARASVLSGGELDKWEKIRLRPGRKKQYKLKHIVWASRELERFAINPSL   [SEQ ID NO:64]

LETSEGCRQILGQLQPSLQTGSEELKSLYNTIAVLYCVHQRINVKDTKEA

LDKVEEQNKSKKKAQQAAADTGNKSSQVSQNY

>gi|17999742|gb|AAK76328.1| gag protein
[Human immunodeficiency virus type 1]
MGARASVLSGGELDKWEKIRLRPGRKKQYKLKHIVWASRELERFAINPSL   [SEQ ID NO:65]

LETSEGCRQILGQLQPSLQTGSEELKSLYNTIAVLYCVHQRINVKDTKEA

LDKVEEQNKSKKKAQQAAADTGNKSSQVSQNY

>gi|17999740|gb|AAK76327.1| gag protein
[Human immunodeficiency virus type 1]
MGARASVLSGGELDKWEKIRLRPGRKKQYKLKHIVWASRELERFAINPSL   [SEQ ID NO:66]

LETSEGCRQILGQLQPSLQTGSEELKSLYNTIAVLYCVHQRINVKDTKEA

LDKVEEQNKSKKKAQQAAADTGNKSSQVSQNY

>gi|17999738|gb|AAK76326.1| gag protein
[Human immunodeficiency virus type 1]
MGARASVLSGGELDKWEKIRLRPGRKKQYKLKHIVWASRELERFAINPSL   SEQ ID NO:67]

LETSEGCRQILGQLQPSLQTGSEELKSLYNTIAVLYCVHQRINVKDTKEA

LDKVEEQNKSKKKAQQAAADTGNKSSQVSQNY
```

```
-continued
>gi|17999736|gb|AAK76325.1| gag protein
[Human immunodeficiency virus type 1]
MGARASVLSGGELDKWEKIRLRPGRKKQYKLKHIVWASRELERFAINPSL    [SEQ ID NO:68]

LETSEGCRQILGQLQPSLQTGSEELKSLYNTIAVLYCVHQRINVKDTKEA

LDKVEEEQNKSKKKAQQAAADTGNKSSQVSQNY

>gi|17999734|gb|AAK76324.1| gag protein
[Human immunodeficiency virus type 1]
MGARASVLSGGELDKWEKIRLRPGRKKQYKLKHIVWASRELERFAINPSL    [SEQ ID NO:69]

LETSEGCRQILGQLQPSLQTGSEELKSLYNTIAVLYCVHQRINVKDTKEA

LDKVEEEQNKSKKKAQQAAADTGNKSSQVSQNY

>gi|17999732|gb|AAK76323.1| gag protein
[Human immunodeficiency virus type 1]
MGARASVLSGGELDKWEKIRLRPGRKKQYKLKHIVWASRELERFAINPSL    [SEQ ID NO:70]

LETSEGCRQILGQLQPSLQTGSEELKSLYNTIAVLYCVHQRINVKDTKEA

LDKVEEEQNKSKKKAQQAAADTGNKSSQVSQNY

>gi|17999730|gb|AAK76322.1| gag protein
[Human immunodeficiency virus type 1]
MGARASVLSGGELDKWEKIRLRPGRKKQYKLKHIVWASRELERFAINPSL    [SEQ ID NO:71]

LETSEGCRQILGQLQPSLQTGSEELKSLYNTIAVLYCVHQRINVKDTKEA

LDKVEEEQNKSKKKAQQAAADTGNKSSQVSQNY

>gi|17999728|gb|AAK76321.1| gag protein
[Human immunodeficiency virus type 1]
MGARASVLSGGELDKWEKIRLRPGRKKQYKLKHIVWASRELERFAINPSL    [SEQ ID NO:72]

LETSEGCRQILGQLQPSLQTGSEELKSLYNTIAVLYCVHQRINVKDTKEA

LDKVEEEQNKSKKKAQQAAADTGNKSSQVSQNY

>gi|17999726|gb|AAK76320.1| gag protein
[Human immunodeficiency virus type 1]
MGARASVLSGGELDKWEKIRLRPGRKKQYKLKHIVWASRELERFAINPSL    [SEQ ID NO:73]

LETSEGCRQILGQLQPSLQTGSEELKSLYNTIAVLYCVHQRINVKDTKEA

LDKVEEEQNKSKKKAQQAAADTGNKSSQVSQNY

>gi|17999724|gb|AAK76319.1| gag protein
[Human immunodeficiency virus type 1]
MGARASVLSGGELDKWEKIRLRPGRKKQYKLKHIVWASRELERFAINPSL    [SEQ ID NO:74]

LETSEGCRQILGQLQPSLQTGSEELKSLYNTIAVLYCVHQRINVKDTKEA

LDKVEEEQNKSKKKAQQAAADTGNKSSQVSQNY

>gi|17999722|gb|AAK76318.1| gag protein
[Human immunodeficiency virus type 1]
MGARASVLSGGELDKWEKIRLRPGRKKQYKLKHIVWASRELERFAINPSL    [SEQ ID NO:75]

LETSEGCRQILGQLQPSLQTGSEELKSLYNTIAVLYCVHQRINVKDTKEA

LDKVEEEQNKSKKKAQQAAADTGNKSSQVSQNY

>gi|17999720|gb|AAK76317.1| gag protein
[Human immunodeficiency virus type 1]
MGARASVLSGGELDKWEKIRLRPGRKKQYKLKHIVWASRELERFAINPSL    [SEQ ID NO:76]

LETSEGCRQILGQLQPSLQTGSEELKSLYNTIAVLYCVHQRINVKDTKEA

LDKVEEEQNKSKKKAQQAAADTGNKSSQVSQNY

>gi|17999718|gb|AAK76316.1| gag protein
[Human immunodeficiency virus type 1]
MGARASVLSGGELDKWEKIRLRPGRKKQYKLKHIVWASRELERFAINPSL    [SEQ ID NO:77]

LETSEGCRQILGQLQPSLQTGSEELKSLYNTIAVLYCVHQRINVKDTKEA

LDKVEEEQNKSKKKAQQAAADTGNKSSQVSQNY
```

-continued

\>gi|17999716|gb|AAK76315.1| gag protein
[Human immunodeficiency virus type 1]
MGARASVLSGGELDKWEKIRLRPGRKKQYKLKHIVWASRELERFAINPSL  [SEQ ID NO:78]

LETSEGCRQILGQLQPSLQTGSEELKSLYNTIAVLYCVHQRINVKDTKEA

LDKVEEEQNKSKKKAQQAAADTGNKSSQVSQNY

\>gi|17999714|gb|AAK76314.1| gag protein
[Human immunodeficiency virus type 1]
MGARASVLSGGELDKWEKIRLRPGRKKQYKLKHIVWASRELERFAINPSL  [SEQ ID NO:79]

LETSEGCRQILGQLQPSLQTGSEELKSLYNTIAVLYCVHQRINVKDTKEA

LDKVEEEQNKSKKKAQQAAADTGNKSSQVSQNY

\>gi|17999712|gb|AAK76313.1| gag protein
[Human immunodeficiency virus type 1]
MGARASVLSGGELDKWEKIRLRPGRKKQYKLKHIVWASRELERFAINPSL  [SEQ ID NO:80]

LETSEGCRQILGQLQPSLQTGSEELKSLYNTIAVLYCVHQRINVKDTKEA

LDKVEEEQNKSKKKAQQAAADTGNKSSQVSQNY

\>gi|17999710|gb|AAK76312.1| gag protein
[Human immunodeficiency virus type 1]
MGARASVLSGGELDKWEKIRLRPGRKKQYKLKHIVWASRELERFAINPSL  [SEQ ID NO:81]

LETSEGCRQILGQLQPSLQTGSEELKSLYNTIAVLYCVHQRINVKDTKEA

LDKVEEEQNKSKKKAQQAAADTGNKSSQVSQNY

\>gi|17999708|gb|AAK76311.1| gag protein
[Human immunodeficiency virus type 1]
MGARASVLSGGELDKWEKIRLRPGRKKQYKLKHIVWASRELERFAINPSL  [SEQ ID NO:82]

LETSEGCRQILGQLQPSLQTGSEELKSLYNTIAVLYCVHQRINVKDTKEA

LDKVEEEQNKSKKKAQQAAADTGNKSSQVSQNY

\>gi|17999706|gb|AAK76310.1| gag protein
[Human immunodeficiency virus type 1]
MGARASVLSGGELDKWEKIRLRPGRKKQYKLKHIVWASRELERFAINPSL  [SEQ ID NO:83]

LETSEGCRQILGQLQPSLQTGSEELKSLYNTIAVLYCVHQRINVKDTKEA

LDKVEEEQNKSKKKAQQAAADTGNKSSQVSQNY

\>gi|17999704|gb|AAK76309.1| gag protein
[Human immunodeficiency virus type 1]
MGARASVLSGGELDKWEKIRLRPGRKKQYKLKHIVWASRELERFAINPSL  [SEQ ID NO:84]

LETSEGCRQILGQLQPSLQTGSEELKSLYNTIAVLYCVHQRINVKDTKEA

LDKVEEEQNKSKKKAQQAAADTGNKSSQVSQNY

\>gi|17999702|gb|AAK76308.1| gag protein
[Human immunodeficiency virus type 1]
MGARASVLSGGELDKWEKIRLRPGRKKQYKLKHIVWASRELERFAINPSL  [SEQ ID NO:85]

LETSEGCRQILGQLQPSLQTGSEELKSLYNTIAVLYCVHQRINVKDTKEA

LDKVEEEQNKSKKKAQQAAADTGNKSSQVSQNY

\>gi|17999700|gb|AAK76307.1| gag protein
[Human immunodeficiency virus type 1]
MGARASVLSGGELDKWEKIRLRPGRKKQYKLKHIVWASRELERFAINPSL  [SEQ ID NO:86]

LETSEGCRQILGQLQPSLQTGSEELKSLYNTIAVLYCVHQRINVKDTKEA

LDKVEEEQNKSNKKAQQAAADTGNKSSQVSQNY

\>gi|17999698|gb|AAK76306.1| gag protein
[Human immunodeficiency virus type 1]
MGARASVLSGGELDKWEKIRLRPGRKKQYKLKHIVWASRELERFAINPSL  [SEQ ID NO:87]

LETSEGCRQILGQLQPSLQTGSEELKSLYNTIAVLYCVHQRINVKDTKEA

LDKVEEEQNKSKKKAQQAAADTGNKSSQVSQNY

-continued

\>gi|17999696|gb|AAK76305.1| gag protein
[Human immunodeficiency virus type 1]
MGARASVLSGGELDKWEKIRLRPGRKKQYKLKHIVWASRELERFAINPSL  [SEQ ID NO:88]

LETSEGCRQILGQLQPSLQTGSEELKSLYNTIAVLYCVHQRINVKDTKEA

LDKVEEEQNKSKKKAQQAAADTGNKSSQVSQNY

\>gi|17999689|gb|AAK76304.1| gag protein
[Human immunodeficiency virus type 1]
MGARASVLSGGKLDKWEKTRLRPGGKKKYQLKHIVWASRELGRFAVNPGL  [SEQ ID NO:89]

LETADGCRQILGQLQPSLQTGSEELKSLFNTVATLYCVHQNIEVKDTKEA

LDKVEEEQNKSKKNAQQAAADTRNSQVSQNY

\>gi|17999685|gb|AAK76303.1| gag protein
[Human immunodeficiency virus type 1]
MGARASVLSGGKLDKWEKTRLRPGGKKKYQLKHIVWASRELERSAVNPGL  [SEQ ID NO:90]

LETADGCRQILGQLQPSLQTGSEELKSLFNTIATLYCVHQNIEVKDTKEA

LDKVEEEQNKSKKNAQQAAADTRNSQVSQNY

\>gi|17999683|gb|AAK76302.1| gag protein
[Human immunodeficiency virus type 1]
MGARASVLSGGKLDKWEKTRLRPGGKKKYQLKHIVWASRELERFAVNPGL  [SEQ ID NO:91]

LETADGCRQILGQLQPSLQTGSEELKSLFNTIATLYCVHQNIEVKDTKEA

LDKVEEEQNKSKKNAQQAAADTRNSQVSQNY

\>gi|17999680|gb|AAK76301.1| gag protein
[Human immunodeficiency virus type 1]
MGARASVLSGGKLDKWEKTRLRPGGKKKYQLKHIVWASRELERFAVNPGL  [SEQ ID NO:92]

LETADGCRQILGQLQPSLQTGSEELKSLFNTVATLYCVHQNIEVKDTKEA

LDKVEEEQNKSKKNAQQAAADTRNSQVSQNY

\>gi|17999678|gb|AAK76300.1| gag protein
[Human immunodeficiency virus type 1]
MGARASVLSGGKLDKWEKTRLRPGGKKKYQLKHIVWASRELERFAVNPGL  [SEQ ID NO:93]

LETADGCRQILGQLQPSLQTGSEELKSLFNTIATLYCVHQNIEVKDTKEA

LDKVEEEQNKSKKNAQQAAADTRNSQVSQNY

\>gi|17999676|gb|AAK76299.1| gag protein
[Human immunodeficiency virus type 1]
MGARASVLSGGKLDKWEKTRLRPGGKKKYQLKHIVWASRELERFAVNPGL  [SEQ ID NO:94]

LETADGCRQILGQLQPSLQTGSEELKSLFNTIATLYCVHQNIEVKDTKEA

LDKVEEEQNKSKKNAQQAAADTRNSQVSQNY

\>gi|17999673|gb|AAK76298.1| gag protein
[Human immunodeficiency virus type 1]
MGARASVLSGGKLDKWEKTRLRPGGKKKYQLKHIVWASRELERFAVNPGL  [SEQ ID NO:95]

LETADGCRQILGQLQPSLQTGSEELKSLFNTIATLYCVHQNIEVKDTKEA

LDKVEEEQNKSKKNAQQAAADTRNSQVSQNY

\>gi|17999670|gb|AAK76297.1| gag protein
[Human immunodeficiency virus type 1]
MGARSVLSGGKLDKWEKTRLRPGGRKKYQLKHIVWASRELERFAVNPGL  [SEQ ID NO:96]

LETADGCRQILGQLQPSLQTGSEELKSLFNTIATLYCVHQNIEVKDTKEA

LDKVEEEQNKSKKNAQQAAADTRNSQVSQNY

\>gi|17999668|gb|AAK76296.1| gag protein
[Human immunodeficiency virus type 1]
MGARSVLSGGKLDKWEKTRLRPGGRKKYQLKHIVWASRELERFAVNPGL  [SEQ ID NO:97]

LETADGCRQILGQLQPSLQTGSEELKSLFNTIATLYCVHQNIEVKDTKEA

LDKVEEEQNKSKKNAQQAAADTRNSQVSQNY

-continued

>gi|17999663|gb|AAK76295.1| gag protein
[Human immunodeficiency virus type 1]
MGARASVLSGGKLDQWEKIRLRPGGKKKYKLKHIVWASRELERFAVNPGL   [SEQ ID NO:98]

LETAEGCRQILGQLQPALQTGSEELKSLYNTVATLYCVHQRIDIKDTKEA

LDKIEEEQNQSKKKAQQAAADTGNSNQVSQNY

>gi|17902137|gb|AAL47802.1| gag protein
[Human immunodeficiency virus type 1]
MGARASVLSGGKLDAWEKIRLRPGGKKKYRMKHLVWASRELERFALNPDL   [SEQ ID NO:99]

LETTEGCQQIMGQLQPALXTGTEEIRSLFNTVATLYCVHQKIEVKDTKEA

LEEVEKAQKKSQKNQQAAMDEGNNSQVSQNYPIVQNAQGQMVHQAISPRT

LNAWVKVVEEKAFSPEVIPMFSALSEGATPQDLNTMLNTVGGHQAAMQML

KDTINEEAAEWDRMHPPQAGPIPPGQIREPRGSDIAGTTSTLQEQIRWMT

SNPPIPVGEIYKRWIILGLNKIVRMYSPVSILDIRQGPKEPFRDYVDRFF

KTLRAEQATQEVKGWMTDTLLVQNANPDCKTILRALGPGATLEEMMTACQ

GVGGPSHKARVLAEAMSQASGATVMMQKSNFKGPRRNIKCFNCGKEGHLA

RNCRAPRKRGCWKCGKEGHQMKDCTESKANFLGKIWPSNKGRPGNFLQNR

PEPTAPPAESFGFGEEIAPSPKPEPKEKEMYPLASLKSLFGSDP

>gi|17902126|gb|AAL47793.1| gag protein
[Human immunodeficiency virus type 1]
MGARASVLSGGKLDAWEKIRLRPGGKKKYRXKHLVWASRELERFALNPGL   [SEQ ID NO:100]

LETAEGCQQIMGQLQPALQTGTEEIRSLFNTVATLYCVHQKIEVKDTKEA

LEEVEKAQKKSQKKQQAAMDEGNNSQASQNYPIVQNAQGQMVHQAISPRT

LNAWVKVVEEKAFSPEVIPMFSALSEGATPQDLNTMLNTVGGHQAAMQML

KDTINEEAAEWDRMHPQQAGPIPPGQIREPRGSDIAGTTSTLQEQIRWMT

SNPPIPVGEIYKRWIILGLNKIVRMYSPVSILDIRQGPKEPFRDYVDRFF

KTLRAEQATQEVKGWMTDTLLVQNANPDCKTILRALGPGATLEEMMTACQ

GVGGPSHKARVLAEAMSLASGATVMMQKSNFKGPRRNIKCFNCGKEGHLA

RNCRAPRKKGCWKCGKEGHQMKDCTESKANFLGKIWPSNKGRPGNFLQNR

PEPTAPPAESFGFGEEIAPSPKPEPKEKEMYPLASLKSLFGSDP

>gi|17902115|gb|AAL47784.1| gag protein
[Human immunodeficiency virus type 1]
MGARASVLSGGKLDAWEKIRLRPGGKKKYRMKHLVWASRELERFALNPDL   [SEQ ID NO:101]

LETADGCQQIMGQLQPXLQTGTEEIRSLFNTVATLYCVHQKIEVKDTKEA

LEXVEKAQKKSQKQQQAAMDEGNNSQASQNYPIVQNAQGQMVHQPISPRT

LNAWVKVVEEKAFSPEVIPMFSALSEGATPQDLNTMLNTVGGHQAAMQML

KDTINEEAAEWDRIHPQQAGPIPPGQIREPRGSDIAGTTSTLQEQIRWMT

SNPPIPVGEIYKRWIILGLNKIVRMYSPVSILDIRQGPKEPFRDYVDRFF

KTLRAEQATQEVKGWMTDTLLVQNANPDCKTILRALGPGATLEEMMTACQ

GVGGPSHKARVLAEAMSLASGATIMMQKSNFKGPRRNIKCFNCGKEGHLA

RNCRAPRKKGCWKCGKEGHQMKDCTESKANFLGKIWPSNKGRPGNFLQNR

PEPTAPPAESFGFGEEIAPSPKQEPKEKEIYPLASLKSLFGSDP

-continued

>gi|17646691|gb|AAL41005.1| gag protein
[Human immunodeficiency virus type 1]
QGRELERFALNPGLLETAEGCQQLIEQLQSTLTTGSEELKSLFNTIATLW  [SEQ ID NO:102]

CVHQKIEVKDTKEALDKVEEAQKRSQQKTQQAAAGTGSSSKVSQNYPIVQ

NAQGQMVHQPVSPRTLNAWVKVVEEKGFNPEVIPMFSALSEGATPQDLNM

MLNIVGGHQAAMQMLKDTINEEAADWDRVHPVHAGPIPPGQMREPRGSDI

AGTTSTLQEQIGWMT

>gi|17646689|gb|AAL41004.1| gag protein
[Human immunodeficiency virus type 1]
RFALNPGLLETSEGCKQIIKQLQPALQTGTEELRSLYNTVATLYCVHKRI  [SEQ ID NO:103]

EVKDTKEALDKVEEEQNKIQQKTQQAKEADGKVSQNYPIVQNLQGQMVHQ

AISPRTLNAWVKVIEEKAFSPEIIPMFTALSEGATPQDLNTMLNTVGGHQ

AAMQMLKDTINEEAADWDRLHPVHAGPIAPGQMREPRGSDIAGTTSSLQE

Q

>gi|15011375|gb|AAK77528.1|AF391267_1 gag protein
[Human immunodeficiency virus type 1]
MGARASILRGEKLDKWEKIRLRPGGRKHYMLKHLVWASRELERFALNPGL  [SEQ ID NO:104]

LETSQGCKQIIKQLHPALKTGTEELRSLYNTVATLYCVHENIEVRDTKEA

LDKIEEEQNKSQQKTQQAKAADEGVSQNYPIVQNLQGQMVHQAISPRTLN

AWVKVIEEKAFSPEVIPMFTALSEGATPQDLNTMLNTVGGHQAAMQMLKD

TINEEAAEWDRLHPVHAGPAAPGQMREPRGSDIAGTTSTLQEQIAWMTGN

PPVPVGDIYKRWIILGLNKIVRMYSPVSILDIKQGPKEPFRDYVDRFFKV

LRAEQATQDVKNWMTDTLLIQNANPDCKTILKALGPAASLEEMMTACQGV

GGPGHKARVLAEAMSQANSNIMMQRSNFKGSKRIVKCFNCGKEGHIARNC

RAPRKKGCWKCGQEGHQMKDCTERQANFLGKIWPSHKGRPGNFLQSRPEP

TAPPAESFRFEETTPAPKQESKDREPLISLKSLFGSDPSSQ

>gi|15011373|gb|AAK77527.1|AF391266_1 gag protein
[Human immunodeficiency virus type 1]
MGARASILRGTKLDAWEKIRLRPGGKKHYMLKHLVWASRELERFALNPGL  [SEQ ID NO:105]

LETSEGCKQIMKQLHPALQTGTEELKSLYNTVATLYCVHENIKVRDTKEA

LDKIEEEQNKIKSQQKTQQAKAADEKVSQNYPIVQNLQGQMVHQNLSPRT

LNAWVKVIEEKAFSPEVIPMFTALSEGATPQDLSTMLNTVGGHQAAMQML

KDTINEEAAEWDRLHPVHAGPMAPGQLREPRGSDIAGTTSTLREQIAWMT

SNPPIPVGDIYKRWIILGLNKIVRMYSPVSILDIRQGPKEPFRDYVDRFF

KALRAEQATQDVKNWMTETLLVQNANPDCKTILKALGIGATLEEMMTACQ

GVGGPSHKARVLAEAMSQANNTNIMMQRSNFKSSKRIVKCSNCGKEGHIA

RNCRAPRKKGCWKCGKEGHQMKDCTERQANFLGKIWPSHKGRPGNFLQNR

PEPTAPPAESFRNRPEPTAPPAESFRFEETTPTPKQEPKDRDPLTSLKSL

FGSDPSSQ

-continued

\>gi|15011348|gb|AAK77515.1|AF391253_1 gag protein
[Human immunodeficiency virus type 1]
MGARASVLKGKKLDTWERIRLRPGGKKHYMLKHLVWASRELERFALNPGL   [SEQ ID NO:106]

LETAEGCKQIMQQLQSALQTGTEELRSLYNTVATLYCVHKEIDVRDTKEA

LDKIEEEQNKSQQKTQQAEAADKGKVSQNYPIVQNLQGQMVHQAISPRTL

NAWVKVIEEKAFSPEVIPMFTALSEGATPQDLNTMLNTVGGHQAAMQMLK

DTINEEAAEWDRLHPVHAGPIAPGQMREPRGSDIAGTTSTLQEQIAWMTS

NPPIPVGDIYKRWIILGLNKIVRMYSPVSILDIKQGPKEPFRDYVDRFFK

TLRAEQSSQEVKNWMTDTLLVQNANPDCKTILRALGPGATLEEMMTACQG

VGGPGHKARVLAEAMSQANTNIMMQKSNFKGPKRTVKCFNCGKEGHIARN

CRAPRKKGCWKCGKEGHQMKDCTERQANFLGKIWPSYKGRSGNFLQSRPE

PSAPPAESFRFEEREPKDKEPPLTSLKSLFGSDPSSQ

\>gi|15011346|gb|AAK77514.1|AF391252_1 gag protein
[Human immunodeficiency virus type 1]
MGARASILSGGKLDKWERIRLRPGGKKHYMLKHLVWASRELERFALNPGL   [SEQ ID NO:107]

LETAEGCKQIIKQLQPALQTGTEELRSLFNTVATLYCVHKGIEVRDTKEA

LDKIEEEQNKCQQKAQQAKAADEKVSQNYPIVQNAQGQMVHQAISPRTLN

AWVKVIEEKAFNPEVIPMFTALSEGATPQDLNTMLNTVGGHQAAMQMLKD

TINEEAAEWDRTHPVHAGPVAPGQMREPRGSDIAGTTSTLQEQIAWMTSN

PPIPVGDIYKRWIILGLNKIVRMYSPVSILDIKQGPKEPFRDYVDRFFKT

LRAEQATQDVKNWMTDTLLVQNANPDCKTILRALGPGASLEEMMTACQGV

GGPSHKARVLAEAMSQTNSNILVQRSNFKGSNRIVKCFNCGKVGHIVRNC

RAPRKKGCWKCGQEGHQMKDCTERQANFLGKIWPSHKGRPGNFLQNRPEP

TAPPAEPTAPPAESFRFEETTPVPKREKEREPLTSLKSLFGNDPSSQ

\>gi|17046898|gb|AAL34900.1| gag protein
[Human immunodeficiency virus type 1]
MGARASILRGGKLDKWEKIRLRPGGKKKYMLKHLVWASRELERFALNSGL   [SEQ ID NO:108]

LETSDGCKQIIQQLQPALKTGTEELRSLYNTVATLYCVHNNIEIRDTKEA

LDRIEEEQKKCQQKTQQQKTQQVEAADGKVSQNYPIVQNLQGQMVHQSLS

PRTLNAWVKVIEEKAFSPEIIPMFTALSEGATPQDLNTMLNTVGGHQAAM

QMLKDTINEEAAEWDRLHPVHAGPVAPGQMREPRGSDIAGTTSNLQEQIN

WMTANPPIPVGDIYKRWIILGLNKIVRMYSPVSILDIKQGPKEPFRDYVD

RFFKTLRAEQATQDVKNWMTDTLLVQNANPDCKTILRALGPGATLEEMMT

ACQGVGGPSHKARVLAEAMSQTNSNIMMQNSNFKGSRRIVKCFNCGKVGH

IARNCRAPRKKGCWKCGKEGHQMKDCTERQANFLGRIWPSHKGRPGNFLQ

SRPEPTAPPAESFRFEEITPVPKQEPKDREPLTSLKSLFGSDPLSQ

-continued

```
>gi|17046722|gb|AAL34742.1| gag protein
[Human immunodeficiency virus type 1]
MGASASILRGGKLDKWEKIRLRPGGKKKYRLKHLVWASRELERFALNSGL    [SEQ ID NO:109]

LETAEGCKQIIKQLQPALQTGTEELKSLYNTVATLYCVHAGIEVRDTKEA

LDKIEEEQNKCQQKTQQAKEADGKVSQNYPIVQNLQGQMVHQPISPRTLN

AWVKVIEEKAFSPEVIPMFTALSEGATPQDLNTMLNTVGGHQAAMQMLKD

TINEEAAEWDRLHPVHAGPVAPGQMREPRGSDIAGTTSTLQEQITWMTSN

PPVPVGDIYKRWIILGLNKIVRMYSPVSILDIKQGPKEPFRDYVDRFFKV

LRAEQATQDVKNWMTDTLLVQNANPDCKTILRALGPAASLEEMMTACQGV

GGPSHKARVLAEAMSQANTTNIMMQKSNFKGPRRTVKCFNCGKEGHIAKN

CRAPRKKGCWKCGKEGHQMKDCTERQANFLGKIWPSHKGRPGNFLQSRPE

PTAPPAESFRFEETTPAPKQEPKDREPLTSLKSLFGSDPLSQ

>gi|16751229|gb|AAL05307.1| gag protein
[Human immunodeficiency virus type 1]
MGARASILRGEKLDTWEKIRLRPGGKKCYMLKHIVWASRELERFSLNPGL    [SEQ ID NO:110]

LETSEGCKQIMKQLQPALQTGTEELKSLYNTVATLFCVHEKIAVRDTKEA

LDKIEEEQNKSQQKTQQAKAADGTVSQNYPIVQNLQGQMVHQAISPRTLN

AWVKVIEEKAFSPEVIPMFTALSEGATPQDLNTMLNTVGGHQAAMQMLKD

TINEEAAEWDRLHPVHAGPIAPGQMREPRGSDIAGTTSTLQEQIAWMTNN

PPVPVGDIYKRWIILGLNKIVRMYSPVSILDIRQGPKEPFRDYVDRFFKT

LRAEQATQDVKNWMTDTLLVQNANPDCKTILRALGPGATLEEMMTACQGV

GGPSHKARVLAEAMSQTNNANIMMQRSNFKGPRRIIKCFNCGKEGHLARN

CRAPRKKGCWKCGKEGHQMKDCTERQANFLGKIWPSHKGRPGNFLQNRPE

PTAPPAESFRFEETTPAPKQEPREREPLTSLKSLFGSDPLSQ

>gi|16118350|gb|AAL12718.1| gag protein
[Human immunodeficiency virus type 1]
SRASILSGGKLDKWEKIRLRPGGKKRYKLKHIVWASRELERFAVNPGLLE    [SEQ ID NO:111]

TTEGCQKIIAQLQPSIQTGSEELKSLYNTVAVLYFVHQEVDVKDTKEALD

KLEEEQNSKKKAQQAAAGTGNSSQTSQNFPIVQNIQGQMVHQALSPRTLN

AWVKVVEEKAFSPEVIPMFSALSEGATPQDLNTMLNTVGGHQAAMQMLKD

TINEEAAEWDRVHPVHAGPIPPGQMREPRGSDIAGTTSTLQEQIQWMTSN

PPVPVGEIYKRWIILGLNKIVRMYSPVSILDIRQGPKEPFRDYVDRFFKT

LRAEQATQEVKNWMTDTLLIQNANPDCKTILKALGPGASLEEMMTACQGV

GGPGHKARVLAEAMSQATNTTVMMQRGNFKGQRRIVKCFNCGKEGHIAKN

CRAPRKKGCWKCGKEGHQMKDCTERQANFLGKIWPSHKGRPGNFLQNRPE

PTAPPAESFGFGEEMTPSPKQEQKEEGLYPPLASLRSLFGNDH

>gi|15626839|gb|AAL04322.1|AF409833_1 gag protein
[Human immunodeficiency virus type 1]
GGKKKYKLKHIVWASRELERFAVNPGLLETSEGCRQILEQLQPSLKTGSE    [SEQ ID NO:112]

ELKSLFNTVATLYCVHRRIEVKDTKEALDKIEEEQNKSKKKAQQAAADTG

NNSQAAAGTGDSSQISQDYPVVRNLQGQMVHQAISPRTLN
```

-continued

\>gi|15626743|gb|AAL04274.1|AF409785_1 gag protein
[Human immunodeficiency virus type 1]
GGKKKYRLRHIVWASRELERFAVNPGLLETSEGCRQLLEQLQPSLKTGSE [SEQ ID NO:113]

ELRSLFNTVATLYCVHQKIDVKDTKEALDKIEEEQNKSKKKAQQAAAGTG

NNSQVSQNYPIVQNMQGQMVHQAISPRTLN

\>gi|15626667|gb|AAL04236.1|AF409747_1 gag protein
[Human immunodeficiency virus type 1]
GGKKKYLLKHIVWASRELERFSINPGLLETSEGCRQILTQLQPALKTGSE [SEQ ID NO:114]

ELKSLYNTVAVLYCVHQKIDVKDTKEALDKIEEEQNKSKEKAQQAAAGTG

NSSQVSQNYPIVQNMQGQMVHQAISPRTLN

\>gi|15626609|gb|AAL04207.1|AF409718_1 gag protein
[Human immunodeficiency virus type 1]
GGKKKYKLKHVAWASRELERFSINPGLLETSEGCRQILTQLQPALKTGSE [SEQ ID NO:115]

ELKSLYNTVAVLYCVHQKIDVKDTKEALDKIEEEQNKSKEKAQQAAAGTG

NSSQVSQNYPIVQNIQGQMVHQAISPRTLN

\>gi|15626575|gb|AAL04190.1|AF409701_1 gag protein
[Human immunodeficiency virus type 1]
GGKKKYRLKHIAWASRELERFAVNPGLLETSGGCKQILEQLQPSLQTGSE [SEQ ID NO:116]

ELRSLYNTVATLYCVHQKIDVKDTKEALDKIEEEQNKSKKKAQQAAAGTG

NSSQVSQNYPIVQNMQGQMVHQAISPRTLN

\>gi|4322932|gb|AAD16135.1| gag protein
[Human immunodeficieney virus type 1]
MGARASVLSGGKLDAWEKIRLRPGGKKKYRMKHLVWASRELERFALNPSL [SEQ ID NO:117]

LETAEGCQQIMEQIQPALKTGSEELRSLFNTVATLYCVHQRIDVKDTKEA

LDKIEEIQNKSKQKTQQAAADTGNSSKVSQNYPIVQNAQGQMIHQNLSPR

TLNAWVKVIEEKAFSPEVIPMFSALSEGATPQDLNVMLNIVGGHQAAMQM

LKDTINEEAAEWNRMHPVHAGPIPPGQIREPRGTDIA

\>gi|14537771|gb|AAK66725.1| gag protein
[Human immunodeficiency virus type 1]
MKVCTERQANFLGKIWPSHKGRPGNFLQNRPEPTAPPEESFKFGEETTAP [SEQ ID NO:118]

SQKQEPIDKELYPLTSPQITLGNDPSSQ

\>gi|6007375|gb|AAF00893.1| gag protein
[Human immunodeficiency virus type 1]
GGKKKYKLKHIVWASRVLERFAVNPGLLETSEGCRQILEQLQPSLKTGSE [SEQ ID NO:119]

ELKSLFNTVATLYCVHRRIEVKDTKEALDKIEEEQNKSKKKAQQAAADTG

NNSQAAAGTGNSXQVSQNYPIVRNLQGQMVHQAISPRT

\>gi|13625270|gb|AAK34994.1| gag protein
[Human immunodeficieney virus type 1]
GGKKHYMLKHIVWASRELDRFALNPGLLETSEGCKQIMQQLQPALQTGTE [SEQ ID NO:120]

ELRSLFNTVATLYCVHAGIEVRDTKEALDKIEEEQNKSQRKTQQAKEADG

KVSQNYPIVQNLQGQMVHQALSP

```
-continued
>gi|13540172|gb|AAK29339.1| gag protein
[Human immunodeficiency virus type 1]
MGARASVLSGGKLDEWEKIRLRPGGKKKYRLKHLVWASRELERFALNPGL    [SEQ ID NO:121]

LETSEGCKQIIGQLQPAIQTGSEEIKSLYNTVATLYCVHERIQVKDTKEA

LDKIGEEQTKSKKKAQQATADTRNSSQVSQNYPIVQNTQGQMVYQSISPR

TLNAWVKVIEEKAFSPEVIPMFSALSEGATPQDLNTMLNTVGGHQGAMQM

LKETINEEAAEWDRLHPVHAGPVAPGQMREPRGSDIAGTTSTLQEQIGWM

TGNPVIPVGEIYKRWIILGLNKIVRMYSPISILDIRQGPKEPFRDYVDRF

YKTLRAEQASQDVKNWMTETLLVQNANPDCKTILKALGPAATLEEMMTAC

QGVGGPGHKARVLAEAMSQATKGNAIMMQRGNFKGPKRIIKCFNCGKGGH

IAKNCRAPRKKGCWKCGREGHQMKDCTERQANFLGKIWPSHKGRPGNFLQ

SRPEPTAPPAESFGFGEEMTPFQKQEQKDKEELYLLASLKSLFGNDPLSQ

>gi|13540162|gb|AAK29330.1| gag protein
[Human immunodeficiency virus type 1]
MGARASVLSGGKLDEWEKIRLRPGGKKQYKLKHLVWASRELDRFAINPGL    [SEQ ID NO:122]

LETSEGCKQIIGQLQPAIQTGSEEIKSLYNTVATLYCVHERIKVADTKEA

LDKIEEEQTKSKKKAQQATADTGNSSQVSQNYPIVQNLQGQMVHQPLTPR

TLNAWVKVVEEKAFSPEVIPMFSALSEGATPQDLNTMLNTVGGHQAAMQM

LKETINEEAAEWDRLHPVQAGPVAPGQIREPRGSDIAGTTSTLQEQIRWM

TSNPPIPVGEIYKRWIILGLNKIVRMYSPVSILDIRQGPKEPFRDYVDRF

YKTLRAEQASQDVKNWMTETLLVQNANPDCKTILKALGPAATLEEMMTAC

QGVGGPSHKARVLAEAMSQATGGNTIMMQRGNFKGPKKSIKCFNCGKEGH

TAKNCRAPRRRGCWKCGREGHQLKDCPERRQANFLGKIWPSNKGRPGNFL

QSRPEPTAPPAESFGFGEEITPSQKQEQKDKEPHPLASLKSLFGNDPLSQ

>gi|13445626|gb|AAK26319.1| gag protein
[Human immunodeficiency virus type 1]
GARASVLSGGKLDAWEKIRLRPGGKKKYRLKHLVWASRELERFALNPGLL    [SEQ ID NO:123]

ESAXGCQQLIEQLQSTLKTGSEELKSLFNTIATLWCVHQRIEVKDTKEAL

DKLEEVQKKSQQKTQQAAAGPGSSSKVSQNYPIVQNAQGQMVHQPVSPRT

LNAWVKVVEEKGFNPEVIPMFSALSEGATPQDLNMMLNIVGGHQAAMQML

KETINEEAAEWDRXHPVHAGPIPPGQMREPRGSDIAGTTSTLQEQIGWMT

SNPXIPVGDIYKRWIILGLNKIV

>gi|13445623|gb|AAK26318.1| gag protein
[Human immunodeficiency virus type 1]
GARASVLSGGKLDAWEXIRLRPGGKKKYKHLVWASRELERFAVNPGLLES    [SEQ ID NO:124]

XEGCQQIIEQLQXXLKTGSEELKSLYNTVVTLWCVHQRIEIXDTKEALDK

XEEVQXKSQQKTQQAAAGTGSSGKVSQNYPIVQNAQGQMVHQALSPRTLN

AWVKVVEEKGFNPEVIPMFSALSEGATPQDLNMMLNIVGGHQAAMQMLKE

TINEEAAEWDRVHPVHAGPIPPGQMREPRGSDIAGTTSTLQEQIGWMTNN

XPIPVGDIYKRWIILGLNKIVRMY
```

-continued

>gi|13445579|gb|AAK26296.1| gag protein
[Human immunodeficiency virus type 1]
GARASVLXGGKLDAWEKIRLRPGGKKKYRMKHLVWASRELERFALNPGLL  [SEQ ID NO:125]

ETAEGCQQILEQLQSTLKTGSEELKSLFNTVATLWCVHQRIEVKDTKEAL

DKIEEVQNKSQQKTQQAAAGTGSSSKVSQNYPIVQNAQGQMAHQPLSPRT

LNAWVKVVEEKGFNPEVIPMFSALSEGATPQDLNMMLNIVGGHQAAMQML

KETINEEAAEWDRVHPVHAGPIPPGQMREPRGSDIAGTTSTLQEQIGWMT

NNPPIPVGDIYKRWIILGLNKIVRMYS

>gi|16093157|emb|CAB58988.1| GAG protein
[Human immunodeficiency virus type 1]
GARASVLSGGKLDAWEKIRLRPGGKKKYKLKHLVWASRELERFLNPGLLE  [SEQ ID NO:126]

TTEGCRQIITQIQPSIQTGSEEIKSLYNTIAVLYFVHQKIEVKDTKEALD

KLEEEQNKSQRKTQQEAADKGVSQNYPIVQNLQGQMVHQALSPRTLNAWV

KVIEEKAFSPEVIPMFTALSEGATPQDLNTMLNTVGGHQAAMQMLKDTIN

DEAAEWDRLHPVHAGPIPPGQMREPRGSDIAGTTSTLQEQIAWMTSNPPV

PVGEIYKRWIILGLNKIVRMYSPVSILDIRQGPKEPFRDYVDRFFKTLRA

EQATQEVKNWMTDTLLVQNANPDCKTILKALGPGASLEEMMTACQGVGGP

SHKARILAEAMSQVTNPVVMMQKGNFKGHRKIVKCFNCGKEGHIARNCRA

PRKKGCWKCGKEGHQMKDCTERQANFLGKIWPSHKGRPGNFLQSRPEPTA

PPAESFGFGEEITPSPRQETKDKEQSPPLTSLKSLFGNDPLSQ

>gi|10436102|gb|AAG16784.1| gag protein
[Human immunodeficiency virus type 1]
MGARASILSGGGLDRWEKIRLRPGGKKKYRLKHLVWASRELERFAVNPGL  [SEQ ID NO:127]

LETSEGCRQILGQLQPSLQTGSEELRSLYNTVATLYCVHQKIDVKDTKEA

LDKIEEEQNKSKKKAQQAAADTGNSSQVSQNYPIVQNIQGQMVHQAISPR

TLNAWVKVVEEKAFSPEVIPMFSALSEGATPQDLNTMLNTVGGHQAAMQM

LKETINEEAAEWDRLHPVHAGPNPPGQMREPRGSDIAGTTSTLQEQIAWM

TNNPPIPVGEIYKRWIILGLNKIVRMYSPTSILDIKQGPKEPFRDYVDRF

YKTLRAEQASQEVKNWMTETLLVQNANPDCKTILKALGPASTLEEMMTAC

QGVGGPGHKARVLAEAMSQVTNSATIMMQKGNFRNQRKIVKCFNCGKEGH

IAKNCRAPRKRGCWKCGKEGHQMKDCTERQANFLGKIWPSHRGRPGNFPQ

NRLEPTAPPAPPEEIFRFGEETTTPSQKQEMIDKELYPSASLKSLFGNDP

LSQ

-continued

\>gi|9886945|gb|AAG01668.1| gag protein
[Human immunodeficiency virus type 1]
GGKKQYKMKHLIWASRELERFALNPSLLETGEGCQQIMEQLQSALRTGSE   [SEQ ID NO:128]

EFKSLYNTVATLYCVHQRIAVKDTKEALDKIEEIQSKSKQKAQQAAAATG

NSSNLSQNYPIVQNAQGQMVHQPISPRTLNAWVKVVEEKAFSPEVIPMFS

ALSEGATPQDLNMMLNIVGGHQAAMQMLKDTINEEAADWDRTHPVQAGPI

PPGQIREPRGSDIAGTTSNLQEQIRWMTSNPPNPVGEIYKRWIILGLNKI

VRMYSPVSILDIRQGPKEPFRDYVDRFFKTLRAEQATQEVKGWMTDTLLV

QNANPDCKTILKALGPGATLEEMMTACQGVGGPSHKARVLAEAMNQASGR

AIMMQKSNFKGPRRSIKCFNCGKEGHLARNCRAPRKKGCWKCGKEGHQMK

DCTERQANFLGKIWPSNKGRPGNFLQNRPEPTAPPAESFGFGEEIASSPK

QEPKKKELYPLASLKSLFGNDP

\>gi|3808251|gb|AAC69288.1| gag protein
[Human immunodeficiency virus type 1]
ARASVLSGGKLDAWEKIRLRPGGKKKYRMKHLVWASRELERFALNPSLLE   [SEQ ID NO:129]

TTEGCQQIMEQLQSALKTGTEELRSLFNTVAVLYCVHQRIEIKDTKEALD

KIEEIQKKSKQKAQQAAADTGNSSKVSQNYPIVQNAQGQMVHQSLSPRTL

NAWVKVIEEKAFSPEVIPVFSALSEGATPQDLNMMLNIVGGHQAAMQMLK

DTINEEAAEWDRLHPAHAGPVAPGQMREPRGSDIAGTTSTPQEQIGWMTG

NPPIPVGDIYKRWIILGLNKIVRMYSPVSILDIKQGPKEPFRDYVDRFFK

TLRAEQATQDVKNWMTETLLVQNANPDCKSILRALGAGATLEEMMSACQG

VGGPSHKARVLAEAMSQAQQHTTVMMQRANFRGQKRIKCFNCGKEGHLAR

NCRAPRKKGCWKCGKEGHQMKDCTERQANFLGKMWPSSKGRPGNFPQSRP

EPTAPPAELFGMGEEIASPPKQEQKDREQNSPSVSLKSLFGNDLLSQ

\>gi|3808241|gb|AAC69279.1| gag protein
[Human immunodeficiency virus type 1]
ARASVLSGGRLDAWEKIRLRPGGKKKYRMKHLVWASRELDRFALNPSLLE   [SEQ ID NO:130]

TTEGCQQIIGQLQPAFKTGTEELKSLYNTVATLWCVHQRIDVKDTKEALD

KLEEIQKKSKQKTQQAVADTGSSSKVSHNYPVVQNAQGQMIHQNLSPRTL

NAWVKVIEEKGFNPEVIPMFSALSEGATPQDLNTMLNIVGGHQAAMQMLK

DTINEEAAEWDRLHPVHAGPIPPGQMREPRGSDIAGTTSTPQEQLQWMTS

NPPIPVGDIYKRWIILGLNKIVRMYSPVSILDIRQGPKEPFRDYVDRFFK

ALRAEQATQEVKGWMTETLLVQNANPDCKSILKALGTGATLEEMMTACQG

VGGPGHKARVLAEAMSQVQQPNIMMQRGNFRGQRRIKCFNCGKEGHLAKN

CRAPRKKGCWKCGKEGHQMKDCTERQANFLGKIWPSSKGRPGNFPQSRPE

PTAPPAEIFGMGEVITSPPKQEQKDKEQVPPLVSLKSLFGNDPLSQ

\>gi|9651238|gb|AAF91101.1|AF196654_1 gag protein
[Human immunodeficiency virus type 1]
GGKKCYMMKHIVWASRELERFALDPGLLETSEGCKQILKQLQPALPTGTK   [SEQ ID NO:131]

ELISLYNTVATLYCVHEKIEVRDTKEALDKLKEEQNKSQQQTQQAAMADK

GKVSQNYPIVQNLQGQMVHQAISPRTLNAWVKVIEEKAFSPEVIPMFTAL

SEGATPQDLNTMLNTVGGHQAAMQMLKDTINEEAAEWDRLHPVQAGPVAP

GQVREPRGSDIAGTTSTLQEQIAWMTSNPPIPVGEIYKRWI

-continued

\>gi|8927258|gb|AAF82028.1|AF208027_1 gag protein
[Human immunodeficiency virus type 2]
MGARSSVLSGKKADELEKVRLRPGGKKKYMLKHVVWAANELDRFGLAESL  [SEQ ID NO:132]

LESKEGCQKILSVLAPLVPTGSENLKSLYNTVCVIWCLHAEQKVKHTEEA

KQVVQRHLVVETGTTEKVPATSRPIAPPSGRGGNYPVQQVGGNYVHLPLS

PRTLNAWVKLVEEKKFGAEVVPGFQALSEGCLPYDINQMLNCVGEHQAAM

QIIREIINEEAAXWDLQHPQQGPPPAGQXREPTGSDIAGTTSTIEEQIQW

THRQQNPIPVGNIYRRWIQLGLQKCVRMYNPTNILDVKQGPKEPFQSYVD

RFYKSLRAEQTDPAVKNWMTQTLLIQNANPDCKLVLKGLGMNPTLEEMLT

ACQGXGGPGQKARLMAEALKEALNPTALPFAAAQQKTGGKRSTIKCWNCG

KEGHTVRQCRAPRRQGCWKCGKPGHIMAKCPERQAGFLGFGPWGKKPRNF

PMTQVPQGLTPSAPPMDPAVDLLKNYMQLGRKQKEQRNKPYKEVTEXLLH

LSSLFGDDQ

\>gi|7767291|gb|AAF69055.1|AF144829_1 gag protein
[Human immunodeficiency virus type 1]
ELERFALNPDLLETTEGCQQALIQLQPALKIGIEELKSLYNTVATLYCVH  [SEQ ID NO:133]

RGIDVKDTKEALDKIEEIQIKSKNS

\>gi|8118014|gb|AAF72863.1| gag protein
[Human immunodeficiency virus type 1]
GGKKKYRMKHLVWASRELXRFAVDPGLLETPEGCRKIIGQLQPSLQTGSD  [SEQ ID NO:134]

ELRSLYNAVVVLYYVHQKIDVKDTKEALEKLEEEQHRSQQKTQQAAADKG

VSQNYPIVQNLQGQMVHQALSPRTLNAWVKVIEEKAFSPEVIPMXSALSE

GATPQDLNTMLNTVGGHQAAMQILKDTINEEAADWDRLHPVHAGPIPPGQ

MREPRGSDIAGTTSTLXEQIQWMTSNPPVPVGDIYKRWI

\>gi|8050682|gb|AAF71735.1| gag protein
[Human immunodeficiency virus type 1]
GGKKKYRLKHLVWASRELERFALNPGLLETTEGCKQIIGQLQPSLQTGTE  [SEQ ID NO:135]

ELKSLYNLVVVLYCVHRKIDVRDTKEALDKLQEEQAKCQQKTQQATADKG

VSQNYPIVQNLQGQMVHQAISPRTLNAWVKVIEEKAFSPEVIPMFSALSE

GATPQDLNTMLNTVGGHQAAMQMLKDTINEEAAEWDRVHPVQAGPNPPGQ

MREPRGSDIAGTTSTLQEQIAWMTGNPPVPVGEIYKRWISLVVNKIVRMY

SPVSILDIRQGPKEPFRDYVDRFFKTLRAEQATQEVKGWMTDTLLVQNAN

PDCKTILKALGPGATLEEMMTACQGVGGPSHKARVLAEAMSRATNTSIMM

QKSNFRGQRKMVKCFNCGKEGHIAKNCRAPRKRGCWKCGKEGHQMKDCTE

RQANFLGKIWPSNKGRPGNF

-continued

```
>gi|5668955|gb|AAD46099.1|AF076998_1 gag protein
[Human immunodeficiency virus type 1]
MGARASVLSGGKLDAWEKIRLRPGGKKKYRLKHIVWASRELERFAINPGL   [SEQ ID NO:136]

LETSEGCKQIIAQLQPAIQTGSEELRSLYNTVATLYCVHEKIEVKDTKEA

LEKIEEEQNKSKSKRAQQAEAGTKNSGPVSQNFPIVQNLQGQMVHQALSP

RTLNAWVKVIEEKAFSPEVIPMFTALSEGATPQDLNTMLNTVGGHQAAMQ

MLKETINEEAAEWDRVHPAQAGPIAPGQIREPRGSDIAGTTSTLQEQITW

MTNNPPIPVGEIYKRWIILGLNKIVRMYSPVSILDIRQGPKEPFRDYVDR

FYKTLRAEQASQDVKNWMTETLLVQNANPDCKTILKALGPQATLEEMMTA

CQGVGGPSHKARVLAEAMSQATGSPAVMMQRGNFKGPRKSIKCFNCGKEG

HTAKNCRAPRKRGCWKCGREGHQMKDCIEGQANFLGRVWLSHKGRPGNFL

QSRPEPSAPPAESFGFGEEITPSPKQEQKDEGKYPPLASLKSLFGNDPLS

Q

>gi|6815749|gb|AAF28699.1|AF184567_1 gag protein
[Human immunodeficieney virus type 1]
PMFTALSEGATPQDLNTMLNTVGGHQAAMQMLKDTINEEAAEWDRLHPVH   [SEQ ID NO:137]

AGPVAPGQMRDPRGSDIAGTTSTLQEQIAWMTNNPPIPVGDIYKRWIILG

LNKIVRMYSPVSILDIKQGPKEPFRDYVDRFFKTLRAEQSTQEVKNWMTD

TLLIQNANPDCKTILRSLGPGATLEEMMTACQGVGGPGHKARVLAEAMSQ

VNQTNIMMQKSNFKGPRRMVKCFNCGKEGHIAKNCRAPRKKGCWKCGKEG

YQMKDCTE

>gi|6815670|gb|AAF28620.1|AF184488_1 gag protein
[Human immunodeficiency virus type 1]
PQDLNTMLNTVGGHQAAMQMLKETINEEAAEWDRMHPVHAGPIAPGQLRE   [SEQ ID NO:138]

PRGSDIAGTTSTLQEQIGWMTNNPPIPVGEIYKRWIILGLNKIVRMYSPV

SILDIRQGPKEPFRDYVDRFYKTLRAEQASQDVKNWMTETLLVQNANPDC

KTILKALGPGATLEEMMTACQGVGGPSHKARVLAEAMSQATNNVNAAIMM

QRGNFKGQRKIIKCFNCGKEGHIAKNCRAPRKKGCWKCGKEGHQMKDCTD

RQANFLG

>gi|6815596|gb|AAF28546.1|AF184414_1 gag protein
[Human immunodeficiency virus type 1]
IPVGEIYKRWIVLGLNKIVRMYSPVSILDIRQGPKEPFRDYVDRFFKTLR   [SEQ ID NO:139]

AEQATQEVKSWMTGTLLVQNANPDCKTILRALGPATIEEMMTACQGVGE

PGHKARVLAEAMSQVQNTNILMQRGNFKGQRIKCFNCGKEGHLARNCRA

PRKKGCWKCGKEGHQMKDCTEKQANFLG
```

-continued

```
>gi|6653669|gb|AAF22839.1|AF209990_1 gag protein
[Human immunodeficiency virus type 1]
MGARASILRGGKLDKWEKIRLRPGGKKHYMLKHLVWASRELERFAVNPGL   [SEQ ID NO:140]

LETAEGCKQIIKQLQPALQTGTEELRSLYNTVATLYCVHAEIEVRDTKEA

LDRIEEEQNKSQQKTQQANEADGKVSQNYPIVQNLQGQMVHQAISPRTLN

AWVKVIEEKAFSPEVIPMFTALSEGATPQDLNTMLNTVGGHQAAMQMLKD

TINEEAAEWDRLHPVHAGPIAPGQMREPRGSDIAGTTSSLQEIAWMTGN

PPVPVGDIYKRWIILGLNKIVRMYSPVSILDIKQGPKEPFRDYVDRFFKT

LRAEQATQDVKNWMTDTLLVQNANPDCKTILRALGPGASLEEMMTACQGV

GGPSHKARVLAEAMSQTNSTILMQRSNFKGPKRIVKCFNCGKEGHIAKNC

RAPRKKGCWKCGKEGHQMKDCTERQANFLGKIWPSHKGRPGNFLQSRPEP

TAPPAESFRFEETTPALQQGPKDREPLTSLRSLFGSDPLSQ

>gi|4754345|gb|AAD28925.1| gag protein
[Human immunodeficiency virus type 1]
NSSQVSQNYPIVQNMQGQMVHQAISPRTLNAWVKVIEEKAFSPEVIPMFT   [SEQ ID NO:141]

ALSEGATPQDLNTMLNTVGGHQAAMQMLKDTINEEAAEWDRLHPVQAGPI

APGQMREPRGSDIAGTTSTLQEQIGWMTSNPPIPVGEIYKRWIILGLNKI

VRMYSPTSILDIKQGPKEPFRDYVDRFYKTLGAEQASQDVKNWMTETLLV

QNANPDCKTILKALGPAATLEEMMTACQGVGGPGHKARVLAEAMSQVTNS

TVMMQKGNFRNQRKIVKCFNCGKEGHIAKNCRAPRKRGCWKCG

>gi|4754293|gb|AAD28899.1| gag protein
[Human immunodeficiency virus type 1]
NSSQVSQNYPIVQNVQGQMVHQAISPRTLNAWVKVVEEKAFSPEVIPMFS   [SEQ ID NO:142]

ALSEGATPQDLNTMLNTVGGHQAAMQMLKETINEEAAEWDRLHPVHAGPI

APGQMREPRGSDIAGTTSTLQEQIGWMTHNPPIPVGEIYKRWIILGLNKI

VRMYSPTSILDIKQGPKEPFRDYVDRFYKTLRAEQASQEVKNWMTETLLV

QNANPDCKTILKALGPAATLEEMMTACQGVGGPGHKARVLAEAMSQVTNS

ATIMMQKGNFRSQRKIVKCFNCGKEGHIAKNCRAPRKKGCWKCG

>gi|3252937|gb|AAD12087.1| gag protein
[Human immunodeficiency virus type 1]
MGARASILRGGKLDKWEKIRLRPGGKKHYMIKHLVWASRELERFALNPGL   [SEQ ID NO:143]

LETSEGCKQIIKQLQPALQTGTEELRSLHNTVATLYCVHAGIEIRDTKEA

LDKIEEEQEKSQQKTQQAKEADGKVSQNYPIVQNLQGQMVHQALSPRTLN

AWVKVIEEKAFSPEIIPMFTALSEGATPQDLNTMLNTVGGHQAAMQMLKD

TINEEAAEWDRLHPAQAGPIAPGQMREPRGSDIAGTTSTLQEQIAWMTGN

PPVPVGEIYKRWIILGLNKIVRMYSPVSILDIKQGPKEPFRDYVDRFFKT

LRAEQATQDVKNWMTDTLLVQNANPDCKTILRALGPGASLEEMMTACQGV

GGPSHKARVLAEAMSQTNNSILMQRSNFKGFKRTVKCFNCGKEGHIARNC

RAPRKKGCWKCGKEGHQMKDCTERQANFLGKIWPSHKGRPGNFLQNRPEP

TAPPAESFRFEETTPALKQEQKDREPLTSLKSLFGSDPLSQ
```

```
-continued
>gi|3403209|gb|AAC29044.1| gag protein
[Human immunodeficiency virus type 1]
MGARASVLSGGKLDAWEKIRLRPGGKKKYRLKHLVWASREMERFALNPGL   [SEQ ID NO:144]

LETAEGCHQIMSQLQPAIQTGTEEIKSLFNTVATLYCVHQKIEVKDTTEA

LEEVEKIQKKSQQKIQQAARDEGNSSQVSQNYPIVQNAQGQMVHQAISPR

TLNAWVKVVEEKAFSPEVIPMFSALSEGATPQDLNTMLNTVGGHQAAMQM

LKDTINEEAAEWDRMHPPQAGPIPPGQIREPRGSDIAGTTSNLQEQIRWM

TSNPPIPVGEIYKRWIILGLNKIVRMYSPVSILDIRQGPKEPFRDYVDRF

FKTLRAEQATQEVKGWMTDTLLVQNANPDCKTILRALGPGATLEEMMTAC

QGVGGPGHKARVLAEAMSQATGAAAAIMMQKSNFKGPKRNIKCFNCGKEG

HLARNCRAPRKKGCWKCGKEGHQMKDCTERQANFLGKIWPSNKGRPGNFL

QNRPEPTAPPAESFGFGEEIAPSPKPEPKEKETHPLASLKSLFGSDPTLE

EMMTACQGVGGPGHKARVLAEAMSQVQNTNIMMQKGNFRGQKRIKCFNCG

KEGHLAK psi-site of HIV-1 RNA, full length sequence:
5'AGGACUCGGCUUGCUGAAGCGCGCACGGCAAGAGGC[SEQ ID NO:5]

GAGGGGCGGCGACUGGUGAGUACGCCAAAAAUUUUGAC

UAGCGGAGGCUAGAAGGAGAGAUGGGUGCGAGAGCG

UCGGU 3'
(published by A. H. Maki et al., Dept. Chem.,
U. Cal. Berkley

Psi-site of HIV-1 DNA, full length sequence:
DNA sequence is known to one of skill [SEQ ID NO:6]
in the art based upon the RNA sequence
immediately above.

SL3 DNA sequence:
5'-GGACTAGCGGAGGCTAGTCC-3'          [SEQ ID NO:8]

SL3 A4 DNA sequence:
5'-GGACTAGCAAAAGCTAGTCC-3'          [SEQ ID NO:9]
```

In one example of the present invention, the small organic molecule is azodicarbonamide having the structure:

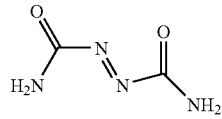

In another example of the present invention, the small organic molecule is a derivative of azodicarbonamide. One example of such a derivative has the following structure:

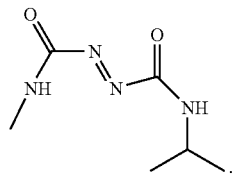

In other preferred examples, the small organic molecules are organic sulfur-containing compounds, such as the compounds having the following formulae:

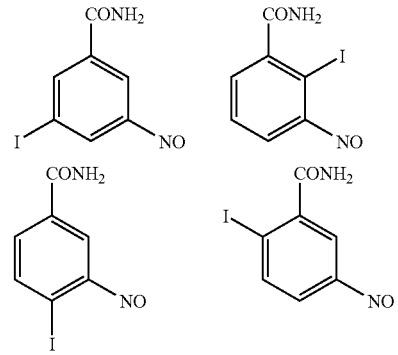

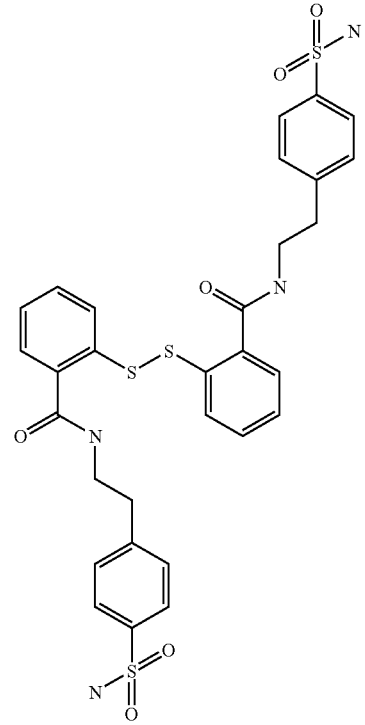

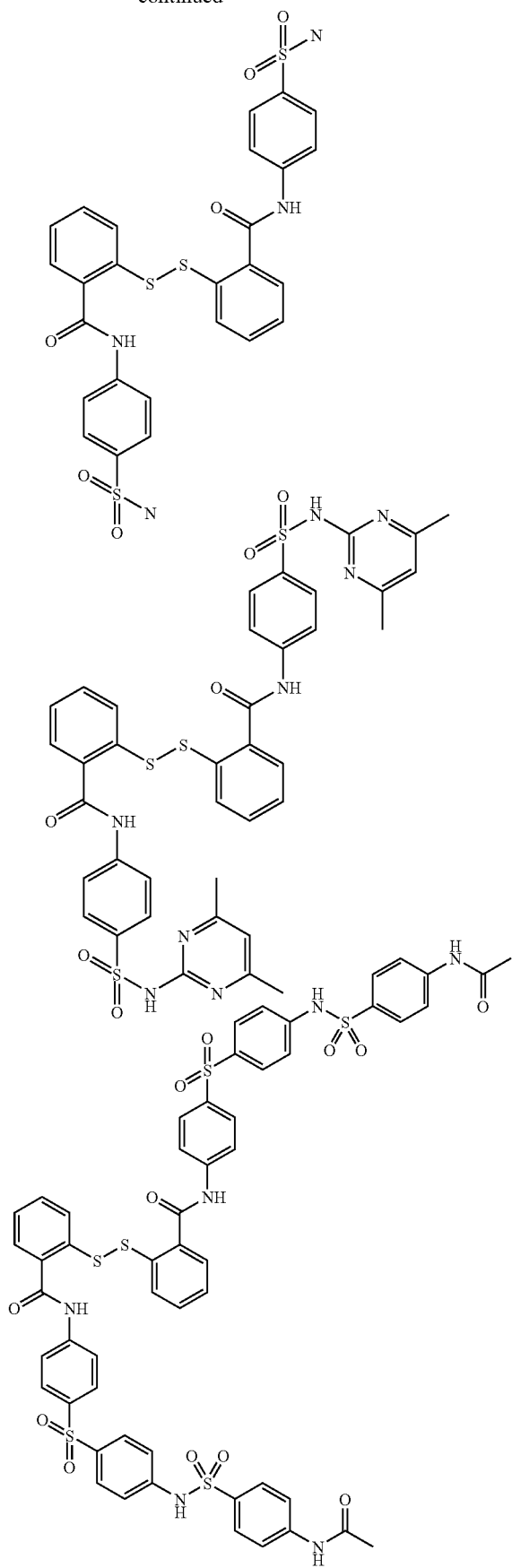
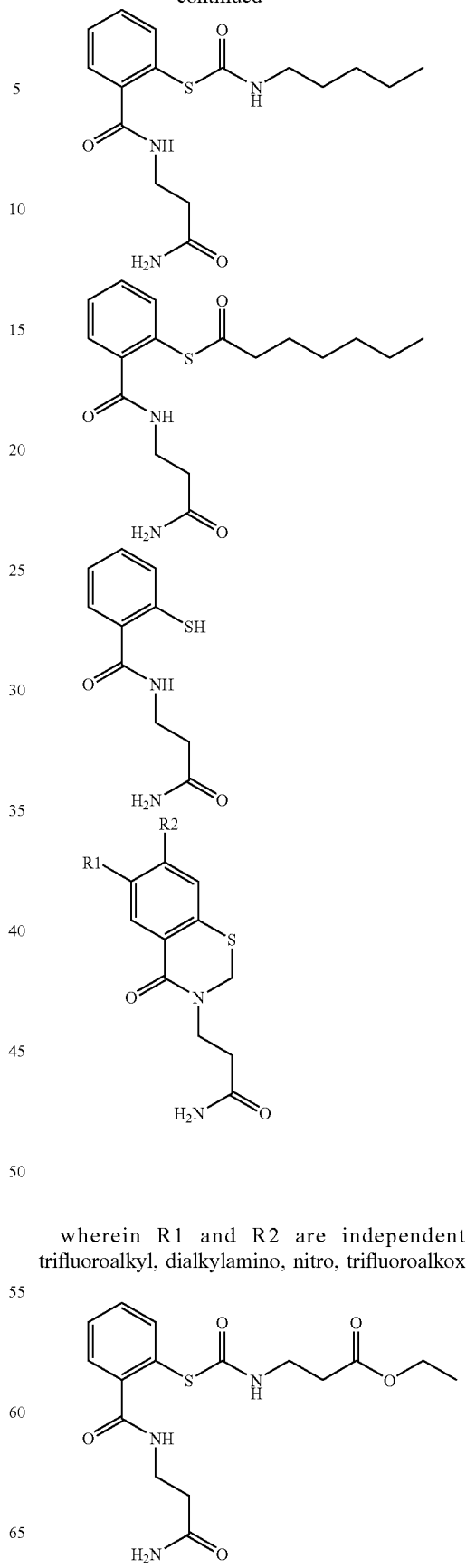
wherein R1 and R2 are independently alkyl, trifluoroalkyl, dialkylamino, nitro, trifluoroalkoxy -continued

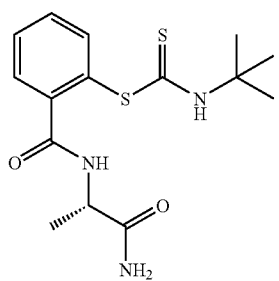
Chiral

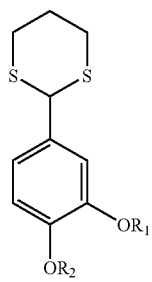

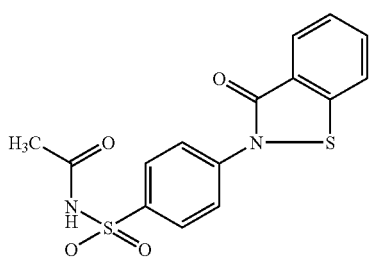

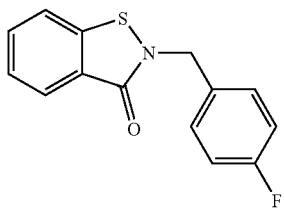

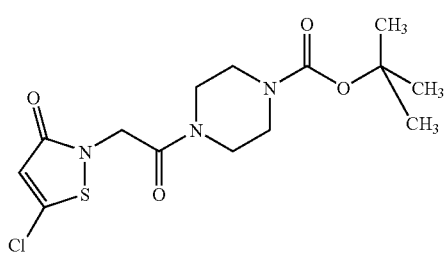

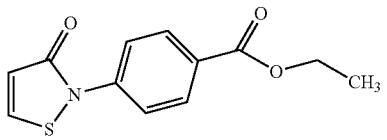

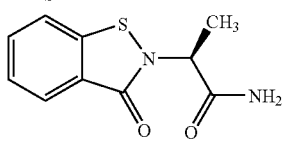

-continued

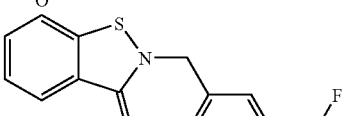

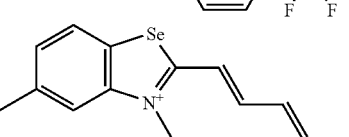

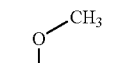

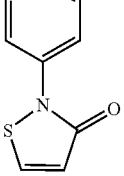

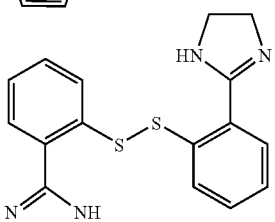

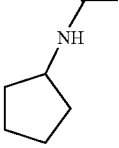

In yet further examples of the present invention, the compound may be any one or a combination of the following: tetramethylthiuram disulfide, tetraethylthiuram disulfide, tetraisopropylthiuram disulfide, tetrabutylthiuram disulfide, dicyclopentamethylenethiuram disulfide, isopropylxanthic disulfide, O,O-diethyl dithiobis-(thioformate), benzoyl disulfide, benzoylmethyl disulfide, formamidine disulfide, 2-(diethylamino)ethyl disulfide, aldrithiol-2, aldrithiol-4, 2,2-dithiobis(pyridine n-oxide), 6,6-dithiodinicotinic acid, 4-methyl-2-quinolyl disulfide, 2-quinolyl disulfide, 2,2 dithiobis(benzothiazole), 2,2-dithiobis(4-tert-butyl-1-isopropyl)-imidazole, 4-(dimethylamino)phenyl disulfide, 2-acetamidophenyl disulfide, 2,3-dimethoxyphenyl disulfide, 4-acetamidophenyl disulfide, 2-(ethoxycarboxamido)phenyl disulfide, 3-nitrophenyl disulfide, 4-nitrophenyl disulfide, 2-aminophenyl disulfide, 2,2 dithiobis(benzonitrile), p-tolyl disulfoxide, 2,4,5-trichlorophenyl disulfide, 4-methylsulfonyl-2-nitrophenyl disulfide, 4-methylsulfonyl-2-nitrophenyl disulfide, 3,3-dithiodipropionic acid, N,N-diformyl-1-cystine, trans-1,2-dithiane-4,5-diol, 2-chloro-5-nitrophenyl disulfide, 2-amino-4-chlorophenyl disulfide, 5,5-dithiobis(2-nitrobenzoic acid), 2,2-dithiobis(1-naphtylamine), 2,4-dinitrophenyl p-tolyl disulfide, 4-nitrophenyl p-tolyl disulfide, and 4-chloro-3-nitrophenyl disulfideformamidine disulfide dihydrochloride.

The U.S. patents listed herein below are hereby incorporated by reference in their entireties. These patents describe molecules which can be evaluated in the screening methods of the invention and which can be useful in the treatment methods of the invention: U.S. Pat. No. 6,242,478 (Five member ring sulfenate esters and thiosulfinate esters); U.S. Pat. No. 6,225,323 (Activated iododerivatives for the treatment of cancer and AIDS); U.S. Pat. No. 6,133,270 (Isothiazolones and pharmaceutical formulations); U.S. Pat. No. 6,046,228 (Anti-viral pharmaceutical compositions containing saturated 1,2-dithiaheterocyclic compounds and uses thereof); U.S. Pat. No. 6,008,190 (Schiff base compounds); U.S. Pat. No. 6,004,978 (Methods of treating cancer with aromatic nitro and nitroso compounds and their metabolites); U.S. Pat. No. 6,001,863 (Isothiazolones); U.S. Pat. No. 5,929,114 (Arylthio compounds); U.S. Pat. No. 5,889,034 (Isothiazolones); U.S. Pat. No. 5,877,185 (Synergistic compositions useful as anti-tumor agents); U.S. Pat. No. 5,753,674 (Adenosine diphosphoribose polymerase binding nitroso aromatic compounds useful as retroviral inactivating agents, anti-retroviral agents, anti-retroviral agents and anti-tumor agents); U.S. Pat. No. 5,734,081 (Arylthio compounds); U.S. Pat. No. 5,733,921 (Isothiazolone compounds); U.S. Pat. No. 5,670,518 (Aromatic nitro and nitroso compounds and their metabolites useful as anti-viral and anti-tumor agents); U.S. Pat. No. 5,668,291 (Arylthio compounds); U.S. Pat. No. 5,652,367 (Halo-nitro-isoquinolinone compounds and pharmaceutical compositions thereof); U.S. Pat. No. 5,652,260 (Adenosine diphosphoribose polymerase binding nitroso aromatic compound useful as retroviral inactivating agents, anti-retroviral agents and anti-tumor agents).

The present invention is not limited to the examples disclosed herein, but encompasses any solid support which could be used in the assays and methods described herein.

The present invention is directed to compound screening methods to identify compounds that inhibit the association of an NCp7 polypeptide with oligonucleotides. This assay allows quantification of association of different oligonucleotide sequences with the NCp7 with high specificity and sensitivity. More specifically, the present invention relates to determination of the effects of different small organic molecules upon the association of the NCp7 with oligonucleotides. This enables the evaluation of these small organic molecules as potential agents to disrupt viral replication, since association of the NCp7 with a target oligonucleotide is required for viral replication to occur. Methods for screening molecules in a high throughput screening (HTS) format are described. The present invention also encompasses high throughput screening assays that identify members of population of compounds (e.g., a library) that are inhibitors of the association of NCp7 protein of HIV-1 and an oligonucleotide. The invention provides methods for identifying compounds which inhibit the interaction of or binding of an oligonucleotide to the NCp7 protein.

The present invention is also directed to methods of treating subjects infected with HIV which comprises administering to the subject a composition which comprises a compound identified as an inhibitor of NCp7 binding to an oligonucleotide consisting essentially of the psi ($\Psi$) sequence of HIV-1 RNA.

The present invention is also directed to isolated compounds identified by the screening methods disclosed herein and to derivatives of those isolated compounds. The present invention is also directed to compositions which comprise the compounds identified by the screening methods of the present invention or derivatives of such compounds and a carrier. The carrier may be a pharmaceutically acceptable carrier.

Nucleocapsid Protein 7 of Human Immunodeficiency Virus (NCp7)

The NCp7 protein of HIV-1 is involved in several steps of the HIV-1 life cycle. The NCp7 polypeptide is initially synthesized inside the cell as part of the gag polypeptide. Within mature virions, the gag polypeptide is proteolytically processed to liberate free mature NCp7 protein. The mature NC product, NCp7, is a small basic protein (72 amino acids) containing two copies of a conserved zinc finger-like domain with the sequence $Cys-X_2-Cys-X_4-His-X_4-Cys$, designated as the CCHC motif. Reverse transcription is a key step in the HIV retroviral life cycle, allowing conversion of the single-stranded RNA genome into double-stranded DNA. The initiation of this process begins with the annealing of a primer tRNA to the viral RNA primer binding site. In HIV-1, the primer binding site sequence, located at the 5' end of the genomic RNA has a strict complementarity with 18 nucleotides in the acceptor stem of $tRNA^{Lys}_3$. The annealing of the tRNA primer to the primer binding site is promoted by nucleocapsid (NC) proteins. The NCp7 protein is also required for transfer of the extended primer to the 3' end of the RNA for the next step in minus DNA synthesis.

NCp7 (within the gag polypeptide framework) was found to be necessary for the dimerization and the encapsidation of the genomic viral RNA. Zinc finger protein-nucleic acid complexes are known to play an important role in a variety of biological processes. The zinc finger structure, which was originally identified as DNA binding structure in the RNA polymerase III transcription factor TFIIIA, is one of the well-known common motifs among transcription factors. For example, DNA-binding proteins are known to play an important role in gene regulation. Genes are typically regulated at the transcriptional level by DNA-binding proteins, which are referred to as transcription factors. Transcription factors regulate gene expression by specifically binding to a target nucleic acid sequence in promoter DNA.

The NCp7 protein of HIV-1 contains two zinc finger motifs. Both motifs have spacing $Cys-X_2-Cys-X_4-His-X_4-Cys$ (CCHC-type). In each motif the three cysteine residues and the histidine residue are involved in ligating a single $Zn^{+2}$ ion in a stable and structurally distinct architecture. The three dimensional structure of the NCp7 protein containing both zinc fingers and in complex with HIV-1 RNA has been determined by nuclear magnetic resonance (Amarasinghe et al, *J Mol Biol* 2000 Aug. 11; 301(2):491–511; De Guzman et al, *Science* 1998 Jan. 16; 279(5349):384–8). These structures demonstrate the critical role that the zinc finger motifs play in maintaining the structure of the NCp7 protein that is required for interaction with RNA and hence the biological function of NCp7.

NMR studies of the NCp7 protein have shown that, whereas the N- and C-terminal parts of the protein are flexible, the zinc finger domains are folded around the divalent ions. Moreover, the two zinc complexed domains are spatially close, a property that has been confirmed as being biologically important. Indeed, mutations of the zinc binding amino acids, or replacement of amino acids in the short sequence linking the CCHC boxes, which alter the NCp7 structure, abolish the virus infectivity in vivo.

The NCp7 CCHC zinc finger motifs are conserved in all retroviral NC proteins with the exception of Spumaviruses. Furthermore, the spacing and metal chelating residues are absolutely conserved in these viruses (Berg, *Science* 1986 Apr. 25; 232(4749):485–7; South T L and Summers M F, *Adv Inorg Biochem* 1990; 8:199–248). The HIV-1 CCHC zinc fingers are required for the selection and packaging of viral genomic RNA and participate in a number of other essential functions in both the early and late stages of the viral life cycle (Darlix, *J Mol Biol* 1995 Dec. 8; 254(4):523–37). Mutation of the zinc chelating residues within the zinc finger results in viruses that are non-infectious (Aldovini A, and Young R A., *J Virol* May 1990, 64(5):1920–6; Dorfman et al, *J Virol* 1993 October; 67(10):6159–69). Thus, the HIV-1 CCHC zinc fingers represent a highly conserved domain that may not permit mutational alterations. Drugs targeted against these zinc fingers may thus be less prone to promote the generation of resistant HIV-1 strains. Consequently, because the CCHC zinc finger motifs are essential for the viability of the HIV-1 virus and because they are highly conserved and intolerant of mutations, they are attractive targets for the development of anti-viral drugs. Zinc finger domains have been shown to be amenable to chemical modification by select electrophilic agents. For example, such agents can selectively target the HIV-1 NCp7 zinc finger domains and lead to selective anti-HIV-1 activity in the absence of cellular toxicity (Huang, *J Med Chem.* 1998 Apr. 23; 41(9):1371–81). Therefore, precedent exists for the rationale of selective targeting of zinc finger domains by therapeutic agents. The HIV-1 NCp7 zinc finger domains represent conserved, essential entities that can be targeted by particular chemical agents or compounds, and such agents can serve as human anti-HIV therapeutic agents. Methods to identify agents that will target the HIV-1 NCp7 zinc finger domains are described.

Due to the biological importance of protein-nucleic acid interaction, a variety of methods for studying protein-nucleic acid binding characteristics have been proposed. See, e.g., Hill et al. and the references cited therein. U.S. Pat. No. 5,783,384 to Verdine discloses methods for determining the affinity of a DNA-binding protein for a target nucleic acid sequence. Verdine teaches methods comprising providing a reversible bond between a DNA-binding protein and a target nucleic acid sequence, and determining the relative strength of the reversible bond (and, thus, the affinity of the protein for the nucleic acid) by breaking it under supervised conditions. The more stringent the conditions necessary to break the bond, the higher the affinity of the protein for the nucleic acid.

Radioactive labeling remains the most popular method for analyzing protein-nucleic acid interactions, despite being relatively slow, a health and environmental hazard, and relatively labor-intensive. Conventional radioactive labeling methods typically require radioactively end-labeling DNA probes with $^{32}P$ using specialized enzymes. Purification of labeled DNA from unincorporated $^{32}P$ can involve polyacrylamide gel electrophoresis, overnight elution, gel filtration and concentration steps. Since the half-life of $^{32}P$ is only 14 days, radiolabeling is required approximately every three weeks for each probe. Moreover, protein-$^{32}P$-DNA complexes need to be separated from unbound $^{32}P$-DNA. This is therefore not readily amenable to a high throughput format, e.g., where a large number of samples (tens to thousands per day) require quantification. Thus, a need has existed in the art for a simple, effective and rapid method for analyzing HIV nucleocapsid protein-nucleic acid interaction, and determining how this is modulated by small organic molecules which could potentially inhibit this interaction and thereby possess utility as potential therapeutic agents directed against HIV. It is therefore an object of the present invention to provide compositions and methods for designing and identifying compositions effective as anti-HIV compounds.

The following are illustrative embodiments of the methods and compositions of the invention:

Derivatives of Compounds

This invention encompasses derivatives of compounds or molecules which are identified as inhibitors of the association or binding of NCp7 polypeptide and the psi ($\Psi$)-based oligonucleotide having the sequence shown in SEQ ID NO:4. Such derivatives are based on the compound or molecule which is tested in the screening methods disclosed herein. The derivative may be the result of a modification of the lead compound or molecule to produce a more pharmaceutically acceptable compound or molecule. The derivative may include an association of the compound or molecule to a carrier which is pharmaceutically acceptable. The derivative may alternatively result in a less pharmaceutically acceptable derivative, but one that is more potent.

Methods of Treating a Subject Infected with HIV

This invention provides methods for treating a subject infected with HIV which comprises administering to the subject an effective amount of a composition comprising a molecule or a derivative thereof which is identified as an inhibitor of binding of NCp7 and an oligonucleotide. The composition administered is a therapeutic composition and the dose of such therapeutic composition may be optimized based on subject size, age and progression of the disease.

As used herein, a "therapeutic composition" refers to a composition comprising an active ingredient required to cause a desired effect when a therapeutically effective amount of the composition is administered to a mammal in need thereof.

As used herein, a "therapeutically effective amount" of a composition is that amount of each active component of the therapeutic composition that is sufficient to show a benefit (e.g., a reduction in a symptom associated with the disorder, disease, or condition being treated). When applied to an individual active ingredient, administered alone, the term refers to that ingredient alone. When applied to a combination, the term refers to combined amounts of the active ingredients that result in the benefit, whether administered in combination, serially, or simultaneously.

As used herein, the term "pharmaceutically acceptable delivery vehicle" refers to carriers that facilitate administration of a compound and preferably do not reduce the biological function of the compound. However, it is possible to have a carrier or delivery vehicle that does reduce the biological activity of the compound in exchange for enhanced delivery. The characteristics of the delivery vehicle will depend on the route of administration. Therapeutic compositions may contain, in addition to the active compound, diluents, fillers, salts, buffers, stabilizers, solubilizers, and other materials well known in the art.

There are many methods of administration of the identified compound or pharmaceutical composition which are useful in the methods of treating a subject. The administration of such a molecule, compound or composition comprises intralesional, intraperitoneal, intramuscular or intravenous injection; infusion, liposome-mediated delivery, topical delivery, or nasal, oral, anal, ocular or otic delivery. The invention encompasses the formulation of the identified molecule into a tablet or powder or liquid which can be taken orally by the subject. The invention encompasses any type of administration which would successfully bring the molecule, compound or composition to the location necessary in the subject to inhibit association of the HIV genomic RNA sequence with the NCp7 polypeptide. The invention encompasses the use of any carrier to enhance the delivery of the molecule, compound or composition.

Throughout this application, various publications are referenced within the text. Full citations for these publications may be found listed at the end of the specification immediately preceding the claims. All patents, patent applications and publications cited herein, whether supra or infra, are hereby incorporated by reference in their entirety. The disclosures of these publications in their entireties are hereby incorporated by reference into this application in order to more fully describe the state of the art as known to those skilled therein as of the date of the invention described and claimed herein.

This invention is illustrated in the Experimental Details section which follows. These examples are set forth to aid in an understanding of the invention but are not intended to, and should not be construed to, limit in any way the invention as set forth in the claims which follow thereafter. It is to be understood that the foregoing general description and the following detailed description are exemplary and explanatory, and are intended to provide further explanation of the invention claimed.

Experimental Details

To confirm the assay methods that are presented herein as part of the invention, the following examples are provided.

"µM" means micromolar;
"ml" or "mL" means milliliter;
"µl" means microliter;
"mg" means milligram;
"nM" means nanomolar

EXAMPLE 1

Expression and Purification of HIV-1 NCp7 in *E. coli*

ZB media (10 g tryptone/5 g NaCl per liter $H_2O$) (25 ml) containing 100 µg/ml ampicillin and 30 µg/ml chloramphenicol (ZB/Amp/Chl) was inoculated with 30 µl of a 10% glycerol stock of BL21 (DE3) cells harboring plasmid pET-3α-NC55 previously stored at −80° C. The culture was grown with shaking (250 rpm) at 37° C. overnight. The overnight culture was centrifuged at 1000 rpm for 5 min, the supernatant discarded, and the pellet resuspended in 20 ml of fresh ZB/Amp/Chl. A portion (20 ml) of the resuspended culture was used to inoculate 2 liters of ZB/Chl/Amp also containing 200 ml of 10×M9 salts (10 g of $NH_4Cl$, 30 g of $KH_2PO_4$, and 31.8 g of $Na_2HPO_4$ per liter of $H_2O$), 40 ml of 20% glucose, 2 ml of 1M $MgSO_4$, and 1 ml of 0.2M $ZnCl_2$. This culture was incubated at 37° C. and 250 rpm. The $OD^{600}$ was measured and at $OD^{600}$=0.55, isopropyl-thiogalactopyranoside was added to 1 mM. Incubation was continued at 37° C., 250 rpm for 4 hrs. After incubation, the culture was centrifuged at 8,000 rpm for 12 min. The supernatant was decanted and the pellet stored at −80° C. Stored pellets were allowed to thaw on ice and then resuspended in 20 ml of lysis buffer (50 mM Tris.HCl, pH 8.0, 0.1 mM $ZnCl_2$, 100 mM NaCl, 5 mM DTT, 2 mM EDTA, 10% glycerol at 4° C.). Protease inhibitor cocktail (200 µl, Calbiochem) was added and the resuspended pellets were sonicated on ice six times at 20 seconds on, 40 seconds off with a Branson Sonifier 250 at power setting 4. To the lysed resuspended pellets was added 2 ml of 4% polyethylenimine (PEI, Sigma Chemical Co., St. Louis, Mo., prepared by diluting 50% PEI to 4% with lysis buffer and adjusting the pH to 7.5 with 12N HCl) dropwise with stirring over 15 min at 4° C. The solution was then centrifuged at 21,000×g for 30 minutes at 4° C. The supernatant was decanted, stored on ice, and the pellet discarded.

The supernatant was filtered through a 0.45 micron filter and loaded at 0.5 ml/min onto a HILOAD™ 16/10 Q Sepharose column (Pharmacia) connected in series to a HILOAD™ 16/10 SP Sepharose column (Pharmacia) both previously equilibrated with Buffer A (50 mM Tris.HCl, pH 8.0, 10% glycerol, 100 mM NaCl, 100 mM $ZnCl_2$, 10 mM β-ME). The columns were washed with a total of 130 ml of buffer A after which the Q Sepharose column was removed and the SP Sepharose column washed with an additional 30 ml of Buffer A at 1 ml/min. The buffer was stepped to 60% Buffer A with 40% Buffer B (Buffer A containing 1M NaCl) and then the protein eluted at 1 ml/min with a gradient of 40% Buffer B to 50% Buffer B over 100 min. Fractions containing NCp7 were combined and concentrated to 5 ml in a CENTRIPLUS™ YM-3 ultrafiltration device (Amicon).

The concentrated NCp7-containing fractions were loaded on a HILOAD™ 16/60 Superdex 75 column (Pharmacia). The protein was eluted at 0.5 ml/min with Buffer A containing 200 mM NaCl. NCp7-containing fractions were combined, concentrated in CENTRIPLUS™ YM-3 devices, and stored at −80° C.

EXAMPLE 2

High-Throughput Screening Assay for Detection of Biotinylated-SL3 Binding to Immobilized NCp7 Protein NCp7 protein (15 µl, 2 mg/ml in 50 mM Tris pH 8.0, 200 mM NaCl, 0.1 mM $ZnCl_2$, 10 mM beta-mercaptoethanol, 10% glycerol from stock stored at −80° C.) was added to 10 mls of phosphate-buffered saline. The solution was vortexed gently and 100 µl was added to each well of a MAXISORP™ 96-well plate (NUNC™). Uncoated wells received buffer with no protein, BSA coated wells received buffer with no NCp7 protein but containing 2% BSA. The plates were covered and incubated at 4° C. overnight. Following incubation, unbound protein was removed and the plates washed twice with 200 µl/well of phosphate buffered saline at room temperature. Biotinylated-SL3 (15 pmol in 50 mM Tris HCl pH 7.5, containing 50 mM KCl and 10 mM $MgCl_2$) was added to each well and incubated at room temperature for 2 hours. Unbound biotinylated-SL3 was removed and the wells washed twice with 200 µl/well of phosphate buffered saline, 0.05% Tween. To each well was added 110 µl of streptavidin-HRP conjugate (1:4000, ZYMED™) in phosphate buffered saline, 0.05% Tween, 3% bovine serum albumin, and the plate was incubated at room temperature for 60 minutes. The wells were washed twice with 200 µl 1× phosphate buffered saline, 0.05% Tween, followed by one wash with 200 µl of distilled $H_2O$. To each well was added 110 µl of HRP substrate (DAKO TMB™ One Step Substrate). After two minutes, the development reaction was stopped by adding 110 µl/well of 0.2N HCl. The absorbance at $OD^{450}$ was determined in a plate reader (Molecular Devices, Sunnyvale, Calif.). FIG. 1 illustrates the results of this example. The lack of the use of a blocking agent resulted in an $OD^{450}$ of between 1.0 and 1.5. However, when BSA was used as a blocking agent, there is very little background and the binding is shown to be due to the presence of NCp7 on the plates (FIG. 1, last bar).

EXAMPLE 3

Screening Assay for Detection of Biotinylated-SL3 Binding to Immobilized NCp7 Protein NCp7 protein (15 µl, 2 mg/ml in 50 mM Tris pH 8.0, 200 mM NaCl, 0.1 mM $ZnCl_2$, 10 mM beta-mercaptoethanol, 10% glycerol from stock stored at −80° C.) was added to 10 mls of phosphate-buffered saline. The solution was vortexed gently and 100 µl was added to each well of a MAXISORP™ 96-well black plate (NUNC™). Uncoated wells received buffer with no protein, BSA coated wells received buffer with no NCp7 protein but containing 2% BSA. The plates were covered and incubated at 4° C. overnight. Following incubation, unbound protein was removed and the plates washed three (3) times with 200 µl/well of phosphate buffered saline at room temperature. Biotinylated-SL3 (5 pmol in 50 mM Tris.HCl pH 7.5, containing 50 mM KCl and 10 mM $MgCl_2$) was added to each well and incubated at room temperature for 2 hours. Unbound biotinylated-SL3 was removed and the wells washed three (3) times with 200 µl/well of phosphate buffered saline. To each well was added 110 µl of streptavidin-HRP conjugate (1:4000, ZYMED™) in phosphate buffered saline, 0.05% Tween, 0.5% bovine serum albumin, and the plate was incubated at room temperature for 60 minutes. The wells were washed 3× with 200 µl 1× phosphate buffered saline. To each well was added 110 µl of chemiluminescent HRP substrate (SUPERSIGNAL™ ELISA Pico Chemiluminescent substrate, Pierce, Rockford, Ill.). Resultant chemiluminescence was determined by reading in a Wallac Microbeta (luminescent program).

EXAMPLE 4

High Throughput Screening Assay to Detect Compounds that Alter Binding of Biotinylated-SL3 to HIV-1 NCp7

Figure 2:
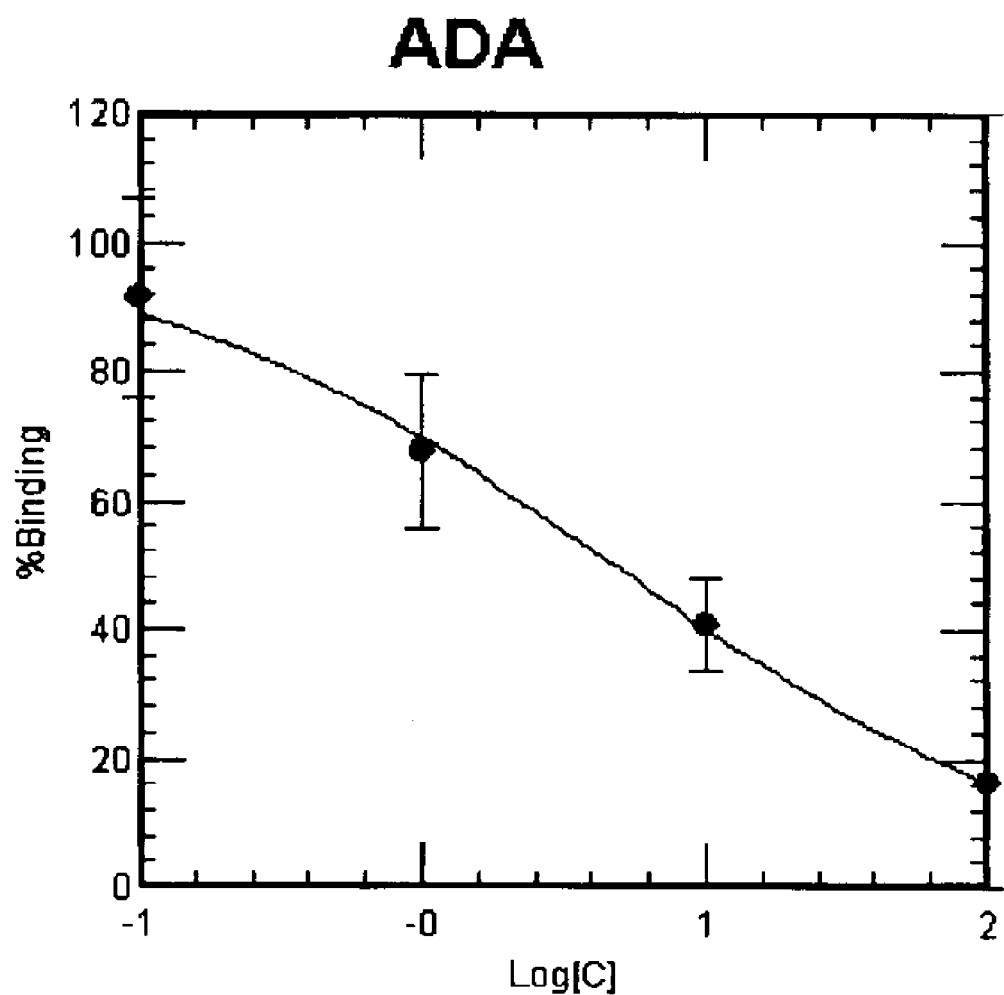
FIG. 2 illustrates percent binding of biotinylated SL3 to plate immobilized NCp7 proteins vs. azodicarbonamide (ADA) concentration.
Figure 3:
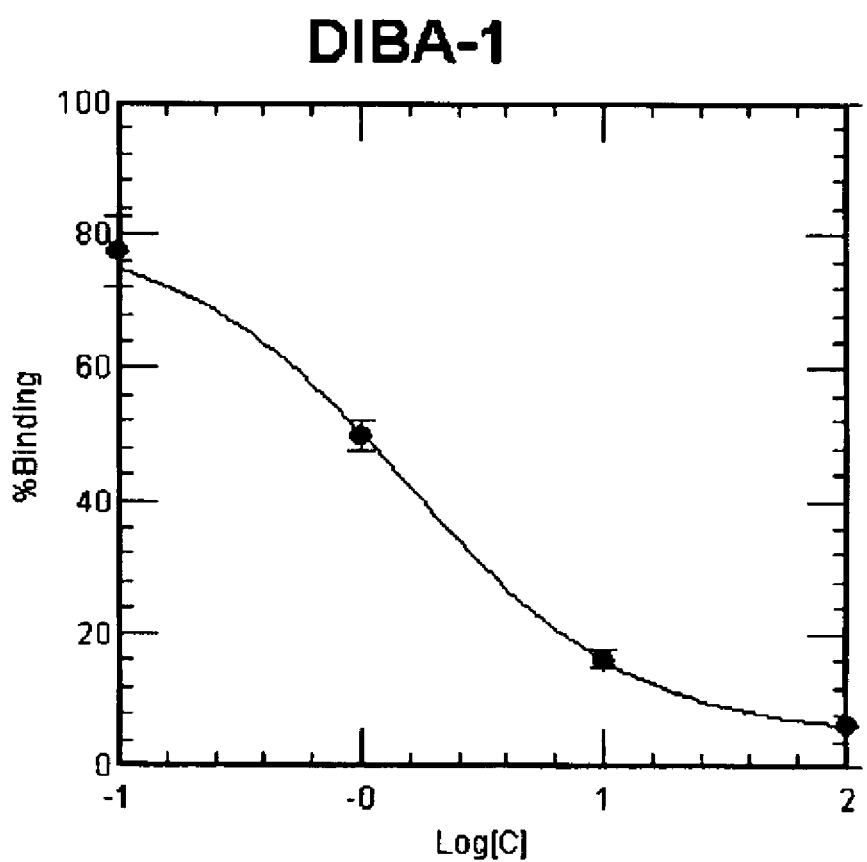
FIG. 3 illustrates percent binding of biotinylated SL3 to plate immobilized NCp7 proteins vs. 2,2'-dithiobisbenzamide (DIBA-1) concentration.
Figure 4:
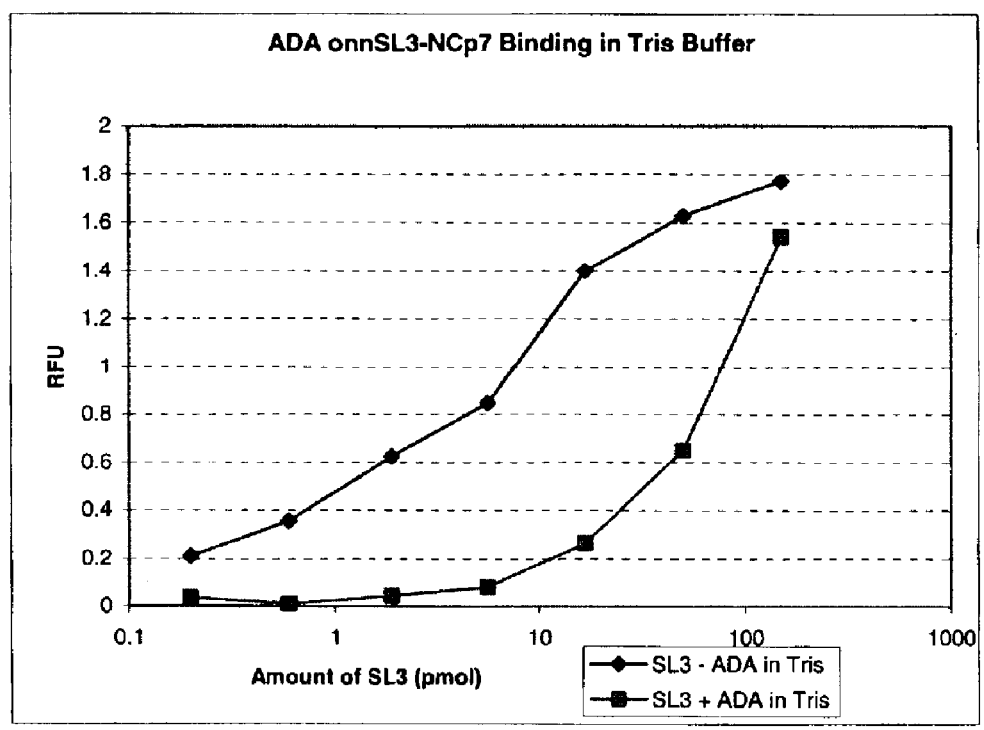
FIG. 4 illustrates the effect of ADA SL3 binding to NCp7 in Tris buffer.

Plates (96-well, NUNC™) were coated with NCp7 protein as described in Example 2. To treated wells was added 200 µl of azodicarbonamide (ADA) at the indicated concentrations (see FIG. 2) or 2,2'-dithiobisbenzamide (DIBA-1) stock solutions at the indicated concentrations (see FIG. 3), both in 50 mM Tris.HCl pH 7.5, 50 mM KCl, 10 mM $MgCl_2$, 10% glycerol, 1% DMSO. To control wells was added 200 µl of buffer minus compounds. The plates were incubated at room temperature for 60 minutes. After treatment, each well was washed twice with 200 µl/well of phosphate buffered saline. Biotinylated-SL3 (15 pmol in 50 mM Tris.HCl pH 7.5, containing 50 mM KCl and 10 mM $MgCl_2$) was added to each well and incubated at room temperature for 2 hours. Unbound biotinylated-SL3 was removed and the wells washed twice with 200 µl/well of phosphate buffered saline, 0.05% TWEEN™. Bound biotinylated-SL3 was detected as described in Example 2.

EXAMPLE 5

Figure 5:
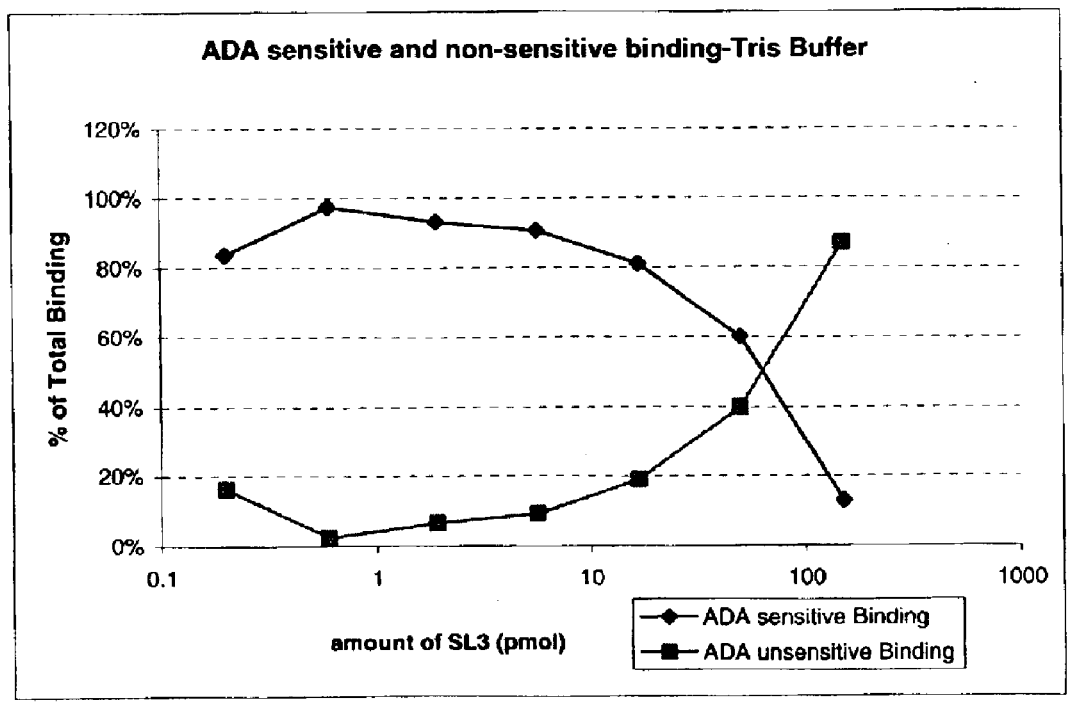
FIG. 5 illustrates ADA sensitive and non-sensitive SL3 binding to NCp7 in Tris buffer.

Demonstration of Specific Binding of Biotin labeled-SL3 Stem Loop to Immobilized HIV-1 NCp7 Protein NCp7 protein (15 µl, 2 mg/ml in 50 mM Tris pH 8.0, 200 mM NaCl, 0.1 mM $ZnCl_2$, 10 mM beta-mercaptoethanol, 10% glycerol) was added to 10 mls 1× phosphate buffered saline. The solution was vortexed gently and 100 µl was added to each well of a MAXISORP™ 96-well plate (NUNC™). The plates were covered and incubated at 4° C. overnight. Following incubation unbound protein was removed and the plates washed twice with 200 µl/well of 1× phosphate buffered saline at room temperature. Azodicarbonamide (Lancaster, Pelham, N.H., 200 µl at 100 µM in 50 mM Tris.HCl pH 7.5, 50 mM KCl, 10 mM $MgCl_2$, 10% glycerol, 1% DMSO) was added to each well. The plates were incubated at room temperature for 60 minutes. After treatment, each well was washed twice with 200 µl/well of phosphate buffered saline. Biotinylated SL3 starting at 0.150 pmol/well and increasing to 150 pmol/well in 50 mM Tris.HCl pH 7.5, containing 50 mM KCl and 10 mM $MgCl_2$ was added to each well and incubated at room temperature for a 2 hour-period. Unbound biotinylated SL3 was removed and the wells washed twice with 200 µl/well of 1× phosphate buffered saline, 0.05% TWEEN™. To each well was added 110 µl of streptavidin-HRP conjugate (1:4000, ZYMED™) in 1× phosphate buffered saline, 0.05% TWEEN™, 3% bovine serum albumin and the plate was incubated at room temperature for 60 minutes. The wells were washed twice with 200 µl 1× phosphate buffered saline, 0.05% TWEEN™, followed by one wash with 200 µl of distilled $H_2O$. To each well was added 110 µl of HRP substrate (DAKO TMB™ One Step Substrate). After two minutes the development reaction was stopped by adding 110 µl/well of 0.2N HCl. The absorbance at $OD^{450}$ was determined in a plate reader (Molecular Devices, Sunnyvale, Calif.). The percent ADA-sensitive and ADA-nonsensitive binding at each concentration of biotinylated SL3 was calculated using the following equation:

[Relative Fluorescence Units (0 µM ADA)−*RFU*(100 µM ADA)/ *RFU*(0 µM ADA)]×100=% specific binding The results are shown in FIG. 5.

EXAMPLE 6

Specificity of Binding of DNA Oligos by Immobilized NCp7

Figure 6:
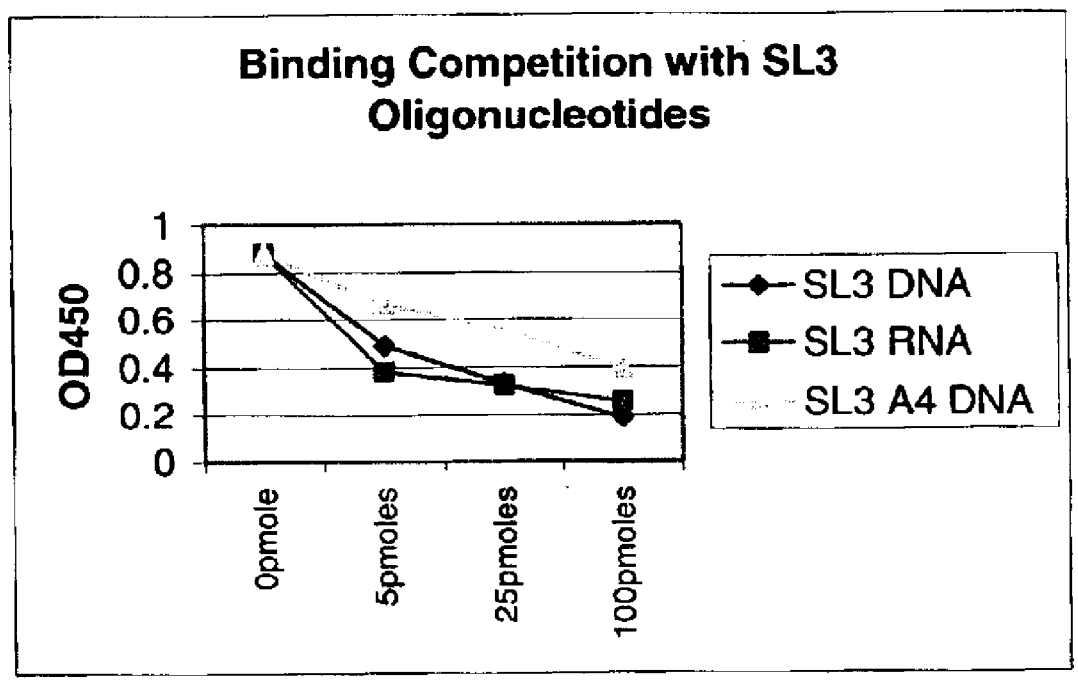
FIG. 6 illustrates a binding competition with three different SL3 oligonucleotides, i.e., SL3 DNA (SEQ ID NO:8), SL3 RNA (SEQ ID NO:7) and SL3 A4 DNA (SEQ ID NO:9).
Figure 7:
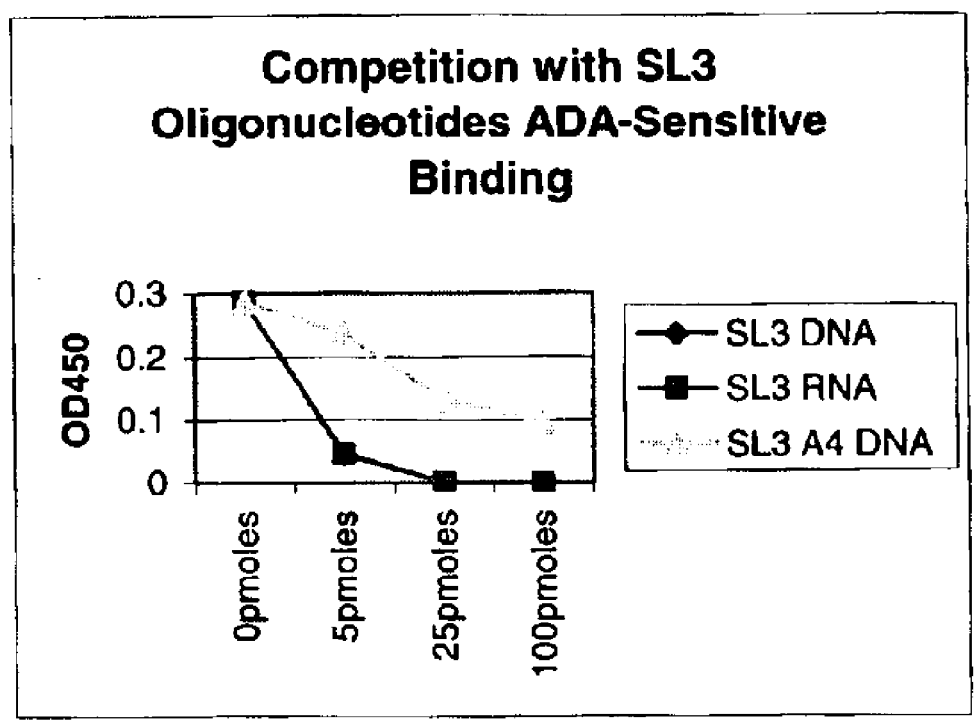
FIG. 7 illustrates competition with SL3 oligonucleotides ADA-sensitive binding.

Plates (96-well, NUNC™) were coated with NCp7 protein as described in Example 2. To treated wells was added 200 µl of 100 µM azodicarbonamide (ADA) in 50 mM Tris.HCl pH 7.5, 50 mM KCl, 10 mM $MgCl_2$, 10% glycerol, 1% DMSO. To control wells was added 200 µl of buffer minus azodicarbonamide. Plates were incubated at room temperature for 3 hours. Following incubation, plates were washed twice with 200 µl/well of phosphate buffered saline. Binding buffer (100 µl/well, 50 mM Tris.HCl pH 7.5, 50 mM KCl, 10 mM $MgCl_2$, 10% glycerol) containing 2 pmoles biotinylated SL3 and also containing either 0, 1, 5, 10, 25, 50, or 100 pmoles unlabeled competitor oligonucleotide, was added. Plates were incubated for 2 hours at room temp. Unbound oligonucleotides were removed and wells washed twice with 200 µl/well 1× phosphate buffered saline, 0.5% TWEEN-20™. Bound biotinylated SL3 was detected as described in Example 2. The $OD^{450}$ was plotted against pmoles of competitor oligonucleotide (see FIG. 6) added as well as the azodicarbonamide-sensitive binding against pmoles of competitor oligonucleotide added (see FIG. 7). Azodicarbonamide-sensitive binding was calculated as described in Example 4.

Sequences of unlabeled competitor oligos.
SL3 DNA:    5'-GGACTAGCGGAGGCTAGTCC-3' (SEQ ID NO:8)

SL3 RNA:    5'-GGACUAGCGGAGGCUAGUCC-3' (SEQ ID NO:7)

SL3 A4 DNA: 5'-GGACTAGCAAAAGCTAGTCC-3' (SEQ ID NO:9)

In the NCp7 assay, NCp7 protein is coated onto the surface of a 96-well plate. This is followed with a blocking step with bovine serum albumin (BSA). If the BSA step is omitted and the assay performed as usual, the biotinylated SL3 oligo binds well to each well of the plate. However, this binding is non-specific and it is not possible to prevent or abolish this binding with compounds like ADA or DIBA-1. Thus, without the BSA block almost all of the binding of the biotinylated oligo is non-specific. If the BSA blocking step is carried out, then almost all of the binding is specific.

In the NCp7 assay, adding increasing amounts of biotinylated oligonucleotide to each NCp7-coated well of a 96-well plate results in increasing amounts of oligonucleotide binding to the plate. However, past a certain point the increase in binding is entirely non-specific binding. Thus, as the amount of oligonucleotide is increased, the percent of total binding that is specific binding decreases. To obtain a useable signal from the assay requires using an amount of oligonucleotide within a fairly narrow concentration window that gives a reasonable signal but yet maximizes the percent of total binding that is specific. Thus, it is possible to optimize the signal to noise ratio.

In the same way different buffers give different percentages of specific binding against non-specific binding. Experiments were carried out using phosphate buffer, Tris buffer, and HEPES buffer. It was found that phosphate gives the maximum specific binding.

EXAMPLE 7

High-Throughput Screening Assay for Detection of HIV-1 NCp7 Protein Binding to Immobilized SL3

Biotinylated-SL3 oligonucleotide (10 pmoles in 100 µl phosphate buffered saline) was added to each well of a streptavidin-coated black 96-well microtiter plate (Pierce Biotechnology, Rockford, Ill.) and incubated at room temperature for one hour. Unbound biotinylated-SL3 was removed and the wells washed three times with 200 µl/well of phosphate buffered saline containing 0.05% Tween-20. Casein (2.5% in phosphate-buffered saline, 200 µl) was added to each well and incubation continued for one hour at room temperature. Each well was washed three times with 200 µl/well of phosphate buffered saline containing 0.05% Tween-20. NCp7 protein (10 ng in 100 µl of 50 mM Tris, pH 7.3, 25 mM KCl, 15 mM NaCl, 5 mM MgCl$_2$, 10% glycerol, 0.05% Tween-20) was added to each well. Incubation was continued for 30 minutes at room temperature. Following incubation, the wells were washed three times with 200 µl/well of phosphate buffered saline containing 0.05% Tween-20. Anti-NCp7 rabbit sera (1:4,000 dilution in 100 µl phosphate buffered saline containing 0.05% Tween-20) was added to each well and incubated for 30 minutes at room temperature. The anti-sera solution was removed and each well washed three times with 200 µl/well of phosphate buffered saline containing 0.05% Tween-20. Europium-labeled anti-rabbit antibody (1:15,000 dilution in 100 µl 50 mM Tris, pH 7.3, 0.5% BSA, 0.05% Tween-20, Perkin Elmer Life Sciences, Boston, Mass.) was added and incubated for one hour at room temperature. The antibody solution was removed and the wells washed three times with 200 µl/well of phosphate buffered saline containing 0.05% Tween-20. Europium enhancement solution (100 µl/well, Perkin Elmer Life Sciences) was added and fluorescence read at 615 nm with excitation at 340 nm.

EXAMPLE 8

High Throughput Screening Assay to Detect Compounds that Alter Binding of HIV-1 NCp7 to Immobilized SL3

Plates (streptavidin-coated, black, 96-well, Pierce Biotechnology) were coated with biotinylated-SL3 and blocked with 2.5% casein as described in Example 7. NCp7 (10 ng in 100 µl of 50 µmM Tris, pH 7.3, 25 mM KCl, 15 mM NaCl, 5 mM MgCl$_2$, 10% glycerol, 0.05% Tween-20, 1% DMSO) was incubated with the test compound at the desired concentration in a clear 96-well microtiter plate (previously blocked with 2.5% casein for 30 minutes at room temperature and washed three times to remove blocking solution.). The plates were incubated at room temperature for 30 minutes. The contents of this plate were then transferred to the SL3-coated plate and incubated for 30 minutes at room temperature. After incubation, unbound NCp7 was removed, the plates washed, and bound NCp7 quantitated as described in Example 7.

REFERENCES

Basrur V, Song Y, Mazur S J, Higashimoto Y, Turpin J A, Rice W G, Inman J K, Appella E., Inactivation of HIV-1 nucleocapsid protein P7 by pyridinioalkanoyl thioesters. Characterization of reaction products and proposed mechanism of action. *J. Biol. Chem.* 2000 May 19; 275(20):14890–7.

de Rocquigny H, Ficheux D, Gabus C, Fournie-Zaluski M C, Darlix J L, Roques B P. Related Articles, First large scale chemical synthesis of the 72 amino acid HIV-1 nucleocapsid protein NCp7 in an active form. *Biochem. Biophys. Res. Commun.* 1991 Oct. 31; 180(2):1010–8.

Gorelick R J, Gagliardi T D, Bosche W J, Wiltrout T A, Coren L V, Chabot D J, Lifson J D, Henderson L E, Arthur L O. Strict conservation of the retroviral nucleocapsid protein zinc finger is strongly influenced by its role in viral infection processes: characterization of HIV-1 particles containing mutant nucleocapsid zinc-coordinating sequences. *Virology.* 1999 Mar. 30; 256(1):92–104.

Guo J, Wu T, Anderson J, Kane B F, Johnson D G, Gorelick R J, Henderson L E, Levin J G., Zinc finger structures in the human immunodeficiency virus type 1 nucleocapsid protein facilitate efficient minus- and plus-strand transfer. *J. Virol.* 2000 October; 74(19):8980–8.

Huang M, Maynard A, Turpin J A, Graham L, Janini G M, Covell D G, Rice W G. Anti-HIV agents that selectively target retroviral nucleocapsid protein zinc fingers without affecting cellular zinc finger proteins. *J. Med. Chem.* 1998 Apr. 23; 41(9):1371–81.

Maynard A T, Covell D G, Reactivity of zinc finger cores: analysis of protein packing and electrostatic screening. *J. Am. Chem. Soc.* 2001 Feb. 14; 123(6): 1047–58.

Maynard A T, Huang M, Rice W G, Covell D G. Reactivity of the HIV-1 nucleocapsid protein p7 zinc finger domains from the perspective of density-functional theory. *Proc. Natl. Acad. Sci., U.S.A.* 1998 Sep. 29; 95(20):11578–83.

McDonnell N B, De Guzman R N, Rice W G, Turpin J A, Summers M F. Zinc ejection as a new rationale for the use of cystamine and related disulfide-containing antiviral agents in the treatment of AIDS. *J. Med. Chem.*, 1997 Jun. 20; 40(13): 1969–76.

Ramboarina S, Morellet N, Fournie-Zaluski M C, Roques B P, Moreller N. Structural investigation on the requirement of CCHH zinc finger type in nucleocapsid protein of human immunodeficiency virus 1. Biochemistry. 1999 Jul. 27; 38(30):9600–7.

Rice W G, Supko J G, Malspeis L, Buckheit R W Jr, Clanton D, Bu M, Graham L, Schaeffer C A, Turpin J A, Domagala J, et al. Inhibitors of HIV nucleocapsid protein zinc fingers as candidates for the treatment of AIDS. *Science*. 1995 Nov. 17; 270(5239):1194.

Rice W G, Schaeffer C A, Graham L, Bu M, McDougal J S, Orloff S L, Villinger F, Young M, Oroszlan S, Fesen M R, et al. The site of antiviral action of 3-nitrosobenzamide on the infectivity process of human immunodeficiency virus in human lymphocytes. *Proc. Natl. Acad. Sci. U.S.A.* 1993 Oct. 15; 90(20):9721–4.

Rice W G, Baker D C, Schaeffer C A, Graham L, Bu M, Terpening S, Clanton D, Schultz R, Bader J P, Buckheit R W Jr, Field L, Singh P K, Turpin J A. Inhibition of multiple phases of human immunodeficiency virus type 1 replication by a dithiane compound that attacks the conserved zinc fingers of retroviral nucleocapsid proteins. *Antimicrob. Agents Chemother.* 1997 February; 41(2):419–26.

South T L, Blake P R, Sowder R C 3rd, Arthur L O, Henderson L E, Summers M F. The nucleocapsid protein isolated from HIV-1 particles binds zinc and forms retroviral-type zinc fingers. *Biochemistry*. 1990 Aug. 28; 29(34):7786–9.

Takahashi K, Baba S, Koyanagi Y, Yamamoto N, Takaku H, Kawai, Two basic regions of NCp7 are sufficient for conformational conversion of HIV-1 dimerization initiation site from kissing-loop dimer to extended-duplex dimer. *J. Biol. Chem.* 2001 Aug. 17; 276(33):31274–8.

Tummino P J, Scholten J D, Harvey P J, Holler T P, Maloney L, Gogliotti R, Domagala J, Hupe D. The in vitro ejection of zinc from human immunodeficiency virus (HIV) type 1 nucleocapsid protein by disulfide benzamides with cellular anti-HIV activity. *Proc Natl Acad Sci USA*. 1996 Feb. 6; 93(3):969–73.

Turpin J A, Song Y, Inman J K, Huang M, Wallqvist A, Maynard A, Covell D G, Rice W G, Appella E. Synthesis and biological properties of novel pyridinioalkanoyl thiolesters (PATE) as anti-HIV-1 agents that target the viral nucleocapsid protein zinc fingers. *J Med Chem.* 1999 Jan. 14; 42(1):67–86.

Vuilleumier C, Bombarda E, Morellet N, Gerard D, Roques B P, Mely Y. Nucleic acid sequence discrimination by the HIV-1 nucleocapsid protein NCp7: a fluorescence study. *Biochemistry*. 1999 Dec. 21; 38(51):16816–25.

Williams M C, Rouzina I, Wenner J R, Gorelick R J, Musier-Forsyth K, Bloomfield V A. Mechanism for nucleic acid chaperone activity of HIV-1 nucleocapsid protein revealed by single molecule stretching. *Proc Natl Acad Sci U.S.A.* 2001 May 22; 98(11):6121–6.

---

What is claimed is:

1. A method for determining whether a compound inhibits formation of a complex between an HIV nucleocapsid protein 7 (NCp7) polypeptide and an HIV Ψ-site oligonucleotide comprising the steps of:
   (a) admixing an NCp7 polypeptide with a compound;
   (b) adding an HIV Ψ-site oligonucleotide selected from SEQ ID NO:7 and SEQ ID NO:8 to the admixture of step (a) so as to form an HIV Ψ-site oligonucleotide-NCp7 polypeptide complex;
   (c) determining amounts of complex formed in step (b); and
   (d) comparing the amount of complex formed in step (b) in the presence of the compound with the amount of complex formed in the absence of the compound, thereby determining whether the compound inhibits complex formation, wherein a decrease in the amount of complex formed in the presence of the compound indicates that the compound inhibits complex formation.

2. The method of claim 1, wherein the NCp7 polypeptide consists the amino acid sequence set forth in any one of SEQ ID NOS: 10–18, 20, 22–32, 35, 99–101, 104–111, 121–122, 126–130, 132, and 135–144.

3. The method of claim 1, wherein the NCp7 polypeptide consists essentially of two zinc finger binding domains and an amino acid sequence which links the two zinc finger binding domains.

4. A method for determining whether a compound inhibits binding of human immunodeficiency virus (HIV) nucleocapsid 7 polypeptide (NCp7) to an oligonucleotide which comprises:
- (a) attaching an NCp7 polypeptide to a solid support;
- (b) incubating the solid support with the NCp7 polypeptide linked thereto with a blocking agent;
- (c) incubating the solid support with the NCp7 polypeptide linked thereto with:
  - (i) at least one labeled oligonucleotide selected from SEQ ID NO:7 and SEQ ID NO:8, and
  - (ii) an amount of the compound; and
- (d) determining the amount of labeled oligonucleotide bound to the NCp7 polypeptide, wherein a decrease in the amount of oligonucleotide bound to the NCp7 polypeptide in the presence of the compound compared with the amount of oligonucleotide bound to the NCp7 polypeptide in the absence of the compound indicates that the compound inhibits binding of NCp7 polypeptide to the oligonucleotide.

5. The method of claim 4, wherein the NCp7 polypeptide consists of the amino acid sequence set forth in any one of SEQ ID NOS:10–18, 20, 22–32, 35, 99–101, 104–111, 121–122, 126–130, 132, and 135–144.

6. The method of claim 4, wherein the NCp7 polypeptide consists essentially of two zinc finger binding domains and an amino acid sequence which links the two zinc finger binding domains.

7. The method of claim 4, wherein the blocking agent is selected from the group consisting of: bovine serum albumin (BSA), poly-L-lysine, poly-DL-lysine, poly-L-glutamic acid, poly-DL-glutamic acid polyethyleneimine, poly-4-vinylpyridine, poly-2-vinylpyridine, poly-3-vinylpyridine, polyethylene oxide, bacterial tRNA, yeast tRNA, casein, ovalbumin gamma-globulin, heparin, polybrene, polyacrylic acid, polymethacrylic acid, ampholytic copolymers of acrylic acid with acrylamide, poly-N-carboxyethylacrylamide, poly-N-carboxymethylacrylamide poly-N-carboxypropylacrylamide, poly(glycolic acid), a copolymer of polyacrylic acid, poly(glycolic acid), polylactic acid oligomers and any combination thereof.

8. A kit for detection of agents that inhibit binding of an HIV nucleocapsid polypeptide to an HIV Ψ-site oligonucleotide, comprising:
- (a) an NCp7 polypeptide; (b) an isolated HIV Ψ-site oligonucleotide selected from SEQ ID NO:7 and SEQ ID NO:8;
- (c) instructions describing how to create the appropriate binding conditions.

9. The kit of claim 8, wherein the NCp7 polypeptide is affixed to a solid support.

* * * * *